United States Patent
Karplus et al.

(10) Patent No.: US 11,434,263 B2
(45) Date of Patent: Sep. 6, 2022

(54) STABILIZED POLYPEPTIDES AND USES THEREOF

(71) Applicant: PRESIDENT AND FELLOWS OF HARVARD COLLEGE, Cambridge, MA (US)

(72) Inventors: Martin Karplus, Cambridge, MA (US); Victor G Ovchinnkov, Watertown, MA (US)

(73) Assignee: PRESIDENT AND FELLOWS OF HARVARD COLLEGE, Cambridge, MA (US)

( * ) Notice: Subject to any disclaimer, the term of this patent is extended or adjusted under 35 U.S.C. 154(b) by 64 days.

(21) Appl. No.: 16/955,557

(22) PCT Filed: Jan. 4, 2019

(86) PCT No.: PCT/US2019/012291
§ 371 (c)(1),
(2) Date: Jun. 18, 2020

(87) PCT Pub. No.: WO2019/136209
PCT Pub. Date: Jul. 11, 2019

(65) Prior Publication Data
US 2020/0317736 A1 Oct. 8, 2020

Related U.S. Application Data

(60) Provisional application No. 62/613,994, filed on Jan. 5, 2018, provisional application No. 62/714,464, filed on Aug. 3, 2018.

(51) Int. Cl.
*A61K 38/10* (2006.01)
*C07K 7/08* (2006.01)
*C07K 14/195* (2006.01)
*A61K 38/00* (2006.01)

(52) U.S. Cl.
CPC .............. *C07K 14/195* (2013.01); *C07K 7/08* (2013.01); *A61K 38/00* (2013.01); *A61K 38/10* (2013.01)

(58) Field of Classification Search
CPC ........ A61K 38/10; A61K 38/164; C07K 7/08; C07K 14/195
See application file for complete search history.

(56) References Cited

U.S. PATENT DOCUMENTS

| 2014/0256912 A1 | 9/2014 | Moellering et al. |
| 2016/0244494 A1 | 8/2016 | Verdine et al. |
| 2017/0008930 A1 | 1/2017 | Walensky et al. |
| 2019/0352339 A1* | 11/2019 | Deber ...................... C07K 7/08 |

OTHER PUBLICATIONS

Bay et al. Small multidrug resistance proteins: A multidrug transporter family that continues to grow. Biochimica et Biophysica Acta. 2008, vol. 1778, pp. 1814-1838. (Year: 2008).*
Poulsen et al. Drug Efflux by a Small Multidrug Resistance Protein Is Inhibited by a Transmembrane Peptide. Antimicrobial Agents and Chemotherapy. Jul. 2012, vol. 56, No. 7, pp. 3911-3916. (Year: 2012).*
International Search Report and Written Opinion for PCT/US2019/012291 dated Mar. 29, 2019.
Bellman-Sickert et al., "Efflux by Small Multidrug Resistance Proteins Is Inhibited by Membrane-interactive Helix-stapled Peptides," The Journal of Biological Chemistry, Nov. 25, 2014, vol. 290, No. 3, pp. 1752-1759.
Ovchinnikov et al., "Structure of the EmrE multidrug transported and its user of inhibitor peptide design," PNAS, Aug. 6, 2018, vol. 115, No. 34, pp. E7932-E7941.
Wang et al., "Functional response of the small multidrug resistance protein EmrE to mutations in transmembrane helix 2," FEBS Letters, Oct. 16, 2014, vol. 588, Iss. 20, pp. 3720-3725.

* cited by examiner

*Primary Examiner* — Jeffrey E. Russel
(74) *Attorney, Agent, or Firm* — Hogan Lovells US LLP

(57) ABSTRACT

The present invention features polypeptides which inhibit dimerization of small multidrug resistance transporters including a stabilized α-helix, and the use of such polypeptides in the treatment of bacterial infections.

20 Claims, 2 Drawing Sheets
Specification includes a Sequence Listing.

SEQUENCE LISTING

```
<160> NUMBER OF SEQ ID NOS: 439

<210> SEQ ID NO 1
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Asp Leu Pro Ala Ile Ile Gly Met Met Leu Ile Cys Ala Gly Val Leu
1               5                   10                  15

Ile Ile Asn Leu Leu Ser
            20

<210> SEQ ID NO 2
```

```
<211> LENGTH: 110
<212> TYPE: PRT
<213> ORGANISM: Escherichia coli

<400> SEQUENCE: 2

Met Asn Pro Tyr Ile Tyr Leu Gly Gly Ala Ile Leu Ala Glu Val Ile
1               5                   10                  15

Gly Thr Thr Leu Met Lys Phe Ser Glu Gly Phe Thr Arg Leu Trp Pro
            20                  25                  30

Ser Val Gly Thr Ile Ile Cys Tyr Cys Ala Ser Phe Trp Leu Leu Ala
        35                  40                  45

Gln Thr Leu Ala Tyr Ile Pro Thr Gly Ile Ala Tyr Ala Ile Trp Ser
    50                  55                  60

Gly Val Gly Ile Val Leu Ile Ser Leu Leu Ser Trp Gly Phe Phe Gly
65                  70                  75                  80

Gln Arg Leu Asp Leu Pro Ala Ile Ile Gly Met Met Leu Ile Cys Ala
                85                  90                  95

Gly Val Leu Ile Ile Asn Leu Leu Ser Arg Ser Thr Pro His
            100                 105                 110

<210> SEQ ID NO 3
<211> LENGTH: 115
<212> TYPE: PRT
<213> ORGANISM: Escherichia coli

<400> SEQUENCE: 3

Met Lys Gly Trp Leu Phe Leu Val Ile Ala Ile Val Gly Glu Val Ile
1               5                   10                  15

Ala Thr Ser Ala Leu Lys Ser Ser Glu Gly Phe Thr Lys Leu Ala Pro
            20                  25                  30

Ser Ala Val Val Ile Ile Gly Tyr Gly Ile Ala Phe Tyr Phe Leu Ser
        35                  40                  45

Leu Val Leu Lys Ser Ile Pro Val Gly Val Ala Tyr Ala Val Trp Ser
    50                  55                  60

Gly Leu Gly Val Val Ile Ile Thr Ala Ile Ala Trp Leu Leu His Gly
65                  70                  75                  80

Gln Lys Leu Asp Ala Trp Gly Phe Val Gly Met Gly Leu Ile Ile Ala
                85                  90                  95

Ala Phe Leu Leu Ala Arg Ser Pro Ser Trp Lys Ser Leu Arg Arg Pro
            100                 105                 110

Thr Pro Trp
        115

<210> SEQ ID NO 4
<211> LENGTH: 110
<212> TYPE: PRT
<213> ORGANISM: Escherichia coli

<400> SEQUENCE: 4

Met Asn Pro Tyr Ile Tyr Leu Gly Gly Ala Ile Leu Ala Glu Val Ile
1               5                   10                  15

Gly Thr Thr Leu Met Lys Phe Ser Glu Gly Phe Thr Arg Leu Trp Pro
            20                  25                  30

Ser Val Gly Thr Ile Ile Cys Tyr Cys Ala Ser Phe Trp Leu Leu Ala
        35                  40                  45

Gln Thr Leu Ala Tyr Ile Pro Thr Gly Ile Ala Tyr Ala Ile Trp Ser
    50                  55                  60
```

```
Gly Val Gly Ile Val Leu Ile Ser Leu Leu Ser Trp Gly Phe Phe Gly
65                  70                  75                  80

Gln Arg Leu Asp Leu Pro Ala Ile Ile Gly Met Met Leu Ile Cys Ala
                85                  90                  95

Gly Val Leu Val Ile Asn Leu Leu Ser Arg Ser Ala Pro His
            100                 105                 110

<210> SEQ ID NO 5
<211> LENGTH: 62
<212> TYPE: PRT
<213> ORGANISM: Mycobacterium tuberculosis

<400> SEQUENCE: 5

Met Tyr Ile Arg Thr Gln Gly Glu Val Leu Thr Tyr Leu Phe Pro Leu
1               5                   10                  15

Cys Ala Ile Ala Ala Glu Ala Ala Ala Thr Ser Leu Phe Lys Gly Ser
            20                  25                  30

Phe Gly Asp Phe Arg Val Cys Ser Pro Gly His Asp Gly Ala Ile Thr
        35                  40                  45

Ala Met Pro Ser Val Leu Ala Ala Ser Arg Ile Arg Ser Ser
    50                  55                  60

<210> SEQ ID NO 6
<211> LENGTH: 107
<212> TYPE: PRT
<213> ORGANISM: Mycobacterium orygis

<400> SEQUENCE: 6

Met Ile Tyr Leu Tyr Leu Leu Cys Ala

```
Gly Leu Gly Val Val Ile Ile Thr Ala Ile Ala Trp Leu Leu His Gly
 65                  70                  75                  80

Gln Lys Leu Asp Ala Trp Gly Phe Val Gly Met Gly Leu Ile Ile Ala
                 85                  90                  95

Ala Phe Leu Leu Ala Arg Ser Pro Ser Trp Lys Ser Leu Arg Arg Pro
            100                 105                 110

Thr Pro Trp
        115

<210> SEQ ID NO 8
<211> LENGTH: 115
<212> TYPE: PRT
<213> ORGANISM: Klebsiella pneumoniae

<400> SEQUENCE: 8

Met Lys Gly Trp Leu Phe Leu Val Ile Ala Ile Val Gly Glu Val Ile
  1               5                  10                  15

Ala Thr Ser Ala Leu Lys Ser Ser Glu Gly Phe Thr Lys Leu Ala Pro
                 20                  25                  30

Ser Ala Val Val Ile Ile Gly Tyr Gly Ile Ala Phe Tyr Phe Leu Ser
             35                  40                  45

Leu Val Leu Lys Ser Ile Pro Val Gly Val Ala Tyr Ala Val Trp Ser
 50                  55                  60

Gly Leu Gly Val Val Ile Ile Thr Ala Ile Ala Trp Leu Leu His Gly
 65                  70                  75                  80

Gln Lys Leu Asp Ala Trp Gly Phe Val Gly Met Gly Leu Ile Ile Ala
                 85                  90                  95

Ala Phe Leu Leu Ala Arg Ser Pro Ser Trp Lys Ser Leu Arg Arg Pro
            100                 105                 110

Thr Pro Trp
        115

<210> SEQ ID NO 9
<211> LENGTH: 115
<212> TYPE: PRT
<213> ORGANISM: Escherichia coli

<400> SEQUENCE: 9

Met Lys Gly Trp Leu Phe Leu Val Ile Ala Ile Val Gly Glu Val Ile
  1               5                  10                  15

Ala Thr Ser Ala Leu Lys Ser Ser Glu Gly Phe Thr Lys Leu Ala Pro
                 20                  25                  30

Ser Ala Val Val Ile Ile Gly Tyr Gly Ile Ala Phe Tyr Phe Leu Ser
             35                  40                  45

Leu Val Leu Lys Ser Ile Pro Val Gly Val Ala Tyr Ala Val Trp Ser
 50                  55                  60

Gly Leu Gly Val Val Ile Ile Thr Ala Ile Ala Trp Leu Leu His Gly
 65                  70                  75                  80

Gln Lys Leu Asp Ala Trp Gly Phe Val Gly Met Gly Leu Ile Ile Ala
                 85                  90                  95

Ala Phe Leu Leu Ala Arg Ser Pro Ser Trp Lys Ser Leu Arg Arg Pro
            100                 105                 110

Thr Pro Trp
        115

<210> SEQ ID NO 10
```

```
<211> LENGTH: 115
<212> TYPE: PRT
<213> ORGANISM: Pseudomonas aeruginosa

<400> SEQUENCE: 10

Met Lys Gly Trp Leu Phe Leu Val Ile Ala Ile Val Gly Glu Val Ile
1               5                   10                  15

Ala Thr Ser Ala Leu Lys Ser Ser Glu Gly Phe Thr Lys Leu Ala Pro
                20                  25                  30

Ser Ala Val Val Ile Ile Gly Tyr Gly Ile Ala Phe Tyr Phe Leu Ser
            35                  40                  45

Leu Val Leu Lys Ser Ile Pro Val Gly Val Ala Tyr Ala Val Trp Ser
50                  55                  60

Gly Leu Gly Val Val Ile Ile Thr Ala Ile Ala Trp Leu Leu His Gly
65                  70                  75                  80

Gln Lys Leu Asp Ala Trp Gly Phe Val Gly Met Gly Leu Ile Ile Ala
                85                  90                  95

Ala Phe Leu Leu Ala Arg Ser Pro Ser Trp Lys Ser Leu Arg Arg Pro
            100                 105                 110

Thr Pro Trp
        115

<210> SEQ ID NO 11
<211> LENGTH: 115
<212> TYPE: PRT
<213> ORGANISM: Providencia rettgeri

<400> SEQUENCE: 11

Met Lys Gly Trp Leu Phe Leu Val Ile Ala Ile Val Gly Glu Val Ile
1               5                   10                  15

Ala Thr Ser Ala Leu Lys Ser Ser Glu Gly Phe Thr Lys Leu Ala Pro
                20                  25                  30

Ser Ala Val Val Ile Ile Gly Tyr Gly Ile Ala Phe Tyr Phe Leu Ser
            35                  40                  45

Leu Val Leu Lys Ser Ile Pro Val Gly Val Ala Tyr Ala Val Trp Ser
50                  55                  60

Gly Leu Gly Val Val Ile Ile Thr Ala Ile Ala Trp Leu Leu His Gly
65                  70                  75                  80

Gln Lys Leu Asp Ala Trp Gly Phe Val Gly Met Gly Leu Ile Ile Ala
                85                  90                  95

Ala Phe Leu Leu Ala Arg Ser Pro Ser Trp Lys Ser Leu Arg Arg Pro
            100                 105                 110

Thr Pro Trp
        115

<210> SEQ ID NO 12
<211> LENGTH: 110
<212> TYPE: PRT
<213> ORGANISM: Pseudomonas citronellolis

<400> SEQUENCE: 12

Met Pro Gly Tyr Leu Tyr Leu Ala Ile Ala Ile Val Ala Glu Val Ile
1               5                   10                  15

Ala Thr Ala Ser Leu Lys Ser Val Lys Gly Leu Ser Thr Pro Leu Pro
                20                  25                  30

Leu Leu Leu Val Ile Val Gly Tyr Ala Ile Ser Phe Trp Met Leu Thr
            35                  40                  45
```

```
Leu Val Val Arg Ser Ile Pro Val Gly Ile Ala Tyr Ala Ile Trp Ala
            50                  55                  60

Gly Leu Gly Ile Val Leu Val Ser Val Ala Ala Leu Val Leu Tyr Gln
 65                  70                  75                  80

Gln Lys Leu Asp Ala Pro Ala Leu Leu Gly Met Gly Leu Ile Val Ser
                85                  90                  95

Gly Val Val Ile Gln Leu Phe Ser Gly Ser Val Ser His
               100                 105                 110

<210> SEQ ID NO 13
<211> LENGTH: 110
<212> TYPE: PRT
<213> ORGANISM: Pseudomonas aeruginosa

<400> SEQUENCE: 13

Met Thr Asn Tyr Leu Tyr Leu Ala Ile Ala Ile Ala Ala Glu Val Val
 1               5                  10                  15

Ala Thr Thr Ser Leu Lys Ala Val Ala Gly Phe Ser Lys Pro Leu Pro
                20                  25                  30

Leu Leu Leu Val Val Gly Gly Tyr Val Leu Ala Phe Ser Met Leu Val
            35                  40                  45

Leu Val Met Arg Thr Leu Pro Val Gly Val Val Tyr Ala Ile Trp Ser
 50                  55                  60

Gly Leu Gly Ile Val Leu Val Ser Leu Val Ala Met Phe Val Tyr Gly
 65                  70                  75                  80

Gln Arg Leu Asp Pro Ala Ala Leu Leu Gly Ile Gly Leu Ile Ile Ala
                85                  90                  95

Gly Val Leu Val Ile Gln Leu Phe Ser Arg Ala Ser Gly His
               100                 105                 110

<210> SEQ ID NO 14
<211> LENGTH: 110
<212> TYPE: PRT
<213> ORGANISM: Pseudomonas aeruginosa

<400> SEQUENCE: 14

Met Asn Pro Tyr Ile Tyr Leu Ala Ala Ala Ile Val Leu Glu Val Ile
 1               5                  10                  15

Ala Thr Ser Leu Leu Lys Ala Ser Asp Gly Met Ser Arg Leu Trp Pro
                20                  25                  30

Thr Val Gly Ala Leu Val Gly Tyr Gly Leu Cys Phe Tyr Leu Leu Ser
            35                  40                  45

Val Thr Met Lys Ser Val Pro Thr Gly Ile Ala Tyr Ala Ile Trp Ser
 50                  55                  60

Gly Val Gly Ile Val Leu Ile Ser Leu Ile Gly Leu Val Phe Lys
 65                  70                  75                  80

Gln Arg Leu Asp Ala Pro Ala Leu Ile Gly Ile Gly Leu Ile Cys Ala
                85                  90                  95

Gly Val Leu Val Ile Asn Leu Phe Ser Arg Ser Ser Ala His
               100                 105                 110

<210> SEQ ID NO 15
<211> LENGTH: 110
<212> TYPE: PRT
<213> ORGANISM: Bordetella pertussis
```

<400> SEQUENCE: 15

Met Asn Ser Trp Ile His Leu Ser Met Ala Ile Val Ala Glu Ile Ile
1               5                   10                  15

Ala Thr Ser Ala Leu Lys Ser Ser Glu Gly Phe Thr Arg Leu Leu Pro
            20                  25                  30

Ser Leu Val Thr Val Ala Gly Tyr Ala Ile Ala Phe Tyr Phe Leu Ala
        35                  40                  45

Leu Thr Leu Arg Val Ile Pro Val Gly Val Ala Tyr Ala Ile Trp Ser
    50                  55                  60

Gly Val Gly Ile Val Leu Ile Ser Leu Val Gly Ala Leu Leu Phe Lys
65                  70                  75                  80

Gln His Leu Asp Leu Pro Ala Ile Ile Gly Ile Ala Leu Ile Leu Ala
                85                  90                  95

Gly Val Val Val Met Asn Val Phe Ser Lys Ser Val Gly His
            100                 105                 110

<210> SEQ ID NO 16
<211> LENGTH: 74
<212> TYPE: PRT
<213> ORGANISM: Bordetella pertussis

<400> SEQUENCE: 16

Met Ala Gly Tyr Ala Ile Ala Phe Tyr Phe Leu Ala Leu Thr Leu Arg
1               5                   10                  15

Val Ile Pro Val Gly Val Ala Tyr Ala Ile Trp Ser Gly Val Gly Ile
            20                  25                  30

Val Leu Ile Ser Leu Val Gly Ala Leu Leu Phe Lys Gln His Leu Asp
        35                  40                  45

Leu Pro Ala Ile Ile Gly Ile Ala Leu Ile Leu Ala Gly Val Val Val
    50                  55                  60

Met Asn Val Phe Ser Lys Ser Val Gly His
65                  70

<210> SEQ ID NO 17
<211> LENGTH: 55
<212> TYPE: PRT
<213> ORGANISM: Bordetella pertussis

<400> SEQUENCE: 17

Met Gly Val Ala Tyr Ala Ile Trp Ser Gly Val Gly Ile Val Leu Ile
1               5                   10                  15

Ser Leu Val Gly Ala Leu Leu Phe Lys Gln His Leu Asp Leu Pro Ala
            20                  25                  30

Ile Ile Gly Ile Ala Leu Ile Leu Ala Gly Val Val Val Met Asn Val
        35                  40                  45

Phe Ser Lys Ser Val Gly His
    50                  55

<210> SEQ ID NO 18
<211> LENGTH: 57
<212> TYPE: PRT
<213> ORGANISM: Neisseria meningitidis

<400> SEQUENCE: 18

Met Pro Leu Ala Thr Ala Tyr Ala Ile Trp Ala Gly Val Gly Leu Val
1               5                   10                  15

Leu Thr Ala Leu Val Ser Val Val Phe Phe Gly Glu Lys Ala Asp Phe
20 25 30

Ile Gly Ile Val Ser Ile Gly Leu Ile Leu Leu Gly Val Val Leu Leu
35 40 45

Asn Thr Met Ser His Met Ser Gly His
50 55

<210> SEQ ID NO 19
<211> LENGTH: 114
<212> TYPE: PRT
<213> ORGANISM: Bacillus cereus

<400> SEQUENCE: 19

Met Lys Asn Lys Ala Trp Leu Tyr Val Ile Leu Thr Cys Ile Phe Glu
1 5 10 15

Val Phe Trp Val Phe Gly Phe Asn Thr Ala Asn Thr Trp Trp His Trp
20 25 30

Ile Ile Ile Leu Gly Val Ile Ala Val Asp Phe His Phe Leu Ser Lys
35 40 45

Ala Cys Glu His Leu Ala Thr Gly Thr Val Tyr Ala Val Phe Ala Gly
50 55 60

Ala Gly Thr Val Gly Thr Phe Leu Met Asp Val Phe Leu Phe Gly Gly
65 70 75 80

Ser Phe Ser Val Gly Lys Leu Phe Phe Ile Val Met Val Val Ala Gly
85 90 95

Val Ile Gly Leu Lys Leu Ala Asp Asn Lys Glu Glu Thr Val Glu Gly
100 105 110

Ala Ala

<210> SEQ ID NO 20
<211> LENGTH: 107
<212> TYPE: PRT
<213> ORGANISM: Staphylococcus aureus

<400> SEQUENCE: 20

Met Pro Tyr Ile Tyr Leu Ile Ile Ala Ile Ser Thr Glu Val Ile Gly
1 5 10 15

Ser Ala Phe Leu Lys Ser Ser Glu Gly Phe Ser Lys Phe Ile Pro Ser
20 25 30

Leu Gly Thr Ile Ile Ser Phe Gly Ile Cys Phe Tyr Phe Leu Ser Lys
35 40 45

Thr Met Gln His Leu Pro Leu Asn Ile Thr Tyr Ala Thr Trp Ala Gly
50 55 60

Leu Gly Leu Val Leu Thr Thr Val Val Ser Ile Ile Ile Phe Lys Glu
65 70 75 80

Gln Ile Asn Leu Ile Thr Ile Val Ser Ile Val Leu Ile Ile Val Gly
85 90 95

Val Val Ser Leu Asn Ile Phe Gly Thr Ser His
100 105

<210> SEQ ID NO 21
<211> LENGTH: 110
<212> TYPE: PRT
<213> ORGANISM: Fundulus heteroclitus

<400> SEQUENCE: 21

Met Asn Pro Tyr Ile Tyr Leu Gly Gly Ala Ile Leu Ala Glu Val Ile
1               5                   10                  15

Gly Thr Thr Leu Met Lys Phe Ser Glu Gly Phe Thr Arg Leu Trp Pro
            20                  25                  30

Ser Val Gly Thr Ile Ile Cys Tyr Cys Ala Ser Phe Trp Leu Leu Ala
        35                  40                  45

Gln Thr Leu Ala Tyr Ile Pro Thr Gly Ile Ala Tyr Ala Ile Trp Ser
    50                  55                  60

Gly Val Gly Ile Val Leu Ile Ser Leu Ser Trp Gly Phe Phe Gly
65                  70                  75                  80

Gln Arg Leu Asp Leu Pro Ala Ile Ile Gly Met Met Leu Ile Cys Ala
                85                  90                  95

Gly Val Leu Ile Ile Asn Leu Leu Ser Arg Ser Thr Pro His
            100                 105                 110

<210> SEQ ID NO 22
<211> LENGTH: 110
<212> TYPE: PRT
<213> ORGANISM: Escherichia coli

<400> SEQUENCE: 22

Met Asn Pro Tyr Ile Tyr Leu Gly Gly Ala Ile Leu Ala Glu Val Ile
1               5                   10                  15

Gly Thr Thr Leu Met Lys Phe Ser Glu Gly Phe Thr Arg Leu Trp Pro
            20                  25                  30

Ser Val Gly Thr Ile Ile Cys Tyr Cys Ala Ser Phe Trp Leu Leu Ala
        35                  40                  45

Gln Thr Leu Ala Tyr Ile Pro Thr Gly Ile Ala Tyr Ala Ile Trp Ser
    50                  55                  60

Gly Val Gly Ile Val Leu Ile Ser Leu Ser Trp Gly Phe Phe Gly
65                  70                  75                  80

Gln Arg Leu Asp Leu Pro Ala Ile Ile Gly Met Met Leu Ile Cys Ala
                85                  90                  95

Gly Val Leu Ile Ile Asn Leu Leu Ser Arg Ser Thr Pro His
            100                 105                 110

<210> SEQ ID NO 23
<211> LENGTH: 110
<212> TYPE: PRT
<213> ORGANISM: Escherichia coli

<400> SEQUENCE: 23

Met Asn Pro Tyr Ile Tyr Leu Gly Gly Ala Ile Leu Ala Glu Val Ile
1               5                   10                  15

Gly Thr Thr Leu Met Lys Phe Ser Glu Gly Phe Thr Arg Leu Trp Pro
            20                  25                  30

Ser Val Gly Thr Ile Ile Cys Tyr Cys Ala Ser Phe Trp Leu Leu Ala
        35                  40                  45

Gln Thr Leu Ala Tyr Ile Pro Thr Gly Ile Ala Tyr Ala Ile Trp Ser
    50                  55                  60

Gly Val Gly Ile Val Leu Ile Ser Leu Ser Trp Gly Phe Phe Gly
65                  70                  75                  80

Gln Arg Leu Asp Leu Pro Ala Ile Ile Gly Met Met Leu Ile Cys Ala
                85                  90                  95

Gly Val Leu Ile Ile Asn Leu Leu Ser Arg Ser Thr Pro His
                100                 105                 110

<210> SEQ ID NO 24
<211> LENGTH: 110
<212> TYPE: PRT
<213> ORGANISM: Escherichia coli

<400> SEQUENCE: 24

Met Asn Pro Tyr Ile Tyr Leu Gly Gly Ala Ile Leu Ala Glu Val Ile
1               5                   10                  15

Gly Thr Thr Leu Met Lys Phe Ser Glu Gly Phe Thr Arg Leu Trp Pro
                20                  25                  30

Ser Val Gly Thr Ile Ile Cys Tyr Cys Ala Ser Phe Trp Leu Leu Ala
            35                  40                  45

Gln Thr Leu Ala Tyr Ile Pro Thr Gly Ile Ala Tyr Ala Ile Trp Ser
        50                  55                  60

Gly Val Gly Ile Val Leu Ile Ser Leu Leu Ser Trp Gly Phe Phe Gly
65                  70                  75                  80

Gln Arg Leu Asp Leu Pro Ala Ile Ile Gly Met Met Leu Ile Cys Ala
                85                  90                  95

Gly Val Leu Ile Ile Asn Leu Leu Ser Arg Ser Thr Pro His
                100                 105                 110

<210> SEQ ID NO 25
<211> LENGTH: 110
<212> TYPE: PRT
<213> ORGANISM: Escherichia coli

<400> SEQUENCE: 25

Met Asn Pro Tyr Ile Tyr Leu Gly Gly Ala Ile Leu Ala Glu Val Ile
1               5                   10                  15

Gly Thr Thr Leu Met Lys Phe Ser Glu Gly Phe Thr Arg Leu Trp Pro
                20                  25                  30

Ser Val Gly Thr Ile Ile Cys Tyr Cys Ala Ser Phe Trp Leu Leu Ala
            35                  40                  45

Gln Thr Leu Ala Tyr Ile Pro Thr Gly Ile Ala Tyr Ala Ile Trp Ser
        50                  55                  60

Gly Val Gly Ile Val Leu Ile Ser Leu Leu Ser Trp Gly Phe Phe Gly
65                  70                  75                  80

Gln Arg Leu Asp Leu Pro Ala Ile Ile Gly Met Met Leu Ile Cys Ala
                85                  90                  95

Gly Val Leu Ile Ile Asn Leu Leu Ser Arg Ser Thr Pro His
                100                 105                 110

<210> SEQ ID NO 26
<211> LENGTH: 110
<212> TYPE: PRT
<213> ORGANISM: Escherichia coli

<400> SEQUENCE: 26

Met Asn Pro Tyr Ile Tyr Leu Gly Gly Ala Ile Leu Ala Glu Val Ile
1               5                   10                  15

Gly Thr Thr Leu Met Lys Phe Ser Glu Gly Phe Thr Arg Leu Trp Pro
                20                  25                  30

Ser Val Gly Thr Ile Ile Cys Tyr Cys Ala Ser Phe Trp Leu Leu Ala
            35                  40                  45

```
Gln Thr Leu Ala Tyr Ile Pro Thr Gly Ile Ala Tyr Ala Ile Trp Ser
        50                  55                  60

Gly Val Gly Ile Val Leu Ile Ser Leu Leu Ser Trp Gly Phe Phe Gly
 65                  70                  75                  80

Gln Arg Leu Asp Leu Pro Ala Ile Ile Gly Met Met Leu Ile Cys Ala
                85                  90                  95

Gly Val Leu Val Ile Asn Leu Leu Ser Arg Ser Thr Pro His
            100                 105                 110

<210> SEQ ID NO 27
<211> LENGTH: 110
<212> TYPE: PRT
<213> ORGANISM: Escherichia coli

<400> SEQUENCE: 27

Met Asn Pro Tyr Ile Tyr Leu Gly Gly Ala Ile Leu Ala Glu Val Ile
 1               5                  10                  15

Gly Thr Thr Leu Met Lys Phe Ser Glu Gly Phe Thr Arg Leu Trp Pro
                20                  25                  30

Ser Val Gly Thr Ile Ile Cys Tyr Cys Ala Ser Phe Trp Leu Leu Ala
            35                  40                  45

Gln Thr Leu Ala Tyr Ile Pro Thr Gly Ile Ala Tyr Ala Ile Trp Ser
        50                  55                  60

Gly Val Gly Ile Val Leu Ile Ser Leu Leu Ser Trp Gly Phe Phe Gly
 65                  70                  75                  80

Gln Arg Leu Asp Leu Pro Ala Ile Ile Gly Met Met Leu Ile Cys Ala
                85                  90                  95

Gly Val Leu Val Ile Asn Leu Leu Ser Arg Ser Thr Pro His
            100                 105                 110

<210> SEQ ID NO 28
<211> LENGTH: 110
<212> TYPE: PRT
<213> ORGANISM: Escherichia coli

<400> SEQUENCE: 28

Met Asn Pro Tyr Ile Tyr Leu Gly Gly Ala Ile Leu Ala Glu Val Ile
 1               5                  10                  15

Gly Thr Thr Leu Met Lys Phe Ser Glu Gly Phe Thr Arg Leu Trp Pro
                20                  25                  30

Ser Val Gly Thr Ile Ile Cys Tyr Cys Ala Ser Phe Trp Leu Leu Ala
            35                  40                  45

Gln Thr Leu Ala Tyr Ile Pro Thr Gly Ile Ala Tyr Ala Ile Trp Ser
        50                  55                  60

Gly Val Gly Ile Val Leu Ile Ser Leu Leu Ser Trp Gly Phe Phe Gly
 65                  70                  75                  80

Gln Arg Leu Asp Leu Pro Ala Ile Ile Gly Met Met Leu Ile Cys Ala
                85                  90                  95

Gly Val Leu Val Ile Asn Leu Leu Ser Arg Ser Thr Pro His
            100                 105                 110

<210> SEQ ID NO 29
<211> LENGTH: 110
<212> TYPE: PRT
<213> ORGANISM: Escherichia coli
```

<400> SEQUENCE: 29

Met Asn Pro Tyr Ile Tyr Leu Gly Gly Ala Ile Leu Ala Glu Val Ile
1               5                   10                  15

Gly Thr Thr Leu Met Lys Phe Ser Glu Gly Phe Thr Arg Leu Trp Pro
            20                  25                  30

Ser Val Gly Thr Ile Ile Cys Tyr Cys Ala Ser Phe Trp Leu Leu Ala
        35                  40                  45

Gln Thr Leu Ala Tyr Ile Pro Thr Gly Ile Ala Tyr Ala Ile Trp Ser
    50                  55                  60

Gly Val Gly Ile Val Leu Ile Ser Leu Leu Ser Trp Gly Phe Phe Gly
65                  70                  75                  80

Gln Arg Leu Asp Leu Pro Ala Ile Ile Gly Met Met Leu Ile Cys Ala
                85                  90                  95

Gly Val Leu Val Ile Asn Leu Leu Ser Arg Ser Thr Pro His
            100                 105                 110

<210> SEQ ID NO 30
<211> LENGTH: 110
<212> TYPE: PRT
<213> ORGANISM: Escherichia coli

<400> SEQUENCE: 30

Met Asn Pro Tyr Ile Tyr Leu Gly Gly Ala Ile Leu Ala Glu Val Ile
1               5                   10                  15

Gly Thr Thr Leu Met Lys Phe Ser Glu Gly Phe Thr Arg Leu Trp Pro
            20                  25                  30

Ser Val Gly Thr Ile Ile Cys Tyr Cys Ala Ser Phe Trp Leu Leu Ala
        35                  40                  45

Gln Thr Leu Ala Tyr Ile Pro Thr Gly Ile Ala Tyr Ala Ile Trp Ser
    50                  55                  60

Gly Val Gly Ile Val Leu Ile Ser Leu Leu Ser Trp Gly Phe Phe Gly
65                  70                  75                  80

Gln Arg Leu Asp Leu Pro Ala Ile Ile Gly Met Met Leu Ile Cys Ala
                85                  90                  95

Gly Val Leu Val Ile Asn Leu Leu Ser Arg Ser Thr Pro His
            100                 105                 110

<210> SEQ ID NO 31
<211> LENGTH: 110
<212> TYPE: PRT
<213> ORGANISM: Escherichia coli

<400> SEQUENCE: 31

Met Asn Pro Tyr Ile Tyr Leu Gly Gly Ala Ile Leu Ala Glu Val Ile
1               5                   10                  15

Gly Thr Thr Leu Met Lys Phe Ser Glu Gly Phe Thr Arg Leu Trp Pro
            20                  25                  30

Ser Val Gly Thr Ile Ile Cys Tyr Cys Ala Ser Phe Trp Leu Leu Ala
        35                  40                  45

Gln Thr Leu Ala Tyr Ile Pro Thr Gly Ile Ala Tyr Ala Ile Trp Ser
    50                  55                  60

Gly Val Gly Ile Val Leu Ile Ser Leu Leu Ser Trp Gly Phe Phe Gly
65                  70                  75                  80

Gln Arg Leu Asp Leu Pro Ala Ile Ile Gly Met Met Leu Ile Cys Ala
                85                  90                  95

```
Gly Val Leu Val Ile Asn Leu Leu Ser Arg Ser Thr Pro His
            100                 105                 110
```

<210> SEQ ID NO 32
<211> LENGTH: 110
<212> TYPE: PRT
<213> ORGANISM: Escherichia coli

<400> SEQUENCE: 32

```
Met Asn Pro Tyr Ile Tyr Leu Gly Gly Ala Ile Leu Ala Glu Val Ile
1               5                   10                  15

Gly Thr Thr Leu Met Lys Phe Ser Glu Gly Phe Thr Arg Leu Trp Pro
            20                  25                  30

Ser Val Gly Thr Ile Ile Cys Tyr Cys Ala Ser Phe Trp Leu Leu Ala
        35                  40                  45

Gln Thr Leu Ala Tyr Ile Pro Thr Gly Ile Ala Tyr Ala Ile Trp Ser
    50                  55                  60

Gly Val Gly Ile Val Leu Ile Ser Leu Leu Ser Trp Gly Phe Phe Gly
65                  70                  75                  80

Gln Arg Leu Asp Leu Pro Ala Ile Ile Gly Met Met Leu Ile Cys Ala
                85                  90                  95

Gly Val Leu Val Ile Asn Leu Leu Ser Arg Ser Thr Pro His
            100                 105                 110
```

<210> SEQ ID NO 33
<211> LENGTH: 110
<212> TYPE: PRT
<213> ORGANISM: Escherichia coli

<400> SEQUENCE: 33

```
Met Asn Pro Tyr Ile Tyr Leu Gly Gly Ala Ile Leu Ala Glu Val Ile
1               5                   10                  15

Gly Thr Thr Leu Met Lys Phe Ser Glu Gly Phe Thr Arg Leu Trp Pro
            20                  25                  30

Ser Val Gly Thr Ile Ile Cys Tyr Cys Ala Ser Phe Trp Leu Leu Ala
        35                  40                  45

Gln Thr Leu Ala Tyr Ile Pro Thr Gly Ile Ala Tyr Ala Ile Trp Ser
    50                  55                  60

Gly Val Gly Ile Val Leu Ile Ser Leu Leu Ser Trp Gly Phe Phe Gly
65                  70                  75                  80

Gln Arg Leu Asp Leu Pro Ala Ile Ile Gly Met Met Leu Ile Cys Ala
                85                  90                  95

Gly Val Leu Val Ile Asn Leu Leu Ser Arg Ser Thr Pro His
            100                 105                 110
```

<210> SEQ ID NO 34
<211> LENGTH: 110
<212> TYPE: PRT
<213> ORGANISM: Escherichia coli

<400> SEQUENCE: 34

```
Met Asn Pro Tyr Ile Tyr Leu Gly Gly Ala Ile Leu Ala Glu Val Ile
1               5                   10                  15

Gly Thr Thr Leu Met Lys Phe Ser Glu Gly Phe Thr Arg Leu Trp Pro
            20                  25                  30

Ser Val Gly Thr Ile Ile Cys Tyr Cys Ala Ser Phe Trp Leu Leu Ala
        35                  40                  45
```

Gln Thr Leu Ala Tyr Ile Pro Thr Gly Ile Ala Tyr Ala Ile Trp Ser
            50                  55                  60

Gly Val Gly Ile Val Leu Ile Ser Leu Leu Ser Trp Gly Phe Phe Gly
65                  70                  75                  80

Gln Arg Leu Asp Leu Pro Ala Ile Ile Gly Met Met Leu Ile Cys Ala
                85                  90                  95

Gly Val Leu Val Ile Asn Leu Leu Ser Arg Ser Thr Pro His
            100                 105                 110

<210> SEQ ID NO 35
<211> LENGTH: 110
<212> TYPE: PRT
<213> ORGANISM: Escherichia coli

<400> SEQUENCE: 35

Met Asn Pro Tyr Ile Tyr Leu Gly Gly Ala Ile Leu Ala Glu Val Ile
1               5                   10                  15

Gly Thr Thr Leu Met Lys Phe Ser Glu Gly Phe Thr Arg Leu Trp Pro
            20                  25                  30

Ser Val Gly Thr Ile Ile Cys Tyr Cys Ala Ser Phe Trp Leu Leu Ala
        35                  40                  45

Gln Thr Leu Ala Tyr Ile Pro Thr Gly Ile Ala Tyr Ala Ile Trp Ser
            50                  55                  60

Gly Val Gly Ile Val Leu Ile Ser Leu Leu Ser Trp Gly Phe Phe Gly
65                  70                  75                  80

Gln Arg Leu Asp Leu Pro Ala Ile Ile Gly Met Met Leu Ile Cys Ala
                85                  90                  95

Gly Val Leu Val Ile Asn Leu Leu Ser Arg Ser Thr Pro His
            100                 105                 110

<210> SEQ ID NO 36
<211> LENGTH: 110
<212> TYPE: PRT
<213> ORGANISM: Escherichia coli

<400> SEQUENCE: 36

Met Asn Pro Tyr Ile Tyr Leu Gly Gly Ala Ile Leu Ala Glu Val Ile
1               5                   10                  15

Gly Thr Thr Leu Met Lys Phe Ser Glu Gly Phe Thr Arg Leu Trp Pro
            20                  25                  30

Ser Val Gly Thr Ile Ile Cys Tyr Cys Ala Ser Phe Trp Leu Leu Ala
        35                  40                  45

Gln Thr Leu Ala Tyr Ile Pro Thr Gly Ile Ala Tyr Ala Ile Trp Ser
            50                  55                  60

Gly Val Gly Ile Val Leu Ile Ser Leu Leu Ser Trp Gly Phe Phe Gly
65                  70                  75                  80

Gln Arg Leu Asp Leu Pro Ala Ile Ile Gly Met Met Leu Ile Cys Ala
                85                  90                  95

Gly Val Leu Val Ile Asn Leu Leu Ser Arg Ser Thr Pro His
            100                 105                 110

<210> SEQ ID NO 37
<211> LENGTH: 110
<212> TYPE: PRT
<213> ORGANISM: Escherichia coli

<400> SEQUENCE: 37

Met Asn Pro Tyr Ile Tyr Leu Gly Gly Ala Ile Leu Ala Glu Val Ile
1               5                   10                  15

Gly Thr Thr Leu Met Lys Phe Ser Glu Gly Phe Thr Arg Leu Trp Pro
            20                  25                  30

Ser Val Gly Thr Ile Ile Cys Tyr Cys Ala Ser Phe Trp Leu Leu Ala
        35                  40                  45

Gln Thr Leu Ala Tyr Ile Pro Thr Gly Ile Ala Tyr Ala Ile Trp Ser
    50                  55                  60

Gly Val Gly Ile Val Leu Ile Ser Leu Ser Trp Gly Phe Phe Gly
65                  70                  75                  80

Gln Arg Leu Asp Leu Pro Ala Ile Ile Gly Met Met Leu Ile Cys Ala
                85                  90                  95

Gly Val Leu Val Ile Asn Leu Leu Ser Arg Ser Thr Pro His
            100                 105                 110

<210> SEQ ID NO 38
<211> LENGTH: 110
<212> TYPE: PRT
<213> ORGANISM: Escherichia coli

<400> SEQUENCE: 38

Met Asn Pro Tyr Ile Tyr Leu Gly Gly Ala Ile Leu Ala Glu Val Ile
1               5                   10                  15

Gly Thr Thr Leu Met Lys Phe Ser Glu Gly Phe Thr Arg Leu Trp Pro
            20                  25                  30

Ser Val Gly Thr Ile Ile Cys Tyr Cys Ala Ser Phe Trp Leu Leu Ala
        35                  40                  45

Gln Thr Leu Ala Tyr Ile Pro Thr Gly Ile Ala Tyr Ala Ile Trp Ser
    50                  55                  60

Gly Val Gly Ile Val Leu Ile Ser Leu Ser Trp Gly Phe Phe Gly
65                  70                  75                  80

Gln Arg Leu Asp Leu Pro Ala Ile Ile Gly Met Met Leu Ile Cys Ala
                85                  90                  95

Gly Val Leu Val Ile Asn Leu Leu Ser Arg Ser Thr Pro His
            100                 105                 110

<210> SEQ ID NO 39
<211> LENGTH: 110
<212> TYPE: PRT
<213> ORGANISM: Escherichia coli

<400> SEQUENCE: 39

Met Asn Pro Tyr Ile Tyr Leu Gly Gly Ala Ile Leu Ala Glu Val Ile
1               5                   10                  15

Gly Thr Thr Leu Met Lys Phe Ser Glu Gly Phe Thr Arg Leu Trp Pro
            20                  25                  30

Ser Val Gly Thr Ile Ile Cys Tyr Cys Ala Ser Phe Trp Leu Leu Ala
        35                  40                  45

Gln Thr Leu Ala Tyr Ile Pro Thr Gly Ile Ala Tyr Ala Ile Trp Ser
    50                  55                  60

Gly Val Gly Ile Val Leu Ile Ser Leu Ser Trp Gly Phe Phe Gly
65                  70                  75                  80

Gln Arg Leu Asp Leu Pro Ala Ile Ile Gly Met Met Leu Ile Cys Ala
                85                  90                  95

```
Gly Val Leu Val Ile Asn Leu Leu Ser Arg Ser Thr Pro His
            100                 105                 110
```

<210> SEQ ID NO 40
<211> LENGTH: 110
<212> TYPE: PRT
<213> ORGANISM: Escherichia coli

<400> SEQUENCE: 40

```
Met Asn Pro Tyr Ile Tyr Leu Gly Gly Ala Ile Leu Ala Glu Val Ile
1               5                   10                  15

Gly Thr Thr Leu Met Lys Phe Ser Glu Gly Phe Thr Arg Leu Trp Pro
            20                  25                  30

Ser Val Gly Thr Ile Ile Cys Tyr Cys Ala Ser Phe Trp Leu Leu Ala
        35                  40                  45

Gln Thr Leu Ala Tyr Ile Pro Thr Gly Ile Ala Tyr Ala Ile Trp Ser
    50                  55                  60

Gly Val Gly Ile Val Leu Ile Ser Leu Leu Ser Trp Gly Phe Phe Gly
65                  70                  75                  80

Gln Arg Leu Asp Leu Pro Ala Ile Ile Gly Met Met Leu Ile Cys Ala
                85                  90                  95

Gly Val Leu Val Ile Asn Leu Leu Ser Arg Ser Thr Pro His
            100                 105                 110
```

<210> SEQ ID NO 41
<211> LENGTH: 110
<212> TYPE: PRT
<213> ORGANISM: Escherichia coli

<400> SEQUENCE: 41

```
Met Asn Pro Tyr Ile Tyr Leu Gly Gly Ala Ile Leu Ala Glu Val Ile
1               5                   10                  15

Gly Thr Thr Leu Met Lys Phe Ser Glu Gly Phe Thr Arg Leu Trp Pro
            20                  25                  30

Ser Val Gly Thr Ile Ile Cys Tyr Cys Ala Ser Phe Trp Leu Leu Ala
        35                  40                  45

Gln Thr Leu Ala Tyr Ile Pro Thr Gly Ile Ala Tyr Ala Ile Trp Ser
    50                  55                  60

Gly Val Gly Ile Val Leu Ile Ser Leu Leu Ser Trp Gly Phe Phe Gly
65                  70                  75                  80

Gln Arg Leu Asp Leu Pro Ala Ile Ile Gly Met Met Leu Ile Cys Ala
                85                  90                  95

Gly Val Leu Val Ile Asn Leu Leu Ser Arg Ser Thr Pro His
            100                 105                 110
```

<210> SEQ ID NO 42
<211> LENGTH: 110
<212> TYPE: PRT
<213> ORGANISM: Escherichia coli

<400> SEQUENCE: 42

```
Met Asn Pro Tyr Ile Tyr Leu Gly Gly Ala Ile Leu Ala Glu Val Ile
1               5                   10                  15

Gly Thr Thr Leu Met Lys Phe Ser Glu Gly Phe Thr Arg Leu Trp Pro
            20                  25                  30

Ser Val Gly Thr Ile Ile Cys Tyr Cys Ala Ser Phe Trp Leu Leu Ala
        35                  40                  45
```

Gln Thr Leu Ala Tyr Ile Pro Thr Gly Ile Ala Tyr Ala Ile Trp Ser
            50                  55                  60

Gly Val Gly Ile Val Leu Ile Ser Leu Leu Ser Trp Gly Phe Phe Gly
 65                  70                  75                  80

Gln Arg Leu Asp Leu Pro Ala Ile Ile Gly Met Met Leu Ile Cys Ala
                85                  90                  95

Gly Val Leu Val Ile Asn Leu Leu Ser Arg Ser Thr Pro His
            100                 105                 110

<210> SEQ ID NO 43
<211> LENGTH: 110
<212> TYPE: PRT
<213> ORGANISM: Escherichia coli

<400> SEQUENCE: 43

Met Asn Pro Tyr Ile Tyr Leu Gly Gly Ala Ile Leu Ala Glu Val Ile
 1               5                  10                  15

Gly Thr Thr Leu Met Lys Phe Ser Glu Gly Phe Thr Arg Leu Trp Pro
                20                  25                  30

Ser Val Gly Thr Ile Ile Cys Tyr Cys Ala Ser Phe Trp Leu Leu Ala
            35                  40                  45

Gln Thr Leu Ala Tyr Ile Pro Thr Gly Ile Ala Tyr Ala Ile Trp Ser
            50                  55                  60

Gly Val Gly Ile Val Leu Ile Ser Leu Leu Ser Trp Gly Phe Phe Gly
 65                  70                  75                  80

Gln Arg Leu Asp Leu Pro Ala Ile Ile Gly Met Met Leu Ile Cys Ala
                85                  90                  95

Gly Val Leu Val Ile Asn Leu Leu Ser Arg Ser Thr Pro His
            100                 105                 110

<210> SEQ ID NO 44
<211> LENGTH: 110
<212> TYPE: PRT
<213> ORGANISM: Escherichia coli

<400> SEQUENCE: 44

Met Asn Pro Tyr Ile Tyr Leu Gly Gly Ala Ile Leu Ala Glu Val Ile
 1               5                  10                  15

Gly Thr Thr Leu Met Lys Phe Ser Glu Gly Phe Thr Arg Leu Trp Pro
                20                  25                  30

Ser Val Gly Thr Ile Ile Cys Tyr Cys Ala Ser Phe Trp Leu Leu Ala
            35                  40                  45

Gln Thr Leu Ala Tyr Ile Pro Thr Gly Ile Ala Tyr Ala Ile Trp Ser
            50                  55                  60

Gly Val Gly Ile Val Leu Ile Ser Leu Leu Ser Trp Gly Phe Phe Gly
 65                  70                  75                  80

Gln Arg Leu Asp Leu Pro Ala Ile Ile Gly Met Met Leu Ile Cys Ala
                85                  90                  95

Gly Val Leu Val Ile Asn Leu Leu Ser Arg Ser Thr Pro His
            100                 105                 110

<210> SEQ ID NO 45
<211> LENGTH: 117
<212> TYPE: PRT
<213> ORGANISM: Escherichia coli

```
<400> SEQUENCE: 45

Met Asn Arg Lys Glu Tyr Ala Met Asn Pro Tyr Ile Tyr Leu Gly Gly
1               5                   10                  15

Ala Ile Leu Ala Glu Val Ile Gly Thr Thr Leu Met Lys Phe Ser Glu
                20                  25                  30

Gly Phe Thr Arg Leu Trp Pro Ser Val Gly Thr Ile Ile Cys Tyr Cys
            35                  40                  45

Ala Ser Phe Trp Leu Leu Ala Gln Thr Leu Ala Tyr Ile Pro Thr Gly
    50                  55                  60

Ile Ala Tyr Ala Ile Trp Ser Gly Val Gly Ile Val Leu Ile Ser Leu
65                  70                  75                  80

Leu Ser Trp Gly Phe Phe Gly Gln Arg Leu Asp Leu Pro Ala Ile Ile
                85                  90                  95

Gly Met Met Leu Ile Cys Ala Gly Val Leu Val Ile Asn Leu Leu Ser
            100                 105                 110

Arg Ser Thr Pro His
        115

<210> SEQ ID NO 46
<211> LENGTH: 110
<212> TYPE: PRT
<213> ORGANISM: Escherichia coli

<400> SEQUENCE: 46

Met Asn Pro Tyr Ile Tyr Leu Gly Gly Ala Ile Leu Ala Glu Val Ile
1               5                   10                  15

Gly Thr Thr Leu Met Lys Phe Ser Glu Gly Phe Thr Arg Leu Trp Pro
                20                  25                  30

Ser Val Gly Thr Ile Ile Cys Tyr Cys Ala Ser Phe Trp Leu Leu Ala
            35                  40                  45

Gln Thr Leu Ala Tyr Ile Pro Thr Gly Ile Ala Tyr Ala Ile Trp Ser
    50                  55                  60

Gly Val Gly Ile Val Leu Ile Ser Leu Leu Ser Trp Gly Phe Phe Gly
65                  70                  75                  80

Gln Arg Leu Asp Leu Pro Ala Val Ile Gly Met Met Leu Ile Cys Ala
                85                  90                  95

Gly Val Leu Val Ile Asn Leu Leu Ser Arg Ser Thr Pro His
            100                 105                 110

<210> SEQ ID NO 47
<211> LENGTH: 110
<212> TYPE: PRT
<213> ORGANISM: Escherichia coli

<400> SEQUENCE: 47

Met Asn Pro Tyr Ile Tyr Leu Gly Gly Ala Ile Leu Ala Glu Val Ile
1               5                   10                  15

Gly Thr Thr Leu Met Lys Phe Ser Glu Gly Phe Thr Arg Leu Trp Pro
                20                  25                  30

Ser Val Gly Thr Ile Ile Cys Tyr Cys Ala Ser Phe Trp Leu Leu Ala
            35                  40                  45

Gln Thr Leu Ala Tyr Ile Pro Thr Gly Ile Ala Tyr Ala Ile Trp Ser
    50                  55                  60

Gly Val Gly Ile Val Leu Ile Ser Leu Leu Ser Trp Gly Phe Phe Gly
65                  70                  75                  80
```

```
Gln Arg Leu Asp Leu Pro Ala Val Ile Gly Met Met Leu Ile Cys Ala
                85                  90                  95

Gly Val Leu Val Ile Asn Leu Leu Ser Arg Ser Thr Pro His
            100                 105                 110

<210> SEQ ID NO 48
<211> LENGTH: 110
<212> TYPE: PRT
<213> ORGANISM: Escherichia sp.

<400> SEQUENCE: 48

Met Asn Pro Tyr Ile Tyr Leu Gly Gly Ala Ile Leu Ala Glu Val Ile
1               5                   10                  15

Gly Thr Thr Leu Met Lys Phe Ser Glu Gly Phe Thr Arg Leu Trp Pro
                20                  25                  30

Ser Val Gly Thr Ile Ile Cys Tyr Cys Ala Ser Phe Trp Leu Leu Ala
            35                  40                  45

Gln Thr Leu Ala Tyr Ile Pro Thr Gly Ile Ala Tyr Ala Ile Trp Ser
        50                  55                  60

Gly Val Gly Ile Val Leu Ile Ser Leu Leu Ser Trp Gly Phe Phe Gly
65                  70                  75                  80

Gln Arg Leu Asp Leu Pro Ala Val Ile Gly Met Met Leu Ile Cys Ala
                85                  90                  95

Gly Val Leu Val Ile Asn Leu Leu Ser Arg Ser Thr Pro His
            100                 105                 110

<210> SEQ ID NO 49
<211> LENGTH: 110
<212> TYPE: PRT
<213> ORGANISM: Escherichia coli

<400> SEQUENCE: 49

Met Asn Pro Tyr Ile Tyr Leu Gly Gly Ala Ile Leu Ala Glu Val Ile
1               5                   10                  15

Gly Thr Thr Leu Met Lys Phe Ser Glu Gly Phe Thr Arg Leu Trp Pro
                20                  25                  30

Ser Val Gly Thr Ile Ile Cys Tyr Cys Ala Ser Phe Trp Leu Leu Ala
            35                  40                  45

Gln Thr Leu Ala Tyr Ile Pro Thr Gly Ile Ala Tyr Ala Ile Trp Ser
        50                  55                  60

Gly Val Gly Ile Val Leu Ile Ser Leu Leu Ser Trp Gly Phe Phe Gly
65                  70                  75                  80

Gln Arg Leu Asp Leu Pro Ala Val Ile Gly Met Met Leu Ile Cys Ala
                85                  90                  95

Gly Val Leu Val Ile Asn Leu Leu Ser Arg Ser Thr Pro His
            100                 105                 110

<210> SEQ ID NO 50
<211> LENGTH: 110
<212> TYPE: PRT
<213> ORGANISM: Escherichia coli

<400> SEQUENCE: 50

Met Asn Pro Tyr Ile Tyr Leu Gly Gly Ala Ile Leu Ala Glu Val Ile
1               5                   10                  15

Gly Thr Thr Leu Met Lys Phe Ser Glu Gly Phe Thr Arg Leu Trp Pro
                20                  25                  30
```

```
Ser Val Gly Thr Ile Ile Cys Tyr Cys Ala Ser Phe Trp Leu Leu Ala
        35                  40                  45

Gln Thr Leu Ala Tyr Ile Pro Thr Gly Ile Ala Tyr Ala Ile Trp Ser
    50                  55                  60

Gly Val Gly Ile Val Leu Ile Ser Leu Leu Ser Trp Gly Phe Phe Gly
65                  70                  75                  80

Gln Arg Leu Asp Leu Pro Ala Val Ile Gly Met Met Leu Ile Cys Ala
                85                  90                  95

Gly Val Leu Val Ile Asn Leu Leu Ser Arg Ser Thr Pro His
            100                 105                 110

<210> SEQ ID NO 51
<211> LENGTH: 110
<212> TYPE: PRT
<213> ORGANISM: Escherichia coli

<400> SEQUENCE: 51

Met Asn Pro Tyr Ile Tyr Leu Gly Gly Ala Ile Leu Ala Glu Val Ile
1               5                   10                  15

Gly Thr Thr Leu Met Lys Phe Ser Glu Gly Phe Thr Arg Leu Trp Pro
            20                  25                  30

Ser Val Gly Thr Ile Ile Cys Tyr Cys Ala Ser Phe Trp Leu Leu Ala
        35                  40                  45

Gln Thr Leu Ala Tyr Ile Pro Thr Gly Ile Ala Tyr Ala Ile Trp Ser
    50                  55                  60

Gly Val Gly Ile Val Leu Ile Ser Leu Leu Ser Trp Gly Phe Phe Gly
65                  70                  75                  80

Gln Arg Leu Asp Leu Pro Ala Val Ile Gly Met Met Leu Ile Cys Ala
                85                  90                  95

Gly Val Leu Val Ile Asn Leu Leu Ser Arg Ser Thr Pro His
            100                 105                 110

<210> SEQ ID NO 52
<211> LENGTH: 110
<212> TYPE: PRT
<213> ORGANISM: Escherichia coli

<400> SEQUENCE: 52

Met Asn Pro Tyr Ile Tyr Leu Gly Gly Ala Ile Leu Ala Glu Val Ile
1               5                   10                  15

Gly Thr Thr Leu Met Lys Phe Ser Glu Gly Phe Thr Arg Leu Trp Pro
            20                  25                  30

Ser Val Gly Thr Ile Ile Cys Tyr Cys Ala Ser Phe Trp Leu Leu Ala
        35                  40                  45

Gln Thr Leu Ala Tyr Ile Pro Thr Gly Ile Ala Tyr Ala Ile Trp Ser
    50                  55                  60

Gly Val Gly Ile Val Leu Ile Ser Leu Leu Ser Trp Gly Phe Phe Gly
65                  70                  75                  80

Gln Arg Leu Asp Leu Pro Ala Val Ile Gly Met Met Leu Ile Cys Ala
                85                  90                  95

Gly Val Leu Val Ile Asn Leu Leu Ser Arg Ser Thr Pro His
            100                 105                 110

<210> SEQ ID NO 53
<211> LENGTH: 110
<212> TYPE: PRT
<213> ORGANISM: Escherichia coli
```

<400> SEQUENCE: 53

Met Asn Pro Tyr Ile Tyr Leu Gly Gly Ala Ile Leu Ala Glu Val Ile
1               5                   10                  15

Gly Thr Thr Leu Met Lys Phe Ser Glu Gly Phe Thr Arg Leu Trp Pro
            20                  25                  30

Ser Val Gly Thr Ile Ile Cys Tyr Cys Ala Ser Phe Trp Leu Leu Ala
        35                  40                  45

Gln Thr Leu Ala Tyr Ile Pro Thr Gly Ile Ala Tyr Ala Ile Trp Ser
    50                  55                  60

Gly Val Gly Ile Val Leu Ile Ser Leu Ser Trp Gly Phe Phe Gly
65                  70                  75                  80

Gln Arg Leu Asp Leu Pro Ala Val Ile Gly Met Met Leu Ile Cys Ala
                85                  90                  95

Gly Val Leu Val Ile Asn Leu Leu Ser Arg Ser Thr Pro His
            100                 105                 110

<210> SEQ ID NO 54
<211> LENGTH: 110
<212> TYPE: PRT
<213> ORGANISM: Escherichia coli

<400> SEQUENCE: 54

Met Asn Pro Tyr Ile Tyr Leu Gly Gly Ala Ile Leu Ala Glu Val Ile
1               5                   10                  15

Gly Thr Thr Leu Met Lys Phe Ser Glu Gly Phe Thr Arg Leu Trp Pro
            20                  25                  30

Ser Val Gly Thr Ile Ile Cys Tyr Cys Ala Ser Phe Trp Leu Leu Ala
        35                  40                  45

Gln Thr Leu Ala Tyr Ile Pro Thr Gly Ile Ala Tyr Ala Ile Trp Ser
    50                  55                  60

Gly Val Gly Ile Val Leu Ile Ser Leu Ser Trp Gly Phe Phe Gly
65                  70                  75                  80

Gln Arg Leu Asp Met Pro Ala Ile Ile Gly Met Met Leu Ile Cys Ala
                85                  90                  95

Gly Val Leu Val Ile Asn Leu Leu Ser Arg Ser Thr Pro His
            100                 105                 110

<210> SEQ ID NO 55
<211> LENGTH: 110
<212> TYPE: PRT
<213> ORGANISM: Escherichia coli

<400> SEQUENCE: 55

Met Asn Pro Tyr Ile Tyr Leu Gly Gly Ala Ile Leu Ala Gln Val Ile
1               5                   10                  15

Gly Thr Thr Leu Met Lys Phe Ser Glu Gly Phe Thr Arg Leu Trp Pro
            20                  25                  30

Ser Val Gly Thr Ile Ile Cys Tyr Cys Ala Ser Phe Trp Leu Leu Ala
        35                  40                  45

Gln Thr Leu Ala Tyr Ile Pro Thr Gly Ile Ala Tyr Ala Ile Trp Ser
    50                  55                  60

Gly Val Gly Ile Val Leu Ile Ser Leu Ser Trp Gly Phe Phe Gly
65                  70                  75                  80

Gln Arg Leu Asp Leu Pro Ala Ile Ile Gly Met Met Leu Ile Cys Ala
                85                  90                  95

Gly Val Leu Val Ile Asn Leu Leu Ser Arg Ser Thr Pro His
            100             105             110

<210> SEQ ID NO 56
<211> LENGTH: 110
<212> TYPE: PRT
<213> ORGANISM: Escherichia coli

<400> SEQUENCE: 56

Met Asn Pro Tyr Ile Tyr Leu Gly Gly Ala Ile Leu Ala Glu Val Ile
1               5                   10                  15

Gly Thr Thr Leu Met Lys Phe Ser Glu Gly Phe Thr Arg Leu Trp Pro
            20                  25                  30

Ser Val Gly Thr Ile Ile Cys Tyr Cys Ala Ser Phe Trp Leu Leu Ala
        35                  40                  45

Gln Thr Leu Ala Tyr Ile Pro Thr Gly Ile Ala Tyr Ala Ile Trp Ser
    50                  55                  60

Gly Val Gly Ile Val Leu Ile Ser Leu Leu Ser Trp Gly Phe Phe Gly
65                  70                  75                  80

Gln Arg Leu Asp Leu Pro Ala Ile Ile Gly Met Met Leu Ile Cys Ala
                85                  90                  95

Gly Val Leu Val Ile Asn Leu Leu Ser Arg Ser Ala Pro His
            100             105             110

<210> SEQ ID NO 57
<211> LENGTH: 110
<212> TYPE: PRT
<213> ORGANISM: Escherichia coli

<400> SEQUENCE: 57

Met Asn Pro Tyr Ile Tyr Leu Gly Gly Ala Ile Leu Ala Glu Val Ile
1               5                   10                  15

Gly Thr Thr Leu Met Lys Phe Ser Glu Gly Phe Thr Arg Leu Trp Pro
            20                  25                  30

Ser Val Gly Thr Ile Ile Cys Tyr Cys Ala Ser Phe Trp Leu Leu Ala
        35                  40                  45

Gln Thr Leu Ala Tyr Ile Pro Thr Gly Ile Ala Tyr Ala Ile Trp Ser
    50                  55                  60

Gly Val Gly Ile Val Leu Ile Ser Leu Leu Ser Trp Gly Phe Phe Gly
65                  70                  75                  80

Gln Arg Leu Asp Leu Pro Ala Ile Ile Gly Met Met Leu Ile Cys Ala
                85                  90                  95

Gly Val Leu Val Ile Asn Leu Leu Ser Arg Ser Ala Pro His
            100             105             110

<210> SEQ ID NO 58
<211> LENGTH: 110
<212> TYPE: PRT
<213> ORGANISM: Escherichia coli

<400> SEQUENCE: 58

Met Asn Pro Tyr Ile Tyr Leu Gly Gly Ala Ile Leu Ala Glu Val Ile
1               5                   10                  15

Gly Thr Thr Leu Met Lys Phe Ser Glu Gly Phe Thr Arg Leu Trp Pro
            20                  25                  30

Ser Val Gly Thr Ile Ile Cys Tyr Cys Ala Ser Phe Trp Leu Leu Ala
        35                  40                  45

Gln Thr Leu Ala Tyr Ile Pro Thr Gly Ile Ala Tyr Ala Ile Trp Ser
    50                  55                  60

Gly Val Gly Ile Val Leu Ile Ser Leu Leu Ser Trp Gly Phe Phe Gly
65                  70                  75                  80

Gln Arg Leu Asp Leu Pro Ala Ile Ile Gly Met Met Leu Ile Cys Ala
                85                  90                  95

Gly Val Leu Val Ile Asn Leu Leu Ser Arg Ser Ala Pro His
            100                 105                 110

<210> SEQ ID NO 59
<211> LENGTH: 110
<212> TYPE: PRT
<213> ORGANISM: Escherichia coli

<400> SEQUENCE: 59

Met Asn Pro Tyr Ile Tyr Leu Gly Gly Ala Ile Leu Ala Glu Val Ile
1               5                   10                  15

Gly Thr Thr Leu Met Lys Phe Ser Glu Gly Phe Thr Arg Leu Trp Pro
            20                  25                  30

Ser Val Gly Thr Ile Ile Cys Tyr Cys Ala Ser Phe Trp Leu Leu Ala
        35                  40                  45

Gln Thr Leu Ala Tyr Ile Pro Thr Gly Ile Ala Tyr Ala Ile Trp Ser
    50                  55                  60

Gly Val Gly Ile Val Leu Ile Ser Leu Leu Ser Trp Gly Phe Phe Gly
65                  70                  75                  80

Gln Arg Leu Asp Leu Pro Ala Ile Ile Gly Met Met Leu Ile Cys Ala
                85                  90                  95

Gly Val Leu Val Ile Asn Leu Leu Ser Arg Ser Ala Pro His
            100                 105                 110

<210> SEQ ID NO 60
<211> LENGTH: 110
<212> TYPE: PRT
<213> ORGANISM: Escherichia coli

<400> SEQUENCE: 60

Met Asn Pro Tyr Ile Tyr Leu Gly Gly Ala Ile Leu Ala Glu Val Ile
1               5                   10                  15

Gly Thr Thr Leu Met Lys Phe Ser Glu Gly Phe Thr Arg Leu Trp Pro
            20                  25                  30

Ser Val Gly Thr Ile Ile Cys Tyr Cys Ala Ser Phe Trp Leu Leu Ala
        35                  40                  45

Gln Thr Leu Ala Tyr Ile Pro Thr Gly Ile Ala Tyr Ala Ile Trp Ser
    50                  55                  60

Gly Val Gly Ile Val Leu Ile Ser Leu Leu Ser Trp Gly Phe Phe Gly
65                  70                  75                  80

Gln Arg Leu Asp Leu Pro Ala Ile Ile Gly Met Met Leu Ile Cys Ala
                85                  90                  95

Gly Val Leu Val Ile Asn Leu Leu Ser Arg Ser Ala Pro His
            100                 105                 110

<210> SEQ ID NO 61
<211> LENGTH: 110
<212> TYPE: PRT
<213> ORGANISM: Escherichia coli

<400> SEQUENCE: 61

Met Asn Pro Tyr Ile Tyr Leu Gly Gly Ala Ile Leu Ala Glu Val Ile
1               5                   10                  15

Gly Thr Thr Leu Met Lys Phe Ser Glu Gly Phe Thr Arg Leu Trp Pro
            20                  25                  30

Ser Val Gly Thr Ile Ile Cys Tyr Cys Ala Ser Phe Trp Leu Leu Ala
        35                  40                  45

Gln Thr Leu Ala Tyr Ile Pro Thr Gly Ile Ala Tyr Ala Ile Trp Ser
    50                  55                  60

Gly Val Gly Ile Val Leu Ile Ser Leu Leu Ser Trp Gly Phe Phe Gly
65                  70                  75                  80

Gln Arg Leu Asp Leu Pro Ala Ile Ile Gly Met Met Leu Ile Cys Ala
                85                  90                  95

Gly Val Leu Val Ile Asn Leu Leu Ser Arg Ser Ala Pro His
            100                 105                 110

<210> SEQ ID NO 62
<211> LENGTH: 110
<212> TYPE: PRT
<213> ORGANISM: Escherichia coli

<400> SEQUENCE: 62

Met Asn Pro Tyr Ile Tyr Leu Gly Gly Ala Ile Leu Ala Glu Val Ile
1               5                   10                  15

Gly Thr Thr Leu Met Lys Phe Ser Glu Gly Phe Thr Arg Leu Trp Pro
            20                  25                  30

Ser Val Gly Thr Ile Ile Cys Tyr Cys Ala Ser Phe Trp Leu Leu Ala
        35                  40                  45

Gln Thr Leu Ala Tyr Ile Pro Thr Gly Ile Ala Tyr Ala Ile Trp Ser
    50                  55                  60

Gly Val Gly Ile Val Leu Ile Ser Leu Leu Ser Trp Gly Phe Phe Gly
65                  70                  75                  80

Gln Arg Leu Asp Leu Pro Ala Ile Ile Gly Met Met Leu Ile Cys Ala
                85                  90                  95

Gly Val Leu Val Ile Asn Leu Leu Ser Arg Ser Ala Pro His
            100                 105                 110

<210> SEQ ID NO 63
<211> LENGTH: 110
<212> TYPE: PRT
<213> ORGANISM: Escherichia coli

<400> SEQUENCE: 63

Met Asn Pro Tyr Ile Tyr Leu Gly Gly Ala Ile Leu Ala Glu Val Ile
1               5                   10                  15

Gly Thr Thr Leu Met Lys Phe Ser Glu Gly Phe Thr Arg Leu Trp Pro
            20                  25                  30

Ser Val Gly Thr Ile Ile Cys Tyr Cys Ala Ser Phe Trp Leu Leu Ala
        35                  40                  45

Gln Thr Leu Ala Tyr Ile Pro Thr Gly Ile Ala Tyr Ala Ile Trp Ser
    50                  55                  60

Gly Val Gly Ile Val Leu Ile Ser Leu Leu Ser Trp Gly Phe Phe Gly
65                  70                  75                  80

Gln Arg Leu Asp Leu Pro Ala Ile Ile Gly Met Met Leu Ile Cys Ala
                85                  90                  95

Gly Val Leu Val Ile Asn Leu Leu Ser Arg Ser Ala Pro His
            100                 105                 110

<210> SEQ ID NO 64
<211> LENGTH: 110
<212> TYPE: PRT
<213> ORGANISM: Escherichia coli

<400> SEQUENCE: 64

Met Asn Pro Tyr Ile Tyr Leu Gly Gly Ala Ile Leu Ala Glu Val Ile
1               5                   10                  15

Gly Thr Thr Leu Met Lys Phe Ser Glu Gly Phe Thr Arg Leu Trp Pro
            20                  25                  30

Ser Val Gly Thr Ile Ile Cys Tyr Cys Ala Ser Phe Trp Leu Leu Ala
        35                  40                  45

Gln Thr Leu Ala Tyr Ile Pro Thr Gly Ile Ala Tyr Ala Ile Trp Ser
    50                  55                  60

Gly Val Gly Ile Val Leu Ile Ser Leu Leu Ser Trp Gly Phe Phe Gly
65                  70                  75                  80

Gln Arg Leu Asp Leu Pro Ala Ile Ile Gly Met Met Leu Ile Cys Ala
                85                  90                  95

Gly Val Leu Val Ile Asn Leu Leu Ser Arg Ser Ala Pro His
            100                 105                 110

<210> SEQ ID NO 65
<211> LENGTH: 110
<212> TYPE: PRT
<213> ORGANISM: Escherichia coli

<400> SEQUENCE: 65

Met Asn Pro Tyr Ile Tyr Leu Gly Gly Ala Ile Leu Ala Glu Val Ile
1               5                   10                  15

Gly Thr Thr Leu Met Lys Phe Ser Glu Gly Phe Thr Arg Leu Trp Pro
            20                  25                  30

Ser Val Gly Thr Ile Ile Cys Tyr Cys Ala Ser Phe Trp Leu Leu Ala
        35                  40                  45

Gln Thr Leu Ala Tyr Ile Pro Thr Gly Ile Ala Tyr Ala Ile Trp Ser
    50                  55                  60

Gly Val Gly Ile Val Leu Ile Ser Leu Leu Ser Trp Gly Phe Phe Gly
65                  70                  75                  80

Gln Arg Leu Asp Leu Pro Ala Ile Ile Gly Met Met Leu Ile Cys Ala
                85                  90                  95

Gly Val Leu Val Ile Asn Leu Leu Ser Arg Ser Ala Pro His
            100                 105                 110

<210> SEQ ID NO 66
<211> LENGTH: 110
<212> TYPE: PRT
<213> ORGANISM: Escherichia fergusonii

<400> SEQUENCE: 66

Met Asn Pro Tyr Ile Tyr Leu Gly Gly Ala Ile Leu Ala Glu Val Ile
1               5                   10                  15

Gly Thr Thr Leu Met Lys Phe Ser Glu Gly Phe Thr Arg Leu Trp Pro
            20                  25                  30

Ser Val Gly Thr Ile Ile Cys Tyr Cys Ala Ser Phe Trp Leu Leu Ala
        35                  40                  45

Gln Thr Leu Ala Tyr Ile Pro Thr Gly Ile Ala Tyr Ala Ile Trp Ser
            50                  55                  60

Gly Val Gly Ile Val Leu Ile Ser Leu Leu Ser Trp Gly Phe Phe Gly
 65                  70                  75                  80

Gln Arg Leu Asp Leu Pro Ala Ile Ile Gly Met Met Leu Ile Cys Ala
                85                  90                  95

Gly Val Leu Val Ile Asn Leu Leu Ser Arg Ser Ala Pro His
            100                 105                 110

<210> SEQ ID NO 67
<211> LENGTH: 110
<212> TYPE: PRT
<213> ORGANISM: Escherichia coli

<400> SEQUENCE: 67

Met Asn Pro Tyr Ile Tyr Leu Gly Gly Ala Ile Leu Ala Glu Val Ile
  1               5                  10                  15

Gly Thr Thr Leu Met Lys Phe Ser Glu Gly Phe Thr Arg Leu Trp Pro
                20                  25                  30

Ser Val Gly Thr Ile Ile Cys Tyr Cys Ala Ser Phe Trp Leu Leu Ala
            35                  40                  45

Gln Thr Leu Ala Tyr Ile Pro Thr Gly Ile Ala Tyr Ala Ile Trp Ser
            50                  55                  60

Gly Val Gly Ile Val Leu Ile Ser Leu Leu Ser Trp Gly Phe Phe Gly
 65                  70                  75                  80

Gln Arg Leu Asp Leu Pro Ala Ile Ile Gly Met Met Leu Ile Cys Ala
                85                  90                  95

Gly Val Leu Val Ile Asn Leu Leu Ser Arg Ser Ala Pro His
            100                 105                 110

<210> SEQ ID NO 68
<211> LENGTH: 110
<212> TYPE: PRT
<213> ORGANISM: Escherichia coli

<400> SEQUENCE: 68

Met Asn Pro Tyr Ile Tyr Leu Gly Gly Ala Ile Leu Ala Glu Val Ile
  1               5                  10                  15

Gly Thr Thr Leu Met Lys Phe Ser Glu Gly Phe Thr Arg Leu Trp Pro
                20                  25                  30

Ser Val Gly Thr Ile Ile Cys Tyr Cys Ala Ser Phe Trp Leu Leu Ala
            35                  40                  45

Gln Thr Leu Ala Tyr Ile Pro Thr Gly Ile Ala Tyr Ala Ile Trp Ser
            50                  55                  60

Gly Val Gly Ile Val Leu Ile Ser Leu Leu Ser Trp Gly Phe Phe Gly
 65                  70                  75                  80

Gln Arg Leu Asp Leu Pro Ala Ile Ile Gly Met Met Leu Ile Cys Ala
                85                  90                  95

Gly Val Leu Val Ile Asn Leu Leu Ser Arg Ser Ala Pro His
            100                 105                 110

<210> SEQ ID NO 69
<211> LENGTH: 110
<212> TYPE: PRT
<213> ORGANISM: Escherichia coli

<400> SEQUENCE: 69

Met Asn Pro Tyr Ile Tyr Leu Gly Gly Ala Ile Leu Ala Glu Val Ile
1               5                   10                  15

Gly Thr Thr Leu Met Lys Phe Ser Glu Gly Phe Thr Arg Leu Trp Pro
            20                  25                  30

Ser Val Gly Thr Ile Ile Cys Tyr Cys Ala Ser Phe Trp Leu Leu Ala
        35                  40                  45

Gln Thr Leu Ala Tyr Ile Pro Thr Gly Ile Ala Tyr Ala Ile Trp Ser
    50                  55                  60

Gly Val Gly Ile Val Leu Ile Ser Leu Leu Ser Trp Gly Phe Phe Gly
65                  70                  75                  80

Gln Arg Leu Asp Leu Pro Ala Ile Ile Gly Met Met Leu Ile Cys Ala
                85                  90                  95

Gly Val Leu Val Ile Asn Leu Leu Ser Arg Ser Ala Pro His
            100                 105                 110

<210> SEQ ID NO 70
<211> LENGTH: 110
<212> TYPE: PRT
<213> ORGANISM: Escherichia coli

<400> SEQUENCE: 70

Met Asn Pro Tyr Ile Tyr Leu Gly Gly Ala Ile Leu Ala Glu Val Ile
1               5                   10                  15

Gly Thr Thr Leu Met Lys Phe Ser Glu Gly Phe Thr Arg Leu Trp Pro
            20                  25                  30

Ser Val Gly Thr Ile Ile Cys Tyr Cys Ala Ser Phe Trp Leu Leu Ala
        35                  40                  45

Gln Thr Leu Ala Tyr Ile Pro Thr Gly Ile Ala Tyr Ala Ile Trp Ser
    50                  55                  60

Gly Val Gly Ile Val Leu Ile Ser Leu Leu Ser Trp Gly Phe Phe Gly
65                  70                  75                  80

Gln Arg Leu Asp Leu Pro Ala Ile Ile Gly Met Met Leu Ile Cys Ala
                85                  90                  95

Gly Val Leu Val Ile Asn Leu Leu Ser Arg Ser Ala Pro His
            100                 105                 110

<210> SEQ ID NO 71
<211> LENGTH: 110
<212> TYPE: PRT
<213> ORGANISM: Escherichia sp.

<400> SEQUENCE: 71

Met Asn Pro Tyr Ile Tyr Leu Gly Gly Ala Ile Leu Ala Glu Val Ile
1               5                   10                  15

Gly Thr Thr Leu Met Lys Phe Ser Glu Gly Phe Thr Arg Leu Trp Pro
            20                  25                  30

Ser Val Gly Thr Ile Ile Cys Tyr Cys Ala Ser Phe Trp Leu Leu Ala
        35                  40                  45

Gln Thr Leu Ala Tyr Ile Pro Thr Gly Ile Ala Tyr Ala Ile Trp Ser
    50                  55                  60

Gly Val Gly Ile Val Leu Ile Ser Leu Leu Ser Trp Gly Phe Phe Gly
65                  70                  75                  80

Gln Arg Leu Asp Leu Pro Ala Ile Ile Gly Met Met Leu Ile Cys Ala
                85                  90                  95

Gly Val Leu Val Ile Asn Leu Leu Ser Arg Ser Ala Pro His
            100                 105                 110

<210> SEQ ID NO 72
<211> LENGTH: 110
<212> TYPE: PRT
<213> ORGANISM: Escherichia coli

<400> SEQUENCE: 72

Met Asn Pro Tyr Ile Tyr Leu Gly Gly Ala Ile Leu Ala Glu Val Ile
1               5                   10                  15

Gly Thr Thr Leu Met Lys Phe Ser Glu Gly Phe Thr Arg Leu Trp Pro
            20                  25                  30

Ser Val Gly Thr Ile Ile Cys Tyr Cys Ala Ser Phe Trp Leu Leu Ala
        35                  40                  45

Gln Thr Leu Ala Tyr Ile Pro Thr Gly Ile Ala Tyr Ala Ile Trp Ser
    50                  55                  60

Gly Val Gly Ile Val Leu Ile Ser Leu Leu Ser Trp Gly Phe Phe Gly
65                  70                  75                  80

Gln Arg Leu Asp Leu Pro Ala Ile Ile Gly Met Met Leu Ile Cys Ala
                85                  90                  95

Gly Val Leu Val Ile Asn Leu Leu Ser Arg Ser Ala Pro His
            100                 105                 110

<210> SEQ ID NO 73
<211> LENGTH: 110
<212> TYPE: PRT
<213> ORGANISM: Escherichia coli

<400> SEQUENCE: 73

Met Asn Pro Tyr Ile Tyr Leu Gly Gly Ala Ile Leu Ala Glu Val Ile
1               5                   10                  15

Gly Thr Thr Leu Met Lys Phe Ser Glu Gly Phe Thr Arg Leu Trp Pro
            20                  25                  30

Ser Val Gly Thr Ile Ile Cys Tyr Cys Ala Ser Phe Trp Leu Leu Ala
        35                  40                  45

Gln Thr Leu Ala Tyr Ile Pro Thr Gly Ile Ala Tyr Ala Ile Trp Ser
    50                  55                  60

Gly Val Gly Ile Val Leu Ile Ser Leu Leu Ser Trp Gly Phe Phe Gly
65                  70                  75                  80

Gln Arg Leu Asp Leu Pro Ala Ile Ile Gly Met Met Leu Ile Cys Ala
                85                  90                  95

Gly Val Leu Val Ile Asn Leu Leu Ser Arg Ser Ala Pro His
            100                 105                 110

<210> SEQ ID NO 74
<211> LENGTH: 110
<212> TYPE: PRT
<213> ORGANISM: Escherichia coli

<400> SEQUENCE: 74

Met Asn Pro Tyr Ile Tyr Leu Gly Gly Ala Ile Leu Ala Glu Val Ile
1               5                   10                  15

Gly Thr Thr Leu Met Lys Phe Ser Glu Gly Phe Thr Arg Leu Trp Pro
            20                  25                  30

Ser Val Gly Thr Ile Ile Cys Tyr Cys Ala Ser Phe Trp Leu Leu Ala
        35                  40                  45

Gln Thr Leu Ala Tyr Ile Pro Thr Gly Ile Ala Tyr Ala Ile Trp Ser
    50                  55                  60

Gly Val Gly Ile Val Leu Ile Ser Leu Leu Ser Trp Gly Phe Phe Gly
65                  70                  75                  80

Gln Arg Leu Asp Leu Pro Ala Ile Ile Gly Met Met Leu Ile Cys Ala
                85                  90                  95

Gly Val Leu Val Ile Asn Leu Leu Ser Arg Ser Ala Pro His
            100                 105                 110

<210> SEQ ID NO 75
<211> LENGTH: 110
<212> TYPE: PRT
<213> ORGANISM: Achromobacter sp.

<400> SEQUENCE: 75

Met Asn Pro Tyr Ile Tyr Leu Gly Gly Ala Ile Leu Ala Glu Val Ile
1               5                   10                  15

Gly Thr Thr Leu Met Lys Phe Ser Glu Gly Phe Thr Arg Leu Trp Pro
            20                  25                  30

Ser Val Gly Thr Ile Ile Cys Tyr Cys Ala Ser Phe Trp Leu Leu Ala
        35                  40                  45

Gln Thr Leu Ala Tyr Ile Pro Thr Gly Ile Ala Tyr Ala Ile Trp Ser
    50                  55                  60

Gly Val Gly Ile Val Leu Ile Ser Leu Leu Ser Trp Gly Phe Phe Gly
65                  70                  75                  80

Gln Arg Leu Asp Leu Pro Ala Ile Ile Gly Met Met Leu Ile Cys Ala
                85                  90                  95

Gly Val Leu Val Ile Asn Leu Leu Ser Arg Ser Ala Pro His
            100                 105                 110

<210> SEQ ID NO 76
<211> LENGTH: 110
<212> TYPE: PRT
<213> ORGANISM: Escherichia coli

<400> SEQUENCE: 76

Met Asn Pro Tyr Ile Tyr Leu Gly Gly Ala Ile Leu Ala Glu Val Ile
1               5                   10                  15

Gly Thr Thr Leu Met Lys Phe Ser Glu Gly Phe Thr Arg Leu Trp Pro
            20                  25                  30

Ser Val Gly Thr Ile Ile Cys Tyr Cys Ala Ser Phe Trp Leu Leu Ala
        35                  40                  45

Gln Thr Leu Ala Tyr Ile Pro Thr Gly Ile Ala Tyr Ala Ile Trp Ser
    50                  55                  60

Gly Val Gly Ile Val Leu Ile Ser Leu Leu Ser Trp Gly Phe Phe Gly
65                  70                  75                  80

Gln Arg Leu Asp Leu Pro Ala Ile Ile Gly Met Met Leu Ile Cys Ala
                85                  90                  95

Gly Val Leu Val Ile Asn Leu Leu Ser Arg Ser Ala Pro His
            100                 105                 110

<210> SEQ ID NO 77
<211> LENGTH: 110
<212> TYPE: PRT
<213> ORGANISM: Escherichia coli

<400> SEQUENCE: 77

Met Asn Pro Tyr Ile Tyr Leu Gly Gly Ala Ile Leu Ala Glu Val Ile
1               5                   10                  15

Gly Thr Thr Leu Met Lys Phe Ser Glu Gly Phe Thr Arg Leu Trp Pro
            20                  25                  30

Ser Val Gly Thr Ile Ile Cys Tyr Cys Ala Ser Phe Trp Leu Leu Ala
        35                  40                  45

Gln Thr Leu Ala Tyr Ile Pro Thr Gly Ile Ala Tyr Ala Ile Trp Ser
    50                  55                  60

Gly Val Gly Ile Val Leu Ile Ser Leu Ser Trp Gly Phe Phe Gly
65                  70                  75                  80

Gln Arg Leu Asp Leu Pro Ala Ile Ile Gly Met Met Leu Ile Cys Ala
                85                  90                  95

Gly Val Leu Val Ile Asn Leu Leu Ser Arg Ser Ala Pro His
            100                 105                 110

<210> SEQ ID NO 78
<211> LENGTH: 110
<212> TYPE: PRT
<213> ORGANISM: Escherichia coli

<400> SEQUENCE: 78

Met Asn Pro Tyr Ile Tyr Leu Gly Gly Ala Ile Leu Ala Glu Val Ile
1               5                   10                  15

Gly Thr Thr Leu Met Lys Phe Ser Glu Gly Phe Thr Arg Leu Trp Pro
            20                  25                  30

Ser Val Gly Thr Ile Ile Cys Tyr Cys Ala Ser Phe Trp Leu Leu Ala
        35                  40                  45

Gln Thr Leu Ala Tyr Ile Pro Thr Gly Ile Ala Tyr Ala Ile Trp Ser
    50                  55                  60

Gly Val Gly Ile Val Leu Ile Ser Leu Ser Trp Gly Phe Phe Gly
65                  70                  75                  80

Gln Arg Leu Asp Leu Pro Ala Ile Ile Gly Met Met Leu Ile Cys Ala
                85                  90                  95

Gly Val Leu Val Ile Asn Leu Leu Ser Arg Ser Ala Pro His
            100                 105                 110

<210> SEQ ID NO 79
<211> LENGTH: 110
<212> TYPE: PRT
<213> ORGANISM: Escherichia coli

<400> SEQUENCE: 79

Met Asn Pro Tyr Ile Tyr Leu Gly Gly Ala Ile Leu Ala Glu Val Ile
1               5                   10                  15

Gly Thr Thr Leu Met Lys Phe Ser Glu Gly Phe Thr Arg Leu Trp Pro
            20                  25                  30

Ser Val Gly Thr Ile Ile Cys Tyr Cys Ala Ser Phe Trp Leu Leu Ala
        35                  40                  45

Gln Thr Leu Ala Tyr Ile Pro Thr Gly Ile Ala Tyr Ala Ile Trp Ser
    50                  55                  60

Gly Val Gly Ile Val Leu Ile Ser Leu Ser Trp Gly Phe Phe Gly
65                  70                  75                  80

Gln Arg Leu Asp Leu Pro Ala Ile Ile Gly Met Met Leu Ile Cys Ala
                85                  90                  95

Gly Val Leu Val Ile Asn Leu Leu Ser Arg Ser Ala Pro His
            100                 105                 110

<210> SEQ ID NO 80
<211> LENGTH: 110
<212> TYPE: PRT
<213> ORGANISM: Escherichia coli

<400> SEQUENCE: 80

Met Asn Pro Tyr Ile Tyr Leu Gly Gly Ala Ile Leu Ala Glu Val Ile
1               5                   10                  15

Gly Thr Thr Leu Met Lys Phe Ser Glu Gly Phe Thr Arg Leu Trp Pro
            20                  25                  30

Ser Val Gly Thr Ile Ile Cys Tyr Cys Ala Ser Phe Trp Leu Leu Ala
        35                  40                  45

Gln Thr Leu Ala Tyr Ile Pro Thr Gly Ile Ala Tyr Ala Ile Trp Ser
    50                  55                  60

Gly Val Gly Ile Val Leu Ile Ser Leu Leu Ser Trp Gly Phe Phe Gly
65                  70                  75                  80

Gln Arg Leu Asp Leu Pro Ala Ile Ile Gly Met Met Leu Ile Cys Ala
                85                  90                  95

Gly Val Leu Val Ile Asn Leu Leu Ser Arg Ser Ala Pro His
            100                 105                 110

<210> SEQ ID NO 81
<211> LENGTH: 110
<212> TYPE: PRT
<213> ORGANISM: Escherichia coli

<400> SEQUENCE: 81

Met Asn Pro Tyr Ile Tyr Leu Gly Gly Ala Ile Leu Ala Glu Val Ile
1               5                   10                  15

Gly Thr Thr Leu Met Lys Phe Ser Glu Gly Phe Thr Arg Leu Trp Pro
            20                  25                  30

Ser Val Gly Thr Ile Ile Cys Tyr Cys Ala Ser Phe Trp Leu Leu Ala
        35                  40                  45

Gln Thr Leu Ala Tyr Ile Pro Thr Gly Ile Ala Tyr Ala Ile Trp Ser
    50                  55                  60

Gly Val Gly Ile Val Leu Ile Ser Leu Leu Ser Trp Gly Phe Phe Gly
65                  70                  75                  80

Gln Arg Leu Asp Leu Pro Ala Ile Ile Gly Met Met Leu Ile Cys Ala
                85                  90                  95

Gly Val Leu Val Ile Asn Leu Leu Ser Arg Ser Ala Pro His
            100                 105                 110

<210> SEQ ID NO 82
<211> LENGTH: 110
<212> TYPE: PRT
<213> ORGANISM: Escherichia coli

<400> SEQUENCE: 82

Met Asn Pro Tyr Ile Tyr Leu Gly Gly Ala Ile Leu Ala Glu Val Ile
1               5                   10                  15

Gly Thr Thr Leu Met Lys Phe Ser Glu Gly Phe Thr Arg Leu Trp Pro
            20                  25                  30

Ser Val Gly Thr Ile Ile Cys Tyr Cys Ala Ser Phe Trp Leu Leu Ala
        35                  40                  45

Gln Thr Leu Ala Tyr Ile Pro Thr Gly Ile Ala Tyr Ala Ile Trp Ser
    50                  55                  60

Gly Val Gly Ile Val Leu Ile Ser Leu Leu Ser Trp Gly Phe Phe Gly
65                  70                  75                  80

Gln Arg Leu Asp Leu Pro Ala Ile Ile Gly Met Met Leu Ile Cys Ala
                85                  90                  95

Gly Val Leu Val Ile Asn Leu Leu Ser Arg Ser Ala Pro His
            100                 105                 110

<210> SEQ ID NO 83
<211> LENGTH: 110
<212> TYPE: PRT
<213> ORGANISM: Escherichia coli

<400> SEQUENCE: 83

Met Asn Pro Tyr Ile Tyr Leu Gly Gly Ala Ile Leu Ala Glu Val Ile
1               5                   10                  15

Gly Thr Thr Leu Met Lys Phe Ser Glu Gly Phe Thr Arg Leu Trp Pro
                20                  25                  30

Ser Val Gly Thr Ile Ile Cys Tyr Cys Ala Ser Phe Trp Leu Leu Ala
            35                  40                  45

Gln Thr Leu Ala Tyr Ile Pro Thr Gly Ile Ala Tyr Ala Ile Trp Ser
    50                  55                  60

Gly Val Gly Ile Val Leu Ile Ser Leu Leu Ser Trp Gly Phe Phe Gly
65                  70                  75                  80

Gln Arg Leu Asp Leu Pro Ala Ile Ile Gly Met Met Leu Ile Cys Ala
                85                  90                  95

Gly Val Leu Val Ile Asn Leu Leu Ser Arg Ser Ala Pro His
            100                 105                 110

<210> SEQ ID NO 84
<211> LENGTH: 110
<212> TYPE: PRT
<213> ORGANISM: Escherichia coli

<400> SEQUENCE: 84

Met Asn Pro Tyr Ile Tyr Leu Gly Gly Ala Ile Leu Ala Glu Val Ile
1               5                   10                  15

Gly Thr Thr Leu Met Lys Phe Ser Glu Gly Phe Thr Arg Leu Trp Pro
                20                  25                  30

Ser Val Gly Thr Ile Ile Cys Tyr Cys Ala Ser Phe Trp Leu Leu Ala
            35                  40                  45

Gln Thr Leu Ala Tyr Ile Pro Thr Gly Ile Ala Tyr Ala Ile Trp Ser
    50                  55                  60

Gly Val Gly Ile Val Leu Ile Ser Leu Leu Ser Trp Gly Phe Phe Gly
65                  70                  75                  80

Gln Arg Leu Asp Leu Pro Ala Ile Ile Gly Met Met Leu Ile Cys Ala
                85                  90                  95

Gly Val Leu Val Ile Asn Leu Leu Ser Arg Ser Ala Pro His
            100                 105                 110

<210> SEQ ID NO 85
<211> LENGTH: 110
<212> TYPE: PRT
<213> ORGANISM: Escherichia coli

<400> SEQUENCE: 85

Met Asn Pro Tyr Ile Tyr Leu Gly Gly Ala Ile Leu Ala Glu Val Ile
1               5                   10                  15

Gly Thr Thr Leu Met Lys Phe Ser Glu Gly Phe Thr Arg Leu Trp Pro
            20                  25                  30

Ser Val Gly Thr Ile Ile Cys Tyr Cys Ala Ser Phe Trp Leu Leu Ala
        35                  40                  45

Gln Thr Leu Ala Tyr Ile Pro Thr Gly Ile Ala Tyr Ala Ile Trp Ser
    50                  55                  60

Gly Val Gly Ile Val Leu Ile Ser Leu Leu Ser Trp Gly Phe Phe Gly
65                  70                  75                  80

Gln Arg Leu Asp Leu Pro Ala Ile Ile Gly Met Met Leu Ile Cys Ala
                85                  90                  95

Gly Val Leu Val Ile Asn Leu Leu Ser Arg Ser Ala Pro His
            100                 105                 110

<210> SEQ ID NO 86
<211> LENGTH: 110
<212> TYPE: PRT
<213> ORGANISM: Shigella flexneri

<400> SEQUENCE: 86

Met Asn Pro Tyr Ile Tyr Leu Gly Gly Ala Ile Leu Ala Glu Val Ile
1               5                   10                  15

Gly Thr Thr Leu Met Lys Phe Ser Glu Gly Phe Thr Arg Leu Trp Pro
            20                  25                  30

Ser Val Gly Thr Ile Ile Cys Tyr Cys Ala Ser Phe Trp Leu Leu Ala
        35                  40                  45

Gln Thr Leu Ala Tyr Ile Pro Thr Gly Ile Ala Tyr Ala Ile Trp Ser
    50                  55                  60

Gly Val Gly Ile Val Leu Ile Ser Leu Leu Ser Trp Gly Phe Phe Gly
65                  70                  75                  80

Gln Arg Leu Asp Leu Pro Ala Ile Ile Gly Met Met Leu Ile Cys Ala
                85                  90                  95

Gly Val Leu Val Ile Asn Leu Leu Ser Arg Ser Ala Pro His
            100                 105                 110

<210> SEQ ID NO 87
<211> LENGTH: 110
<212> TYPE: PRT
<213> ORGANISM: Shigella flexneri

<400> SEQUENCE: 87

Met Asn Pro Tyr Ile Tyr Leu Gly Gly Ala Ile Leu Ala Glu Val Ile
1               5                   10                  15

Gly Thr Thr Leu Met Lys Phe Ser Glu Gly Phe Thr Arg Leu Trp Pro
            20                  25                  30

Ser Val Gly Thr Ile Ile Cys Tyr Cys Ala Ser Phe Trp Leu Leu Ala
        35                  40                  45

Gln Thr Leu Ala Tyr Ile Pro Thr Gly Ile Ala Tyr Ala Ile Trp Ser
    50                  55                  60

Gly Val Gly Ile Val Leu Ile Ser Leu Leu Ser Trp Gly Phe Phe Gly
65                  70                  75                  80

Gln Arg Leu Asp Leu Pro Ala Ile Ile Gly Met Met Leu Ile Cys Ala
                85                  90                  95

```
Gly Val Leu Val Ile Asn Leu Leu Ser Arg Ser Ala Pro His
            100                 105                 110

<210> SEQ ID NO 88
<211> LENGTH: 110
<212> TYPE: PRT
<213> ORGANISM: Shigella sunnier

<400> SEQUENCE: 88

Met Asn Pro Tyr Ile Tyr Leu Gly Gly Ala Ile Leu Ala Glu Val Ile
1               5                   10                  15

Gly Thr Thr Leu Met Lys Phe Ser Glu Gly Phe Thr Arg Leu Trp Pro
            20                  25                  30

Ser Val Gly Thr Ile Ile Cys Tyr Cys Ala Ser Phe Trp Leu Leu Ala
        35                  40                  45

Gln Thr Leu Ala Tyr Ile Pro Thr Gly Ile Ala Tyr Ala Ile Trp Ser
    50                  55                  60

Gly Val Gly Ile Val Leu Ile Ser Leu Leu Ser Trp Gly Phe Phe Gly
65                  70                  75                  80

Gln Arg Leu Asp Leu Pro Ala Ile Ile Gly Met Met Leu Ile Cys Ala
                85                  90                  95

Gly Val Leu Val Ile Asn Leu Leu Ser Arg Ser Ala Pro His
            100                 105                 110

<210> SEQ ID NO 89
<211> LENGTH: 110
<212> TYPE: PRT
<213> ORGANISM: Escherichia coli

<400> SEQUENCE: 89

Met Asn Pro Tyr Ile Tyr Leu Gly Gly Ala Ile Leu Ala Glu Val Ile
1               5                   10                  15

Gly Thr Thr Leu Met Lys Phe Ser Glu Gly Phe Thr Arg Leu Trp Pro
            20                  25                  30

Ser Val Gly Thr Ile Ile Cys Tyr Cys Ala Ser Phe Trp Leu Leu Ala
        35                  40                  45

Gln Thr Leu Ala Tyr Ile Pro Thr Gly Ile Ala Tyr Ala Ile Trp Ser
    50                  55                  60

Gly Val Gly Ile Val Leu Ile Ser Leu Leu Ser Trp Gly Phe Phe Gly
65                  70                  75                  80

Gln Arg Leu Asp Leu Pro Ala Ile Ile Gly Met Met Leu Ile Cys Ala
                85                  90                  95

Gly Val Leu Val Ile Asn Leu Leu Ser Arg Ser Ala Pro His
            100                 105                 110

<210> SEQ ID NO 90
<211> LENGTH: 110
<212> TYPE: PRT
<213> ORGANISM: Escherichia coli

<400> SEQUENCE: 90

Met Asn Pro Tyr Ile Tyr Leu Gly Gly Ala Ile Leu Ala Glu Val Ile
1               5                   10                  15

Gly Thr Thr Leu Met Lys Phe Ser Glu Gly Phe Thr Arg Leu Trp Pro
            20                  25                  30

Ser Val Gly Thr Ile Ile Cys Tyr Cys Ala Ser Phe Trp Leu Leu Ala
        35                  40                  45
```

```
Gln Thr Leu Ala Tyr Ile Pro Thr Gly Ile Ala Tyr Ala Ile Trp Ser
    50                  55                  60

Gly Val Gly Ile Val Leu Ile Ser Leu Leu Ser Trp Gly Phe Phe Gly
65                  70                  75                  80

Gln Arg Leu Asp Leu Pro Ala Ile Ile Gly Met Met Leu Ile Cys Ala
                85                  90                  95

Gly Val Leu Val Ile Asn Leu Leu Ser Arg Ser Ala Pro His
            100                 105                 110

<210> SEQ ID NO 91
<211> LENGTH: 110
<212> TYPE: PRT
<213> ORGANISM: Escherichia coli

<400> SEQUENCE: 91

Met Asn Pro Tyr Ile Tyr Leu Gly Gly Ala Ile Leu Ala Glu Val Ile
1               5                   10                  15

Gly Thr Thr Leu Met Lys Phe Ser Glu Gly Phe Thr Arg Leu Trp Pro
                20                  25                  30

Ser Val Gly Thr Ile Ile Cys Tyr Cys Ala Ser Phe Trp Leu Leu Ala
            35                  40                  45

Gln Thr Leu Ala Tyr Ile Pro Thr Gly Ile Ala Tyr Ala Ile Trp Ser
    50                  55                  60

Gly Val Gly Ile Val Leu Ile Ser Leu Leu Ser Trp Gly Phe Phe Gly
65                  70                  75                  80

Gln Arg Leu Asp Leu Pro Ala Ile Ile Gly Met Met Leu Ile Cys Ala
                85                  90                  95

Gly Val Leu Val Ile Asn Leu Leu Ser Arg Ser Ala Pro His
            100                 105                 110

<210> SEQ ID NO 92
<211> LENGTH: 110
<212> TYPE: PRT
<213> ORGANISM: Escherichia coli

<400> SEQUENCE: 92

Met Asn Pro Tyr Ile Tyr Leu Gly Gly Ala Ile Leu Ala Glu Val Ile
1               5                   10                  15

Gly Thr Thr Leu Met Lys Phe Ser Glu Gly Phe Thr Arg Leu Trp Pro
                20                  25                  30

Ser Val Gly Thr Ile Ile Cys Tyr Cys Ala Ser Phe Trp Leu Leu Ala
            35                  40                  45

Gln Thr Leu Ala Tyr Ile Pro Thr Gly Ile Ala Tyr Ala Ile Trp Ser
    50                  55                  60

Gly Val Gly Ile Val Leu Ile Ser Leu Leu Ser Trp Gly Phe Phe Gly
65                  70                  75                  80

Gln Arg Leu Asp Leu Pro Ala Ile Ile Gly Met Met Leu Ile Cys Ala
                85                  90                  95

Gly Val Leu Val Ile Asn Leu Leu Ser Arg Ser Ala Pro His
            100                 105                 110

<210> SEQ ID NO 93
<211> LENGTH: 110
<212> TYPE: PRT
<213> ORGANISM: Escherichia coli
```

<400> SEQUENCE: 93

Met Asn Pro Tyr Ile Tyr Leu Gly Gly Ala Ile Leu Ala Glu Val Ile
1               5                   10                  15

Gly Thr Thr Leu Met Lys Phe Ser Glu Gly Phe Thr Arg Leu Trp Pro
            20                  25                  30

Ser Val Gly Thr Ile Ile Cys Tyr Cys Ala Ser Phe Trp Leu Leu Ala
        35                  40                  45

Gln Thr Leu Ala Tyr Ile Pro Thr Gly Ile Ala Tyr Ala Ile Trp Ser
    50                  55                  60

Gly Val Gly Ile Val Leu Ile Ser Leu Leu Ser Trp Gly Phe Phe Gly
65                  70                  75                  80

Gln Arg Leu Asp Leu Pro Ala Ile Ile Gly Met Met Leu Ile Cys Ala
                85                  90                  95

Gly Val Leu Val Ile Asn Leu Leu Ser Arg Ser Ala Pro His
            100                 105                 110

<210> SEQ ID NO 94
<211> LENGTH: 110
<212> TYPE: PRT
<213> ORGANISM: Escherichia coli

<400> SEQUENCE: 94

Met Asn Pro Tyr Ile Tyr Leu Gly Gly Ala Ile Leu Ala Glu Val Ile
1               5                   10                  15

Gly Thr Thr Leu Met Lys Phe Ser Glu Gly Phe Thr Arg Leu Trp Pro
            20                  25                  30

Ser Val Gly Thr Ile Ile Cys Tyr Cys Ala Ser Phe Trp Leu Leu Ala
        35                  40                  45

Gln Thr Leu Ala Tyr Ile Pro Thr Gly Ile Ala Tyr Ala Ile Trp Ser
    50                  55                  60

Gly Val Gly Ile Val Leu Ile Ser Leu Leu Ser Trp Gly Phe Phe Gly
65                  70                  75                  80

Gln Arg Leu Asp Leu Pro Ala Ile Ile Gly Met Met Leu Ile Cys Ala
                85                  90                  95

Gly Val Leu Val Ile Asn Leu Leu Ser Arg Ser Ala Pro His
            100                 105                 110

<210> SEQ ID NO 95
<211> LENGTH: 110
<212> TYPE: PRT
<213> ORGANISM: Escherichia coli

<400> SEQUENCE: 95

Met Asn Pro Tyr Ile Tyr Leu Gly Gly Ala Ile Leu Ala Glu Val Ile
1               5                   10                  15

Gly Thr Thr Leu Met Lys Phe Ser Glu Gly Phe Thr Arg Leu Trp Pro
            20                  25                  30

Ser Val Gly Thr Ile Ile Cys Tyr Cys Ala Ser Phe Trp Leu Leu Ala
        35                  40                  45

Gln Thr Leu Ala Tyr Ile Pro Thr Gly Ile Ala Tyr Ala Ile Trp Ser
    50                  55                  60

Gly Val Gly Ile Val Leu Ile Ser Leu Leu Ser Trp Gly Phe Phe Gly
65                  70                  75                  80

Gln Arg Leu Asp Leu Pro Ala Ile Ile Gly Met Met Leu Ile Cys Ala
                85                  90                  95

Gly Val Leu Val Ile Asn Leu Leu Ser Arg Ser Ala Pro His
            100                 105                 110

<210> SEQ ID NO 96
<211> LENGTH: 110
<212> TYPE: PRT
<213> ORGANISM: Escherichia coli

<400> SEQUENCE: 96

Met Asn Pro Tyr Ile Tyr Leu Gly Gly Ala Ile Leu Ala Glu Val Ile
1               5                   10                  15

Gly Thr Thr Leu Met Lys Phe Ser Glu Gly Phe Thr Arg Leu Trp Pro
            20                  25                  30

Ser Val Gly Thr Ile Ile Cys Tyr Cys Ala Ser Phe Trp Leu Leu Ala
        35                  40                  45

Gln Thr Leu Ala Tyr Ile Pro Thr Gly Ile Ala Tyr Ala Ile Trp Ser
    50                  55                  60

Gly Val Gly Ile Val Leu Ile Ser Leu Leu Ser Trp Gly Phe Phe Gly
65                  70                  75                  80

Gln Arg Leu Asp Leu Pro Ala Ile Ile Gly Met Met Leu Ile Cys Ala
                85                  90                  95

Gly Val Leu Val Ile Asn Leu Leu Ser Arg Ser Ala Pro His
            100                 105                 110

<210> SEQ ID NO 97
<211> LENGTH: 110
<212> TYPE: PRT
<213> ORGANISM: Escherichia coli

<400> SEQUENCE: 97

Met Asn Pro Tyr Ile Tyr Leu Gly Gly Ala Ile Leu Ala Glu Val Ile
1               5                   10                  15

Gly Thr Thr Leu Met Lys Phe Ser Glu Gly Phe Thr Arg Leu Trp Pro
            20                  25                  30

Ser Val Gly Thr Ile Ile Cys Tyr Cys Ala Ser Phe Trp Leu Leu Ala
        35                  40                  45

Gln Thr Leu Ala Tyr Ile Pro Thr Gly Ile Ala Tyr Ala Ile Trp Ser
    50                  55                  60

Gly Val Gly Ile Val Leu Ile Ser Leu Leu Ser Trp Gly Phe Phe Gly
65                  70                  75                  80

Gln Arg Leu Asp Leu Pro Ala Ile Ile Gly Met Met Leu Ile Cys Ala
                85                  90                  95

Gly Val Leu Val Ile Asn Leu Leu Ser Arg Ser Ala Pro His
            100                 105                 110

<210> SEQ ID NO 98
<211> LENGTH: 110
<212> TYPE: PRT
<213> ORGANISM: Escherichia coli

<400> SEQUENCE: 98

Met Asn Pro Tyr Ile Tyr Leu Gly Gly Ala Ile Leu Ala Glu Val Ile
1               5                   10                  15

Gly Thr Thr Leu Met Lys Phe Ser Glu Gly Phe Thr Arg Leu Trp Pro
            20                  25                  30

Ser Val Gly Thr Ile Ile Cys Tyr Cys Ala Ser Phe Trp Leu Leu Ala
        35                  40                  45

Gln Thr Leu Ala Tyr Ile Pro Thr Gly Ile Ala Tyr Ala Ile Trp Ser
            50                  55                  60

Gly Val Gly Ile Val Leu Ile Ser Leu Leu Ser Trp Gly Phe Phe Gly
65                  70                  75                  80

Gln Arg Leu Asp Leu Pro Ala Ile Ile Gly Met Met Leu Ile Cys Ala
                85                  90                  95

Gly Val Leu Val Ile Asn Leu Leu Ser Arg Ser Ala Pro His
            100                 105                 110

<210> SEQ ID NO 99
<211> LENGTH: 110
<212> TYPE: PRT
<213> ORGANISM: Escherichia coli

<400> SEQUENCE: 99

Met Asn Pro Tyr Ile Tyr Leu Gly Gly Ala Ile Leu Ala Glu Val Ile
1               5                   10                  15

Gly Thr Thr Leu Met Lys Phe Ser Glu Gly Phe Thr Arg Leu Trp Pro
                20                  25                  30

Ser Val Gly Thr Ile Ile Cys Tyr Cys Ala Ser Phe Trp Leu Leu Ala
            35                  40                  45

Gln Thr Leu Ala Tyr Ile Pro Thr Gly Ile Ala Tyr Ala Ile Trp Ser
        50                  55                  60

Gly Val Gly Ile Val Leu Ile Ser Leu Leu Ser Trp Gly Phe Phe Gly
65                  70                  75                  80

Gln Arg Leu Asp Leu Pro Ala Ile Ile Gly Met Met Leu Ile Cys Ala
                85                  90                  95

Gly Val Leu Val Ile Asn Leu Leu Ser Arg Ser Ala Pro His
            100                 105                 110

<210> SEQ ID NO 100
<211> LENGTH: 110
<212> TYPE: PRT
<213> ORGANISM: Escherichia coli

<400> SEQUENCE: 100

Met Asn Pro Tyr Ile Tyr Leu Gly Gly Ala Ile Leu Ala Glu Val Ile
1               5                   10                  15

Gly Thr Thr Leu Met Lys Phe Ser Glu Gly Phe Thr Arg Leu Trp Pro
                20                  25                  30

Ser Val Gly Thr Ile Ile Cys Tyr Cys Ala Ser Phe Trp Leu Leu Ala
            35                  40                  45

Gln Thr Leu Ala Tyr Ile Pro Thr Gly Ile Ala Tyr Ala Ile Trp Ser
        50                  55                  60

Gly Val Gly Ile Val Leu Ile Ser Leu Leu Ser Trp Gly Phe Phe Gly
65                  70                  75                  80

Gln Arg Leu Asp Leu Pro Ala Ile Ile Gly Met Met Leu Ile Cys Ala
                85                  90                  95

Gly Val Leu Val Ile Asn Leu Leu Ser Arg Ser Ala Pro His
            100                 105                 110

<210> SEQ ID NO 101
<211> LENGTH: 110
<212> TYPE: PRT
<213> ORGANISM: Escherichia coli

<400> SEQUENCE: 101

Met Asn Pro Tyr Ile Tyr Leu Gly Gly Ala Ile Leu Ala Glu Val Ile
1               5                   10                  15

Gly Thr Thr Leu Met Lys Phe Ser Glu Gly Phe Thr Arg Leu Trp Pro
            20                  25                  30

Ser Val Gly Thr Ile Ile Cys Tyr Cys Ala Ser Phe Trp Leu Leu Ala
        35                  40                  45

Gln Thr Leu Ala Tyr Ile Pro Thr Gly Ile Ala Tyr Ala Ile Trp Ser
    50                  55                  60

Gly Val Gly Ile Val Leu Ile Ser Leu Ser Trp Gly Phe Phe Gly
65                  70                  75                  80

Gln Arg Leu Asp Leu Pro Ala Ile Ile Gly Met Met Leu Ile Cys Ala
                85                  90                  95

Gly Val Leu Val Ile Asn Leu Leu Ser Arg Ser Ala Pro His
            100                 105                 110

<210> SEQ ID NO 102
<211> LENGTH: 110
<212> TYPE: PRT
<213> ORGANISM: Escherichia coli

<400> SEQUENCE: 102

Met Asn Pro Tyr Ile Tyr Leu Gly Gly Ala Ile Leu Ala Glu Val Ile
1               5                   10                  15

Gly Thr Thr Leu Met Lys Phe Ser Glu Gly Phe Thr Arg Leu Trp Pro
            20                  25                  30

Ser Val Gly Thr Ile Ile Cys Tyr Cys Ala Ser Phe Trp Leu Leu Ala
        35                  40                  45

Gln Thr Leu Ala Tyr Ile Pro Thr Gly Ile Ala Tyr Ala Ile Trp Ser
    50                  55                  60

Gly Val Gly Ile Val Leu Ile Ser Leu Ser Trp Gly Phe Phe Gly
65                  70                  75                  80

Gln Arg Leu Asp Leu Pro Ala Ile Ile Gly Met Met Leu Ile Cys Ala
                85                  90                  95

Gly Val Leu Val Ile Asn Leu Leu Ser Arg Ser Ala Pro His
            100                 105                 110

<210> SEQ ID NO 103
<211> LENGTH: 110
<212> TYPE: PRT
<213> ORGANISM: Escherichia coli

<400> SEQUENCE: 103

Met Asn Pro Tyr Ile Tyr Leu Gly Gly Ala Ile Leu Ala Glu Val Ile
1               5                   10                  15

Gly Thr Thr Leu Met Lys Phe Ser Glu Gly Phe Thr Arg Leu Trp Pro
            20                  25                  30

Ser Val Gly Thr Ile Ile Cys Tyr Cys Ala Ser Phe Trp Leu Leu Ala
        35                  40                  45

Gln Thr Leu Ala Tyr Ile Pro Thr Gly Ile Ala Tyr Ala Ile Trp Ser
    50                  55                  60

Gly Val Gly Ile Val Leu Ile Ser Leu Ser Trp Gly Phe Phe Gly
65                  70                  75                  80

Gln Arg Leu Asp Leu Pro Ala Ile Ile Gly Met Met Leu Ile Cys Ala
                85                  90                  95

-continued

Gly Val Leu Val Ile Asn Leu Leu Ser Arg Ser Ala Pro His
                100                 105                 110

<210> SEQ ID NO 104
<211> LENGTH: 110
<212> TYPE: PRT
<213> ORGANISM: Escherichia coli

<400> SEQUENCE: 104

Met Asn Pro Tyr Ile Tyr Leu Gly Gly Ala Ile Leu Ala Glu Val Ile
1               5                   10                  15

Gly Thr Thr Leu Met Lys Phe Ser Glu Gly Phe Thr Arg Leu Trp Pro
            20                  25                  30

Ser Val Gly Thr Ile Ile Cys Tyr Cys Ala Ser Phe Trp Leu Leu Ala
        35                  40                  45

Gln Thr Leu Ala Tyr Ile Pro Thr Gly Ile Ala Tyr Ala Ile Trp Ser
    50                  55                  60

Gly Val Gly Ile Val Leu Ile Ser Leu Leu Ser Trp Gly Phe Phe Gly
65                  70                  75                  80

Gln Arg Leu Asp Leu Pro Ala Ile Ile Gly Met Met Leu Ile Cys Ala
                85                  90                  95

Gly Val Leu Val Ile Asn Leu Leu Ser Arg Ser Ala Pro His
                100                 105                 110

<210> SEQ ID NO 105
<211> LENGTH: 110
<212> TYPE: PRT
<213> ORGANISM: Escherichia coli

<400> SEQUENCE: 105

Met Asn Pro Tyr Ile Tyr Leu Gly Gly Ala Ile Leu Ala Glu Val Ile
1               5                   10                  15

Gly Thr Thr Leu Met Lys Phe Ser Glu Gly Phe Thr Arg Leu Trp Pro
            20                  25                  30

Ser Val Gly Thr Ile Ile Cys Tyr Cys Ala Ser Phe Trp Leu Leu Ala
        35                  40                  45

Gln Thr Leu Ala Tyr Ile Pro Thr Gly Ile Ala Tyr Ala Ile Trp Ser
    50                  55                  60

Gly Val Gly Ile Val Leu Ile Ser Leu Leu Ser Trp Gly Phe Phe Gly
65                  70                  75                  80

Gln Arg Leu Asp Leu Pro Ala Ile Ile Gly Met Met Leu Ile Cys Ala
                85                  90                  95

Gly Val Leu Val Ile Asn Leu Leu Ser Arg Ser Ala Pro His
                100                 105                 110

<210> SEQ ID NO 106
<211> LENGTH: 110
<212> TYPE: PRT
<213> ORGANISM: Escherichia coli

<400> SEQUENCE: 106

Met Asn Pro Tyr Ile Tyr Leu Gly Gly Ala Ile Leu Ala Glu Val Ile
1               5                   10                  15

Gly Thr Thr Leu Met Lys Phe Ser Glu Gly Phe Thr Arg Leu Trp Pro
            20                  25                  30

Ser Val Gly Thr Ile Ile Cys Tyr Cys Ala Ser Phe Trp Leu Leu Ala
        35                  40                  45

-continued

Gln Thr Leu Ala Tyr Ile Pro Thr Gly Ile Ala Tyr Ala Ile Trp Ser
    50                  55                  60

Gly Val Gly Ile Val Leu Ile Ser Leu Leu Ser Trp Gly Phe Phe Gly
65                  70                  75                  80

Gln Arg Leu Asp Leu Pro Ala Ile Ile Gly Met Met Leu Ile Cys Ala
                85                  90                  95

Gly Val Leu Val Ile Asn Leu Leu Ser Arg Ser Ala Pro His
            100                 105                 110

<210> SEQ ID NO 107
<211> LENGTH: 110
<212> TYPE: PRT
<213> ORGANISM: Escherichia coli

<400> SEQUENCE: 107

Met Asn Pro Tyr Ile Tyr Leu Gly Gly Ala Ile Leu Ala Glu Val Ile
1               5                   10                  15

Gly Thr Thr Leu Met Lys Phe Ser Glu Gly Phe Thr Arg Leu Trp Pro
                20                  25                  30

Ser Val Gly Thr Ile Ile Cys Tyr Cys Ala Ser Phe Trp Leu Leu Ala
            35                  40                  45

Gln Thr Leu Ala Tyr Ile Pro Thr Gly Ile Ala Tyr Ala Ile Trp Ser
    50                  55                  60

Gly Val Gly Ile Val Leu Ile Ser Leu Leu Ser Trp Gly Phe Phe Gly
65                  70                  75                  80

Gln Arg Leu Asp Leu Pro Ala Ile Ile Gly Met Met Leu Ile Cys Ala
                85                  90                  95

Gly Val Leu Val Ile Asn Leu Leu Ser Arg Ser Ala Pro His
            100                 105                 110

<210> SEQ ID NO 108
<211> LENGTH: 110
<212> TYPE: PRT
<213> ORGANISM: Escherichia coli

<400> SEQUENCE: 108

Met Asn Pro Tyr Ile Tyr Leu Gly Gly Ala Ile Leu Ala Glu Val Ile
1               5                   10                  15

Gly Thr Thr Leu Met Lys Phe Ser Glu Gly Phe Thr Arg Leu Trp Pro
                20                  25                  30

Ser Val Gly Thr Ile Ile Cys Tyr Cys Ala Ser Phe Trp Leu Leu Ala
            35                  40                  45

Gln Thr Leu Ala Tyr Ile Pro Thr Gly Ile Ala Tyr Ala Ile Trp Ser
    50                  55                  60

Gly Val Gly Ile Val Leu Ile Ser Leu Leu Ser Trp Gly Phe Phe Gly
65                  70                  75                  80

Gln Arg Leu Asp Leu Pro Ala Ile Ile Gly Met Met Leu Ile Cys Ala
                85                  90                  95

Gly Val Leu Val Ile Asn Leu Leu Ser Arg Ser Ala Pro His
            100                 105                 110

<210> SEQ ID NO 109
<211> LENGTH: 110
<212> TYPE: PRT
<213> ORGANISM: Escherichia coli

<400> SEQUENCE: 109

Met Asn Pro Tyr Ile Tyr Leu Gly Gly Ala Ile Leu Ala Glu Val Ile
1               5                   10                  15

Gly Thr Thr Leu Met Lys Phe Ser Glu Gly Phe Thr Arg Leu Trp Pro
            20                  25                  30

Ser Val Gly Thr Ile Ile Cys Tyr Cys Ala Ser Phe Trp Leu Leu Ala
        35                  40                  45

Gln Thr Leu Ala Tyr Ile Pro Thr Gly Ile Ala Tyr Ala Ile Trp Ser
    50                  55                  60

Gly Val Gly Ile Val Leu Ile Ser Leu Leu Ser Trp Gly Phe Phe Gly
65                  70                  75                  80

Gln Arg Leu Asp Leu Pro Ala Ile Ile Gly Met Met Leu Ile Cys Ala
                85                  90                  95

Gly Val Leu Val Ile Asn Leu Leu Ser Arg Ser Ala Pro His
            100                 105                 110

<210> SEQ ID NO 110
<211> LENGTH: 110
<212> TYPE: PRT
<213> ORGANISM: Escherichia coli

<400> SEQUENCE: 110

Met Asn Pro Tyr Ile Tyr Leu Gly Gly Ala Ile Leu Ala Glu Val Ile
1               5                   10                  15

Gly Thr Thr Leu Met Lys Phe Ser Glu Gly Phe Thr Arg Leu Trp Pro
            20                  25                  30

Ser Val Gly Thr Ile Ile Cys Tyr Cys Ala Ser Phe Trp Leu Leu Ala
        35                  40                  45

Gln Thr Leu Ala Tyr Ile Pro Thr Gly Ile Ala Tyr Ala Ile Trp Ser
    50                  55                  60

Gly Val Gly Ile Val Leu Ile Ser Leu Leu Ser Trp Gly Phe Phe Gly
65                  70                  75                  80

Gln Arg Leu Asp Leu Pro Ala Ile Ile Gly Met Met Leu Ile Cys Ala
                85                  90                  95

Gly Val Leu Val Ile Asn Leu Leu Ser Arg Ser Ala Pro His
            100                 105                 110

<210> SEQ ID NO 111
<211> LENGTH: 110
<212> TYPE: PRT
<213> ORGANISM: Escherichia coli

<400> SEQUENCE: 111

Met Asn Pro Tyr Ile Tyr Leu Gly Gly Ala Ile Leu Ala Glu Val Ile
1               5                   10                  15

Gly Thr Thr Leu Met Lys Phe Ser Glu Gly Phe Thr Arg Leu Trp Pro
            20                  25                  30

Ser Val Gly Thr Ile Ile Cys Tyr Cys Ala Ser Phe Trp Leu Leu Ala
        35                  40                  45

Gln Thr Leu Ala Tyr Ile Pro Thr Gly Ile Ala Tyr Ala Ile Trp Ser
    50                  55                  60

Gly Val Gly Ile Val Leu Ile Ser Leu Leu Ser Trp Gly Phe Phe Gly
65                  70                  75                  80

Gln Arg Leu Asp Leu Pro Ala Ile Ile Gly Met Met Leu Ile Cys Ala
                85                  90                  95

Gly Val Leu Val Ile Asn Leu Leu Ser Arg Ser Ala Pro His
              100                 105                 110

<210> SEQ ID NO 112
<211> LENGTH: 110
<212> TYPE: PRT
<213> ORGANISM: Shigella flexneri

<400> SEQUENCE: 112

Met Asn Pro Tyr Ile Tyr Leu Gly Gly Ala Ile Leu Ala Glu Val Ile
1               5                   10                  15

Gly Thr Thr Leu Met Lys Phe Ser Glu Gly Phe Thr Arg Leu Trp Pro
            20                  25                  30

Ser Val Gly Thr Ile Ile Cys Tyr Cys Ala Ser Phe Trp Leu Leu Ala
        35                  40                  45

Gln Thr Leu Ala Tyr Ile Pro Thr Gly Ile Ala Tyr Ala Ile Trp Ser
    50                  55                  60

Gly Val Gly Ile Val Leu Ile Ser Leu Leu Ser Trp Gly Phe Phe Gly
65                  70                  75                  80

Gln Arg Leu Asp Leu Pro Ala Ile Ile Gly Met Met Leu Ile Cys Ala
                85                  90                  95

Gly Val Leu Val Ile Asn Leu Leu Ser Arg Ser Ala Pro His
              100                 105                 110

<210> SEQ ID NO 113
<211> LENGTH: 110
<212> TYPE: PRT
<213> ORGANISM: Escherichia coli

<400> SEQUENCE: 113

Met Asn Pro Tyr Ile Tyr Leu Gly Gly Ala Ile Leu Ala Glu Val Ile
1               5                   10                  15

Gly Thr Thr Leu Met Lys Phe Ser Glu Gly Phe Thr Arg Leu Trp Pro
            20                  25                  30

Ser Val Gly Thr Ile Ile Cys Tyr Cys Ala Ser Phe Trp Leu Leu Ala
        35                  40                  45

Gln Thr Leu Ala Tyr Ile Pro Thr Gly Ile Ala Tyr Ala Ile Trp Ser
    50                  55                  60

Gly Val Gly Ile Val Leu Ile Ser Leu Leu Ser Trp Gly Phe Phe Gly
65                  70                  75                  80

Gln Arg Leu Asp Leu Pro Ala Ile Ile Gly Met Met Leu Ile Cys Ala
                85                  90                  95

Gly Val Leu Val Ile Asn Leu Leu Ser Arg Ser Ala Pro His
              100                 105                 110

<210> SEQ ID NO 114
<211> LENGTH: 110
<212> TYPE: PRT
<213> ORGANISM: Shigella flexneri

<400> SEQUENCE: 114

Met Asn Pro Tyr Ile Tyr Leu Gly Gly Ala Ile Leu Ala Glu Val Ile
1               5                   10                  15

Gly Thr Thr Leu Met Lys Phe Ser Glu Gly Phe Thr Arg Leu Trp Pro
            20                  25                  30

Ser Val Gly Thr Ile Ile Cys Tyr Cys Ala Ser Phe Trp Leu Leu Ala
        35                  40                  45

Gln Thr Leu Ala Tyr Ile Pro Thr Gly Ile Ala Tyr Ala Ile Trp Ser
        50                  55                  60

Gly Val Gly Ile Val Leu Ile Ser Leu Leu Ser Trp Gly Phe Phe Gly
65                  70                  75                  80

Gln Arg Leu Asp Leu Pro Ala Ile Ile Gly Met Met Leu Ile Cys Ala
                85                  90                  95

Gly Val Leu Val Ile Asn Leu Leu Ser Arg Ser Ala Pro His
            100                 105                 110

<210> SEQ ID NO 115
<211> LENGTH: 110
<212> TYPE: PRT
<213> ORGANISM: Shigella flexneri

<400> SEQUENCE: 115

Met Asn Pro Tyr Ile Tyr Leu Gly Gly Ala Ile Leu Ala Glu Val Ile
1               5                   10                  15

Gly Thr Thr Leu Met Lys Phe Ser Glu Gly Phe Thr Arg Leu Trp Pro
            20                  25                  30

Ser Val Gly Thr Ile Ile Cys Tyr Cys Ala Ser Phe Trp Leu Leu Ala
        35                  40                  45

Gln Thr Leu Ala Tyr Ile Pro Thr Gly Ile Ala Tyr Ala Ile Trp Ser
        50                  55                  60

Gly Val Gly Ile Val Leu Ile Ser Leu Leu Ser Trp Gly Phe Phe Gly
65                  70                  75                  80

Gln Arg Leu Asp Leu Pro Ala Ile Ile Gly Met Met Leu Ile Cys Ala
                85                  90                  95

Gly Val Leu Val Ile Asn Leu Leu Ser Arg Ser Ala Pro His
            100                 105                 110

<210> SEQ ID NO 116
<211> LENGTH: 110
<212> TYPE: PRT
<213> ORGANISM: Escherichia coli

<400> SEQUENCE: 116

Met Asn Pro Tyr Ile Tyr Leu Gly Gly Ala Ile Leu Ala Glu Val Ile
1               5                   10                  15

Gly Thr Thr Leu Met Lys Phe Ser Glu Gly Phe Thr Arg Leu Trp Pro
            20                  25                  30

Ser Val Gly Thr Ile Ile Cys Tyr Cys Ala Ser Phe Trp Leu Leu Ala
        35                  40                  45

Gln Thr Leu Ala Tyr Ile Pro Thr Gly Ile Ala Tyr Ala Ile Trp Ser
        50                  55                  60

Gly Val Gly Ile Val Leu Ile Ser Leu Leu Ser Trp Gly Phe Phe Gly
65                  70                  75                  80

Gln Arg Leu Asp Leu Pro Ala Ile Ile Gly Met Met Leu Ile Cys Ala
                85                  90                  95

Gly Val Leu Val Ile Asn Leu Leu Ser Arg Ser Ala Pro His
            100                 105                 110

<210> SEQ ID NO 117
<211> LENGTH: 110
<212> TYPE: PRT
<213> ORGANISM: Shigella sonnei

<400> SEQUENCE: 117

Met Asn Pro Tyr Ile Tyr Leu Gly Gly Ala Ile Leu Ala Glu Val Ile
1               5                   10                  15

Gly Thr Thr Leu Met Lys Phe Ser Glu Gly Phe Thr Arg Leu Trp Pro
            20                  25                  30

Ser Val Gly Thr Ile Ile Cys Tyr Cys Ala Ser Phe Trp Leu Leu Ala
        35                  40                  45

Gln Thr Leu Ala Tyr Ile Pro Thr Gly Ile Ala Tyr Ala Ile Trp Ser
    50                  55                  60

Gly Val Gly Ile Val Leu Ile Ser Leu Ser Trp Gly Phe Phe Gly
65                  70                  75                  80

Gln Arg Leu Asp Leu Pro Ala Ile Ile Gly Met Met Leu Ile Cys Ala
                85                  90                  95

Gly Val Leu Val Ile Asn Leu Leu Ser Arg Ser Ala Pro His
            100                 105                 110

<210> SEQ ID NO 118
<211> LENGTH: 110
<212> TYPE: PRT
<213> ORGANISM: Escherichia coli

<400> SEQUENCE: 118

Met Asn Pro Tyr Ile Tyr Leu Gly Gly Ala Ile Leu Ala Glu Val Ile
1               5                   10                  15

Gly Thr Thr Leu Met Lys Phe Ser Glu Gly Phe Thr Arg Leu Trp Pro
            20                  25                  30

Ser Val Gly Thr Ile Ile Cys Tyr Cys Ala Ser Phe Trp Leu Leu Ala
        35                  40                  45

Gln Thr Leu Ala Tyr Ile Pro Thr Gly Ile Ala Tyr Ala Ile Trp Ser
    50                  55                  60

Gly Val Gly Ile Val Leu Ile Ser Leu Ser Trp Gly Phe Phe Gly
65                  70                  75                  80

Gln Arg Leu Asp Leu Pro Ala Ile Ile Gly Met Met Leu Ile Cys Ala
                85                  90                  95

Gly Val Leu Val Ile Asn Leu Leu Ser Arg Ser Ala Pro His
            100                 105                 110

<210> SEQ ID NO 119
<211> LENGTH: 110
<212> TYPE: PRT
<213> ORGANISM: Escherichia coli

<400> SEQUENCE: 119

Met Asn Pro Tyr Ile Tyr Leu Gly Gly Ala Ile Leu Ala Glu Val Ile
1               5                   10                  15

Gly Thr Thr Leu Met Lys Phe Ser Glu Gly Phe Thr Arg Leu Trp Pro
            20                  25                  30

Ser Val Gly Thr Ile Ile Cys Tyr Cys Ala Ser Phe Trp Leu Leu Ala
        35                  40                  45

Gln Thr Leu Ala Tyr Ile Pro Thr Gly Ile Ala Tyr Ala Ile Trp Ser
    50                  55                  60

Gly Val Gly Ile Val Leu Ile Ser Leu Ser Trp Gly Phe Phe Gly
65                  70                  75                  80

Gln Arg Leu Asp Leu Pro Ala Ile Ile Gly Met Met Leu Ile Cys Ala
                85                  90                  95

Gly Val Leu Val Ile Asn Leu Leu Ser Arg Ser Ala Pro His
                100                 105                 110

<210> SEQ ID NO 120
<211> LENGTH: 110
<212> TYPE: PRT
<213> ORGANISM: Escherichia coli

<400> SEQUENCE: 120

Met Asn Pro Tyr Ile Tyr Leu Gly Gly Ala Ile Leu Ala Glu Val Ile
1               5                   10                  15

Gly Thr Thr Leu Met Lys Phe Ser Glu Gly Phe Thr Arg Leu Trp Pro
            20                  25                  30

Ser Val Gly Thr Ile Ile Cys Tyr Cys Ala Ser Phe Trp Leu Leu Ala
        35                  40                  45

Gln Thr Leu Ala Tyr Ile Pro Thr Gly Ile Ala Tyr Ala Ile Trp Ser
    50                  55                  60

Gly Val Gly Ile Val Leu Ile Ser Leu Leu Ser Trp Gly Phe Phe Gly
65                  70                  75                  80

Gln Arg Leu Asp Leu Pro Ala Ile Ile Gly Met Met Leu Ile Cys Ala
                85                  90                  95

Gly Val Leu Val Ile Asn Leu Leu Ser Arg Ser Ala Pro His
                100                 105                 110

<210> SEQ ID NO 121
<211> LENGTH: 110
<212> TYPE: PRT
<213> ORGANISM: Escherichia coli

<400> SEQUENCE: 121

Met Asn Pro Tyr Ile Tyr Leu Gly Gly Ala Ile Leu Ala Glu Val Ile
1               5                   10                  15

Gly Thr Thr Leu Met Lys Phe Ser Glu Gly Phe Thr Arg Leu Trp Pro
            20                  25                  30

Ser Val Gly Thr Ile Ile Cys Tyr Cys Ala Ser Phe Trp Leu Leu Ala
        35                  40                  45

Gln Thr Leu Ala Tyr Ile Pro Thr Gly Ile Ala Tyr Ala Ile Trp Ser
    50                  55                  60

Gly Val Gly Ile Val Leu Ile Ser Leu Leu Ser Trp Gly Phe Phe Gly
65                  70                  75                  80

Gln Arg Leu Asp Leu Pro Ala Ile Ile Gly Met Met Leu Ile Cys Ala
                85                  90                  95

Gly Val Leu Val Ile Asn Leu Leu Ser Arg Ser Ala Pro His
                100                 105                 110

<210> SEQ ID NO 122
<211> LENGTH: 110
<212> TYPE: PRT
<213> ORGANISM: Escherichia coli

<400> SEQUENCE: 122

Met Asn Pro Tyr Ile Tyr Leu Gly Gly Ala Ile Leu Ala Glu Val Ile
1               5                   10                  15

Gly Thr Thr Leu Met Lys Phe Ser Glu Gly Phe Thr Arg Leu Trp Pro
            20                  25                  30

Ser Val Gly Thr Ile Ile Cys Tyr Cys Ala Ser Phe Trp Leu Leu Ala
        35                  40                  45

```
Gln Thr Leu Ala Tyr Ile Pro Thr Gly Ile Ala Tyr Ala Ile Trp Ser
    50                  55                  60

Gly Val Gly Ile Val Leu Ile Ser Leu Leu Ser Trp Gly Phe Phe Gly
65                  70                  75                  80

Gln Arg Leu Asp Leu Pro Ala Ile Ile Gly Met Met Leu Ile Cys Ala
                85                  90                  95

Gly Val Leu Val Ile Asn Leu Leu Ser Arg Ser Ala Pro His
            100                 105                 110

<210> SEQ ID NO 123
<211> LENGTH: 110
<212> TYPE: PRT
<213> ORGANISM: Escherichia coli

<400> SEQUENCE: 123

Met Asn Pro Tyr Ile Tyr Leu Gly Gly Ala Ile Leu Ala Glu Val Ile
1               5                   10                  15

Gly Thr Thr Leu Met Lys Phe Ser Glu Gly Phe Thr Arg Leu Trp Pro
                20                  25                  30

Ser Val Gly Thr Ile Ile Cys Tyr Cys Ala Ser Phe Trp Leu Leu Ala
            35                  40                  45

Gln Thr Leu Ala Tyr Ile Pro Thr Gly Ile Ala Tyr Ala Ile Trp Ser
    50                  55                  60

Gly Val Gly Ile Val Leu Ile Ser Leu Leu Ser Trp Gly Phe Phe Gly
65                  70                  75                  80

Gln Arg Leu Asp Leu Pro Ala Ile Ile Gly Met Met Leu Ile Cys Ala
                85                  90                  95

Gly Val Leu Val Ile Asn Leu Leu Ser Arg Ser Ala Pro His
            100                 105                 110

<210> SEQ ID NO 124
<211> LENGTH: 110
<212> TYPE: PRT
<213> ORGANISM: Shigella boydii

<400> SEQUENCE: 124

Met Asn Pro Tyr Ile Tyr Leu Gly Gly Ala Ile Leu Ala Glu Val Ile
1               5                   10                  15

Gly Thr Thr Leu Met Lys Phe Ser Glu Gly Phe Thr Arg Leu Trp Pro
                20                  25                  30

Ser Val Gly Thr Ile Ile Cys Tyr Cys Ala Ser Phe Trp Leu Leu Ala
            35                  40                  45

Gln Thr Leu Ala Tyr Ile Pro Thr Gly Ile Ala Tyr Ala Ile Trp Ser
    50                  55                  60

Gly Val Gly Ile Val Leu Ile Ser Leu Leu Ser Trp Gly Phe Phe Gly
65                  70                  75                  80

Gln Arg Leu Asp Leu Pro Ala Ile Ile Gly Met Met Leu Ile Cys Ala
                85                  90                  95

Gly Val Leu Val Ile Asn Leu Leu Ser Arg Ser Ala Pro His
            100                 105                 110

<210> SEQ ID NO 125
<211> LENGTH: 110
<212> TYPE: PRT
<213> ORGANISM: Shigella flexneri
```

<400> SEQUENCE: 125

Met Asn Pro Tyr Ile Tyr Leu Gly Gly Ala Ile Leu Ala Glu Val Ile
1               5                   10                  15

Gly Thr Thr Leu Met Lys Phe Ser Glu Gly Phe Thr Arg Leu Trp Pro
                20                  25                  30

Ser Val Gly Thr Ile Ile Cys Tyr Cys Ala Ser Phe Trp Leu Leu Ala
            35                  40                  45

Gln Thr Leu Ala Tyr Ile Pro Thr Gly Ile Ala Tyr Ala Ile Trp Ser
    50                  55                  60

Gly Val Gly Ile Val Leu Ile Ser Leu Ser Trp Gly Phe Phe Gly
65              70                  75                  80

Gln Arg Leu Asp Leu Pro Ala Ile Ile Gly Met Met Leu Ile Cys Ala
                85                  90                  95

Gly Val Leu Val Ile Asn Leu Leu Ser Arg Ser Ala Pro His
                100                 105                 110

<210> SEQ ID NO 126
<211> LENGTH: 117
<212> TYPE: PRT
<213> ORGANISM: Escherichia coli

<400> SEQUENCE: 126

Met Asn Arg Lys Glu Tyr Ala Met Asn Pro Tyr Ile Tyr Leu Gly Gly
1               5                   10                  15

Ala Ile Leu Ala Glu Val Ile Gly Thr Thr Leu Met Lys Phe Ser Glu
                20                  25                  30

Gly Phe Thr Arg Leu Trp Pro Ser Val Gly Thr Ile Ile Cys Tyr Cys
            35                  40                  45

Ala Ser Phe Trp Leu Leu Ala Gln Thr Leu Ala Tyr Ile Pro Thr Gly
    50                  55                  60

Ile Ala Tyr Ala Ile Trp Ser Gly Val Gly Ile Val Leu Ile Ser Leu
65              70                  75                  80

Leu Ser Trp Gly Phe Phe Gly Gln Arg Leu Asp Leu Pro Ala Ile Ile
                85                  90                  95

Gly Met Met Leu Ile Cys Ala Gly Val Leu Val Ile Asn Leu Leu Ser
                100                 105                 110

Arg Ser Ala Pro His
        115

<210> SEQ ID NO 127
<211> LENGTH: 117
<212> TYPE: PRT
<213> ORGANISM: Escherichia coli

<400> SEQUENCE: 127

Met Asn Arg Lys Glu Tyr Ala Met Asn Pro Tyr Ile Tyr Leu Gly Gly
1               5                   10                  15

Ala Ile Leu Ala Glu Val Ile Gly Thr Thr Leu Met Lys Phe Ser Glu
                20                  25                  30

Gly Phe Thr Arg Leu Trp Pro Ser Val Gly Thr Ile Ile Cys Tyr Cys
            35                  40                  45

Ala Ser Phe Trp Leu Leu Ala Gln Thr Leu Ala Tyr Ile Pro Thr Gly
    50                  55                  60

Ile Ala Tyr Ala Ile Trp Ser Gly Val Gly Ile Val Leu Ile Ser Leu
65              70                  75                  80

Leu Ser Trp Gly Phe Phe Gly Gln Arg Leu Asp Leu Pro Ala Ile Ile
                85                  90                  95

Gly Met Met Leu Ile Cys Ala Gly Val Leu Val Ile Asn Leu Leu Ser
            100                 105                 110

Arg Ser Ala Pro His
        115

<210> SEQ ID NO 128
<211> LENGTH: 117
<212> TYPE: PRT
<213> ORGANISM: Escherichia coli

<400> SEQUENCE: 128

Met Asn Arg Lys Glu Tyr Ala Met Asn Pro Tyr Ile Tyr Leu Gly Gly
1               5                   10                  15

Ala Ile Leu Ala Glu Val Ile Gly Thr Thr Leu Met Lys Phe Ser Glu
            20                  25                  30

Gly Phe Thr Arg Leu Trp Pro Ser Val Gly Thr Ile Ile Cys Tyr Cys
        35                  40                  45

Ala Ser Phe Trp Leu Leu Ala Gln Thr Leu Ala Tyr Ile Pro Thr Gly
    50                  55                  60

Ile Ala Tyr Ala Ile Trp Ser Gly Val Gly Ile Val Leu Ile Ser Leu
65                  70                  75                  80

Leu Ser Trp Gly Phe Phe Gly Gln Arg Leu Asp Leu Pro Ala Ile Ile
                85                  90                  95

Gly Met Met Leu Ile Cys Ala Gly Val Leu Val Ile Asn Leu Leu Ser
            100                 105                 110

Arg Ser Ala Pro His
        115

<210> SEQ ID NO 129
<211> LENGTH: 117
<212> TYPE: PRT
<213> ORGANISM: Escherichia coli

<400> SEQUENCE: 129

Met Asn Arg Lys Glu Tyr Ala Met Asn Pro Tyr Ile Tyr Leu Gly Gly
1               5                   10                  15

Ala Ile Leu Ala Glu Val Ile Gly Thr Thr Leu Met Lys Phe Ser Glu
            20                  25                  30

Gly Phe Thr Arg Leu Trp Pro Ser Val Gly Thr Ile Ile Cys Tyr Cys
        35                  40                  45

Ala Ser Phe Trp Leu Leu Ala Gln Thr Leu Ala Tyr Ile Pro Thr Gly
    50                  55                  60

Ile Ala Tyr Ala Ile Trp Ser Gly Val Gly Ile Val Leu Ile Ser Leu
65                  70                  75                  80

Leu Ser Trp Gly Phe Phe Gly Gln Arg Leu Asp Leu Pro Ala Ile Ile
                85                  90                  95

Gly Met Met Leu Ile Cys Ala Gly Val Leu Val Ile Asn Leu Leu Ser
            100                 105                 110

Arg Ser Ala Pro His
        115

<210> SEQ ID NO 130
<211> LENGTH: 117
<212> TYPE: PRT
<213> ORGANISM: Escherichia coli -continued

<400> SEQUENCE: 130

Met Asn Arg Lys Glu Tyr Ala Met Asn Pro Tyr Ile Tyr Leu Gly Gly
1               5                   10                  15

Ala Ile Leu Ala Glu Val Ile Gly Thr Thr Leu Met Lys Phe Ser Glu
            20                  25                  30

Gly Phe Thr Arg Leu Trp Pro Ser Val Gly Thr Ile Ile Cys Tyr Cys
        35                  40                  45

Ala Ser Phe Trp Leu Leu Ala Gln Thr Leu Ala Tyr Ile Pro Thr Gly
    50                  55                  60

Ile Ala Tyr Ala Ile Trp Ser Gly Val Gly Ile Val Leu Ile Ser Leu
65                  70                  75                  80

Leu Ser Trp Gly Phe Phe Gly Gln Arg Leu Asp Leu Pro Ala Ile Ile
                85                  90                  95

Gly Met Met Leu Ile Cys Ala Gly Val Leu Val Ile Asn Leu Leu Ser
            100                 105                 110

Arg Ser Ala Pro His
        115

<210> SEQ ID NO 131
<211> LENGTH: 117
<212> TYPE: PRT
<213> ORGANISM: Escherichia coli

<400> SEQUENCE: 131

Met Asn Arg Lys Glu Tyr Ala Met Asn Pro Tyr Ile Tyr Leu Gly Gly
1               5                   10                  15

Ala Ile Leu Ala Glu Val Ile Gly Thr Thr Leu Met Lys Phe Ser Glu
            20                  25                  30

Gly Phe Thr Arg Leu Trp Pro Ser Val Gly Thr Ile Ile Cys Tyr Cys
        35                  40                  45

Ala Ser Phe Trp Leu Leu Ala Gln Thr Leu Ala Tyr Ile Pro Thr Gly
    50                  55                  60

Ile Ala Tyr Ala Ile Trp Ser Gly Val Gly Ile Val Leu Ile Ser Leu
65                  70                  75                  80

Leu Ser Trp Gly Phe Phe Gly Gln Arg Leu Asp Leu Pro Ala Ile Ile
                85                  90                  95

Gly Met Met Leu Ile Cys Ala Gly Val Leu Val Ile Asn Leu Leu Ser
            100                 105                 110

Arg Ser Ala Pro His
        115

<210> SEQ ID NO 132
<211> LENGTH: 117
<212> TYPE: PRT
<213> ORGANISM: Escherichia coli

<400> SEQUENCE: 132

Met Asn Arg Lys Glu Tyr Ala Met Asn Pro Tyr Ile Tyr Leu Gly Gly
1               5                   10                  15

Ala Ile Leu Ala Glu Val Ile Gly Thr Thr Leu Met Lys Phe Ser Glu
            20                  25                  30

Gly Phe Thr Arg Leu Trp Pro Ser Val Gly Thr Ile Ile Cys Tyr Cys
        35                  40                  45

Ala Ser Phe Trp Leu Leu Ala Gln Thr Leu Ala Tyr Ile Pro Thr Gly
    50                  55                  60

Ile Ala Tyr Ala Ile Trp Ser Gly Val Gly Ile Val Leu Ile Ser Leu
65                  70                  75                  80

Leu Ser Trp Gly Phe Phe Gly Gln Arg Leu Asp Leu Pro Ala Ile Ile
                85                  90                  95

Gly Met Met Leu Ile Cys Ala Gly Val Leu Val Ile Asn Leu Leu Ser
            100                 105                 110

Arg Ser Ala Pro His
        115

<210> SEQ ID NO 133
<211> LENGTH: 117
<212> TYPE: PRT
<213> ORGANISM: Escherichia coli

<400> SEQUENCE: 133

Met Asn Arg Lys Glu Tyr Ala Met Asn Pro Tyr Ile Tyr Leu Gly Gly
1               5                   10                  15

Ala Ile Leu Ala Glu Val Ile Gly Thr Thr Leu Met Lys Phe Ser Glu
                20                  25                  30

Gly Phe Thr Arg Leu Trp Pro Ser Val Gly Thr Ile Ile Cys Tyr Cys
            35                  40                  45

Ala Ser Phe Trp Leu Leu Ala Gln Thr Leu Ala Tyr Ile Pro Thr Gly
        50                  55                  60

Ile Ala Tyr Ala Ile Trp Ser Gly Val Gly Ile Val Leu Ile Ser Leu
65                  70                  75                  80

Leu Ser Trp Gly Phe Phe Gly Gln Arg Leu Asp Leu Pro Ala Ile Ile
                85                  90                  95

Gly Met Met Leu Ile Cys Ala Gly Val Leu Val Ile Asn Leu Leu Ser
            100                 105                 110

Arg Ser Ala Pro His
        115

<210> SEQ ID NO 134
<211> LENGTH: 117
<212> TYPE: PRT
<213> ORGANISM: Escherichia coli

<400> SEQUENCE: 134

Met Asn Arg Lys Glu Tyr Ala Met Asn Pro Tyr Ile Tyr Leu Gly Gly
1               5                   10                  15

Ala Ile Leu Ala Glu Val Ile Gly Thr Thr Leu Met Lys Phe Ser Glu
                20                  25                  30

Gly Phe Thr Arg Leu Trp Pro Ser Val Gly Thr Ile Ile Cys Tyr Cys
            35                  40                  45

Ala Ser Phe Trp Leu Leu Ala Gln Thr Leu Ala Tyr Ile Pro Thr Gly
        50                  55                  60

Ile Ala Tyr Ala Ile Trp Ser Gly Val Gly Ile Val Leu Ile Ser Leu
65                  70                  75                  80

Leu Ser Trp Gly Phe Phe Gly Gln Arg Leu Asp Leu Pro Ala Ile Ile
                85                  90                  95

Gly Met Met Leu Ile Cys Ala Gly Val Leu Val Ile Asn Leu Leu Ser
            100                 105                 110

Arg Ser Ala Pro His
        115

<210> SEQ ID NO 135

<211> LENGTH: 110
<212> TYPE: PRT
<213> ORGANISM: Escherichia sp.

<400> SEQUENCE: 135

Met Asn Pro Tyr Ile Tyr Leu Gly Gly Ala Ile Leu Ala Glu Val Ile
1               5                   10                  15
Gly Thr Thr Leu Met Lys Phe Ser Glu Gly Phe Thr Arg Leu Trp Pro
            20                  25                  30
Ser Val Gly Thr Ile Ile Cys Tyr Cys Ala Ser Phe Trp Leu Leu Ala
        35                  40                  45
Gln Thr Leu Ala Tyr Ile Pro Thr Gly Ile Ala Tyr Ala Ile Trp Ser
    50                  55                  60
Gly Val Gly Ile Val Leu Ile Ser Leu Leu Ser Trp Gly Leu Phe Gly
65                  70                  75                  80
Gln Arg Leu Asp Leu Pro Ala Ile Ile Gly Met Met Leu Ile Cys Ala
                85                  90                  95
Gly Val Leu Val Ile Asn Leu Leu Ser Arg Ser Thr Pro His
            100                 105                 110

<210> SEQ ID NO 136
<211> LENGTH: 110
<212> TYPE: PRT
<213> ORGANISM: Escherichia fergusonii

<400> SEQUENCE: 136

Met Asn Pro Tyr Ile Tyr Leu Gly Gly Ala Ile Leu Ala Glu Val Ile
1               5                   10                  15
Gly Thr Thr Leu Met Lys Phe Ser Glu Gly Phe Thr Arg Leu Trp Pro
            20                  25                  30
Ser Val Gly Thr Ile Ile Cys Tyr Cys Ala Ser Phe Trp Leu Leu Ala
        35                  40                  45
Gln Thr Leu Ala Tyr Ile Pro Thr Gly Ile Ala Tyr Ala Ile Trp Ser
    50                  55                  60
Gly Val Gly Ile Val Leu Ile Ser Leu Leu Ser Trp Gly Leu Phe Gly
65                  70                  75                  80
Gln Arg Leu Asp Leu Pro Ala Ile Ile Gly Met Met Leu Ile Cys Ala
                85                  90                  95
Gly Val Leu Val Ile Asn Leu Leu Ser Arg Ser Thr Pro His
            100                 105                 110

<210> SEQ ID NO 137
<211> LENGTH: 110
<212> TYPE: PRT
<213> ORGANISM: Escherichia coli

<400> SEQUENCE: 137

Met Asn Pro Tyr Ile Tyr Leu Gly Gly Ala Ile Leu Ala Glu Val Ile
1               5                   10                  15
Gly Thr Thr Leu Met Lys Phe Ser Glu Gly Phe Thr Arg Leu Trp Pro
            20                  25                  30
Ser Val Gly Thr Ile Ile Cys Tyr Cys Ala Ser Phe Trp Leu Leu Ala
        35                  40                  45
Gln Thr Leu Ala Tyr Ile Pro Thr Gly Ile Ala Tyr Ala Ile Trp Ser
    50                  55                  60
Gly Val Gly Ile Val Leu Ile Ser Leu Leu Ser Trp Gly Leu Phe Gly
65                  70                  75                  80

Gln Arg Leu Asp Leu Pro Ala Ile Ile Gly Met Met Leu Ile Cys Ala
                85                  90                  95

Gly Val Leu Val Ile Asn Leu Leu Ser Arg Ser Thr Pro His
            100                 105                 110

<210> SEQ ID NO 138
<211> LENGTH: 110
<212> TYPE: PRT
<213> ORGANISM: Klebsiella oxytoca

<400> SEQUENCE: 138

Met Asn Pro Tyr Ile Tyr Leu Gly Gly Ala Ile Leu Ala Glu Val Ile
1               5                   10                  15

Gly Thr Thr Leu Met Lys Phe Ser Glu Gly Phe Thr Arg Leu Trp Pro
            20                  25                  30

Ser Val Gly Thr Ile Ile Cys Tyr Cys Ala Ser Phe Trp Leu Leu Ala
        35                  40                  45

Gln Thr Leu Ala Tyr Ile Pro Thr Gly Ile Ala Tyr Ala Ile Trp Ser
    50                  55                  60

Gly Val Gly Ile Val Leu Ile Ser Leu Leu Ser Trp Gly Leu Phe Gly
65                  70                  75                  80

Gln Arg Leu Asp Leu Pro Ala Ile Ile Gly Met Met Leu Ile Cys Ala
                85                  90                  95

Gly Val Leu Val Ile Asn Leu Leu Ser Arg Ser Thr Pro His
            100                 105                 110

<210> SEQ ID NO 139
<211> LENGTH: 110
<212> TYPE: PRT
<213> ORGANISM: Escherichia coli

<400> SEQUENCE: 139

Met Asn Pro Tyr Ile Tyr Leu Gly Gly Ala Ile Leu Ala Glu Val Ile
1               5                   10                  15

Gly Thr Thr Leu Met Lys Phe Ser Glu Gly Phe Thr Arg Leu Trp Pro
            20                  25                  30

Ser Val Gly Thr Ile Ile Cys Tyr Cys Ala Ser Phe Trp Leu Leu Ala
        35                  40                  45

Gln Thr Leu Ala Tyr Ile Pro Thr Gly Ile Ala Tyr Ala Ile Trp Ser
    50                  55                  60

Gly Val Gly Ile Val Leu Ile Ser Leu Leu Ser Trp Gly Leu Phe Gly
65                  70                  75                  80

Gln Arg Leu Asp Leu Pro Ala Ile Ile Gly Met Met Leu Ile Cys Ala
                85                  90                  95

Gly Val Leu Val Ile Asn Leu Leu Ser Arg Ser Thr Pro His
            100                 105                 110

<210> SEQ ID NO 140
<211> LENGTH: 110
<212> TYPE: PRT
<213> ORGANISM: Escherichia coli

<400> SEQUENCE: 140

Met Asn Pro Tyr Ile Tyr Leu Gly Gly Ala Ile Leu Ala Glu Val Ile
1               5                   10                  15

Gly Thr Thr Leu Met Lys Phe Ser Glu Gly Phe Thr Arg Leu Trp Pro
            20                  25                  30

```
Ser Val Gly Thr Ile Ile Cys Tyr Cys Ala Ser Phe Trp Leu Leu Ala
        35                  40                  45

Gln Thr Leu Ala Tyr Ile Pro Thr Gly Ile Ala Tyr Ala Ile Trp Ser
    50                  55                  60

Gly Val Gly Ile Val Leu Ile Ser Leu Leu Ser Trp Gly Leu Phe Gly
65                  70                  75                  80

Gln Arg Leu Asp Leu Pro Ala Ile Ile Gly Met Met Leu Ile Cys Ala
                85                  90                  95

Gly Val Leu Val Ile Asn Leu Leu Ser Arg Ser Thr Pro His
            100                 105                 110

<210> SEQ ID NO 141
<211> LENGTH: 110
<212> TYPE: PRT
<213> ORGANISM: Escherichia coli

<400> SEQUENCE: 141

Met Asn Pro Tyr Ile Tyr Leu Gly Gly Ala Ile Leu Ala Glu Val Ile
1               5                   10                  15

Gly Thr Thr Leu Met Lys Phe Ser Glu Gly Phe Thr Arg Leu Trp Pro
            20                  25                  30

Ser Val Gly Thr Ile Ile Cys Tyr Cys Ala Ser Phe Trp Leu Leu Ala
        35                  40                  45

Gln Thr Leu Ala Tyr Ile Pro Thr Gly Ile Ala Tyr Ala Ile Trp Ser
    50                  55                  60

Gly Val Gly Ile Val Leu Ile Ser Leu Leu Ser Trp Gly Leu Phe Gly
65                  70                  75                  80

Gln Arg Leu Asp Leu Pro Ala Ile Ile Gly Met Met Leu Ile Cys Ala
                85                  90                  95

Gly Val Leu Val Ile Asn Leu Leu Ser Arg Ser Thr Pro His
            100                 105                 110

<210> SEQ ID NO 142
<211> LENGTH: 110
<212> TYPE: PRT
<213> ORGANISM: Escherichia coli

<400> SEQUENCE: 142

Met Asn Pro Tyr Ile Tyr Leu Gly Gly Ala Ile Leu Ala Glu Val Ile
1               5                   10                  15

Gly Thr Thr Leu Met Lys Phe Ser Glu Gly Phe Thr Arg Leu Trp Pro
            20                  25                  30

Ser Val Gly Thr Ile Ile Cys Tyr Cys Ala Ser Phe Trp Leu Leu Ala
        35                  40                  45

Gln Thr Leu Ala Tyr Ile Pro Thr Gly Ile Ala Tyr Ala Ile Trp Ser
    50                  55                  60

Gly Val Gly Ile Val Leu Ile Ser Leu Leu Ser Trp Gly Leu Phe Gly
65                  70                  75                  80

Gln Arg Leu Asp Leu Pro Ala Ile Ile Gly Met Met Leu Ile Cys Ala
                85                  90                  95

Gly Val Leu Val Ile Asn Leu Leu Ser Arg Ser Thr Pro His
            100                 105                 110

<210> SEQ ID NO 143
<211> LENGTH: 110
<212> TYPE: PRT
<213> ORGANISM: Escherichia coli
```

<400> SEQUENCE: 143

Met Asn Pro Tyr Ile Tyr Leu Gly Gly Ala Ile Leu Ala Glu Val Ile
1               5                   10                  15

Gly Thr Thr Leu Met Lys Phe Ser Glu Gly Phe Thr Arg Leu Trp Pro
            20                  25                  30

Ser Val Gly Thr Ile Ile Cys Tyr Cys Ala Ser Phe Trp Leu Leu Ala
        35                  40                  45

Gln Thr Leu Ala Tyr Ile Pro Thr Gly Ile Ala Tyr Ala Ile Trp Ser
    50                  55                  60

Gly Val Gly Ile Val Leu Ile Ser Leu Leu Ser Trp Gly Leu Phe Gly
65                  70                  75                  80

Gln Arg Leu Asp Leu Pro Ala Ile Ile Gly Met Met Leu Ile Cys Ala
                85                  90                  95

Gly Val Leu Val Ile Asn Leu Leu Ser Arg Ser Thr Pro His
            100                 105                 110

<210> SEQ ID NO 144
<211> LENGTH: 110
<212> TYPE: PRT
<213> ORGANISM: Escherichia coli

<400> SEQUENCE: 144

Met Asn Pro Tyr Ile Tyr Leu Gly Gly Ala Ile Leu Ala Glu Val Ile
1               5                   10                  15

Gly Thr Thr Leu Met Lys Phe Ser Glu Gly Phe Thr Arg Leu Trp Pro
            20                  25                  30

Ser Val Gly Thr Ile Ile Cys Tyr Cys Ala Ser Phe Trp Leu Leu Ala
        35                  40                  45

Gln Thr Leu Ala Tyr Ile Pro Thr Gly Ile Ala Tyr Ala Ile Trp Ser
    50                  55                  60

Gly Val Gly Ile Val Leu Ile Ser Leu Leu Ser Trp Gly Leu Phe Gly
65                  70                  75                  80

Gln Arg Leu Asp Leu Pro Ala Ile Ile Gly Met Met Leu Ile Cys Ala
                85                  90                  95

Gly Val Leu Val Ile Asn Leu Leu Ser Arg Ser Thr Pro His
            100                 105                 110

<210> SEQ ID NO 145
<211> LENGTH: 110
<212> TYPE: PRT
<213> ORGANISM: Escherichia coli

<400> SEQUENCE: 145

Met Asn Pro Tyr Ile Tyr Leu Gly Gly Ala Ile Leu Ala Glu Val Ile
1               5                   10                  15

Gly Thr Thr Leu Met Lys Phe Ser Glu Gly Phe Thr Arg Leu Trp Pro
            20                  25                  30

Ser Val Gly Thr Ile Ile Cys Tyr Cys Ala Ser Phe Trp Leu Leu Ala
        35                  40                  45

Gln Thr Leu Ala Tyr Ile Pro Thr Gly Ile Ala Tyr Ala Ile Trp Ser
    50                  55                  60

Gly Val Gly Ile Val Leu Ile Ser Leu Leu Ser Trp Gly Leu Phe Gly
65                  70                  75                  80

Gln Arg Leu Asp Leu Pro Ala Ile Ile Gly Met Met Leu Ile Cys Ala
                85                  90                  95

```
Gly Val Leu Val Ile Asn Leu Leu Ser Arg Ser Thr Pro His
            100                 105                 110
```

<210> SEQ ID NO 146
<211> LENGTH: 110
<212> TYPE: PRT
<213> ORGANISM: Escherichia coli

<400> SEQUENCE: 146

```
Met Asn Pro Tyr Ile Tyr Leu Gly Gly Ala Ile Leu Ala Glu Val Ile
1               5                   10                  15

Gly Thr Thr Leu Met Lys Phe Ser Glu Gly Phe Thr Arg Leu Trp Pro
                20                  25                  30

Ser Val Gly Thr Ile Ile Cys Tyr Cys Ala Ser Phe Trp Leu Leu Ala
            35                  40                  45

Gln Thr Leu Ala Tyr Ile Pro Thr Gly Ile Ala Tyr Ala Ile Trp Ser
        50                  55                  60

Gly Val Gly Ile Val Leu Ile Ser Leu Leu Ser Trp Gly Leu Phe Gly
65                  70                  75                  80

Gln Arg Leu Asp Leu Pro Ala Ile Ile Gly Met Met Leu Ile Cys Ala
                85                  90                  95

Gly Val Leu Val Ile Asn Leu Leu Ser Arg Ser Thr Pro His
            100                 105                 110
```

<210> SEQ ID NO 147
<211> LENGTH: 110
<212> TYPE: PRT
<213> ORGANISM: Escherichia sp.

<400> SEQUENCE: 147

```
Met Asn Pro Tyr Ile Tyr Leu Gly Gly Ala Ile Leu Ala Glu Val Ile
1               5                   10                  15

Gly Thr Thr Leu Met Lys Tyr Ser Glu Gly Phe Thr Arg Leu Trp Pro
                20                  25                  30

Ser Val Gly Thr Ile Ile Cys Tyr Cys Ala Ser Phe Trp Leu Leu Ala
            35                  40                  45

Gln Thr Leu Ala Tyr Ile Pro Thr Gly Ile Ala Tyr Ala Ile Trp Ser
        50                  55                  60

Gly Val Gly Ile Val Leu Ile Ser Leu Leu Ser Trp Gly Phe Phe Gly
65                  70                  75                  80

Gln Arg Leu Asp Leu Pro Ala Ile Ile Gly Met Met Leu Ile Cys Ala
                85                  90                  95

Gly Val Leu Val Ile Asn Leu Leu Ser Arg Ser Ala Pro His
            100                 105                 110
```

<210> SEQ ID NO 148
<211> LENGTH: 110
<212> TYPE: PRT
<213> ORGANISM: Escherichia coli

<400> SEQUENCE: 148

```
Met Asn Pro Tyr Ile Tyr Leu Gly Gly Ala Ile Leu Ala Glu Val Ile
1               5                   10                  15

Gly Thr Thr Leu Met Lys Phe Ser Glu Gly Phe Thr Arg Leu Trp Pro
                20                  25                  30

Ser Val Gly Thr Ile Ile Cys Tyr Cys Ala Ser Phe Trp Leu Leu Ala
            35                  40                  45
```

Gln Thr Leu Ala Tyr Ile Pro Thr Gly Ile Ala Tyr Ala Ile Trp Ser
    50                  55                  60

Gly Val Gly Ile Val Leu Ile Ser Leu Leu Ser Trp Gly Phe Phe Gly
65                  70                  75                  80

Gln Arg Leu Asp Leu Pro Ala Ile Ile Gly Met Met Leu Ile Cys Ser
                85                  90                  95

Gly Val Leu Val Ile Asn Leu Leu Ser Arg Ser Ala Pro His
            100                 105                 110

<210> SEQ ID NO 149
<211> LENGTH: 110
<212> TYPE: PRT
<213> ORGANISM: Escherichia coli

<400> SEQUENCE: 149

Met Asn Pro Tyr Ile Tyr Leu Gly Gly Ala Ile Leu Ala Glu Val Ile
1               5                   10                  15

Gly Thr Thr Leu Met Lys Tyr Ser Glu Gly Phe Thr Arg Leu Trp Pro
                20                  25                  30

Ser Val Gly Thr Ile Ile Cys Tyr Cys Ala Ser Phe Trp Leu Leu Ala
            35                  40                  45

Gln Thr Leu Ala Tyr Ile Pro Thr Gly Ile Ala Tyr Ala Ile Trp Ser
    50                  55                  60

Gly Val Gly Ile Val Leu Ile Ser Leu Leu Ser Trp Gly Phe Phe Gly
65                  70                  75                  80

Gln Arg Leu Asp Leu Pro Ala Ile Ile Gly Met Met Leu Ile Cys Ala
                85                  90                  95

Gly Val Leu Val Ile Asn Leu Leu Ser Arg Ser Ala Pro His
            100                 105                 110

<210> SEQ ID NO 150
<211> LENGTH: 110
<212> TYPE: PRT
<213> ORGANISM: Shigella flexneri

<400> SEQUENCE: 150

Met Asn Pro Tyr Ile Tyr Leu Gly Gly Ala Ile Leu Ala Glu Val Ile
1               5                   10                  15

Gly Thr Thr Leu Met Lys Phe Ser Glu Gly Phe Thr Arg Leu Trp Pro
                20                  25                  30

Ser Val Gly Thr Ile Ile Cys Tyr Cys Ala Ser Phe Trp Leu Leu Ala
            35                  40                  45

Gln Thr Leu Ala Tyr Ile Pro Thr Gly Ile Ala Tyr Ala Ile Trp Ser
    50                  55                  60

Gly Val Gly Ile Val Leu Ile Ser Leu Leu Ser Trp Gly Phe Phe Gly
65                  70                  75                  80

Gln Arg Leu Asp Leu Pro Ala Ile Ile Gly Met Met Leu Ile Cys Thr
                85                  90                  95

Gly Val Leu Val Ile Asn Leu Leu Ser Arg Ser Ala Pro His
            100                 105                 110

<210> SEQ ID NO 151
<211> LENGTH: 110
<212> TYPE: PRT
<213> ORGANISM: Escherichia sp.

<400> SEQUENCE: 151

Met Asn Pro Tyr Ile Tyr Leu Gly Gly Ala Ile Leu Ala Glu Val Ile
1               5                   10                  15

Gly Thr Thr Leu Met Lys Phe Ser Glu Gly Phe Thr Arg Leu Trp Pro
            20                  25                  30

Ser Val Gly Thr Ile Ile Cys Tyr Cys Thr Ser Phe Trp Leu Leu Ala
        35                  40                  45

Gln Thr Leu Ala Tyr Ile Pro Thr Gly Ile Ala Tyr Ala Ile Trp Ser
    50                  55                  60

Gly Val Gly Ile Val Leu Ile Ser Leu Leu Ser Trp Gly Phe Phe Gly
65                  70                  75                  80

Gln Arg Leu Asp Leu Pro Ala Ile Ile Gly Met Met Leu Ile Cys Ala
                85                  90                  95

Gly Val Leu Val Ile Asn Leu Leu Ser Arg Ser Ala Pro His
            100                 105                 110

<210> SEQ ID NO 152
<211> LENGTH: 110
<212> TYPE: PRT
<213> ORGANISM: Escherichia sp.

<400> SEQUENCE: 152

Met Asn Pro Tyr Ile Tyr Leu Gly Gly Ala Ile Leu Ala Glu Val Ile
1               5                   10                  15

Gly Thr Thr Leu Met Lys Phe Ser Glu Gly Phe Thr Arg Leu Trp Pro
            20                  25                  30

Ser Val Gly Thr Ile Ile Cys Tyr Cys Thr Ser Phe Trp Leu Leu Ala
        35                  40                  45

Gln Thr Leu Ala Tyr Ile Pro Thr Gly Ile Ala Tyr Ala Ile Trp Ser
    50                  55                  60

Gly Val Gly Ile Val Leu Ile Ser Leu Leu Ser Trp Gly Phe Phe Gly
65                  70                  75                  80

Gln Arg Leu Asp Leu Pro Ala Ile Ile Gly Met Met Leu Ile Cys Ala
                85                  90                  95

Gly Val Leu Val Ile Asn Leu Leu Ser Arg Ser Ala Pro His
            100                 105                 110

<210> SEQ ID NO 153
<211> LENGTH: 110
<212> TYPE: PRT
<213> ORGANISM: Escherichia sp.

<400> SEQUENCE: 153

Met Asn Pro Tyr Ile Tyr Leu Gly Gly Ala Ile Leu Ala Glu Val Ile
1               5                   10                  15

Gly Thr Thr Leu Met Lys Phe Ser Glu Gly Phe Thr Arg Leu Trp Pro
            20                  25                  30

Ser Val Gly Thr Ile Ile Cys Tyr Cys Thr Ser Phe Trp Leu Leu Ala
        35                  40                  45

Gln Thr Leu Ala Tyr Ile Pro Thr Gly Ile Ala Tyr Ala Ile Trp Ser
    50                  55                  60

Gly Val Gly Ile Val Leu Ile Ser Leu Leu Ser Trp Gly Phe Phe Gly
65                  70                  75                  80

Gln Arg Leu Asp Leu Pro Ala Ile Ile Gly Met Met Leu Ile Cys Ala
                85                  90                  95

```
Gly Val Leu Val Ile Asn Leu Leu Ser Arg Ser Ala Pro His
            100                 105                 110
```

<210> SEQ ID NO 154
<211> LENGTH: 110
<212> TYPE: PRT
<213> ORGANISM: Escherichia sp.

<400> SEQUENCE: 154

```
Met Asn Pro Tyr Ile Tyr Leu Gly Gly Ala Ile Leu Ala Glu Val Ile
1               5                   10                  15

Gly Thr Thr Leu Met Lys Phe Ser Glu Gly Phe Thr Arg Leu Trp Pro
            20                  25                  30

Ser Val Gly Thr Ile Ile Cys Tyr Cys Thr Ser Phe Trp Leu Leu Ala
        35                  40                  45

Gln Thr Leu Ala Tyr Ile Pro Thr Gly Ile Ala Tyr Ala Ile Trp Ser
    50                  55                  60

Gly Val Gly Ile Val Leu Ile Ser Leu Leu Ser Trp Gly Phe Phe Gly
65                  70                  75                  80

Gln Arg Leu Asp Leu Pro Ala Ile Ile Gly Met Met Leu Ile Cys Ala
                85                  90                  95

Gly Val Leu Val Ile Asn Leu Leu Ser Arg Ser Ala Pro His
            100                 105                 110
```

<210> SEQ ID NO 155
<211> LENGTH: 110
<212> TYPE: PRT
<213> ORGANISM: Escherichia coli

<400> SEQUENCE: 155

```
Met Asn Pro Tyr Ile Tyr Leu Gly Gly Ala Ile Leu Ala Glu Val Ile
1               5                   10                  15

Gly Thr Thr Leu Met Lys Phe Ser Glu Gly Phe Thr Arg Leu Trp Pro
            20                  25                  30

Ser Ala Gly Thr Ile Ile Cys Tyr Cys Ala Ser Phe Trp Leu Leu Ala
        35                  40                  45

Gln Thr Leu Ala Tyr Ile Pro Thr Gly Ile Ala Tyr Ala Ile Trp Ser
    50                  55                  60

Gly Val Gly Ile Val Leu Ile Ser Leu Leu Ser Trp Gly Phe Phe Gly
65                  70                  75                  80

Gln Arg Leu Asp Leu Pro Ala Ile Ile Gly Met Met Leu Ile Cys Ala
                85                  90                  95

Gly Val Leu Val Ile Asn Leu Leu Ser Arg Ser Ala Pro His
            100                 105                 110
```

<210> SEQ ID NO 156
<211> LENGTH: 110
<212> TYPE: PRT
<213> ORGANISM: Escherichia coli

<400> SEQUENCE: 156

```
Met Asn Pro Tyr Ile Tyr Leu Gly Gly Ala Ile Leu Ala Glu Val Ile
1               5                   10                  15

Gly Thr Thr Leu Met Lys Phe Ser Glu Gly Phe Thr Arg Leu Trp Pro
            20                  25                  30

Ser Val Gly Thr Ile Ile Cys Tyr Cys Thr Ser Phe Trp Leu Leu Ala
        35                  40                  45
```

```
Gln Thr Leu Ala Tyr Ile Pro Thr Gly Ile Ala Tyr Ala Ile Trp Ser
        50                  55                  60

Gly Val Gly Ile Val Leu Ile Ser Leu Leu Ser Trp Gly Phe Phe Gly
65                  70                  75                  80

Gln Arg Leu Asp Leu Pro Ala Ile Ile Gly Met Met Leu Ile Cys Ala
                85                  90                  95

Gly Val Leu Val Ile Asn Leu Leu Ser Arg Ser Ala Pro His
            100                 105                 110

<210> SEQ ID NO 157
<211> LENGTH: 110
<212> TYPE: PRT
<213> ORGANISM: Shigella sonnei

<400> SEQUENCE: 157

Met Asn Pro Tyr Ile Tyr Leu Gly Gly Ala Ile Leu Ala Glu Val Ile
1               5                   10                  15

Gly Thr Thr Leu Met Lys Phe Ser Glu Gly Phe Thr Arg Leu Trp Pro
            20                  25                  30

Ser Val Gly Thr Ile Ile Cys Tyr Cys Ala Ser Phe Trp Leu Leu Ala
        35                  40                  45

Gln Thr Leu Ala Tyr Ile Pro Thr Gly Ile Ala Tyr Ala Ile Trp Ser
        50                  55                  60

Gly Val Gly Ile Val Leu Ile Gly Leu Leu Ser Trp Gly Phe Phe Gly
65                  70                  75                  80

Gln Arg Leu Asp Leu Pro Ala Ile Ile Gly Met Met Leu Ile Cys Ala
                85                  90                  95

Gly Val Leu Val Ile Asn Leu Leu Ser Arg Ser Ala Pro His
            100                 105                 110

<210> SEQ ID NO 158
<211> LENGTH: 110
<212> TYPE: PRT
<213> ORGANISM: Shigella sonnei

<400> SEQUENCE: 158

Met Asn Pro Tyr Ile Tyr Leu Gly Gly Ala Ile Leu Ala Glu Val Ile
1               5                   10                  15

Gly Thr Thr Leu Met Lys Phe Ser Glu Gly Phe Thr Arg Leu Trp Pro
            20                  25                  30

Ser Val Gly Thr Ile Ile Cys Tyr Cys Thr Ser Phe Trp Leu Leu Ala
        35                  40                  45

Gln Thr Leu Ala Tyr Ile Pro Thr Gly Ile Ala Tyr Ala Ile Trp Ser
        50                  55                  60

Gly Val Gly Ile Val Leu Ile Ser Leu Leu Ser Trp Gly Phe Phe Gly
65                  70                  75                  80

Gln Arg Leu Asp Leu Pro Ala Ile Ile Gly Met Met Leu Ile Cys Ala
                85                  90                  95

Gly Val Leu Val Ile Asn Leu Leu Ser Arg Ser Ala Pro His
            100                 105                 110

<210> SEQ ID NO 159
<211> LENGTH: 110
<212> TYPE: PRT
<213> ORGANISM: Escherichia coli
```

<400> SEQUENCE: 159

Met Asn Pro Tyr Ile Tyr Leu Gly Gly Ala Ile Leu Ala Glu Val Ile
1               5                   10                  15

Gly Thr Thr Leu Met Lys Phe Ser Glu Gly Phe Thr Arg Leu Trp Pro
            20                  25                  30

Ser Val Gly Thr Ile Ile Cys Tyr Cys Thr Ser Phe Trp Leu Leu Ala
        35                  40                  45

Gln Thr Leu Ala Tyr Ile Pro Thr Gly Ile Ala Tyr Ala Ile Trp Ser
    50                  55                  60

Gly Val Gly Ile Val Leu Ile Ser Leu Ser Trp Gly Phe Phe Gly
65                  70                  75                  80

Gln Arg Leu Asp Leu Pro Ala Ile Ile Gly Met Met Leu Ile Cys Ala
            85                  90                  95

Gly Val Leu Val Ile Asn Leu Leu Ser Arg Ser Ala Pro His
            100                 105                 110

<210> SEQ ID NO 160
<211> LENGTH: 110
<212> TYPE: PRT
<213> ORGANISM: Escherichia coli

<400> SEQUENCE: 160

Met Asn Pro Tyr Ile Tyr Leu Gly Gly Ala Ile Leu Ala Glu Val Ile
1               5                   10                  15

Gly Thr Thr Leu Met Lys Phe Ser Glu Gly Phe Thr Arg Leu Trp Pro
            20                  25                  30

Ser Val Gly Thr Ile Ile Cys Tyr Cys Ala Ser Phe Trp Leu Leu Ala
        35                  40                  45

Gln Thr Leu Ala Tyr Ile Pro Thr Gly Ile Ala Tyr Ala Ile Trp Ser
    50                  55                  60

Gly Val Gly Ile Val Leu Ile Ser Leu Ser Trp Gly Phe Phe Val
65                  70                  75                  80

Gln Arg Leu Asp Leu Pro Ala Val Ile Gly Met Met Leu Ile Cys Ala
            85                  90                  95

Gly Val Leu Val Ile Asn Leu Leu Ser Arg Ser Thr Pro His
            100                 105                 110

<210> SEQ ID NO 161
<211> LENGTH: 110
<212> TYPE: PRT
<213> ORGANISM: Shigella sp.

<400> SEQUENCE: 161

Met Asn Pro Tyr Ile Tyr Leu Gly Gly Ala Ile Leu Ala Glu Val Ile
1               5                   10                  15

Gly Thr Thr Leu Met Lys Phe Ser Glu Gly Phe Thr Arg Leu Trp Pro
            20                  25                  30

Ser Val Gly Thr Ile Ile Cys Tyr Cys Ala Ser Phe Trp Leu Leu Ala
        35                  40                  45

Gln Thr Leu Ala Tyr Ile Pro Thr Gly Ile Ala Tyr Gly Ile Trp Ser
    50                  55                  60

Gly Val Gly Ile Val Leu Ile Ser Leu Leu Trp Gly Phe Phe Gly
65                  70                  75                  80

Gln Arg Leu Asp Leu Pro Ala Ile Ile Gly Met Met Leu Ile Cys Ala
            85                  90                  95

```
Gly Val Leu Val Ile Asn Leu Leu Ser Arg Ser Thr Pro His
            100                 105                 110
```

<210> SEQ ID NO 162
<211> LENGTH: 110
<212> TYPE: PRT
<213> ORGANISM: Escherichia coli

<400> SEQUENCE: 162

```
Met Asn Pro Tyr Ile Tyr Leu Gly Gly Ala Ile Leu Ala Glu Val Ile
1               5                   10                  15

Gly Thr Thr Leu Met Lys Phe Ser Glu Gly Phe Thr Arg Leu Trp Pro
            20                  25                  30

Ser Val Gly Thr Ile Ile Cys Tyr Cys Ala Ser Phe Trp Leu Leu Ala
        35                  40                  45

Gln Thr Leu Ala Tyr Ile Pro Thr Gly Ile Ala Tyr Gly Ile Trp Ser
50                  55                  60

Gly Val Gly Ile Val Leu Ile Ser Leu Leu Trp Gly Phe Phe Gly
65                  70                  75                  80

Gln Arg Leu Asp Leu Pro Ala Ile Ile Gly Met Met Leu Ile Cys Ala
                85                  90                  95

Gly Val Leu Val Ile Asn Leu Leu Ser Arg Ser Thr Pro His
            100                 105                 110
```

<210> SEQ ID NO 163
<211> LENGTH: 165
<212> TYPE: PRT
<213> ORGANISM: Escherichia coli

<400> SEQUENCE: 163

```
Met Asn Ser Phe Val Ser Leu Gly Phe Leu Leu Ile Ile Ile Val Pro
1               5                   10                  15

Ala Phe Ile Ser Cys His Ala Arg Ala Pro Trp Ile His Ile His Gln
            20                  25                  30

Asp Glu Asn Gly Glu Leu Cys Ser Asn Cys Ser Thr Ile Leu Ser Ser
        35                  40                  45

Met Asn Arg Lys Glu Tyr Ala Met Asn Pro Tyr Ile Tyr Leu Gly Gly
    50                  55                  60

Ala Ile Leu Ala Glu Val Ile Gly Thr Thr Leu Met Lys Phe Ser Glu
65                  70                  75                  80

Gly Phe Thr Arg Leu Trp Pro Ser Val Gly Thr Ile Ile Cys Tyr Cys
                85                  90                  95

Ala Ser Phe Trp Leu Leu Ala Gln Thr Leu Ala Tyr Ile Pro Thr Gly
            100                 105                 110

Ile Ala Tyr Ala Ile Trp Ser Gly Val Gly Ile Val Leu Ile Ser Leu
        115                 120                 125

Leu Ser Trp Gly Phe Phe Gly Gln Arg Leu Asp Leu Pro Ala Ile Ile
130                 135                 140

Gly Met Met Leu Ile Cys Ala Gly Val Leu Val Ile Asn Leu Leu Ser
145                 150                 155                 160

Arg Ser Ala Pro His
                165
```

<210> SEQ ID NO 164
<211> LENGTH: 165
<212> TYPE: PRT
<213> ORGANISM: Shigella flexneri

<400> SEQUENCE: 164

Met Asn Ser Phe Val Ser Leu Gly Phe Leu Leu Ile Ile Ile Val Pro
1               5                   10                  15

Ala Phe Ile Ser Cys His Ala Arg Ala Pro Trp Ile His Ile His Gln
            20                  25                  30

Asp Glu Asn Gly Glu Leu Cys Ser Asn Cys Ser Thr Ile Leu Ser Ser
        35                  40                  45

Met Asn Arg Lys Glu Tyr Ala Met Asn Pro Tyr Ile Tyr Leu Gly Gly
    50                  55                  60

Ala Ile Leu Ala Glu Val Ile Gly Thr Thr Leu Met Lys Phe Ser Glu
65                  70                  75                  80

Gly Phe Thr Arg Leu Trp Pro Ser Val Gly Thr Ile Ile Cys Tyr Cys
                85                  90                  95

Ala Ser Phe Trp Leu Leu Ala Gln Thr Leu Ala Tyr Ile Pro Thr Gly
            100                 105                 110

Ile Ala Tyr Ala Ile Trp Ser Gly Val Gly Ile Val Leu Ile Ser Leu
        115                 120                 125

Leu Ser Trp Gly Phe Phe Gly Gln Arg Leu Asp Leu Pro Ala Ile Ile
    130                 135                 140

Gly Met Met Leu Ile Cys Ala Gly Val Leu Val Ile Asn Leu Leu Ser
145                 150                 155                 160

Arg Ser Ala Pro His
                165

<210> SEQ ID NO 165
<211> LENGTH: 165
<212> TYPE: PRT
<213> ORGANISM: Escherichia coli

<400> SEQUENCE: 165

Met Asn Ser Phe Val Ser Leu Gly Phe Leu Leu Ile Ile Ile Val Pro
1               5                   10                  15

Ala Phe Ile Ser Cys His Ala Arg Ala Pro Trp Ile His Ile His Gln
            20                  25                  30

Asp Glu Asn Gly Glu Leu Cys Ser Asn Cys Ser Thr Ile Leu Ser Ser
        35                  40                  45

Met Asn Arg Lys Glu Tyr Ala Met Asn Pro Tyr Ile Tyr Leu Gly Gly
    50                  55                  60

Ala Ile Leu Ala Glu Val Ile Gly Thr Thr Leu Met Lys Phe Ser Glu
65                  70                  75                  80

Gly Phe Thr Arg Leu Trp Pro Ser Val Gly Thr Ile Ile Cys Tyr Cys
                85                  90                  95

Ala Ser Phe Trp Leu Leu Ala Gln Thr Leu Ala Tyr Ile Pro Thr Gly
            100                 105                 110

Ile Ala Tyr Ala Ile Trp Ser Gly Val Gly Ile Val Leu Ile Ser Leu
        115                 120                 125

Leu Ser Trp Gly Phe Phe Gly Gln Arg Leu Asp Leu Pro Ala Ile Ile
    130                 135                 140

Gly Met Met Leu Ile Cys Ala Gly Val Leu Val Ile Asn Leu Leu Ser
145                 150                 155                 160

Arg Ser Ala Pro His
                165

<210> SEQ ID NO 166
<211> LENGTH: 165

```
<212> TYPE: PRT
<213> ORGANISM: Shigella flexneri

<400> SEQUENCE: 166

Met Asn Ser Phe Val Ser Leu Gly Phe Leu Leu Ile Ile Ile Val Pro
1               5                   10                  15

Ala Phe Ile Ser Cys His Ala Arg Ala Pro Trp Ile His Ile His Gln
            20                  25                  30

Asp Glu Asn Gly Glu Leu Cys Ser Asn Cys Ser Thr Ile Leu Ser Ser
        35                  40                  45

Met Asn Arg Lys Glu Tyr Ala Met Asn Pro Tyr Ile Tyr Leu Gly Gly
    50                  55                  60

Ala Ile Leu Ala Glu Val Ile Gly Thr Thr Leu Met Lys Phe Ser Glu
65                  70                  75                  80

Gly Phe Thr Arg Leu Trp Pro Ser Val Gly Thr Ile Ile Cys Tyr Cys
                85                  90                  95

Ala Ser Phe Trp Leu Leu Ala Gln Thr Leu Ala Tyr Ile Pro Thr Gly
            100                 105                 110

Ile Ala Tyr Ala Ile Trp Ser Gly Val Gly Ile Val Leu Ile Ser Leu
        115                 120                 125

Leu Ser Trp Gly Phe Phe Gly Gln Arg Leu Asp Leu Pro Ala Ile Ile
    130                 135                 140

Gly Met Met Leu Ile Cys Ala Gly Val Leu Val Ile Asn Leu Leu Ser
145                 150                 155                 160

Arg Ser Ala Pro His
                165

<210> SEQ ID NO 167
<211> LENGTH: 165
<212> TYPE: PRT
<213> ORGANISM: Shigella sonnei

<400> SEQUENCE: 167

Met Asn Ser Phe Val Ser Leu Gly Phe Leu Leu Ile Ile Ile Val Pro
1               5                   10                  15

Ala Phe Ile Ser Cys His Ala Arg Ala Pro Trp Ile His Ile His Gln
            20                  25                  30

Asp Glu Asn Gly Glu Leu Cys Ser Asn Cys Ser Thr Ile Leu Ser Ser
        35                  40                  45

Met Asn Arg Lys Glu Tyr Ala Met Asn Pro Tyr Ile Tyr Leu Gly Gly
    50                  55                  60

Ala Ile Leu Ala Glu Val Ile Gly Thr Thr Leu Met Lys Phe Ser Glu
65                  70                  75                  80

Gly Phe Thr Arg Leu Trp Pro Ser Val Gly Thr Ile Ile Cys Tyr Cys
                85                  90                  95

Ala Ser Phe Trp Leu Leu Ala Gln Thr Leu Ala Tyr Ile Pro Thr Gly
            100                 105                 110

Ile Ala Tyr Ala Ile Trp Ser Gly Val Gly Ile Val Leu Ile Ser Leu
        115                 120                 125

Leu Ser Trp Gly Phe Phe Gly Gln Arg Leu Asp Leu Pro Ala Ile Ile
    130                 135                 140

Gly Met Met Leu Ile Cys Ala Gly Val Leu Val Ile Asn Leu Leu Ser
145                 150                 155                 160

Arg Ser Ala Pro His
                165
```

<210> SEQ ID NO 168
<211> LENGTH: 170
<212> TYPE: PRT
<213> ORGANISM: Escherichia coli

<400> SEQUENCE: 168

Met Leu Pro Gly Arg Val Asn Ser Phe Val Ser Leu Gly Phe Leu Leu
1               5                   10                  15

Ile Ile Ile Val Pro Ala Phe Ile Ser Cys His Ala Arg Ala Pro Trp
            20                  25                  30

Ile His Ile His Gln Asp Glu Asn Gly Glu Leu Cys Ser Asn Cys Ser
        35                  40                  45

Thr Ile Leu Ser Ser Met Asn Arg Lys Glu Tyr Ala Met Asn Pro Tyr
    50                  55                  60

Ile Tyr Leu Gly Gly Ala Ile Leu Ala Glu Val Ile Gly Thr Thr Leu
65                  70                  75                  80

Met Lys Phe Ser Glu Gly Phe Thr Arg Leu Trp Pro Ser Val Gly Thr
                85                  90                  95

Ile Ile Cys Tyr Cys Ala Ser Phe Trp Leu Leu Ala Gln Thr Leu Ala
            100                 105                 110

Tyr Ile Pro Thr Gly Ile Ala Tyr Ala Ile Trp Ser Gly Val Gly Ile
        115                 120                 125

Val Leu Ile Ser Leu Leu Ser Trp Gly Phe Phe Gly Gln Arg Leu Asp
    130                 135                 140

Leu Pro Ala Ile Ile Gly Met Met Leu Ile Cys Ala Gly Val Leu Val
145                 150                 155                 160

Ile Asn Leu Leu Ser Arg Ser Ala Pro His
                165                 170

<210> SEQ ID NO 169
<211> LENGTH: 170
<212> TYPE: PRT
<213> ORGANISM: Escherichia coli

<400> SEQUENCE: 169

Met Leu Pro Gly Arg Val Asn Ser Phe Val Ser Leu Gly Phe Leu Leu
1               5                   10                  15

Ile Ile Ile Val Pro Ala Phe Ile Ser Cys His Ala Arg Ala Pro Trp
            20                  25                  30

Ile His Ile His Gln Asp Glu Asn Gly Glu Leu Cys Ser Asn Cys Ser
        35                  40                  45

Thr Ile Leu Ser Ser Met Asn Arg Lys Glu Tyr Ala Met Asn Pro Tyr
    50                  55                  60

Ile Tyr Leu Gly Gly Ala Ile Leu Ala Glu Val Ile Gly Thr Thr Leu
65                  70                  75                  80

Met Lys Phe Ser Glu Gly Phe Thr Arg Leu Trp Pro Ser Val Gly Thr
                85                  90                  95

Ile Ile Cys Tyr Cys Ala Ser Phe Trp Leu Leu Ala Gln Thr Leu Ala
            100                 105                 110

Tyr Ile Pro Thr Gly Ile Ala Tyr Ala Ile Trp Ser Gly Val Gly Ile
        115                 120                 125

Val Leu Ile Ser Leu Leu Ser Trp Gly Phe Phe Gly Gln Arg Leu Asp
    130                 135                 140

Leu Pro Ala Ile Ile Gly Met Met Leu Ile Cys Ala Gly Val Leu Val
145                 150                 155                 160

```
Ile Asn Leu Leu Ser Arg Ser Ala Pro His
            165                 170

<210> SEQ ID NO 170
<211> LENGTH: 170
<212> TYPE: PRT
<213> ORGANISM: Escherichia coli

<400> SEQUENCE: 170

Met Leu Ile Gly Arg Val Asn Ser Phe Val Ser Leu Gly Phe Leu Leu
1               5                   10                  15

Ile Ile Ile Val Pro Ala Phe Ile Ser Cys His Ala Arg Ala Pro Trp
            20                  25                  30

Ile His Ile His Gln Asp Glu Asn Gly Glu Leu Cys Ser Asn Cys Ser
        35                  40                  45

Thr Ile Leu Ser Ser Met Asn Arg Lys Glu Tyr Ala Met Asn Pro Tyr
    50                  55                  60

Ile Tyr Leu Gly Gly Ala Ile Leu Ala Glu Val Ile Gly Thr Thr Leu
65                  70                  75                  80

Met Lys Phe Ser Glu Gly Phe Thr Arg Leu Trp Pro Ser Val Gly Thr
                85                  90                  95

Ile Ile Cys Tyr Cys Ala Ser Phe Trp Leu Leu Ala Gln Thr Leu Ala
            100                 105                 110

Tyr Ile Pro Thr Gly Ile Ala Tyr Ala Ile Trp Ser Gly Val Gly Ile
        115                 120                 125

Val Leu Ile Ser Leu Leu Ser Trp Gly Phe Phe Gly Gln Arg Leu Asp
    130                 135                 140

Leu Pro Ala Ile Ile Gly Met Met Leu Ile Cys Ala Gly Val Leu Val
145                 150                 155                 160

Ile Asn Leu Leu Ser Arg Ser Ala Pro His
            165                 170

<210> SEQ ID NO 171
<211> LENGTH: 170
<212> TYPE: PRT
<213> ORGANISM: Escherichia coli

<400> SEQUENCE: 171

Met Leu Pro Gly Arg Val Asn Ser Phe Val Ser Leu Gly Phe Leu Leu
1               5                   10                  15

Ile Ile Ile Val Pro Ala Phe Ile Ser Cys His Ala Arg Ala Pro Trp
            20                  25                  30

Ile His Ile His Gln Asp Glu Asn Gly Glu Leu Cys Ser Asn Cys Ser
        35                  40                  45

Thr Ile Leu Ser Ser Met Asn Arg Lys Glu Tyr Ala Met Asn Pro Tyr
    50                  55                  60

Ile Tyr Leu Gly Gly Ala Ile Leu Ala Glu Val Ile Gly Thr Thr Leu
65                  70                  75                  80

Met Lys Phe Ser Glu Gly Phe Thr Arg Leu Trp Pro Ser Val Gly Thr
                85                  90                  95

Ile Ile Cys Tyr Cys Ala Ser Phe Trp Leu Leu Ala Gln Thr Leu Ala
            100                 105                 110

Tyr Ile Pro Thr Gly Ile Ala Tyr Ala Ile Trp Ser Gly Val Gly Ile
        115                 120                 125

Val Leu Ile Ser Leu Leu Ser Trp Gly Phe Phe Gly Gln Arg Leu Asp
    130                 135                 140
```

```
Leu Pro Ala Ile Ile Gly Met Met Leu Ile Cys Ala Gly Val Leu Val
145                 150                 155                 160

Ile Asn Leu Leu Ser Arg Ser Ala Pro His
                165                 170

<210> SEQ ID NO 172
<211> LENGTH: 170
<212> TYPE: PRT
<213> ORGANISM: Escherichia coli

<400> SEQUENCE: 172

Met Leu Pro Gly Arg Val Asn Ser Phe Val Ser Leu Gly Phe Leu Leu
1               5                   10                  15

Ile Ile Ile Val Pro Ala Phe Ile Ser Cys His Ala Arg Ala Pro Trp
                20                  25                  30

Ile His Ile His Gln Asp Glu Asn Gly Glu Leu Cys Ser Asn Cys Ser
            35                  40                  45

Thr Ile Leu Ser Ser Met Asn Arg Lys Glu Tyr Ala Met Asn Pro Tyr
        50                  55                  60

Ile Tyr Leu Gly Gly Ala Ile Leu Ala Glu Val Ile Gly Thr Thr Leu
65                  70                  75                  80

Met Lys Phe Ser Glu Gly Phe Thr Arg Leu Trp Pro Ser Val Gly Thr
                85                  90                  95

Ile Ile Cys Tyr Cys Ala Ser Phe Trp Leu Leu Ala Gln Thr Leu Ala
                100                 105                 110

Tyr Ile Pro Thr Gly Ile Ala Tyr Ala Ile Trp Ser Gly Val Gly Ile
            115                 120                 125

Val Leu Ile Ser Leu Leu Ser Trp Gly Phe Phe Gly Gln Arg Leu Asp
        130                 135                 140

Leu Pro Ala Ile Ile Gly Met Met Leu Ile Cys Ala Gly Val Leu Val
145                 150                 155                 160

Ile Asn Leu Leu Ser Arg Ser Ala Pro His
                165                 170

<210> SEQ ID NO 173
<211> LENGTH: 170
<212> TYPE: PRT
<213> ORGANISM: Escherichia coli

<400> SEQUENCE: 173

Met Leu Pro Gly Arg Val Asn Ser Phe Val Ser Leu Gly Phe Leu Leu
1               5                   10                  15

Ile Ile Ile Val Pro Ala Phe Ile Ser Cys His Ala Arg Ala Pro Trp
                20                  25                  30

Ile His Ile His Gln Asp Glu Asn Ser Glu Leu Cys Ser Asn Cys Ser
            35                  40                  45

Thr Ile Leu Ser Ser Met Asn Arg Lys Glu Tyr Ala Met Asn Pro Tyr
        50                  55                  60

Ile Tyr Leu Gly Gly Ala Ile Leu Ala Glu Val Ile Gly Thr Thr Leu
65                  70                  75                  80

Met Lys Phe Ser Glu Gly Phe Thr Arg Leu Trp Pro Ser Val Gly Thr
                85                  90                  95

Ile Ile Cys Tyr Cys Ala Ser Phe Trp Leu Leu Ala Gln Thr Leu Ala
                100                 105                 110

Tyr Ile Pro Thr Gly Ile Ala Tyr Ala Ile Trp Ser Gly Val Gly Ile
            115                 120                 125
```

```
Val Leu Ile Ser Leu Leu Ser Trp Gly Phe Phe Gly Gln Arg Leu Asp
        130                 135                 140

Leu Pro Ala Ile Ile Gly Met Met Leu Ile Cys Ala Gly Val Leu Val
145                 150                 155                 160

Ile Asn Leu Leu Ser Arg Ser Ala Pro His
                165                 170

<210> SEQ ID NO 174
<211> LENGTH: 170
<212> TYPE: PRT
<213> ORGANISM: Escherichia coli

<400> SEQUENCE: 174

Met Leu Pro Gly Arg Val Asn Ser Phe Val Ser Leu Gly Phe Leu Leu
1               5                   10                  15

Ile Ile Ile Val Pro Ala Phe Ile Ser Cys His Ala Arg Ala Pro Trp
                20                  25                  30

Ile His Ile His Gln Asp Glu Asn Ser Glu Leu Cys Ser Asn Cys Ser
            35                  40                  45

Thr Ile Leu Ser Ser Met Asn Arg Lys Glu Tyr Ala Met Asn Pro Tyr
    50                  55                  60

Ile Tyr Leu Gly Gly Ala Ile Leu Ala Glu Val Ile Gly Thr Thr Leu
65                  70                  75                  80

Met Lys Phe Ser Glu Gly Phe Thr Arg Leu Trp Pro Ser Val Gly Thr
                85                  90                  95

Ile Ile Cys Tyr Cys Ala Ser Phe Trp Leu Leu Ala Gln Thr Leu Ala
            100                 105                 110

Tyr Ile Pro Thr Gly Ile Ala Tyr Ala Ile Trp Ser Gly Val Gly Ile
        115                 120                 125

Val Leu Ile Ser Leu Leu Ser Trp Gly Phe Phe Gly Gln Arg Leu Asp
        130                 135                 140

Leu Pro Ala Ile Ile Gly Met Met Leu Ile Cys Ala Gly Val Leu Val
145                 150                 155                 160

Ile Asn Leu Leu Ser Arg Ser Ala Pro His
                165                 170

<210> SEQ ID NO 175
<211> LENGTH: 170
<212> TYPE: PRT
<213> ORGANISM: Escherichia coli

<400> SEQUENCE: 175

Met Leu Ile Gly Arg Val Asn Ser Phe Val Ser Leu Gly Phe Leu Leu
1               5                   10                  15

Ile Ile Ile Val Pro Ala Phe Ile Ser Cys His Ala Arg Ala Pro Trp
                20                  25                  30

Ile His Ile His Gln Asp Glu Asn Gly Glu Leu Cys Ser Asn Cys Ser
            35                  40                  45

Thr Ile Leu Ser Ser Met Asn Arg Lys Glu Tyr Ala Met Asn Pro Tyr
    50                  55                  60

Ile Tyr Leu Gly Gly Ala Ile Leu Ala Glu Val Ile Gly Thr Thr Leu
65                  70                  75                  80

Met Lys Phe Ser Glu Gly Phe Thr Arg Leu Trp Pro Ser Val Gly Thr
                85                  90                  95

Ile Ile Cys Tyr Cys Ala Ser Phe Trp Leu Leu Ala Gln Thr Leu Ala
            100                 105                 110
```

```
Tyr Ile Pro Thr Gly Ile Ala Tyr Ala Ile Trp Ser Gly Val Gly Ile
            115                 120                 125

Val Leu Ile Ser Leu Leu Ser Trp Gly Phe Phe Gly Gln Arg Leu Asp
    130                 135                 140

Leu Pro Ala Ile Ile Gly Met Met Leu Ile Cys Ala Gly Val Leu Val
145                 150                 155                 160

Ile Asn Leu Leu Ser Arg Ser Ala Pro His
                165                 170

<210> SEQ ID NO 176
<211> LENGTH: 110
<212> TYPE: PRT
<213> ORGANISM: Escherichia coli

<400> SEQUENCE: 176

Met Asn Pro Tyr Ile Tyr Leu Gly Gly Ala Ile Leu Ala Glu Val Ile
1               5                   10                  15

Gly Thr Thr Leu Met Lys Phe Ser Glu Gly Phe Thr Arg Leu Trp Pro
            20                  25                  30

Ser Val Gly Thr Ile Ile Cys Tyr Cys Ala Ser Phe Trp Leu Leu Ala
        35                  40                  45

Gln Thr Leu Ala Tyr Ile Pro Thr Gly Ile Ala Tyr Ala Ile Trp Ser
    50                  55                  60

Gly Val Gly Ile Val Leu Ile Ser Leu Leu Ser Trp Gly Phe Phe Ser
65                  70                  75                  80

Gln Arg Leu Asp Leu Pro Ala Ile Ile Gly Met Met Leu Ile Cys Ala
                85                  90                  95

Gly Val Leu Val Ile Asn Leu Leu Ser Arg Ser Ala Pro His
            100                 105                 110

<210> SEQ ID NO 177
<211> LENGTH: 110
<212> TYPE: PRT
<213> ORGANISM: Escherichia coli

<400> SEQUENCE: 177

Met Asn Pro Tyr Ile Tyr Leu Gly Gly Ala Ile Leu Ala Glu Val Ile
1               5                   10                  15

Gly Thr Thr Leu Met Lys Phe Ser Glu Gly Phe Thr Arg Leu Trp Pro
            20                  25                  30

Ser Val Gly Thr Ile Ile Cys Tyr Cys Ala Ser Phe Trp Leu Leu Ala
        35                  40                  45

Gln Thr Leu Ala Tyr Ile Pro Thr Gly Ile Ala Tyr Ala Ile Trp Ser
    50                  55                  60

Gly Val Gly Ile Val Leu Ile Ser Leu Leu Ser Trp Gly Phe Phe Ser
65                  70                  75                  80

Gln Arg Leu Asp Leu Pro Ala Ile Ile Gly Met Met Leu Ile Cys Ala
                85                  90                  95

Gly Val Leu Val Ile Asn Leu Leu Ser Arg Ser Ala Pro His
            100                 105                 110

<210> SEQ ID NO 178
<211> LENGTH: 110
<212> TYPE: PRT
<213> ORGANISM: Escherichia coli
```

<400> SEQUENCE: 178

```
Met Asn Pro Tyr Ile Tyr Leu Gly Gly Ala Ile Leu Ala Glu Val Ile
1               5                   10                  15

Gly Thr Thr Leu Met Lys Phe Ser Glu Gly Phe Thr Arg Leu Trp Pro
            20                  25                  30

Ser Val Gly Thr Ile Ile Cys Tyr Cys Ala Ser Phe Trp Leu Leu Ala
        35                  40                  45

Gln Thr Leu Ala Tyr Ile Pro Thr Gly Ile Ala Tyr Ala Ile Trp Ser
    50                  55                  60

Gly Val Gly Ile Val Leu Ile Ser Leu Ser Trp Gly Phe Phe Ser
65                  70                  75                  80

Gln Arg Leu Asp Leu Pro Ala Ile Ile Gly Met Met Leu Ile Cys Ala
                85                  90                  95

Gly Val Leu Val Ile Asn Leu Leu Ser Arg Ser Ala Pro His
            100                 105                 110
```

<210> SEQ ID NO 179
<211> LENGTH: 110
<212> TYPE: PRT
<213> ORGANISM: Shigella sonnei

<400> SEQUENCE: 179

```
Met Asn Pro Tyr Ile Tyr Leu Gly Gly Ala Ile Leu Ala Glu Val Ile
1               5                   10                  15

Gly Thr Thr Leu Met Lys Phe Ser Glu Gly Phe Thr Arg Leu Trp Pro
            20                  25                  30

Ser Val Gly Thr Ile Ile Cys Tyr Cys Ala Ser Phe Trp Leu Leu Ala
        35                  40                  45

Gln Thr Leu Ala Tyr Ile Pro Lys Gly Ile Ala Tyr Ala Ile Trp Ser
    50                  55                  60

Gly Val Gly Ile Val Leu Ile Ser Leu Ser Trp Gly Phe Phe Gly
65                  70                  75                  80

Gln Arg Leu Asp Leu Pro Ala Ile Ile Gly Met Met Leu Ile Cys Ala
                85                  90                  95

Gly Val Leu Val Ile Asn Leu Leu Ser Arg Ser Ala Pro His
            100                 105                 110
```

<210> SEQ ID NO 180
<211> LENGTH: 110
<212> TYPE: PRT
<213> ORGANISM: Escherichia coli

<400> SEQUENCE: 180

```
Met Asn Pro Tyr Ile Tyr Leu Gly Gly Ala Ile Leu Ala Glu Val Ile
1               5                   10                  15

Gly Thr Thr Leu Met Lys Phe Ser Glu Gly Phe Thr Arg Leu Trp Pro
            20                  25                  30

Ser Val Gly Thr Ile Ile Cys Tyr Cys Ala Ser Phe Trp Leu Leu Ala
        35                  40                  45

Gln Thr Leu Ala Tyr Ile Pro Lys Gly Ile Ala Tyr Ala Ile Trp Ser
    50                  55                  60

Gly Val Gly Ile Val Leu Ile Ser Leu Ser Trp Gly Phe Phe Gly
65                  70                  75                  80

Gln Arg Leu Asp Leu Pro Ala Ile Ile Gly Met Met Leu Ile Cys Ala
                85                  90                  95
```

```
Gly Val Leu Val Ile Asn Leu Leu Ser Arg Ser Ala Pro His
                100                 105                 110
```

<210> SEQ ID NO 181
<211> LENGTH: 110
<212> TYPE: PRT
<213> ORGANISM: Escherichia coli

<400> SEQUENCE: 181

```
Met Asn Pro Tyr Ile Tyr Leu Gly Gly Ala Ile Leu Ala Glu Val Ile
1               5                   10                  15

Gly Thr Thr Leu Met Lys Phe Ser Glu Gly Phe Thr Arg Leu Trp Pro
                20                  25                  30

Ser Val Gly Thr Ile Ile Cys Tyr Cys Ala Ser Phe Trp Leu Leu Ala
            35                  40                  45

Gln Thr Leu Ala Tyr Ile Pro Thr Gly Ile Ala Tyr Ala Ile Trp Ser
    50                  55                  60

Gly Val Gly Ile Val Leu Ile Ser Leu Leu Ser Trp Gly Phe Phe Gly
65                  70                  75                  80

Gln Arg Leu Asp Leu Pro Ala Ile Ile Gly Met Met Leu Ile Cys Ala
                85                  90                  95

Gly Val Leu Val Ile Asn Leu Leu Ser Arg Ser Ala Pro Asn
                100                 105                 110
```

<210> SEQ ID NO 182
<211> LENGTH: 110
<212> TYPE: PRT
<213> ORGANISM: Escherichia coli

<400> SEQUENCE: 182

```
Met Asn Pro Tyr Ile Tyr Leu Gly Gly Ala Ile Leu Ala Glu Val Ile
1               5                   10                  15

Gly Thr Thr Leu Met Lys Phe Ser Glu Gly Phe Thr Arg Leu Trp Pro
                20                  25                  30

Ser Val Gly Thr Ile Ile Cys Tyr Cys Ala Ser Phe Trp Leu Leu Ala
            35                  40                  45

Gln Thr Leu Ala Tyr Ile Pro Thr Gly Ile Ala Tyr Ala Ile Trp Ser
    50                  55                  60

Gly Val Gly Ile Val Leu Ile Ser Leu Leu Ser Trp Gly Phe Phe Gly
65                  70                  75                  80

Gln Arg Leu Asp Leu Pro Ala Ile Ile Gly Met Met Leu Ile Cys Ala
                85                  90                  95

Gly Val Leu Val Ile Asn Leu Leu Ser Arg Ser Ala Pro Asn
                100                 105                 110
```

<210> SEQ ID NO 183
<211> LENGTH: 110
<212> TYPE: PRT
<213> ORGANISM: Escherichia coli

<400> SEQUENCE: 183

```
Met Asn Pro Tyr Ile Tyr Leu Gly Gly Ala Ile Leu Ala Glu Val Ile
1               5                   10                  15

Gly Thr Thr Leu Met Lys Phe Ser Glu Gly Phe Thr Arg Leu Trp Pro
                20                  25                  30

Ser Val Gly Thr Ile Ile Cys Tyr Cys Ala Ser Phe Trp Leu Leu Ala
            35                  40                  45
```

Gln Thr Leu Ala Tyr Ile Pro Thr Gly Ile Ala Tyr Ala Ile Trp Ser
            50                  55                  60

Gly Val Gly Ile Val Leu Ile Ser Leu Leu Ser Trp Gly Leu Phe Asp
 65                  70                  75                  80

Gln Arg Leu Asp Leu Pro Ala Ile Ile Gly Met Met Leu Ile Cys Ala
                85                  90                  95

Gly Val Leu Val Ile Asn Leu Leu Ser Arg Ser Thr Pro His
            100                 105                 110

<210> SEQ ID NO 184
<211> LENGTH: 110
<212> TYPE: PRT
<213> ORGANISM: Shigella sp.

<400> SEQUENCE: 184

Met Asn Pro Tyr Ile Tyr Leu Gly Gly Ala Ile Leu Ala Glu Val Ile
 1               5                  10                  15

Gly Thr Thr Leu Met Lys Phe Ser Glu Gly Phe Thr Arg Leu Trp Pro
                20                  25                  30

Ser Val Gly Thr Ile Ile Cys Tyr Cys Ala Ser Phe Trp Leu Leu Ala
            35                  40                  45

Gln Thr Leu Ala Tyr Ile Pro Thr Gly Ile Ala Tyr Ala Ile Trp Ser
            50                  55                  60

Gly Val Gly Ile Val Leu Ile Ser Leu Leu Ser Trp Gly Phe Phe Gly
 65                  70                  75                  80

Gln Arg Leu Asp Leu Ser Ala Ile Ile Gly Met Met Leu Ile Cys Ala
                85                  90                  95

Gly Val Leu Val Ile Asn Leu Leu Ser Arg Ser Ala Pro His
            100                 105                 110

<210> SEQ ID NO 185
<211> LENGTH: 110
<212> TYPE: PRT
<213> ORGANISM: Escherichia coli

<400> SEQUENCE: 185

Met Asn Pro Tyr Ile Tyr Leu Gly Gly Ala Ile Leu Ala Glu Val Ile
 1               5                  10                  15

Gly Thr Thr Leu Met Lys Phe Ser Glu Gly Phe Thr Arg Leu Trp Pro
                20                  25                  30

Ser Val Gly Thr Ile Ile Cys Tyr Cys Ala Ser Phe Trp Leu Leu Ala
            35                  40                  45

Gln Thr Leu Ala Tyr Ile Pro Thr Gly Ile Ala Tyr Ala Ile Trp Ser
            50                  55                  60

Gly Val Gly Ile Val Leu Ile Ser Leu Leu Ser Trp Gly Leu Phe Asp
 65                  70                  75                  80

Gln Arg Leu Asp Leu Pro Ala Ile Ile Gly Met Met Leu Ile Cys Ala
                85                  90                  95

Gly Val Leu Val Ile Asn Leu Leu Ser Arg Ser Thr Pro His
            100                 105                 110

<210> SEQ ID NO 186
<211> LENGTH: 110
<212> TYPE: PRT
<213> ORGANISM: Escherichia coli

<400> SEQUENCE: 186

Met Asn Pro Tyr Ile Tyr Leu Gly Gly Ala Ile Leu Ala Glu Val Ile
1               5                   10                  15

Gly Thr Thr Leu Met Lys Phe Ser Glu Gly Phe Thr Arg Leu Trp Pro
            20                  25                  30

Ser Val Gly Thr Ile Ile Cys Tyr Cys Ala Ser Phe Trp Leu Leu Ala
        35                  40                  45

Gln Thr Leu Ala Tyr Ile Pro Thr Gly Ile Ala Tyr Ala Ile Trp Ser
    50                  55                  60

Gly Val Gly Ile Val Leu Ile Ser Leu Ser Trp Gly Leu Phe Asp
65                  70                  75                  80

Gln Arg Leu Asp Leu Pro Ala Ile Ile Gly Met Met Leu Ile Cys Ala
                85                  90                  95

Gly Val Leu Val Ile Asn Leu Leu Ser Arg Ser Thr Pro His
            100                 105                 110

<210> SEQ ID NO 187
<211> LENGTH: 110
<212> TYPE: PRT
<213> ORGANISM: Shigella boydii

<400> SEQUENCE: 187

Met Asn Pro Tyr Ile Tyr Leu Gly Gly Ala Ile Leu Ala Glu Val Ile
1               5                   10                  15

Gly Thr Thr Leu Met Lys Phe Ser Glu Gly Phe Thr Arg Leu Trp Pro
            20                  25                  30

Ser Val Gly Thr Ile Ile Cys Tyr Cys Ala Ser Phe Trp Leu Leu Ala
        35                  40                  45

Gln Thr Leu Ala Tyr Ile Pro Thr Gly Ile Ala Tyr Ala Ile Trp Ser
    50                  55                  60

Gly Val Gly Ile Val Leu Ile Ser Leu Ser Trp Gly Leu Phe Asp
65                  70                  75                  80

Gln Arg Leu Asp Leu Pro Ala Ile Ile Gly Met Met Leu Ile Cys Ala
                85                  90                  95

Gly Val Leu Val Ile Asn Leu Leu Ser Arg Ser Thr Pro His
            100                 105                 110

<210> SEQ ID NO 188
<211> LENGTH: 110
<212> TYPE: PRT
<213> ORGANISM: Shigella dysenteriae

<400> SEQUENCE: 188

Met Asn Pro Tyr Ile Tyr Leu Gly Gly Ala Ile Leu Ala Glu Val Ile
1               5                   10                  15

Gly Thr Thr Leu Met Lys Phe Ser Glu Gly Phe Thr Arg Leu Trp Pro
            20                  25                  30

Ser Val Gly Thr Ile Ile Cys Tyr Tyr Ala Ser Phe Trp Leu Leu Ala
        35                  40                  45

Gln Thr Leu Ala Tyr Ile Pro Thr Gly Ile Ala Tyr Ala Ile Trp Ser
    50                  55                  60

Gly Val Gly Ile Val Leu Ile Ser Leu Ser Trp Gly Phe Phe Gly
65                  70                  75                  80

Gln Arg Leu Asp Leu Pro Ala Ile Ile Gly Met Met Leu Ile Cys Ala
                85                  90                  95

```
Gly Val Leu Val Ile Asn Leu Leu Ser Arg Ser Ala Pro His
            100                 105                 110

<210> SEQ ID NO 189
<211> LENGTH: 110
<212> TYPE: PRT
<213> ORGANISM: Shigella dysenteriae

<400> SEQUENCE: 189

Met Asn Pro Tyr Ile Tyr Leu Gly Gly Ala Ile Leu Ala Glu Val Ile
1               5                   10                  15

Gly Thr Thr Leu Met Lys Phe Ser Glu Gly Phe Thr Arg Leu Trp Pro
            20                  25                  30

Ser Val Gly Thr Ile Ile Cys Tyr Tyr Ala Ser Phe Trp Leu Leu Ala
        35                  40                  45

Gln Thr Leu Ala Tyr Ile Pro Thr Gly Ile Ala Tyr Ala Ile Trp Ser
    50                  55                  60

Gly Val Gly Ile Val Leu Ile Ser Leu Leu Ser Trp Gly Phe Phe Gly
65                  70                  75                  80

Gln Arg Leu Asp Leu Pro Ala Ile Ile Gly Met Met Leu Ile Cys Ala
                85                  90                  95

Gly Val Leu Val Ile Asn Leu Leu Ser Arg Ser Ala Pro His
            100                 105                 110

<210> SEQ ID NO 190
<211> LENGTH: 110
<212> TYPE: PRT
<213> ORGANISM: Escherichia sp.

<400> SEQUENCE: 190

Met Asn Pro Tyr Ile Tyr Leu Gly Gly Ala Ile Phe Ala Glu Val Ile
1               5                   10                  15

Gly Thr Thr Leu Met Lys Tyr Ser Asp Gly Phe Thr Arg Leu Trp Pro
            20                  25                  30

Ser Val Gly Thr Ile Ile Cys Tyr Cys Ala Ser Phe Trp Leu Leu Ala
        35                  40                  45

Gln Thr Leu Ala Tyr Ile Pro Thr Gly Ile Ala Tyr Ala Ile Trp Ser
    50                  55                  60

Gly Val Gly Ile Val Leu Ile Ser Leu Leu Ser Trp Gly Phe Phe Gly
65                  70                  75                  80

Gln Arg Leu Asp Leu Pro Ala Ile Ile Gly Met Ile Leu Ile Cys Ala
                85                  90                  95

Gly Val Leu Val Ile Asn Leu Leu Ser Arg Ser Ala Pro His
            100                 105                 110

<210> SEQ ID NO 191
<211> LENGTH: 110
<212> TYPE: PRT
<213> ORGANISM: Escherichia albertii

<400> SEQUENCE: 191

Met Asn Pro Tyr Ile Tyr Leu Gly Gly Ala Ile Leu Ala Glu Val Ile
1               5                   10                  15

Gly Thr Thr Leu Met Lys Phe Ser Glu Gly Phe Thr Arg Leu Trp Pro
            20                  25                  30

Ser Val Gly Thr Ile Ile Cys Tyr Cys Ala Ser Phe Trp Leu Leu Ala
        35                  40                  45
```

```
Gln Thr Leu Ala Tyr Ile Pro Thr Gly Ile Ala Tyr Ala Ile Trp Ser
    50                  55                  60

Gly Val Gly Ile Val Leu Ile Ser Leu Leu Ser Trp Gly Ile Phe Gly
65                  70                  75                  80

Gln Arg Leu Asp Leu Pro Ala Ile Ile Gly Met Met Leu Ile Cys Ala
                85                  90                  95

Gly Val Leu Val Ile Asn Leu Leu Ser Arg Ser Ala Thr His
            100                 105                 110

<210> SEQ ID NO 192
<211> LENGTH: 110
<212> TYPE: PRT
<213> ORGANISM: Escherichia sp.

<400> SEQUENCE: 192

Met Asn Pro Tyr Ile Tyr Leu Gly Gly Ala Ile Phe Ala Glu Val Ile
1               5                   10                  15

Gly Thr Thr Leu Met Lys Tyr Ser Asp Gly Phe Thr Arg Leu Trp Pro
                20                  25                  30

Ser Val Gly Thr Ile Ile Cys Tyr Cys Ala Ser Phe Trp Leu Leu Ala
            35                  40                  45

Gln Thr Leu Ala Tyr Ile Pro Thr Gly Ile Ala Tyr Ala Ile Trp Ser
    50                  55                  60

Gly Val Gly Ile Val Leu Ile Ser Leu Leu Ser Trp Gly Phe Phe Gly
65                  70                  75                  80

Gln Arg Leu Asp Leu Pro Ala Ile Ile Gly Met Ile Leu Ile Cys Ala
                85                  90                  95

Gly Val Leu Val Ile Asn Leu Leu Ser Arg Ser Ala Pro His
            100                 105                 110

<210> SEQ ID NO 193
<211> LENGTH: 110
<212> TYPE: PRT
<213> ORGANISM: Escherichia sp.

<400> SEQUENCE: 193

Met Asn Pro Tyr Ile Tyr Leu Gly Gly Ala Ile Phe Ala Glu Val Ile
1               5                   10                  15

Gly Thr Thr Leu Met Lys Tyr Ser Asp Gly Phe Thr Arg Leu Trp Pro
                20                  25                  30

Ser Val Gly Thr Ile Ile Cys Tyr Cys Ala Ser Phe Trp Leu Leu Ala
            35                  40                  45

Gln Thr Leu Ala Tyr Ile Pro Thr Gly Ile Ala Tyr Ala Ile Trp Ser
    50                  55                  60

Gly Val Gly Ile Val Leu Ile Ser Leu Leu Ser Trp Gly Phe Phe Gly
65                  70                  75                  80

Gln Arg Leu Asp Leu Pro Ala Ile Ile Gly Met Ile Leu Ile Cys Ala
                85                  90                  95

Gly Val Leu Val Ile Asn Leu Leu Ser Arg Ser Ala Pro His
            100                 105                 110

<210> SEQ ID NO 194
<211> LENGTH: 110
<212> TYPE: PRT
<213> ORGANISM: Escherichia coli
```

<400> SEQUENCE: 194

| Met | Asn | Pro | Tyr | Ile | Tyr | Leu | Gly | Gly | Ala | Ile | Leu | Ala | Glu | Val | Ile |
|---|---|---|---|---|---|---|---|---|---|---|---|---|---|---|---|
| 1 | | | | 5 | | | | | 10 | | | | | 15 | |

| Gly | Thr | Thr | Leu | Met | Lys | Phe | Ser | Glu | Gly | Phe | Thr | Arg | Leu | Trp | Pro |
|---|---|---|---|---|---|---|---|---|---|---|---|---|---|---|---|
| | | | | 20 | | | | | 25 | | | | | 30 | |

| Ser | Val | Gly | Thr | Ile | Ile | Cys | Tyr | Cys | Ala | Ser | Phe | Trp | Leu | Leu | Ala |
|---|---|---|---|---|---|---|---|---|---|---|---|---|---|---|---|
| | | | 35 | | | | | 40 | | | | | 45 | | |

| Gln | Thr | Leu | Ala | Tyr | Ile | Pro | Thr | Gly | Ile | Ala | Tyr | Ala | Ile | Trp | Ser |
|---|---|---|---|---|---|---|---|---|---|---|---|---|---|---|---|
| | 50 | | | | | 55 | | | | | 60 | | | | |

| Gly | Val | Gly | Ile | Val | Leu | Ile | Ser | Leu | Leu | Ser | Arg | Gly | Phe | Phe | Gly |
|---|---|---|---|---|---|---|---|---|---|---|---|---|---|---|---|
| 65 | | | | | 70 | | | | | 75 | | | | | 80 |

| Gln | Arg | Leu | Asp | Leu | Pro | Ala | Ile | Ile | Gly | Met | Met | Leu | Ile | Cys | Ala |
|---|---|---|---|---|---|---|---|---|---|---|---|---|---|---|---|
| | | | | 85 | | | | | 90 | | | | | 95 | |

| Gly | Val | Leu | Val | Ile | Asn | Leu | Leu | Ser | Arg | Ser | Ala | Pro | His |
|---|---|---|---|---|---|---|---|---|---|---|---|---|---|
| | | | 100 | | | | | 105 | | | | | 110 |

<210> SEQ ID NO 195
<211> LENGTH: 110
<212> TYPE: PRT
<213> ORGANISM: Escherichia coli

<400> SEQUENCE: 195

| Met | Asn | Pro | Tyr | Ile | Tyr | Leu | Gly | Gly | Ala | Ile | Leu | Ala | Glu | Val | Ile |
|---|---|---|---|---|---|---|---|---|---|---|---|---|---|---|---|
| 1 | | | | 5 | | | | | 10 | | | | | 15 | |

| Gly | Thr | Thr | Leu | Met | Lys | Phe | Ser | Glu | Gly | Phe | Thr | Arg | Leu | Trp | Pro |
|---|---|---|---|---|---|---|---|---|---|---|---|---|---|---|---|
| | | | | 20 | | | | | 25 | | | | | 30 | |

| Ser | Val | Gly | Thr | Ile | Ile | Cys | Tyr | Cys | Ala | Ser | Phe | Trp | Leu | Leu | Ala |
|---|---|---|---|---|---|---|---|---|---|---|---|---|---|---|---|
| | | | 35 | | | | | 40 | | | | | 45 | | |

| Gln | Thr | Leu | Ala | Tyr | Ile | Pro | Thr | Gly | Ile | Ala | Tyr | Ala | Ile | Trp | Ser |
|---|---|---|---|---|---|---|---|---|---|---|---|---|---|---|---|
| | 50 | | | | | 55 | | | | | 60 | | | | |

| Gly | Val | Gly | Ile | Val | Leu | Ile | Ser | Leu | Leu | Ser | Trp | Gly | Ile | Phe | Gly |
|---|---|---|---|---|---|---|---|---|---|---|---|---|---|---|---|
| 65 | | | | | 70 | | | | | 75 | | | | | 80 |

| Gln | Arg | Leu | Asp | Leu | Pro | Ala | Ile | Ile | Gly | Met | Met | Leu | Ile | Cys | Ala |
|---|---|---|---|---|---|---|---|---|---|---|---|---|---|---|---|
| | | | | 85 | | | | | 90 | | | | | 95 | |

| Gly | Val | Leu | Val | Ile | Asn | Leu | Leu | Ser | Arg | Ser | Ala | Thr | His |
|---|---|---|---|---|---|---|---|---|---|---|---|---|---|
| | | | 100 | | | | | 105 | | | | | 110 |

<210> SEQ ID NO 196
<211> LENGTH: 110
<212> TYPE: PRT
<213> ORGANISM: Escherichia albertii

<400> SEQUENCE: 196

| Met | Asn | Pro | Tyr | Ile | Tyr | Leu | Gly | Gly | Ala | Ile | Leu | Ala | Glu | Val | Ile |
|---|---|---|---|---|---|---|---|---|---|---|---|---|---|---|---|
| 1 | | | | 5 | | | | | 10 | | | | | 15 | |

| Gly | Thr | Thr | Leu | Met | Lys | Phe | Ser | Glu | Gly | Phe | Thr | Arg | Leu | Trp | Pro |
|---|---|---|---|---|---|---|---|---|---|---|---|---|---|---|---|
| | | | | 20 | | | | | 25 | | | | | 30 | |

| Ser | Val | Gly | Thr | Ile | Ile | Cys | Tyr | Cys | Ala | Ser | Phe | Trp | Leu | Leu | Ala |
|---|---|---|---|---|---|---|---|---|---|---|---|---|---|---|---|
| | | | 35 | | | | | 40 | | | | | 45 | | |

| Gln | Thr | Leu | Ala | Tyr | Ile | Pro | Thr | Gly | Ile | Ala | Tyr | Ala | Ile | Trp | Ser |
|---|---|---|---|---|---|---|---|---|---|---|---|---|---|---|---|
| | 50 | | | | | 55 | | | | | 60 | | | | |

| Gly | Val | Gly | Ile | Val | Leu | Ile | Ser | Leu | Leu | Ser | Trp | Gly | Ile | Phe | Gly |
|---|---|---|---|---|---|---|---|---|---|---|---|---|---|---|---|
| 65 | | | | | 70 | | | | | 75 | | | | | 80 |

| Gln | Arg | Leu | Asp | Leu | Pro | Ala | Ile | Ile | Gly | Met | Met | Leu | Ile | Cys | Ala |
|---|---|---|---|---|---|---|---|---|---|---|---|---|---|---|---|
| | | | | 85 | | | | | 90 | | | | | 95 | |

```
Gly Val Leu Val Ile Asn Leu Leu Ser Arg Ser Ala Thr His
                100                 105                 110

<210> SEQ ID NO 197
<211> LENGTH: 110
<212> TYPE: PRT
<213> ORGANISM: Escherichia coli

<400> SEQUENCE: 197

Met Asn Pro Tyr Ile Tyr Leu Gly Gly Ala Ile Phe Ala Glu Val Ile
1               5                   10                  15

Gly Thr Thr Leu Met Lys Tyr Ser Asp Gly Phe Thr Arg Leu Trp Pro
                20                  25                  30

Ser Val Gly Thr Ile Ile Cys Tyr Cys Ala Ser Phe Trp Leu Leu Ala
            35                  40                  45

Gln Thr Leu Ala Tyr Ile Pro Thr Gly Ile Ala Tyr Ala Ile Trp Ser
        50                  55                  60

Gly Val Gly Ile Val Leu Ile Ser Leu Leu Ser Trp Gly Phe Phe Gly
65                  70                  75                  80

Gln Arg Leu Asp Leu Pro Ala Ile Ile Gly Met Ile Leu Ile Cys Ala
                85                  90                  95

Gly Val Leu Val Ile Asn Leu Leu Ser Arg Ser Ala Pro His
                100                 105                 110

<210> SEQ ID NO 198
<211> LENGTH: 110
<212> TYPE: PRT
<213> ORGANISM: Escherichia albertii

<400> SEQUENCE: 198

Met Asn Pro Tyr Ile Tyr Leu Gly Gly Ala Ile Leu Ala Glu Val Ile
1               5                   10                  15

Gly Thr Thr Leu Met Lys Phe Ser Glu Gly Phe Thr Arg Leu Trp Pro
                20                  25                  30

Ser Val Gly Thr Ile Ile Cys Tyr Cys Ala Ser Phe Trp Leu Leu Ala
            35                  40                  45

Gln Thr Leu Ala Tyr Ile Pro Thr Gly Ile Ala Tyr Ala Ile Trp Ser
        50                  55                  60

Gly Val Gly Ile Val Leu Ile Ser Leu Leu Ser Trp Gly Ile Phe Gly
65                  70                  75                  80

Gln Arg Leu Asp Leu Pro Ala Ile Ile Gly Met Met Leu Ile Cys Ala
                85                  90                  95

Gly Val Leu Val Ile Asn Leu Phe Ser Arg Ser Ala Thr His
                100                 105                 110

<210> SEQ ID NO 199
<211> LENGTH: 110
<212> TYPE: PRT
<213> ORGANISM: Escherichia albertii

<400> SEQUENCE: 199

Met Asn Pro Tyr Ile Tyr Leu Gly Gly Ala Ile Leu Ala Glu Val Ile
1               5                   10                  15

Gly Thr Thr Leu Met Lys Phe Ser Glu Gly Phe Thr Arg Leu Trp Pro
                20                  25                  30

Ser Val Gly Thr Ile Ile Cys Tyr Cys Thr Ser Phe Trp Leu Leu Ala
            35                  40                  45
```

-continued

Gln Thr Leu Ala Tyr Ile Pro Thr Gly Ile Ala Tyr Ala Ile Trp Ser
            50                  55                  60

Gly Val Gly Ile Val Leu Ile Ser Leu Leu Ser Trp Gly Ile Phe Gly
 65                  70                  75                  80

Gln Arg Leu Asp Leu Pro Ala Ile Ile Gly Met Met Leu Ile Cys Ala
                85                  90                  95

Gly Val Leu Val Ile Asn Leu Leu Ser Arg Ser Ala Thr His
            100                 105                 110

<210> SEQ ID NO 200
<211> LENGTH: 110
<212> TYPE: PRT
<213> ORGANISM: Escherichia sp.

<400> SEQUENCE: 200

Met Asn Pro Tyr Ile Tyr Leu Gly Gly Ala Ile Phe Ala Glu Val Ile
 1               5                  10                  15

Gly Thr Thr Leu Met Lys Tyr Ser Asp Gly Phe Thr Arg Leu Trp Pro
                20                  25                  30

Ser Val Gly Thr Ile Ile Cys Tyr Cys Ala Ser Phe Trp Leu Leu Ala
            35                  40                  45

Gln Thr Leu Ala Tyr Ile Pro Thr Gly Ile Ala Tyr Ala Ile Trp Ser
        50                  55                  60

Gly Val Gly Ile Val Leu Ile Ser Leu Leu Phe Trp Gly Phe Phe Gly
 65                  70                  75                  80

Gln Arg Leu Asp Leu Pro Ala Ile Ile Gly Met Ile Leu Ile Cys Ala
                85                  90                  95

Gly Val Leu Val Ile Asn Leu Leu Ser Arg Ser Ala Pro His
            100                 105                 110

<210> SEQ ID NO 201
<211> LENGTH: 110
<212> TYPE: PRT
<213> ORGANISM: Escherichia albertii

<400> SEQUENCE: 201

Met Asn Pro Tyr Ile Tyr Leu Gly Gly Ala Ile Leu Ala Glu Val Ile
 1               5                  10                  15

Gly Thr Thr Leu Met Lys Phe Ser Glu Gly Phe Thr Arg Leu Trp Pro
                20                  25                  30

Ser Val Gly Thr Ile Ile Cys Tyr Cys Ala Ser Phe Trp Leu Leu Ala
            35                  40                  45

Gln Thr Leu Ala Tyr Ile Pro Thr Gly Ile Ala Asn Ala Ile Trp Ser
        50                  55                  60

Gly Val Gly Ile Val Leu Ile Ser Leu Leu Ser Trp Gly Ile Phe Gly
 65                  70                  75                  80

Gln Arg Leu Asp Leu Pro Ala Ile Ile Gly Met Met Leu Ile Cys Ala
                85                  90                  95

Gly Val Leu Val Ile Asn Leu Leu Ser Arg Ser Ala Thr His
            100                 105                 110

<210> SEQ ID NO 202
<211> LENGTH: 111
<212> TYPE: PRT
<213> ORGANISM: Shigella sonnei -continued

```
<400> SEQUENCE: 202

Met Asn Pro Tyr Ile Tyr Leu Gly Gly Ala Ile Leu Ala Glu Val Ile
1               5                   10                  15

Gly Thr Thr Leu Met Lys Phe Ser Glu Gly Phe Thr Arg Leu Trp Pro
            20                  25                  30

Ser Val Gly Thr Ile Ile Cys Tyr Cys Ala Ser Phe Trp Leu Leu Ala
        35                  40                  45

Gln Thr Leu Ala Tyr Ile Pro Thr Gly Ile Ala Tyr Ala Ile Trp Ser
    50                  55                  60

Gly Val Gly Ile Val Leu Ile Ser Leu Ser Trp Gly Phe Phe Gly
65                  70                  75                  80

Gln Arg Leu Asp Leu Pro Ala Ile Ile Gly Met Met Leu Ile Cys Ala
                85                  90                  95

Gly Val Leu Val Ile Asn Leu Gly Asp Ala Ala Asn Leu Leu Ile
            100                 105                 110

<210> SEQ ID NO 203
<211> LENGTH: 154
<212> TYPE: PRT
<213> ORGANISM: Shigella flexneri

<400> SEQUENCE: 203

Met Asn Ser Phe Val Ser Leu Gly Phe Leu Leu Ile Ile Ile Val Pro
1               5                   10                  15

Ala Phe Ile Ser Cys His Ala Arg Ala Pro Trp Ile His Ile His Gln
            20                  25                  30

Asp Glu Asn Gly Glu Leu Cys Ser Asn Cys Ser Thr Ile Leu Ser Ser
        35                  40                  45

Met Asn Arg Lys Glu Tyr Ala Met Asn Pro Tyr Ile Tyr Leu Gly Gly
    50                  55                  60

Ala Ile Leu Ala Glu Val Ile Gly Thr Thr Leu Met Lys Phe Ser Glu
65                  70                  75                  80

Gly Phe Thr Arg Leu Trp Pro Ser Val Gly Thr Ile Ile Cys Tyr Cys
                85                  90                  95

Ala Ser Phe Trp Leu Leu Ala Gln Thr Leu Ala Tyr Ile Pro Thr Gly
            100                 105                 110

Ile Ala Tyr Ala Ile Trp Ser Gly Val Gly Ile Val Leu Ile Ser Leu
        115                 120                 125

Leu Ser Trp Gly Phe Phe Gly Gln Arg Leu Asp Leu Pro Ala Ile Ile
    130                 135                 140

Gly Met Met Leu Ile Cys Ala Tyr Tyr Gly
145                 150

<210> SEQ ID NO 204
<211> LENGTH: 110
<212> TYPE: PRT
<213> ORGANISM: Citrobacter sp.

<400> SEQUENCE: 204

Met Asn Thr Tyr Ile Tyr Leu Gly Ala Ala Ile Leu Ala Glu Val Thr
1               5                   10                  15

Gly Thr Thr Leu Met Lys Phe Thr Asp Gly Phe Thr Arg Leu Trp Pro
            20                  25                  30

Ser Val Gly Thr Ile Val Cys Tyr Cys Ala Ser Phe Trp Leu Leu Ser
        35                  40                  45
```

```
Gln Thr Leu Ala His Ile Pro Thr Gly Ile Ala Tyr Ala Ile Trp Ser
     50                  55                  60

Gly Val Gly Ile Val Leu Ile Ser Leu Leu Ala Trp Val Ile His Gly
 65                  70                  75                  80

Gln Arg Leu Asp Leu Pro Ala Ile Ile Gly Met Ala Leu Ile Cys Ala
                 85                  90                  95

Gly Val Leu Ile Ile Asn Leu Leu Ser Arg Ser Ala Val His
            100                 105                 110

<210> SEQ ID NO 205
<211> LENGTH: 104
<212> TYPE: PRT
<213> ORGANISM: Escherichia coli

<400> SEQUENCE: 205

Met Asn Pro Tyr Ile Tyr Leu Gly Gly Ala Ile Leu Ala Glu Val Ile
 1               5                  10                  15

Gly Thr Thr Leu Met Lys Phe Ser Glu Gly Phe Thr Arg Leu Trp Pro
             20                  25                  30

Ser Ala Gly Thr Ile Ile Cys Tyr Cys Ala Ser Phe Trp Leu Leu Ala
         35                  40                  45

Gln Thr Leu Ala Tyr Ile Pro Thr Gly Ile Ala Tyr Ala Ile Trp Ser
     50                  55                  60

Gly Val Gly Ile Val Leu Ile Ser Leu Leu Ser Trp Gly Phe Phe Gly
 65                  70                  75                  80

Gln Arg Leu Asp Leu Pro Ala Ile Ile Asp Thr Val Met Ala Cys Lys
                 85                  90                  95

Phe Phe Pro Gly Pro Val Ser Arg
            100

<210> SEQ ID NO 206
<211> LENGTH: 82
<212> TYPE: PRT
<213> ORGANISM: Paenibacillus sp.

<400> SEQUENCE: 206

Met Asn Pro Tyr Ile Tyr Leu Gly Gly Ala Ile Leu Ala Glu Val Ile
 1               5                  10                  15

Gly Thr Thr Leu Met Lys Phe Ser Glu Gly Phe Thr Arg Leu Trp Pro
             20                  25                  30

Ser Val Gly Thr Ile Ile Cys Tyr Cys Ala Ser Phe Trp Leu Leu Ala
         35                  40                  45

Gln Thr Leu Ala Tyr Ile Pro Thr Gly Ile Ala Tyr Ala Ile Trp Ser
     50                  55                  60

Gly Val Gly Ile Val Leu Ile Ser Leu Leu Ser Trp Gly Phe Phe Gly
 65                  70                  75                  80

Gln Arg

<210> SEQ ID NO 207
<211> LENGTH: 101
<212> TYPE: PRT
<213> ORGANISM: Klebsiella pneumoniae

<400> SEQUENCE: 207

Met Asn Pro Tyr Ile Tyr Leu Gly Gly Ala Ile Leu Ala Glu Val Ile
 1               5                  10                  15

Gly Thr Thr Leu Met Lys Phe Ser Glu Gly Phe Thr Arg Leu Trp Pro
             20                  25                  30
```

Ser Val Gly Thr Ile Ile Cys Tyr Cys Ala Ser Phe Trp Leu Leu Ala
            35                  40                  45

Gln Thr Leu Ala Tyr Ile Pro Thr Gly Ile Ala Tyr Gly Ile Trp Ser
    50                  55                  60

Gly Val Gly Ile Val Leu Ile Ser Leu Leu Ser Trp Gly Phe Phe Leu
65                  70                  75                  80

Pro Thr Ala Gly Pro Ala Ser His Tyr Arg His Asp Val Asp Leu Cys
                85                  90                  95

Arg Cys Val Gly Tyr
            100

<210> SEQ ID NO 208
<211> LENGTH: 71
<212> TYPE: PRT
<213> ORGANISM: Shigella sonnei

<400> SEQUENCE: 208

Met Asn Pro Tyr Ile Tyr Leu Gly Gly Ala Ile Leu Ala Glu Val Ile
1               5                   10                  15

Gly Thr Thr Leu Met Lys Phe Ser Glu Gly Phe Thr Arg Leu Trp Pro
            20                  25                  30

Ser Val Gly Thr Ile Ile Cys Tyr Cys Ala Ser Phe Trp Leu Leu Ala
            35                  40                  45

Gln Thr Leu Ala Tyr Ile Pro Thr Gly Ile Ala Tyr Ala Ile Trp Ser
    50                  55                  60

Gly Val Arg Tyr Cys Pro Asp
65                  70

<210> SEQ ID NO 209
<211> LENGTH: 73
<212> TYPE: PRT
<213> ORGANISM: Escherichia coli

<400> SEQUENCE: 209

Met Asn Pro Tyr Ile Tyr Leu Gly Gly Ala Ile Leu Ala Glu Val Ile
1               5                   10                  15

Gly Thr Thr Leu Met Lys Phe Ser Glu Gly Phe Thr Arg Leu Trp Pro
            20                  25                  30

Ser Val Gly Thr Ile Ile Cys Tyr Cys Ala Ser Phe Trp Leu Leu Ala
            35                  40                  45

Gln Thr Leu Ala Tyr Ile Pro Thr Gly Ile Ala Tyr Ala Ile Trp Tyr
    50                  55                  60

Met Arg Thr Phe Ile Ser Cys Lys Arg
65                  70

<210> SEQ ID NO 210
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 210

Pro Ala Ile Ile Gly Met Met Leu Ile Cys Ala Gly
1               5                   10

<210> SEQ ID NO 211
<211> LENGTH: 80

```
<212> TYPE: PRT
<213> ORGANISM: Escherichia coli

<400> SEQUENCE: 211

Met Asn Arg Lys Glu Tyr Ala Met Asn Pro Tyr Ile Tyr Leu Gly Gly
1               5                   10                  15

Ala Ile Leu Ala Glu Val Ile Gly Thr Thr Leu Met Lys Phe Ser Glu
            20                  25                  30

Gly Phe Thr Arg Leu Trp Pro Ser Val Gly Thr Ile Ile Cys Tyr Cys
        35                  40                  45

Ala Ser Phe Trp Leu Leu Ala Gln Thr Leu Ala Tyr Ile Pro Thr Gly
    50                  55                  60

Ile Ala Tyr Ala Ile Trp Tyr Met Arg Thr Phe Ile Ser Cys Lys Arg
65                  70                  75                  80

<210> SEQ ID NO 212
<211> LENGTH: 110
<212> TYPE: PRT
<213> ORGANISM: Fundulus heteroclitus

<400> SEQUENCE: 212

Met Asn Pro Tyr Ile Tyr Leu Gly Gly Ala Ile Leu Ala Glu Val Ile
1               5                   10                  15

Gly Thr Thr Leu Met Lys Phe Ser Glu Gly Phe Thr Arg Leu Trp Pro
            20                  25                  30

Ser Val Gly Thr Ile Ile Cys Tyr Cys Ala Ser Phe Trp Leu Leu Ala
        35                  40                  45

Gln Thr Leu Ala Tyr Ile Pro Thr Gly Ile Ala Tyr Ala Ile Trp Ser
    50                  55                  60

Gly Val Gly Ile Val Leu Ile Ser Leu Leu Ser Trp Gly Phe Phe Gly
65                  70                  75                  80

Gln Arg Leu Asp Leu Pro Ala Ile Ile Gly Met Met Leu Ile Cys Ala
                85                  90                  95

Gly Val Leu Ile Ile Asn Leu Leu Ser Arg Ser Thr Pro His
            100                 105                 110

<210> SEQ ID NO 213
<211> LENGTH: 110
<212> TYPE: PRT
<213> ORGANISM: Escherichia coli

<400> SEQUENCE: 213

Met Asn Pro Tyr Ile Tyr Leu Gly Gly Ala Ile Leu Ala Glu Val Ile
1               5                   10                  15

Gly Thr Thr Leu Met Lys Phe Ser Glu Gly Phe Thr Arg Leu Trp Pro
            20                  25                  30

Ser Val Gly Thr Ile Ile Cys Tyr Cys Ala Ser Phe Trp Leu Leu Ala
        35                  40                  45

Gln Thr Leu Ala Tyr Ile Pro Thr Gly Ile Ala Tyr Ala Ile Trp Ser
    50                  55                  60

Gly Val Gly Ile Val Leu Ile Ser Leu Leu Ser Trp Gly Phe Phe Gly
65                  70                  75                  80

Gln Arg Leu Asp Leu Pro Ala Ile Ile Gly Met Met Leu Ile Cys Ala
                85                  90                  95

Gly Val Leu Ile Ile Asn Leu Leu Ser Arg Ser Thr Pro His
            100                 105                 110
```

-continued

```
<210> SEQ ID NO 214
<211> LENGTH: 110
<212> TYPE: PRT
<213> ORGANISM: Escherichia coli

<400> SEQUENCE: 214

Met Asn Pro Tyr Ile Tyr Leu Gly Gly Ala Ile Leu Ala Glu Val Ile
1               5                   10                  15

Gly Thr Thr Leu Met Lys Phe Ser Glu Gly Phe Thr Arg Leu Trp Pro
            20                  25                  30

Ser Val Gly Thr Ile Ile Cys Tyr Cys Ala Ser Phe Trp Leu Leu Ala
        35                  40                  45

Gln Thr Leu Ala Tyr Ile Pro Thr Gly Ile Ala Tyr Ala Ile Trp Ser
    50                  55                  60

Gly Val Gly Ile Val Leu Ile Ser Leu Leu Ser Trp Gly Phe Phe Gly
65                  70                  75                  80

Gln Arg Leu Asp Leu Pro Ala Ile Ile Gly Met Met Leu Ile Cys Ala
                85                  90                  95

Gly Val Leu Ile Ile Asn Leu Leu Ser Arg Ser Thr Pro His
            100                 105                 110

<210> SEQ ID NO 215
<211> LENGTH: 110
<212> TYPE: PRT
<213> ORGANISM: Escherichia coli

<400> SEQUENCE: 215

Met Asn Pro Tyr Ile Tyr Leu Gly Gly Ala Ile Leu Ala Glu Val Ile
1               5                   10                  15

Gly Thr Thr Leu Met Lys Phe Ser Glu Gly Phe Thr Arg Leu Trp Pro
            20                  25                  30

Ser Val Gly Thr Ile Ile Cys Tyr Cys Ala Ser Phe Trp Leu Leu Ala
        35                  40                  45

Gln Thr Leu Ala Tyr Ile Pro Thr Gly Ile Ala Tyr Ala Ile Trp Ser
    50                  55                  60

Gly Val Gly Ile Val Leu Ile Ser Leu Leu Ser Trp Gly Phe Phe Gly
65                  70                  75                  80

Gln Arg Leu Asp Leu Pro Ala Ile Ile Gly Met Met Leu Ile Cys Ala
                85                  90                  95

Gly Val Leu Ile Ile Asn Leu Leu Ser Arg Ser Thr Pro His
            100                 105                 110

<210> SEQ ID NO 216
<211> LENGTH: 110
<212> TYPE: PRT
<213> ORGANISM: Escherichia coli

<400> SEQUENCE: 216

Met Asn Pro Tyr Ile Tyr Leu Gly Gly Ala Ile Leu Ala Glu Val Ile
1               5                   10                  15

Gly Thr Thr Leu Met Lys Phe Ser Glu Gly Phe Thr Arg Leu Trp Pro
            20                  25                  30

Ser Val Gly Thr Ile Ile Cys Tyr Cys Ala Ser Phe Trp Leu Leu Ala
        35                  40                  45

Gln Thr Leu Ala Tyr Ile Pro Thr Gly Ile Ala Tyr Ala Ile Trp Ser
    50                  55                  60

Gly Val Gly Ile Val Leu Ile Ser Leu Leu Ser Trp Gly Phe Phe Gly
65                  70                  75                  80
```

Gln Arg Leu Asp Leu Pro Ala Ile Ile Gly Met Met Leu Ile Cys Ala
                85                  90                  95

Gly Val Leu Ile Ile Asn Leu Leu Ser Arg Ser Thr Pro His
            100                 105                 110

<210> SEQ ID NO 217
<211> LENGTH: 51
<212> TYPE: PRT
<213> ORGANISM: Shigella sonnei

<400> SEQUENCE: 217

Met Leu Ser Gly Gln Glu Ser Gly Ile Val Leu Ile Ser Leu Leu Ser
1               5                   10                  15

Trp Gly Phe Phe Gly Gln Arg Leu Asp Leu Pro Ala Ile Ile Gly Met
            20                  25                  30

Met Leu Ile Cys Ala Gly Val Leu Val Ile Asn Leu Leu Ser Arg Ser
        35                  40                  45

Thr Pro His
    50

<210> SEQ ID NO 218
<211> LENGTH: 110
<212> TYPE: PRT
<213> ORGANISM: Escherichia coli

<400> SEQUENCE: 218

Met Asn Pro Tyr Ile Tyr Leu Gly Gly Ala Ile Leu Ala Glu Val Ile
1               5                   10                  15

Gly Thr Thr Leu Met Lys Phe Ser Glu Gly Phe Thr Arg Leu Trp Pro
            20                  25                  30

Ser Val Gly Thr Ile Ile Cys Tyr Cys Ala Ser Phe Trp Leu Leu Ala
        35                  40                  45

Gln Thr Leu Ala Tyr Ile Pro Thr Gly Ile Ala Tyr Ala Ile Trp Ser
    50                  55                  60

Gly Val Gly Ile Val Leu Ile Ser Leu Leu Ser Trp Gly Phe Phe Gly
65                  70                  75                  80

Gln Arg Leu Asp Leu Pro Ala Ile Ile Gly Met Met Leu Ile Cys Ala
                85                  90                  95

Gly Val Leu Val Ile Asn Leu Leu Ser Arg Ser Ala Pro His
            100                 105                 110

<210> SEQ ID NO 219
<211> LENGTH: 110
<212> TYPE: PRT
<213> ORGANISM: Escherichia sp.

<400> SEQUENCE: 219

Met Asn Pro Tyr Ile Tyr Leu Gly Gly Ala Ile Leu Ala Glu Val Ile
1               5                   10                  15

Gly Thr Thr Leu Met Lys Phe Ser Glu Gly Phe Thr Arg Leu Trp Pro
            20                  25                  30

Ser Val Gly Thr Ile Ile Cys Tyr Cys Thr Ser Phe Trp Leu Leu Ala
        35                  40                  45

Gln Thr Leu Ala Tyr Ile Pro Thr Gly Ile Ala Tyr Ala Ile Trp Ser
    50                  55                  60

Gly Val Gly Ile Val Leu Ile Ser Leu Leu Ser Trp Gly Phe Phe Gly
65                  70                  75                  80

```
Gln Arg Leu Asp Leu Pro Ala Ile Ile Gly Met Met Leu Ile Cys Ala
                85                  90                  95

Gly Val Leu Val Ile Asn Leu Leu Ser Arg Ser Ala Pro His
            100                 105                 110

<210> SEQ ID NO 220
<211> LENGTH: 110
<212> TYPE: PRT
<213> ORGANISM: Escherichia sp.

<400> SEQUENCE: 220

Met Asn Pro Tyr Ile Tyr Leu Gly Gly Ala Ile Leu Ala Glu Val Ile
1               5                   10                  15

Gly Thr Thr Leu Met Lys Phe Ser Glu Gly Phe Thr Arg Leu Trp Pro
            20                  25                  30

Ser Val Gly Thr Ile Ile Cys Tyr Cys Thr Ser Phe Trp Leu Leu Ala
        35                  40                  45

Gln Thr Leu Ala Tyr Ile Pro Thr Gly Ile Ala Tyr Ala Ile Trp Ser
    50                  55                  60

Gly Val Gly Ile Val Leu Ile Ser Leu Leu Ser Trp Gly Phe Phe Gly
65                  70                  75                  80

Gln Arg Leu Asp Leu Pro Ala Ile Ile Gly Met Met Leu Ile Cys Ala
                85                  90                  95

Gly Val Leu Val Ile Asn Leu Leu Ser Arg Ser Ala Pro His
            100                 105                 110

<210> SEQ ID NO 221
<211> LENGTH: 110
<212> TYPE: PRT
<213> ORGANISM: Escherichia sp.

<400> SEQUENCE: 221

Met Asn Pro Tyr Ile Tyr Leu Gly Gly Ala Ile Leu Ala Glu Val Ile
1               5                   10                  15

Gly Thr Thr Leu Met Lys Phe Ser Glu Gly Phe Thr Arg Leu Trp Pro
            20                  25                  30

Ser Val Gly Thr Ile Ile Cys Tyr Cys Ala Ser Phe Trp Leu Leu Ala
        35                  40                  45

Gln Thr Leu Ala Tyr Ile Pro Thr Gly Ile Ala Tyr Ala Ile Trp Ser
    50                  55                  60

Gly Val Gly Ile Val Leu Ile Ser Leu Leu Ser Trp Gly Leu Phe Gly
65                  70                  75                  80

Gln Arg Leu Asp Leu Pro Ala Ile Ile Gly Met Met Leu Ile Cys Ala
                85                  90                  95

Gly Val Leu Val Ile Asn Leu Leu Ser Arg Ser Thr Pro His
            100                 105                 110

<210> SEQ ID NO 222
<211> LENGTH: 110
<212> TYPE: PRT
<213> ORGANISM: Escherichia coli

<400> SEQUENCE: 222

Met Asn Pro Tyr Ile Tyr Leu Gly Gly Ala Ile Leu Ala Glu Val Ile
1               5                   10                  15

Gly Thr Thr Leu Met Lys Phe Ser Glu Gly Phe Thr Arg Leu Trp Pro
            20                  25                  30
```

```
Ser Val Gly Thr Ile Ile Cys Tyr Cys Ala Ser Phe Trp Leu Leu Ala
        35                  40                  45

Gln Thr Leu Ala Tyr Ile Pro Thr Gly Ile Ala Tyr Ala Ile Trp Ser
    50                  55                  60

Gly Val Gly Ile Val Leu Ile Ser Leu Leu Ser Trp Gly Phe Phe Gly
65                  70                  75                  80

Gln Arg Leu Asp Leu Pro Ala Ile Ile Gly Met Met Leu Ile Cys Ala
                85                  90                  95

Gly Val Leu Val Ile Asn Leu Leu Ser Arg Ser Thr Pro His
            100                 105                 110

<210> SEQ ID NO 223
<211> LENGTH: 110
<212> TYPE: PRT
<213> ORGANISM: Escherichia coli

<400> SEQUENCE: 223

Met Asn Pro Tyr Ile Tyr Leu Gly Gly Ala Ile Leu Ala Glu Val Ile
1               5                   10                  15

Gly Thr Thr Leu Met Lys Phe Ser Glu Gly Phe Thr Arg Leu Trp Pro
            20                  25                  30

Ser Val Gly Thr Ile Ile Cys Tyr Cys Ala Ser Phe Trp Leu Leu Ala
        35                  40                  45

Gln Thr Leu Ala Tyr Ile Pro Thr Gly Ile Ala Tyr Ala Ile Trp Ser
    50                  55                  60

Gly Val Gly Ile Val Leu Ile Ser Leu Leu Ser Trp Gly Phe Phe Gly
65                  70                  75                  80

Gln Arg Leu Asp Leu Pro Ala Ile Ile Gly Met Met Leu Ile Cys Ala
                85                  90                  95

Gly Val Leu Val Ile Asn Leu Leu Ser Arg Ser Ala Pro His
            100                 105                 110

<210> SEQ ID NO 224
<211> LENGTH: 110
<212> TYPE: PRT
<213> ORGANISM: Escherichia coli

<400> SEQUENCE: 224

Met Asn Pro Tyr Ile Tyr Leu Gly Gly Ala Ile Leu Ala Glu Val Ile
1               5                   10                  15

Gly Thr Thr Leu Met Lys Phe Ser Glu Gly Phe Thr Arg Leu Trp Pro
            20                  25                  30

Ser Val Gly Thr Ile Ile Cys Tyr Cys Ala Ser Phe Trp Leu Leu Ala
        35                  40                  45

Gln Thr Leu Ala Tyr Ile Pro Thr Gly Ile Ala Tyr Ala Ile Trp Ser
    50                  55                  60

Gly Val Gly Ile Val Leu Ile Ser Leu Leu Ser Trp Gly Phe Phe Gly
65                  70                  75                  80

Gln Arg Leu Asp Leu Pro Ala Ile Ile Gly Met Met Leu Ile Cys Ala
                85                  90                  95

Gly Val Leu Val Ile Asn Leu Leu Ser Arg Ser Ala Pro His
            100                 105                 110

<210> SEQ ID NO 225
<211> LENGTH: 110
<212> TYPE: PRT
<213> ORGANISM: Escherichia coli
```

<400> SEQUENCE: 225

Met Asn Pro Tyr Ile Tyr Leu Gly Gly Ala Ile Leu Ala Glu Val Ile
1               5                   10                  15

Gly Thr Thr Leu Met Lys Phe Ser Glu Gly Phe Thr Arg Leu Trp Pro
            20                  25                  30

Ser Val Gly Thr Ile Ile Cys Tyr Cys Ala Ser Phe Trp Leu Leu Ala
        35                  40                  45

Gln Thr Leu Ala Tyr Ile Pro Thr Gly Ile Ala Tyr Ala Ile Trp Ser
    50                  55                  60

Gly Val Gly Ile Val Leu Ile Ser Leu Leu Ser Trp Gly Phe Phe Gly
65                  70                  75                  80

Gln Arg Leu Asp Leu Pro Ala Ile Ile Gly Met Met Leu Ile Cys Ala
                85                  90                  95

Gly Val Leu Val Ile Asn Leu Leu Ser Arg Ser Ala Pro His
            100                 105                 110

<210> SEQ ID NO 226
<211> LENGTH: 110
<212> TYPE: PRT
<213> ORGANISM: Escherichia coli

<400> SEQUENCE: 226

Met Asn Pro Tyr Ile Tyr Leu Gly Gly Ala Ile Leu Ala Glu Val Ile
1               5                   10                  15

Gly Thr Thr Leu Met Lys Phe Ser Glu Gly Phe Thr Arg Leu Trp Pro
            20                  25                  30

Ser Val Gly Thr Ile Ile Cys Tyr Cys Ala Ser Phe Trp Leu Leu Ala
        35                  40                  45

Gln Thr Leu Ala Tyr Ile Pro Thr Gly Ile Ala Tyr Ala Ile Trp Ser
    50                  55                  60

Gly Val Gly Ile Val Leu Ile Ser Leu Leu Ser Trp Gly Phe Phe Gly
65                  70                  75                  80

Gln Arg Leu Asp Leu Pro Ala Ile Ile Gly Met Met Leu Ile Cys Ala
                85                  90                  95

Gly Val Leu Val Ile Asn Leu Leu Ser Arg Ser Ala Pro His
            100                 105                 110

<210> SEQ ID NO 227
<211> LENGTH: 110
<212> TYPE: PRT
<213> ORGANISM: Escherichia coli

<400> SEQUENCE: 227

Met Asn Pro Tyr Ile Tyr Leu Gly Gly Ala Ile Leu Ala Glu Val Ile
1               5                   10                  15

Gly Thr Thr Leu Met Lys Phe Ser Glu Gly Phe Thr Arg Leu Trp Pro
            20                  25                  30

Ser Val Gly Thr Ile Ile Cys Tyr Cys Ala Ser Phe Trp Leu Leu Ala
        35                  40                  45

Gln Thr Leu Ala Tyr Ile Pro Thr Gly Ile Ala Tyr Ala Ile Trp Ser
    50                  55                  60

Gly Val Gly Ile Val Leu Ile Ser Leu Leu Ser Trp Gly Phe Phe Gly
65                  70                  75                  80

Gln Arg Leu Asp Leu Pro Ala Ile Ile Gly Met Met Leu Ile Cys Ala
                85                  90                  95

Gly Val Leu Val Ile Asn Leu Leu Ser Arg Ser Ala Pro His
                100                 105                 110

<210> SEQ ID NO 228
<211> LENGTH: 110
<212> TYPE: PRT
<213> ORGANISM: Escherichia coli

<400> SEQUENCE: 228

Met Asn Pro Tyr Ile Tyr Leu Gly Gly Ala Ile Leu Ala Glu Val Ile
1               5                   10                  15

Gly Thr Thr Leu Met Lys Phe Ser Glu Gly Phe Thr Arg Leu Trp Pro
            20                  25                  30

Ser Val Gly Thr Ile Ile Cys Tyr Cys Ala Ser Phe Trp Leu Leu Ala
        35                  40                  45

Gln Thr Leu Ala Tyr Ile Pro Thr Gly Ile Ala Tyr Ala Ile Trp Ser
    50                  55                  60

Gly Val Gly Ile Val Leu Ile Ser Leu Leu Ser Trp Gly Phe Phe Gly
65                  70                  75                  80

Gln Arg Leu Asp Leu Pro Ala Ile Ile Gly Met Met Leu Ile Cys Ala
                85                  90                  95

Gly Val Leu Val Ile Asn Leu Leu Ser Arg Ser Thr Pro His
                100                 105                 110

<210> SEQ ID NO 229
<211> LENGTH: 110
<212> TYPE: PRT
<213> ORGANISM: Escherichia fergusonii

<400> SEQUENCE: 229

Met Asn Pro Tyr Ile Tyr Leu Gly Gly Ala Ile Leu Ala Glu Val Ile
1               5                   10                  15

Gly Thr Thr Leu Met Lys Phe Ser Glu Gly Phe Thr Arg Leu Trp Pro
            20                  25                  30

Ser Val Gly Thr Ile Ile Cys Tyr Cys Ala Ser Phe Trp Leu Leu Ala
        35                  40                  45

Gln Thr Leu Ala Tyr Ile Pro Thr Gly Ile Ala Tyr Ala Ile Trp Ser
    50                  55                  60

Gly Val Gly Ile Val Leu Ile Ser Leu Leu Ser Trp Gly Leu Phe Gly
65                  70                  75                  80

Gln Arg Leu Asp Leu Pro Ala Ile Ile Gly Met Met Leu Ile Cys Ala
                85                  90                  95

Gly Val Leu Val Ile Asn Leu Leu Ser Arg Ser Thr Pro His
                100                 105                 110

<210> SEQ ID NO 230
<211> LENGTH: 110
<212> TYPE: PRT
<213> ORGANISM: Escherichia coli

<400> SEQUENCE: 230

Met Asn Pro Tyr Ile Tyr Leu Gly Gly Ala Ile Leu Ala Glu Val Ile
1               5                   10                  15

Gly Thr Thr Leu Met Lys Phe Ser Glu Gly Phe Thr Arg Leu Trp Pro
            20                  25                  30

Ser Val Gly Thr Ile Ile Cys Tyr Cys Ala Ser Phe Trp Leu Leu Ala
        35                  40                  45

```
Gln Thr Leu Ala Tyr Ile Pro Thr Gly Ile Ala Tyr Ala Ile Trp Ser
        50                  55                  60

Gly Val Gly Ile Val Leu Ile Ser Leu Leu Ser Trp Gly Phe Phe Gly
 65                  70                  75                  80

Gln Arg Leu Asp Leu Pro Ala Ile Ile Gly Met Met Leu Ile Cys Ala
                85                  90                  95

Gly Val Leu Val Ile Asn Leu Leu Ser Arg Ser Ala Pro His
               100                 105                 110

<210> SEQ ID NO 231
<211> LENGTH: 110
<212> TYPE: PRT
<213> ORGANISM: Escherichia coli

<400> SEQUENCE: 231

Met Asn Pro Tyr Ile Tyr Leu Gly Gly Ala Ile Leu Ala Glu Val Ile
 1               5                  10                  15

Gly Thr Thr Leu Met Lys Phe Ser Glu Gly Phe Thr Arg Leu Trp Pro
                20                  25                  30

Ser Val Gly Thr Ile Ile Cys Tyr Cys Ala Ser Phe Trp Leu Leu Ala
                35                  40                  45

Gln Thr Leu Ala Tyr Ile Pro Thr Gly Ile Ala Tyr Ala Ile Trp Ser
        50                  55                  60

Gly Val Gly Ile Val Leu Ile Ser Leu Leu Ser Trp Gly Leu Phe Gly
 65                  70                  75                  80

Gln Arg Leu Asp Leu Pro Ala Ile Ile Gly Met Met Leu Ile Cys Ala
                85                  90                  95

Gly Val Leu Val Ile Asn Leu Leu Ser Arg Ser Thr Pro His
               100                 105                 110

<210> SEQ ID NO 232
<211> LENGTH: 110
<212> TYPE: PRT
<213> ORGANISM: Escherichia coli

<400> SEQUENCE: 232

Met Asn Pro Tyr Ile Tyr Leu Gly Gly Ala Ile Leu Ala Glu Val Ile
 1               5                  10                  15

Gly Thr Thr Leu Met Lys Phe Ser Glu Gly Phe Thr Arg Leu Trp Pro
                20                  25                  30

Ser Val Gly Thr Ile Ile Cys Tyr Cys Ala Ser Phe Trp Leu Leu Ala
                35                  40                  45

Gln Thr Leu Ala Tyr Ile Pro Thr Gly Ile Ala Tyr Ala Ile Trp Ser
        50                  55                  60

Gly Val Gly Ile Val Leu Ile Ser Leu Leu Ser Trp Gly Phe Phe Gly
 65                  70                  75                  80

Gln Arg Leu Asp Leu Pro Ala Ile Ile Gly Met Met Leu Ile Cys Ala
                85                  90                  95

Gly Val Leu Val Ile Asn Leu Leu Ser Arg Ser Ala Pro His
               100                 105                 110

<210> SEQ ID NO 233
<211> LENGTH: 110
<212> TYPE: PRT
<213> ORGANISM: Escherichia coli
```

<400> SEQUENCE: 233

Met Asn Pro Tyr Ile Tyr Leu Gly Gly Ala Ile Leu Ala Glu Val Ile
1               5                   10                  15

Gly Thr Thr Leu Met Lys Phe Ser Glu Gly Phe Thr Arg Leu Trp Pro
            20                  25                  30

Ser Val Gly Thr Ile Ile Cys Tyr Cys Ala Ser Phe Trp Leu Leu Ala
        35                  40                  45

Gln Thr Leu Ala Tyr Ile Pro Thr Gly Ile Ala Tyr Ala Ile Trp Ser
    50                  55                  60

Gly Val Gly Ile Val Leu Ile Ser Leu Ser Trp Gly Phe Phe Gly
65                  70                  75                  80

Gln Arg Leu Asp Leu Pro Ala Ile Ile Gly Met Met Leu Ile Cys Ala
                85                  90                  95

Gly Val Leu Val Ile Asn Leu Leu Ser Arg Ser Thr Pro His
            100                 105                 110

<210> SEQ ID NO 234
<211> LENGTH: 110
<212> TYPE: PRT
<213> ORGANISM: Escherichia coli

<400> SEQUENCE: 234

Met Asn Pro Tyr Ile Tyr Leu Gly Gly Ala Ile Leu Ala Glu Val Ile
1               5                   10                  15

Gly Thr Thr Leu Met Lys Phe Ser Glu Gly Phe Thr Arg Leu Trp Pro
            20                  25                  30

Ser Val Gly Thr Ile Ile Cys Tyr Cys Ala Ser Phe Trp Leu Leu Ala
        35                  40                  45

Gln Thr Leu Ala Tyr Ile Pro Thr Gly Ile Ala Tyr Ala Ile Trp Ser
    50                  55                  60

Gly Val Gly Ile Val Leu Ile Ser Leu Ser Trp Gly Phe Phe Gly
65                  70                  75                  80

Gln Arg Leu Asp Leu Pro Ala Ile Ile Gly Met Met Leu Ile Cys Ala
                85                  90                  95

Gly Val Leu Val Ile Asn Leu Leu Ser Arg Ser Ala Pro His
            100                 105                 110

<210> SEQ ID NO 235
<211> LENGTH: 110
<212> TYPE: PRT
<213> ORGANISM: Klebsiella oxytoca

<400> SEQUENCE: 235

Met Asn Pro Tyr Ile Tyr Leu Gly Gly Ala Ile Leu Ala Glu Val Ile
1               5                   10                  15

Gly Thr Thr Leu Met Lys Phe Ser Glu Gly Phe Thr Arg Leu Trp Pro
            20                  25                  30

Ser Val Gly Thr Ile Ile Cys Tyr Cys Ala Ser Phe Trp Leu Leu Ala
        35                  40                  45

Gln Thr Leu Ala Tyr Ile Pro Thr Gly Ile Ala Tyr Ala Ile Trp Ser
    50                  55                  60

Gly Val Gly Ile Val Leu Ile Ser Leu Ser Trp Gly Leu Phe Gly
65                  70                  75                  80

Gln Arg Leu Asp Leu Pro Ala Ile Ile Gly Met Met Leu Ile Cys Ala
                85                  90                  95

-continued

Gly Val Leu Val Ile Asn Leu Leu Ser Arg Ser Thr Pro His
            100                 105                 110

<210> SEQ ID NO 236
<211> LENGTH: 110
<212> TYPE: PRT
<213> ORGANISM: Escherichia coli

<400> SEQUENCE: 236

Met Asn Pro Tyr Ile Tyr Leu Gly Gly Ala Ile Leu Ala Gln Val Ile
1               5                   10                  15

Gly Thr Thr Leu Met Lys Phe Ser Glu Gly Phe Thr Arg Leu Trp Pro
            20                  25                  30

Ser Val Gly Thr Ile Ile Cys Tyr Cys Ala Ser Phe Trp Leu Leu Ala
        35                  40                  45

Gln Thr Leu Ala Tyr Ile Pro Thr Gly Ile Ala Tyr Ala Ile Trp Ser
    50                  55                  60

Gly Val Gly Ile Val Leu Ile Ser Leu Leu Ser Trp Gly Phe Phe Gly
65                  70                  75                  80

Gln Arg Leu Asp Leu Pro Ala Ile Ile Gly Met Met Leu Ile Cys Ala
                85                  90                  95

Gly Val Leu Val Ile Asn Leu Leu Ser Arg Ser Thr Pro His
            100                 105                 110

<210> SEQ ID NO 237
<211> LENGTH: 110
<212> TYPE: PRT
<213> ORGANISM: Escherichia coli

<400> SEQUENCE: 237

Met Asn Pro Tyr Ile Tyr Leu Gly Gly Ala Ile Leu Ala Glu Val Ile
1               5                   10                  15

Gly Thr Thr Leu Met Lys Phe Ser Glu Gly Phe Thr Arg Leu Trp Pro
            20                  25                  30

Ser Val Gly Thr Ile Ile Cys Tyr Cys Ala Ser Phe Trp Leu Leu Ala
        35                  40                  45

Gln Thr Leu Ala Tyr Ile Pro Thr Gly Ile Ala Tyr Ala Ile Trp Ser
    50                  55                  60

Gly Val Gly Ile Val Leu Ile Ser Leu Leu Ser Trp Gly Phe Phe Ser
65                  70                  75                  80

Gln Arg Leu Asp Leu Pro Ala Ile Ile Gly Met Met Leu Ile Cys Ala
                85                  90                  95

Gly Val Leu Val Ile Asn Leu Leu Ser Arg Ser Ala Pro His
            100                 105                 110

<210> SEQ ID NO 238
<211> LENGTH: 110
<212> TYPE: PRT
<213> ORGANISM: Escherichia coli

<400> SEQUENCE: 238

Met Asn Pro Tyr Ile Tyr Leu Gly Gly Ala Ile Leu Ala Glu Val Ile
1               5                   10                  15

Gly Thr Thr Leu Met Lys Phe Ser Glu Gly Phe Thr Arg Leu Trp Pro
            20                  25                  30

Ser Val Gly Thr Ile Ile Cys Tyr Cys Ala Ser Phe Trp Leu Leu Ala
        35                  40                  45

Gln Thr Leu Ala Tyr Ile Pro Thr Gly Ile Ala Tyr Ala Ile Trp Ser
            50                  55                  60

Gly Val Gly Ile Val Leu Ile Ser Leu Leu Ser Trp Gly Phe Phe Gly
 65                  70                  75                  80

Gln Arg Leu Asp Leu Pro Ala Ile Ile Gly Met Met Leu Ile Cys Ala
                85                  90                  95

Gly Val Leu Val Ile Asn Leu Leu Ser Arg Ser Ala Pro His
            100                 105                 110

<210> SEQ ID NO 239
<211> LENGTH: 110
<212> TYPE: PRT
<213> ORGANISM: Escherichia fergusonii

<400> SEQUENCE: 239

Met Asn Pro Tyr Ile Tyr Leu Gly Gly Ala Ile Leu Ala Glu Val Ile
 1               5                  10                  15

Gly Thr Thr Leu Met Lys Phe Ser Glu Gly Phe Thr Arg Leu Trp Pro
                20                  25                  30

Ser Val Gly Thr Ile Ile Cys Tyr Cys Ala Ser Phe Trp Leu Leu Ala
            35                  40                  45

Gln Thr Leu Ala Tyr Ile Pro Thr Gly Ile Ala Tyr Ala Ile Trp Ser
            50                  55                  60

Gly Val Gly Ile Val Leu Ile Ser Leu Leu Ser Trp Gly Phe Phe Gly
 65                  70                  75                  80

Gln Arg Leu Asp Leu Pro Ala Ile Ile Gly Met Met Leu Ile Cys Ala
                85                  90                  95

Gly Val Leu Val Ile Asn Leu Leu Ser Arg Ser Ala Pro His
            100                 105                 110

<210> SEQ ID NO 240
<211> LENGTH: 110
<212> TYPE: PRT
<213> ORGANISM: Escherichia coli

<400> SEQUENCE: 240

Met Asn Pro Tyr Ile Tyr Leu Gly Gly Ala Ile Leu Ala Glu Val Ile
 1               5                  10                  15

Gly Thr Thr Leu Met Lys Phe Ser Glu Gly Phe Thr Arg Leu Trp Pro
                20                  25                  30

Ser Val Gly Thr Ile Ile Cys Tyr Cys Ala Ser Phe Trp Leu Leu Ala
            35                  40                  45

Gln Thr Leu Ala Tyr Ile Pro Thr Gly Ile Ala Tyr Ala Ile Trp Ser
            50                  55                  60

Gly Val Gly Ile Val Leu Ile Ser Leu Leu Ser Trp Gly Phe Phe Gly
 65                  70                  75                  80

Gln Arg Leu Asp Leu Pro Ala Ile Ile Gly Met Met Leu Ile Cys Ala
                85                  90                  95

Gly Val Leu Val Ile Asn Leu Leu Ser Arg Ser Thr Pro His
            100                 105                 110

<210> SEQ ID NO 241
<211> LENGTH: 110
<212> TYPE: PRT
<213> ORGANISM: Escherichia coli

<400> SEQUENCE: 241

Met Asn Pro Tyr Ile Tyr Leu Gly Gly Ala Ile Leu Ala Glu Val Ile
1               5                   10                  15

Gly Thr Thr Leu Met Lys Phe Ser Glu Gly Phe Thr Arg Leu Trp Pro
            20                  25                  30

Ser Val Gly Thr Ile Ile Cys Tyr Cys Ala Ser Phe Trp Leu Leu Ala
        35                  40                  45

Gln Thr Leu Ala Tyr Ile Pro Thr Gly Ile Ala Tyr Ala Ile Trp Ser
    50                  55                  60

Gly Val Gly Ile Val Leu Ile Ser Leu Leu Ser Trp Gly Phe Phe Gly
65                  70                  75                  80

Gln Arg Leu Asp Leu Pro Ala Ile Ile Gly Met Met Leu Ile Cys Ala
                85                  90                  95

Gly Val Leu Val Ile Asn Leu Leu Ser Arg Ser Ala Pro His
            100                 105                 110

<210> SEQ ID NO 242
<211> LENGTH: 110
<212> TYPE: PRT
<213> ORGANISM: Escherichia coli

<400> SEQUENCE: 242

Met Asn Pro Tyr Ile Tyr Leu Gly Gly Ala Ile Leu Ala Glu Val Ile
1               5                   10                  15

Gly Thr Thr Leu Met Lys Phe Ser Glu Gly Phe Thr Arg Leu Trp Pro
            20                  25                  30

Ser Val Gly Thr Ile Ile Cys Tyr Cys Ala Ser Phe Trp Leu Leu Ala
        35                  40                  45

Gln Thr Leu Ala Tyr Ile Pro Thr Gly Ile Ala Tyr Ala Ile Trp Ser
    50                  55                  60

Gly Val Gly Ile Val Leu Ile Ser Leu Leu Ser Trp Gly Phe Phe Gly
65                  70                  75                  80

Gln Arg Leu Asp Leu Pro Ala Ile Ile Gly Met Met Leu Ile Cys Ala
                85                  90                  95

Gly Val Leu Val Ile Asn Leu Leu Ser Arg Ser Thr Pro His
            100                 105                 110

<210> SEQ ID NO 243
<211> LENGTH: 110
<212> TYPE: PRT
<213> ORGANISM: Escherichia coli

<400> SEQUENCE: 243

Met Asn Pro Tyr Ile Tyr Leu Gly Gly Ala Ile Leu Ala Glu Val Ile
1               5                   10                  15

Gly Thr Thr Leu Met Lys Phe Ser Glu Gly Phe Thr Arg Leu Trp Pro
            20                  25                  30

Ser Val Gly Thr Ile Ile Cys Tyr Cys Ala Ser Phe Trp Leu Leu Ala
        35                  40                  45

Gln Thr Leu Ala Tyr Ile Pro Thr Gly Ile Ala Tyr Ala Ile Trp Ser
    50                  55                  60

Gly Val Gly Ile Val Leu Ile Ser Leu Leu Ser Trp Gly Phe Phe Gly
65                  70                  75                  80

Gln Arg Leu Asp Leu Pro Ala Ile Ile Gly Met Met Leu Ile Cys Ala
                85                  90                  95

Gly Val Leu Val Ile Asn Leu Leu Ser Arg Ser Ala Pro His
            100                 105                 110

<210> SEQ ID NO 244
<211> LENGTH: 110
<212> TYPE: PRT
<213> ORGANISM: Escherichia coli

<400> SEQUENCE: 244

Met Asn Pro Tyr Ile Tyr Leu Gly Gly Ala Ile Leu Ala Glu Val Ile
1               5                   10                  15

Gly Thr Thr Leu Met Lys Phe Ser Glu Gly Phe Thr Arg Leu Trp Pro
            20                  25                  30

Ser Val Gly Thr Ile Ile Cys Tyr Cys Ala Ser Phe Trp Leu Leu Ala
        35                  40                  45

Gln Thr Leu Ala Tyr Ile Pro Thr Gly Ile Ala Tyr Ala Ile Trp Ser
    50                  55                  60

Gly Val Gly Ile Val Leu Ile Ser Leu Leu Ser Trp Gly Phe Phe Gly
65                  70                  75                  80

Gln Arg Leu Asp Leu Pro Ala Ile Ile Gly Met Met Leu Ile Cys Ala
                85                  90                  95

Gly Val Leu Val Ile Asn Leu Leu Ser Arg Ser Ala Pro His
            100                 105                 110

<210> SEQ ID NO 245
<211> LENGTH: 110
<212> TYPE: PRT
<213> ORGANISM: Escherichia coli

<400> SEQUENCE: 245

Met Asn Pro Tyr Ile Tyr Leu Gly Gly Ala Ile Leu Ala Glu Val Ile
1               5                   10                  15

Gly Thr Thr Leu Met Lys Phe Ser Glu Gly Phe Thr Arg Leu Trp Pro
            20                  25                  30

Ser Val Gly Thr Ile Ile Cys Tyr Cys Ala Ser Phe Trp Leu Leu Ala
        35                  40                  45

Gln Thr Leu Ala Tyr Ile Pro Thr Gly Ile Ala Tyr Ala Ile Trp Ser
    50                  55                  60

Gly Val Gly Ile Val Leu Ile Ser Leu Leu Ser Trp Gly Phe Phe Gly
65                  70                  75                  80

Gln Arg Leu Asp Leu Pro Ala Ile Ile Gly Met Met Leu Ile Cys Ala
                85                  90                  95

Gly Val Leu Val Ile Asn Leu Leu Ser Arg Ser Ala Pro His
            100                 105                 110

<210> SEQ ID NO 246
<211> LENGTH: 110
<212> TYPE: PRT
<213> ORGANISM: Escherichia albertii

<400> SEQUENCE: 246

Met Asn Pro Tyr Ile Tyr Leu Gly Gly Ala Ile Leu Ala Glu Val Ile
1               5                   10                  15

Gly Thr Thr Leu Met Lys Phe Ser Glu Gly Phe Thr Arg Leu Trp Pro
            20                  25                  30

Ser Val Gly Thr Ile Ile Cys Tyr Cys Ala Ser Phe Trp Leu Leu Ala
        35                  40                  45

```
Gln Thr Leu Ala Tyr Ile Pro Thr Gly Ile Ala Tyr Ala Ile Trp Ser
            50                  55                  60

Gly Val Gly Ile Val Leu Ile Ser Leu Leu Ser Trp Gly Ile Phe Gly
 65                  70                  75                  80

Gln Arg Leu Asp Leu Pro Ala Ile Ile Gly Met Met Leu Ile Cys Ala
                85                  90                  95

Gly Val Leu Val Ile Asn Leu Leu Ser Arg Ser Ala Thr His
            100                 105                 110

<210> SEQ ID NO 247
<211> LENGTH: 110
<212> TYPE: PRT
<213> ORGANISM: Escherichia sp.

<400> SEQUENCE: 247

Met Asn Pro Tyr Ile Tyr Leu Gly Gly Ala Ile Leu Ala Glu Val Ile
 1               5                  10                  15

Gly Thr Thr Leu Met Lys Phe Ser Glu Gly Phe Thr Arg Leu Trp Pro
                20                  25                  30

Ser Val Gly Thr Ile Ile Cys Tyr Cys Thr Ser Phe Trp Leu Leu Ala
            35                  40                  45

Gln Thr Leu Ala Tyr Ile Pro Thr Gly Ile Ala Tyr Ala Ile Trp Ser
            50                  55                  60

Gly Val Gly Ile Val Leu Ile Ser Leu Leu Ser Trp Gly Phe Phe Gly
 65                  70                  75                  80

Gln Arg Leu Asp Leu Pro Ala Ile Ile Gly Met Met Leu Ile Cys Ala
                85                  90                  95

Gly Val Leu Val Ile Asn Leu Leu Ser Arg Ser Ala Pro His
            100                 105                 110

<210> SEQ ID NO 248
<211> LENGTH: 110
<212> TYPE: PRT
<213> ORGANISM: Escherichia sp.

<400> SEQUENCE: 248

Met Asn Pro Tyr Ile Tyr Leu Gly Gly Ala Ile Leu Ala Glu Val Ile
 1               5                  10                  15

Gly Thr Thr Leu Met Lys Phe Ser Glu Gly Phe Thr Arg Leu Trp Pro
                20                  25                  30

Ser Val Gly Thr Ile Ile Cys Tyr Cys Ala Ser Phe Trp Leu Leu Ala
            35                  40                  45

Gln Thr Leu Ala Tyr Ile Pro Thr Gly Ile Ala Tyr Ala Ile Trp Ser
            50                  55                  60

Gly Val Gly Ile Val Leu Ile Ser Leu Leu Ser Trp Gly Phe Phe Gly
 65                  70                  75                  80

Gln Arg Leu Asp Leu Pro Ala Ile Ile Gly Met Met Leu Ile Cys Ala
                85                  90                  95

Gly Val Leu Val Ile Asn Leu Leu Ser Arg Ser Ala Pro His
            100                 105                 110

<210> SEQ ID NO 249
<211> LENGTH: 110
<212> TYPE: PRT
<213> ORGANISM: Escherichia coli
```

-continued

<400> SEQUENCE: 249

Met Asn Pro Tyr Ile Tyr Leu Gly Gly Ala Ile Leu Ala Glu Val Ile
1               5                   10                  15

Gly Thr Thr Leu Met Lys Phe Ser Glu Gly Phe Thr Arg Leu Trp Pro
            20                  25                  30

Ser Val Gly Thr Ile Ile Cys Tyr Cys Ala Ser Phe Trp Leu Leu Ala
        35                  40                  45

Gln Thr Leu Ala Tyr Ile Pro Thr Gly Ile Ala Tyr Ala Ile Trp Ser
    50                  55                  60

Gly Val Gly Ile Val Leu Ile Ser Leu Ser Trp Gly Phe Phe Gly
65                  70                  75                  80

Gln Arg Leu Asp Leu Pro Ala Ile Ile Gly Met Met Leu Ile Cys Ala
                85                  90                  95

Gly Val Leu Val Ile Asn Leu Leu Ser Arg Ser Ala Pro His
            100                 105                 110

<210> SEQ ID NO 250
<211> LENGTH: 110
<212> TYPE: PRT
<213> ORGANISM: Escherichia coli

<400> SEQUENCE: 250

Met Asn Pro Tyr Ile Tyr Leu Gly Gly Ala Ile Leu Ala Glu Val Ile
1               5                   10                  15

Gly Thr Thr Leu Met Lys Phe Ser Glu Gly Phe Thr Arg Leu Trp Pro
            20                  25                  30

Ser Val Gly Thr Ile Ile Cys Tyr Cys Ala Ser Phe Trp Leu Leu Ala
        35                  40                  45

Gln Thr Leu Ala Tyr Ile Pro Thr Gly Ile Ala Tyr Ala Ile Trp Ser
    50                  55                  60

Gly Val Gly Ile Val Leu Ile Ser Leu Ser Trp Gly Phe Phe Gly
65                  70                  75                  80

Gln Arg Leu Asp Leu Pro Ala Ile Ile Gly Met Met Leu Ile Cys Ala
                85                  90                  95

Gly Val Leu Val Ile Asn Leu Leu Ser Arg Ser Ala Pro His
            100                 105                 110

<210> SEQ ID NO 251
<211> LENGTH: 110
<212> TYPE: PRT
<213> ORGANISM: Escherichia coli

<400> SEQUENCE: 251

Met Asn Pro Tyr Ile Tyr Leu Gly Gly Ala Ile Leu Ala Glu Val Ile
1               5                   10                  15

Gly Thr Thr Leu Met Lys Phe Ser Glu Gly Phe Thr Arg Leu Trp Pro
            20                  25                  30

Ser Val Gly Thr Ile Ile Cys Tyr Cys Ala Ser Phe Trp Leu Leu Ala
        35                  40                  45

Gln Thr Leu Ala Tyr Ile Pro Thr Gly Ile Ala Tyr Ala Ile Trp Ser
    50                  55                  60

Gly Val Gly Ile Val Leu Ile Ser Leu Ser Trp Gly Phe Phe Gly
65                  70                  75                  80

Gln Arg Leu Asp Leu Pro Ala Ile Ile Gly Met Met Leu Ile Cys Ala
                85                  90                  95

```
Gly Val Leu Val Ile Asn Leu Leu Ser Arg Ser Ala Pro His
            100                 105                 110
```

<210> SEQ ID NO 252
<211> LENGTH: 110
<212> TYPE: PRT
<213> ORGANISM: Achromobacter sp.

<400> SEQUENCE: 252

```
Met Asn Pro Tyr Ile Tyr Leu Gly Gly Ala Ile Leu Ala Glu Val Ile
1               5                   10                  15

Gly Thr Thr Leu Met Lys Phe Ser Glu Gly Phe Thr Arg Leu Trp Pro
            20                  25                  30

Ser Val Gly Thr Ile Ile Cys Tyr Cys Ala Ser Phe Trp Leu Leu Ala
        35                  40                  45

Gln Thr Leu Ala Tyr Ile Pro Thr Gly Ile Ala Tyr Ala Ile Trp Ser
    50                  55                  60

Gly Val Gly Ile Val Leu Ile Ser Leu Leu Ser Trp Gly Phe Phe Gly
65                  70                  75                  80

Gln Arg Leu Asp Leu Pro Ala Ile Ile Gly Met Met Leu Ile Cys Ala
                85                  90                  95

Gly Val Leu Val Ile Asn Leu Leu Ser Arg Ser Ala Pro His
            100                 105                 110
```

<210> SEQ ID NO 253
<211> LENGTH: 110
<212> TYPE: PRT
<213> ORGANISM: Escherichia coli

<400> SEQUENCE: 253

```
Met Asn Pro Tyr Ile Tyr Leu Gly Gly Ala Ile Leu Ala Glu Val Ile
1               5                   10                  15

Gly Thr Thr Leu Met Lys Phe Ser Glu Gly Phe Thr Arg Leu Trp Pro
            20                  25                  30

Ser Val Gly Thr Ile Ile Cys Tyr Cys Ala Ser Phe Trp Leu Leu Ala
        35                  40                  45

Gln Thr Leu Ala Tyr Ile Pro Thr Gly Ile Ala Tyr Ala Ile Trp Ser
    50                  55                  60

Gly Val Gly Ile Val Leu Ile Ser Leu Leu Ser Trp Gly Phe Phe Gly
65                  70                  75                  80

Gln Arg Leu Asp Leu Pro Ala Ile Ile Gly Met Met Leu Ile Cys Ala
                85                  90                  95

Gly Val Leu Val Ile Asn Leu Leu Ser Arg Ser Thr Pro His
            100                 105                 110
```

<210> SEQ ID NO 254
<211> LENGTH: 110
<212> TYPE: PRT
<213> ORGANISM: Escherichia coli

<400> SEQUENCE: 254

```
Met Asn Pro Tyr Ile Tyr Leu Gly Gly Ala Ile Leu Ala Glu Val Ile
1               5                   10                  15

Gly Thr Thr Leu Met Lys Phe Ser Glu Gly Phe Thr Arg Leu Trp Pro
            20                  25                  30

Ser Val Gly Thr Ile Ile Cys Tyr Cys Ala Ser Phe Trp Leu Leu Ala
        35                  40                  45
```

Gln Thr Leu Ala Tyr Ile Pro Thr Gly Ile Ala Tyr Ala Ile Trp Ser
    50                  55                  60

Gly Val Gly Ile Val Leu Ile Ser Leu Leu Ser Trp Gly Phe Phe Gly
65                  70                  75                  80

Gln Arg Leu Asp Leu Pro Ala Ile Ile Gly Met Met Leu Ile Cys Ala
                85                  90                  95

Gly Val Leu Val Ile Asn Leu Leu Ser Arg Ser Ala Pro His
            100                 105                 110

<210> SEQ ID NO 255
<211> LENGTH: 110
<212> TYPE: PRT
<213> ORGANISM: Escherichia coli

<400> SEQUENCE: 255

Met Asn Pro Tyr Ile Tyr Leu Gly Gly Ala Ile Leu Ala Glu Val Ile
1               5                   10                  15

Gly Thr Thr Leu Met Lys Phe Ser Glu Gly Phe Thr Arg Leu Trp Pro
                20                  25                  30

Ser Val Gly Thr Ile Ile Cys Tyr Cys Ala Ser Phe Trp Leu Leu Ala
            35                  40                  45

Gln Thr Leu Ala Tyr Ile Pro Thr Gly Ile Ala Tyr Ala Ile Trp Ser
    50                  55                  60

Gly Val Gly Ile Val Leu Ile Ser Leu Leu Ser Trp Gly Phe Phe Gly
65                  70                  75                  80

Gln Arg Leu Asp Leu Pro Ala Ile Ile Gly Met Met Leu Ile Cys Ala
                85                  90                  95

Gly Val Leu Val Ile Asn Leu Leu Ser Arg Ser Ala Pro His
            100                 105                 110

<210> SEQ ID NO 256
<211> LENGTH: 110
<212> TYPE: PRT
<213> ORGANISM: Escherichia coli

<400> SEQUENCE: 256

Met Asn Pro Tyr Ile Tyr Leu Gly Gly Ala Ile Leu Ala Glu Val Ile
1               5                   10                  15

Gly Thr Thr Leu Met Lys Phe Ser Glu Gly Phe Thr Arg Leu Trp Pro
                20                  25                  30

Ser Val Gly Thr Ile Ile Cys Tyr Cys Ala Ser Phe Trp Leu Leu Ala
            35                  40                  45

Gln Thr Leu Ala Tyr Ile Pro Thr Gly Ile Ala Tyr Ala Ile Trp Ser
    50                  55                  60

Gly Val Gly Ile Val Leu Ile Ser Leu Leu Ser Trp Gly Phe Phe Gly
65                  70                  75                  80

Gln Arg Leu Asp Leu Pro Ala Ile Ile Gly Met Met Leu Ile Cys Ala
                85                  90                  95

Gly Val Leu Val Ile Asn Leu Leu Ser Arg Ser Ala Pro His
            100                 105                 110

<210> SEQ ID NO 257
<211> LENGTH: 110
<212> TYPE: PRT
<213> ORGANISM: Escherichia coli

<400> SEQUENCE: 257

Met Asn Pro Tyr Ile Tyr Leu Gly Gly Ala Ile Leu Ala Glu Val Ile
1               5                   10                  15

Gly Thr Thr Leu Met Lys Phe Ser Glu Gly Phe Thr Arg Leu Trp Pro
            20                  25                  30

Ser Val Gly Thr Ile Ile Cys Tyr Cys Ala Ser Phe Trp Leu Leu Ala
        35                  40                  45

Gln Thr Leu Ala Tyr Ile Pro Thr Gly Ile Ala Tyr Ala Ile Trp Ser
    50                  55                  60

Gly Val Gly Ile Val Leu Ile Ser Leu Ser Trp Gly Phe Phe Gly
65                  70                  75                  80

Gln Arg Leu Asp Leu Pro Ala Ile Ile Gly Met Met Leu Ile Cys Ala
                85                  90                  95

Gly Val Leu Val Ile Asn Leu Leu Ser Arg Ser Ala Pro His
            100                 105                 110

<210> SEQ ID NO 258
<211> LENGTH: 110
<212> TYPE: PRT
<213> ORGANISM: Escherichia coli

<400> SEQUENCE: 258

Met Asn Pro Tyr Ile Tyr Leu Gly Gly Ala Ile Leu Ala Glu Val Ile
1               5                   10                  15

Gly Thr Thr Leu Met Lys Phe Ser Glu Gly Phe Thr Arg Leu Trp Pro
            20                  25                  30

Ser Val Gly Thr Ile Ile Cys Tyr Cys Ala Ser Phe Trp Leu Leu Ala
        35                  40                  45

Gln Thr Leu Ala Tyr Ile Pro Thr Gly Ile Ala Tyr Ala Ile Trp Ser
    50                  55                  60

Gly Val Gly Ile Val Leu Ile Ser Leu Ser Trp Gly Phe Phe Gly
65                  70                  75                  80

Gln Arg Leu Asp Leu Pro Ala Ile Ile Gly Met Met Leu Ile Cys Ala
                85                  90                  95

Gly Val Leu Val Ile Asn Leu Leu Ser Arg Ser Ala Pro His
            100                 105                 110

<210> SEQ ID NO 259
<211> LENGTH: 110
<212> TYPE: PRT
<213> ORGANISM: Escherichia coli

<400> SEQUENCE: 259

Met Asn Pro Tyr Ile Tyr Leu Gly Gly Ala Ile Leu Ala Glu Val Ile
1               5                   10                  15

Gly Thr Thr Leu Met Lys Phe Ser Glu Gly Phe Thr Arg Leu Trp Pro
            20                  25                  30

Ser Val Gly Thr Ile Ile Cys Tyr Cys Ala Ser Phe Trp Leu Leu Ala
        35                  40                  45

Gln Thr Leu Ala Tyr Ile Pro Thr Gly Ile Ala Tyr Ala Ile Trp Ser
    50                  55                  60

Gly Val Gly Ile Val Leu Ile Ser Leu Ser Trp Gly Leu Phe Gly
65                  70                  75                  80

Gln Arg Leu Asp Leu Pro Ala Ile Ile Gly Met Met Leu Ile Cys Ala
                85                  90                  95

```
Gly Val Leu Val Ile Asn Leu Leu Ser Arg Ser Thr Pro His
            100                 105                 110
```

```
<210> SEQ ID NO 260
<211> LENGTH: 110
<212> TYPE: PRT
<213> ORGANISM: Shigella dysenteriae

<400> SEQUENCE: 260
```

```
Met Asn Pro Tyr Ile Tyr Leu Gly Gly Ala Ile Leu Ala Glu Val Ile
1               5                   10                  15

Gly Thr Thr Leu Met Lys Phe Ser Glu Gly Phe Thr Arg Leu Trp Pro
            20                  25                  30

Ser Val Gly Thr Ile Ile Cys Tyr Tyr Ala Ser Phe Trp Leu Leu Ala
        35                  40                  45

Gln Thr Leu Ala Tyr Ile Pro Thr Gly Ile Ala Tyr Ala Ile Trp Ser
    50                  55                  60

Gly Val Gly Ile Val Leu Ile Ser Leu Leu Ser Trp Gly Phe Phe Gly
65                  70                  75                  80

Gln Arg Leu Asp Leu Pro Ala Ile Ile Gly Met Met Leu Ile Cys Ala
                85                  90                  95

Gly Val Leu Val Ile Asn Leu Leu Ser Arg Ser Ala Pro His
            100                 105                 110
```

```
<210> SEQ ID NO 261
<211> LENGTH: 110
<212> TYPE: PRT
<213> ORGANISM: Escherichia coli

<400> SEQUENCE: 261
```

```
Met Asn Pro Tyr Ile Tyr Leu Gly Gly Ala Ile Leu Ala Glu Val Ile
1               5                   10                  15

Gly Thr Thr Leu Met Lys Phe Ser Glu Gly Phe Thr Arg Leu Trp Pro
            20                  25                  30

Ser Val Gly Thr Ile Ile Cys Tyr Cys Ala Ser Phe Trp Leu Leu Ala
        35                  40                  45

Gln Thr Leu Ala Tyr Ile Pro Thr Gly Ile Ala Tyr Ala Ile Trp Ser
    50                  55                  60

Gly Val Gly Ile Val Leu Ile Ser Leu Leu Ser Trp Gly Phe Phe Gly
65                  70                  75                  80

Gln Arg Leu Asp Leu Pro Ala Ile Ile Gly Met Met Leu Ile Cys Ala
                85                  90                  95

Gly Val Leu Val Ile Asn Leu Leu Ser Arg Ser Thr Pro His
            100                 105                 110
```

```
<210> SEQ ID NO 262
<211> LENGTH: 110
<212> TYPE: PRT
<213> ORGANISM: Escherichia sp.

<400> SEQUENCE: 262
```

```
Met Asn Pro Tyr Ile Tyr Leu Gly Gly Ala Ile Leu Ala Glu Val Ile
1               5                   10                  15

Gly Thr Thr Leu Met Lys Phe Ser Glu Gly Phe Thr Arg Leu Trp Pro
            20                  25                  30

Ser Val Gly Thr Ile Ile Cys Tyr Cys Thr Ser Phe Trp Leu Leu Ala
        35                  40                  45
```

Gln Thr Leu Ala Tyr Ile Pro Thr Gly Ile Ala Tyr Ala Ile Trp Ser
    50                  55                  60

Gly Val Gly Ile Val Leu Ile Ser Leu Leu Ser Trp Gly Phe Phe Gly
65                  70                  75                  80

Gln Arg Leu Asp Leu Pro Ala Ile Ile Gly Met Met Leu Ile Cys Ala
                85                  90                  95

Gly Val Leu Val Ile Asn Leu Leu Ser Arg Ser Ala Pro His
            100                 105                 110

<210> SEQ ID NO 263
<211> LENGTH: 110
<212> TYPE: PRT
<213> ORGANISM: Escherichia coli

<400> SEQUENCE: 263

Met Asn Pro Tyr Ile Tyr Leu Gly Gly Ala Ile Leu Ala Glu Val Ile
1               5                   10                  15

Gly Thr Thr Leu Met Lys Phe Ser Glu Gly Phe Thr Arg Leu Trp Pro
                20                  25                  30

Ser Val Gly Thr Ile Ile Cys Tyr Cys Ala Ser Phe Trp Leu Leu Ala
            35                  40                  45

Gln Thr Leu Ala Tyr Ile Pro Thr Gly Ile Ala Tyr Ala Ile Trp Ser
    50                  55                  60

Gly Val Gly Ile Val Leu Ile Ser Leu Leu Ser Trp Gly Phe Phe Gly
65                  70                  75                  80

Gln Arg Leu Asp Leu Pro Ala Ile Ile Gly Met Met Leu Ile Cys Ala
                85                  90                  95

Gly Val Leu Val Ile Asn Leu Leu Ser Arg Ser Ala Pro His
            100                 105                 110

<210> SEQ ID NO 264
<211> LENGTH: 110
<212> TYPE: PRT
<213> ORGANISM: Escherichia coli

<400> SEQUENCE: 264

Met Asn Pro Tyr Ile Tyr Leu Gly Gly Ala Ile Leu Ala Glu Val Ile
1               5                   10                  15

Gly Thr Thr Leu Met Lys Phe Ser Glu Gly Phe Thr Arg Leu Trp Pro
                20                  25                  30

Ser Val Gly Thr Ile Ile Cys Tyr Cys Ala Ser Phe Trp Leu Leu Ala
            35                  40                  45

Gln Thr Leu Ala Tyr Ile Pro Thr Gly Ile Ala Tyr Ala Ile Trp Ser
    50                  55                  60

Gly Val Gly Ile Val Leu Ile Ser Leu Leu Ser Trp Gly Phe Phe Gly
65                  70                  75                  80

Gln Arg Leu Asp Leu Pro Ala Ile Ile Gly Met Met Leu Ile Cys Ala
                85                  90                  95

Gly Val Leu Val Ile Asn Leu Leu Ser Arg Ser Thr Pro His
            100                 105                 110

<210> SEQ ID NO 265
<211> LENGTH: 110
<212> TYPE: PRT
<213> ORGANISM: Escherichia coli

<400> SEQUENCE: 265

Met Asn Pro Tyr Ile Tyr Leu Gly Gly Ala Ile Leu Ala Glu Val Ile
1               5                   10                  15

Gly Thr Thr Leu Met Lys Phe Ser Glu Gly Phe Thr Arg Leu Trp Pro
            20                  25                  30

Ser Val Gly Thr Ile Ile Cys Tyr Cys Ala Ser Phe Trp Leu Leu Ala
        35                  40                  45

Gln Thr Leu Ala Tyr Ile Pro Thr Gly Ile Ala Tyr Ala Ile Trp Ser
    50                  55                  60

Gly Val Gly Ile Val Leu Ile Ser Leu Leu Ser Trp Gly Phe Phe Gly
65                  70                  75                  80

Gln Arg Leu Asp Leu Pro Ala Ile Ile Gly Met Met Leu Ile Cys Ala
                85                  90                  95

Gly Val Leu Val Ile Asn Leu Leu Ser Arg Ser Ala Pro His
            100                 105                 110

<210> SEQ ID NO 266
<211> LENGTH: 110
<212> TYPE: PRT
<213> ORGANISM: Escherichia coli

<400> SEQUENCE: 266

Met Asn Pro Tyr Ile Tyr Leu Gly Gly Ala Ile Leu Ala Glu Val Ile
1               5                   10                  15

Gly Thr Thr Leu Met Lys Phe Ser Glu Gly Phe Thr Arg Leu Trp Pro
            20                  25                  30

Ser Val Gly Thr Ile Ile Cys Tyr Cys Ala Ser Phe Trp Leu Leu Ala
        35                  40                  45

Gln Thr Leu Ala Tyr Ile Pro Thr Gly Ile Ala Tyr Ala Ile Trp Ser
    50                  55                  60

Gly Val Gly Ile Val Leu Ile Ser Leu Leu Ser Trp Gly Phe Phe Gly
65                  70                  75                  80

Gln Arg Leu Asp Leu Pro Ala Ile Ile Gly Met Met Leu Ile Cys Ala
                85                  90                  95

Gly Val Leu Val Ile Asn Leu Leu Ser Arg Ser Ala Pro His
            100                 105                 110

<210> SEQ ID NO 267
<211> LENGTH: 110
<212> TYPE: PRT
<213> ORGANISM: Escherichia coli

<400> SEQUENCE: 267

Met Asn Pro Tyr Ile Tyr Leu Gly Gly Ala Ile Leu Ala Glu Val Ile
1               5                   10                  15

Gly Thr Thr Leu Met Lys Phe Ser Glu Gly Phe Thr Arg Leu Trp Pro
            20                  25                  30

Ser Val Gly Thr Ile Ile Cys Tyr Cys Ala Ser Phe Trp Leu Leu Ala
        35                  40                  45

Gln Thr Leu Ala Tyr Ile Pro Thr Gly Ile Ala Tyr Ala Ile Trp Ser
    50                  55                  60

Gly Val Gly Ile Val Leu Ile Ser Leu Leu Ser Trp Gly Phe Phe Gly
65                  70                  75                  80

Gln Arg Leu Asp Leu Pro Ala Ile Ile Gly Met Met Leu Ile Cys Ala
                85                  90                  95

Gly Val Leu Val Ile Asn Leu Leu Ser Arg Ser Ala Pro His
            100                 105                 110

<210> SEQ ID NO 268
<211> LENGTH: 110
<212> TYPE: PRT
<213> ORGANISM: Escherichia coli

<400> SEQUENCE: 268

Met Asn Pro Tyr Ile Tyr Leu Gly Gly Ala Ile Leu Ala Glu Val Ile
1               5                   10                  15

Gly Thr Thr Leu Met Lys Phe Ser Glu Gly Phe Thr Arg Leu Trp Pro
            20                  25                  30

Ser Val Gly Thr Ile Ile Cys Tyr Cys Ala Ser Phe Trp Leu Leu Ala
        35                  40                  45

Gln Thr Leu Ala Tyr Ile Pro Thr Gly Ile Ala Tyr Ala Ile Trp Ser
    50                  55                  60

Gly Val Gly Ile Val Leu Ile Ser Leu Leu Ser Trp Gly Phe Phe Gly
65                  70                  75                  80

Gln Arg Leu Asp Leu Pro Ala Ile Ile Gly Met Met Leu Ile Cys Ala
                85                  90                  95

Gly Val Leu Val Ile Asn Leu Leu Ser Arg Ser Ala Pro His
            100                 105                 110

<210> SEQ ID NO 269
<211> LENGTH: 110
<212> TYPE: PRT
<213> ORGANISM: Shigella flexneri

<400> SEQUENCE: 269

Met Asn Pro Tyr Ile Tyr Leu Gly Gly Ala Ile Leu Ala Glu Val Ile
1               5                   10                  15

Gly Thr Thr Leu Met Lys Phe Ser Glu Gly Phe Thr Arg Leu Trp Pro
            20                  25                  30

Ser Val Gly Thr Ile Ile Cys Tyr Cys Ala Ser Phe Trp Leu Leu Ala
        35                  40                  45

Gln Thr Leu Ala Tyr Ile Pro Thr Gly Ile Ala Tyr Ala Ile Trp Ser
    50                  55                  60

Gly Val Gly Ile Val Leu Ile Ser Leu Leu Ser Trp Gly Phe Phe Gly
65                  70                  75                  80

Gln Arg Leu Asp Leu Pro Ala Ile Ile Gly Met Met Leu Ile Cys Ala
                85                  90                  95

Gly Val Leu Val Ile Asn Leu Leu Ser Arg Ser Ala Pro His
            100                 105                 110

<210> SEQ ID NO 270
<211> LENGTH: 110
<212> TYPE: PRT
<213> ORGANISM: Escherichia coli

<400> SEQUENCE: 270

Met Asn Pro Tyr Ile Tyr Leu Gly Gly Ala Ile Leu Ala Glu Val Ile
1               5                   10                  15

Gly Thr Thr Leu Met Lys Phe Ser Glu Gly Phe Thr Arg Leu Trp Pro
            20                  25                  30

Ser Val Gly Thr Ile Ile Cys Tyr Cys Ala Ser Phe Trp Leu Leu Ala
        35                  40                  45

-continued

Gln Thr Leu Ala Tyr Ile Pro Thr Gly Ile Ala Tyr Ala Ile Trp Ser
            50                  55                  60

Gly Val Gly Ile Val Leu Ile Ser Leu Leu Ser Trp Gly Phe Phe Gly
 65                  70                  75                  80

Gln Arg Leu Asp Leu Pro Ala Ile Ile Gly Met Met Leu Ile Cys Ala
                85                  90                  95

Gly Val Leu Val Ile Asn Leu Leu Ser Arg Ser Thr Pro His
            100                 105                 110

<210> SEQ ID NO 271
<211> LENGTH: 110
<212> TYPE: PRT
<213> ORGANISM: Shigella flexneri

<400> SEQUENCE: 271

Met Asn Pro Tyr Ile Tyr Leu Gly Gly Ala Ile Leu Ala Glu Val Ile
 1               5                  10                  15

Gly Thr Thr Leu Met Lys Phe Ser Glu Gly Phe Thr Arg Leu Trp Pro
                20                  25                  30

Ser Val Gly Thr Ile Ile Cys Tyr Cys Ala Ser Phe Trp Leu Leu Ala
            35                  40                  45

Gln Thr Leu Ala Tyr Ile Pro Thr Gly Ile Ala Tyr Ala Ile Trp Ser
            50                  55                  60

Gly Val Gly Ile Val Leu Ile Ser Leu Leu Ser Trp Gly Phe Phe Gly
 65                  70                  75                  80

Gln Arg Leu Asp Leu Pro Ala Ile Ile Gly Met Met Leu Ile Cys Ala
                85                  90                  95

Gly Val Leu Val Ile Asn Leu Leu Ser Arg Ser Ala Pro His
            100                 105                 110

<210> SEQ ID NO 272
<211> LENGTH: 110
<212> TYPE: PRT
<213> ORGANISM: Shigella sonnei

<400> SEQUENCE: 272

Met Asn Pro Tyr Ile Tyr Leu Gly Gly Ala Ile Leu Ala Glu Val Ile
 1               5                  10                  15

Gly Thr Thr Leu Met Lys Phe Ser Glu Gly Phe Thr Arg Leu Trp Pro
                20                  25                  30

Ser Val Gly Thr Ile Ile Cys Tyr Cys Ala Ser Phe Trp Leu Leu Ala
            35                  40                  45

Gln Thr Leu Ala Tyr Ile Pro Thr Gly Ile Ala Tyr Ala Ile Trp Ser
            50                  55                  60

Gly Val Gly Ile Val Leu Ile Ser Leu Leu Ser Trp Gly Phe Phe Gly
 65                  70                  75                  80

Gln Arg Leu Asp Leu Pro Ala Ile Ile Gly Met Met Leu Ile Cys Ala
                85                  90                  95

Gly Val Leu Val Ile Asn Leu Leu Ser Arg Ser Ala Pro His
            100                 105                 110

<210> SEQ ID NO 273
<211> LENGTH: 110
<212> TYPE: PRT
<213> ORGANISM: Escherichia coli

<400> SEQUENCE: 273

Met Asn Pro Tyr Ile Tyr Leu Gly Gly Ala Ile Leu Ala Glu Val Ile
1               5                   10                  15

Gly Thr Thr Leu Met Lys Phe Ser Glu Gly Phe Thr Arg Leu Trp Pro
            20                  25                  30

Ser Val Gly Thr Ile Ile Cys Tyr Cys Ala Ser Phe Trp Leu Leu Ala
        35                  40                  45

Gln Thr Leu Ala Tyr Ile Pro Thr Gly Ile Ala Tyr Ala Ile Trp Ser
    50                  55                  60

Gly Val Gly Ile Val Leu Ile Ser Leu Leu Ser Trp Gly Phe Phe Gly
65                  70                  75                  80

Gln Arg Leu Asp Leu Pro Ala Ile Ile Gly Met Met Leu Ile Cys Ala
                85                  90                  95

Gly Val Leu Val Ile Asn Leu Leu Ser Arg Ser Ala Pro His
            100                 105                 110

<210> SEQ ID NO 274
<211> LENGTH: 110
<212> TYPE: PRT
<213> ORGANISM: Escherichia coli

<400> SEQUENCE: 274

Met Asn Pro Tyr Ile Tyr Leu Gly Gly Ala Ile Leu Ala Glu Val Ile
1               5                   10                  15

Gly Thr Thr Leu Met Lys Phe Ser Glu Gly Phe Thr Arg Leu Trp Pro
            20                  25                  30

Ser Val Gly Thr Ile Ile Cys Tyr Cys Ala Ser Phe Trp Leu Leu Ala
        35                  40                  45

Gln Thr Leu Ala Tyr Ile Pro Thr Gly Ile Ala Tyr Ala Ile Trp Ser
    50                  55                  60

Gly Val Gly Ile Val Leu Ile Ser Leu Leu Ser Trp Gly Phe Phe Gly
65                  70                  75                  80

Gln Arg Leu Asp Leu Pro Ala Ile Ile Gly Met Met Leu Ile Cys Ala
                85                  90                  95

Gly Val Leu Val Ile Asn Leu Leu Ser Arg Ser Ala Pro His
            100                 105                 110

<210> SEQ ID NO 275
<211> LENGTH: 110
<212> TYPE: PRT
<213> ORGANISM: Escherichia coli

<400> SEQUENCE: 275

Met Asn Pro Tyr Ile Tyr Leu Gly Gly Ala Ile Leu Ala Glu Val Ile
1               5                   10                  15

Gly Thr Thr Leu Met Lys Phe Ser Glu Gly Phe Thr Arg Leu Trp Pro
            20                  25                  30

Ser Val Gly Thr Ile Ile Cys Tyr Cys Ala Ser Phe Trp Leu Leu Ala
        35                  40                  45

Gln Thr Leu Ala Tyr Ile Pro Thr Gly Ile Ala Tyr Ala Ile Trp Ser
    50                  55                  60

Gly Val Gly Ile Val Leu Ile Ser Leu Leu Ser Trp Gly Leu Phe Gly
65                  70                  75                  80

Gln Arg Leu Asp Leu Pro Ala Ile Ile Gly Met Met Leu Ile Cys Ala
                85                  90                  95

```
Gly Val Leu Val Ile Asn Leu Leu Ser Arg Ser Thr Pro His
            100                 105                 110

<210> SEQ ID NO 276
<211> LENGTH: 110
<212> TYPE: PRT
<213> ORGANISM: Escherichia coli

<400> SEQUENCE: 276

Met Asn Pro Tyr Ile Tyr Leu Gly Gly Ala Ile Leu Ala Glu Val Ile
1               5                   10                  15

Gly Thr Thr Leu Met Lys Phe Ser Glu Gly Phe Thr Arg Leu Trp Pro
            20                  25                  30

Ser Val Gly Thr Ile Ile Cys Tyr Cys Ala Ser Phe Trp Leu Leu Ala
        35                  40                  45

Gln Thr Leu Ala Tyr Ile Pro Thr Gly Ile Ala Tyr Ala Ile Trp Ser
    50                  55                  60

Gly Val Gly Ile Val Leu Ile Ser Leu Leu Ser Trp Gly Phe Phe Gly
65                  70                  75                  80

Gln Arg Leu Asp Leu Pro Ala Ile Ile Gly Met Met Leu Ile Cys Ala
                85                  90                  95

Gly Val Leu Val Ile Asn Leu Leu Ser Arg Ser Thr Pro His
            100                 105                 110

<210> SEQ ID NO 277
<211> LENGTH: 110
<212> TYPE: PRT
<213> ORGANISM: Shigella dysenteriae

<400> SEQUENCE: 277

Met Asn Pro Tyr Ile Tyr Leu Gly Gly Ala Ile Leu Ala Glu Val Ile
1               5                   10                  15

Gly Thr Thr Leu Met Lys Phe Ser Glu Gly Phe Thr Arg Leu Trp Pro
            20                  25                  30

Ser Val Gly Thr Ile Ile Cys Tyr Tyr Ala Ser Phe Trp Leu Leu Ala
        35                  40                  45

Gln Thr Leu Ala Tyr Ile Pro Thr Gly Ile Ala Tyr Ala Ile Trp Ser
    50                  55                  60

Gly Val Gly Ile Val Leu Ile Ser Leu Leu Ser Trp Gly Phe Phe Gly
65                  70                  75                  80

Gln Arg Leu Asp Leu Pro Ala Ile Ile Gly Met Met Leu Ile Cys Ala
                85                  90                  95

Gly Val Leu Val Ile Asn Leu Leu Ser Arg Ser Ala Pro His
            100                 105                 110

<210> SEQ ID NO 278
<211> LENGTH: 110
<212> TYPE: PRT
<213> ORGANISM: Escherichia coli

<400> SEQUENCE: 278

Met Asn Pro Tyr Ile Tyr Leu Gly Gly Ala Ile Leu Ala Glu Val Ile
1               5                   10                  15

Gly Thr Thr Leu Met Lys Phe Ser Glu Gly Phe Thr Arg Leu Trp Pro
            20                  25                  30

Ser Val Gly Thr Ile Ile Cys Tyr Cys Ala Ser Phe Trp Leu Leu Ala
        35                  40                  45
```

Gln Thr Leu Ala Tyr Ile Pro Thr Gly Ile Ala Tyr Ala Ile Trp Ser
            50                  55                  60

Gly Val Gly Ile Val Leu Ile Ser Leu Leu Ser Trp Gly Leu Phe Asp
 65                  70                  75                  80

Gln Arg Leu Asp Leu Pro Ala Ile Ile Gly Met Met Leu Ile Cys Ala
                85                  90                  95

Gly Val Leu Val Ile Asn Leu Leu Ser Arg Ser Thr Pro His
            100                 105                 110

<210> SEQ ID NO 279
<211> LENGTH: 110
<212> TYPE: PRT
<213> ORGANISM: Escherichia coli

<400> SEQUENCE: 279

Met Asn Pro Tyr Ile Tyr Leu Gly Gly Ala Ile Leu Ala Glu Val Ile
  1               5                  10                  15

Gly Thr Thr Leu Met Lys Phe Ser Glu Gly Phe Thr Arg Leu Trp Pro
                20                  25                  30

Ser Val Gly Thr Ile Ile Cys Tyr Cys Ala Ser Phe Trp Leu Leu Ala
            35                  40                  45

Gln Thr Leu Ala Tyr Ile Pro Thr Gly Ile Ala Tyr Ala Ile Trp Ser
            50                  55                  60

Gly Val Gly Ile Val Leu Ile Ser Leu Leu Ser Trp Gly Phe Phe Gly
 65                  70                  75                  80

Gln Arg Leu Asp Leu Pro Ala Ile Ile Gly Met Met Leu Ile Cys Ala
                85                  90                  95

Gly Val Leu Val Ile Asn Leu Leu Ser Arg Ser Ala Pro His
            100                 105                 110

<210> SEQ ID NO 280
<211> LENGTH: 110
<212> TYPE: PRT
<213> ORGANISM: Escherichia coli

<400> SEQUENCE: 280

Met Asn Pro Tyr Ile Tyr Leu Gly Gly Ala Ile Leu Ala Glu Val Ile
  1               5                  10                  15

Gly Thr Thr Leu Met Lys Phe Ser Glu Gly Phe Thr Arg Leu Trp Pro
                20                  25                  30

Ser Val Gly Thr Ile Ile Cys Tyr Cys Ala Ser Phe Trp Leu Leu Ala
            35                  40                  45

Gln Thr Leu Ala Tyr Ile Pro Thr Gly Ile Ala Tyr Ala Ile Trp Ser
            50                  55                  60

Gly Val Gly Ile Val Leu Ile Ser Leu Leu Ser Trp Gly Leu Phe Asp
 65                  70                  75                  80

Gln Arg Leu Asp Leu Pro Ala Ile Ile Gly Met Met Leu Ile Cys Ala
                85                  90                  95

Gly Val Leu Val Ile Asn Leu Leu Ser Arg Ser Thr Pro His
            100                 105                 110

<210> SEQ ID NO 281
<211> LENGTH: 110
<212> TYPE: PRT
<213> ORGANISM: Escherichia coli

<400> SEQUENCE: 281

Met Asn Pro Tyr Ile Tyr Leu Gly Gly Ala Ile Leu Ala Glu Val Ile
1               5                   10                  15

Gly Thr Thr Leu Met Lys Phe Ser Glu Gly Phe Thr Arg Leu Trp Pro
            20                  25                  30

Ser Val Gly Thr Ile Ile Cys Tyr Cys Ala Ser Phe Trp Leu Leu Ala
        35                  40                  45

Gln Thr Leu Ala Tyr Ile Pro Thr Gly Ile Ala Tyr Ala Ile Trp Ser
    50                  55                  60

Gly Val Gly Ile Val Leu Ile Ser Leu Leu Ser Trp Gly Phe Phe Ser
65                  70                  75                  80

Gln Arg Leu Asp Leu Pro Ala Ile Ile Gly Met Met Leu Ile Cys Ala
                85                  90                  95

Gly Val Leu Val Ile Asn Leu Leu Ser Arg Ser Ala Pro His
            100                 105                 110

<210> SEQ ID NO 282
<211> LENGTH: 110
<212> TYPE: PRT
<213> ORGANISM: Escherichia coli

<400> SEQUENCE: 282

Met Asn Pro Tyr Ile Tyr Leu Gly Gly Ala Ile Leu Ala Glu Val Ile
1               5                   10                  15

Gly Thr Thr Leu Met Lys Phe Ser Glu Gly Phe Thr Arg Leu Trp Pro
            20                  25                  30

Ser Val Gly Thr Ile Ile Cys Tyr Cys Ala Ser Phe Trp Leu Leu Ala
        35                  40                  45

Gln Thr Leu Ala Tyr Ile Pro Thr Gly Ile Ala Tyr Ala Ile Trp Ser
    50                  55                  60

Gly Val Gly Ile Val Leu Ile Ser Leu Leu Ser Trp Gly Phe Phe Gly
65                  70                  75                  80

Gln Arg Leu Asp Leu Pro Ala Ile Ile Gly Met Met Leu Ile Cys Ala
                85                  90                  95

Gly Val Leu Val Ile Asn Leu Leu Ser Arg Ser Ala Pro His
            100                 105                 110

<210> SEQ ID NO 283
<211> LENGTH: 110
<212> TYPE: PRT
<213> ORGANISM: Escherichia coli

<400> SEQUENCE: 283

Met Asn Pro Tyr Ile Tyr Leu Gly Gly Ala Ile Leu Ala Glu Val Ile
1               5                   10                  15

Gly Thr Thr Leu Met Lys Phe Ser Glu Gly Phe Thr Arg Leu Trp Pro
            20                  25                  30

Ser Val Gly Thr Ile Ile Cys Tyr Cys Ala Ser Phe Trp Leu Leu Ala
        35                  40                  45

Gln Thr Leu Ala Tyr Ile Pro Thr Gly Ile Ala Tyr Ala Ile Trp Ser
    50                  55                  60

Gly Val Gly Ile Val Leu Ile Ser Leu Leu Ser Trp Gly Phe Phe Gly
65                  70                  75                  80

Gln Arg Leu Asp Leu Pro Ala Ile Ile Gly Met Met Leu Ile Cys Ala
                85                  90                  95

Gly Val Leu Val Ile Asn Leu Leu Ser Arg Ser Ala Pro His
            100                 105                 110

<210> SEQ ID NO 284
<211> LENGTH: 110
<212> TYPE: PRT
<213> ORGANISM: Escherichia coli

<400> SEQUENCE: 284

Met Asn Pro Tyr Ile Tyr Leu Gly Gly Ala Ile Leu Ala Glu Val Ile
1               5                   10                  15

Gly Thr Thr Leu Met Lys Phe Ser Glu Gly Phe Thr Arg Leu Trp Pro
            20                  25                  30

Ser Val Gly Thr Ile Ile Cys Tyr Cys Ala Ser Phe Trp Leu Leu Ala
        35                  40                  45

Gln Thr Leu Ala Tyr Ile Pro Thr Gly Ile Ala Tyr Ala Ile Trp Ser
    50                  55                  60

Gly Val Gly Ile Val Leu Ile Ser Leu Leu Ser Trp Gly Phe Phe Gly
65                  70                  75                  80

Gln Arg Leu Asp Leu Pro Ala Ile Ile Gly Met Met Leu Ile Cys Ala
                85                  90                  95

Gly Val Leu Val Ile Asn Leu Leu Ser Arg Ser Ala Pro His
            100                 105                 110

<210> SEQ ID NO 285
<211> LENGTH: 110
<212> TYPE: PRT
<213> ORGANISM: Escherichia coli

<400> SEQUENCE: 285

Met Asn Pro Tyr Ile Tyr Leu Gly Gly Ala Ile Leu Ala Glu Val Ile
1               5                   10                  15

Gly Thr Thr Leu Met Lys Phe Ser Glu Gly Phe Thr Arg Leu Trp Pro
            20                  25                  30

Ser Val Gly Thr Ile Ile Cys Tyr Cys Ala Ser Phe Trp Leu Leu Ala
        35                  40                  45

Gln Thr Leu Ala Tyr Ile Pro Thr Gly Ile Ala Tyr Ala Ile Trp Ser
    50                  55                  60

Gly Val Gly Ile Val Leu Ile Ser Leu Leu Ser Trp Gly Phe Phe Gly
65                  70                  75                  80

Gln Arg Leu Asp Leu Pro Ala Ile Ile Gly Met Met Leu Ile Cys Ala
                85                  90                  95

Gly Val Leu Val Ile Asn Leu Leu Ser Arg Ser Ala Pro His
            100                 105                 110

<210> SEQ ID NO 286
<211> LENGTH: 110
<212> TYPE: PRT
<213> ORGANISM: Escherichia coli

<400> SEQUENCE: 286

Met Asn Pro Tyr Ile Tyr Leu Gly Gly Ala Ile Leu Ala Glu Val Ile
1               5                   10                  15

Gly Thr Thr Leu Met Lys Phe Ser Glu Gly Phe Thr Arg Leu Trp Pro
            20                  25                  30

Ser Val Gly Thr Ile Ile Cys Tyr Cys Ala Ser Phe Trp Leu Leu Ala
        35                  40                  45

Gln Thr Leu Ala Tyr Ile Pro Thr Gly Ile Ala Tyr Ala Ile Trp Ser
            50                      55                      60

Gly Val Gly Ile Val Leu Ile Ser Leu Leu Ser Trp Gly Phe Phe Gly
65                      70                      75                      80

Gln Arg Leu Asp Leu Pro Ala Ile Ile Gly Met Met Leu Ile Cys Ala
                        85                      90                      95

Gly Val Leu Val Ile Asn Leu Leu Ser Arg Ser Ala Pro His
                100                     105                     110

<210> SEQ ID NO 287
<211> LENGTH: 110
<212> TYPE: PRT
<213> ORGANISM: Escherichia sp.

<400> SEQUENCE: 287

Met Asn Pro Tyr Ile Tyr Leu Gly Gly Ala Ile Leu Ala Glu Val Ile
1                       5                       10                      15

Gly Thr Thr Leu Met Lys Tyr Ser Glu Gly Phe Thr Arg Leu Trp Pro
                20                      25                      30

Ser Val Gly Thr Ile Ile Cys Tyr Cys Ala Ser Phe Trp Leu Leu Ala
            35                      40                      45

Gln Thr Leu Ala Tyr Ile Pro Thr Gly Ile Ala Tyr Ala Ile Trp Ser
            50                      55                      60

Gly Val Gly Ile Val Leu Ile Ser Leu Leu Ser Trp Gly Phe Phe Gly
65                      70                      75                      80

Gln Arg Leu Asp Leu Pro Ala Ile Ile Gly Met Met Leu Ile Cys Ala
                        85                      90                      95

Gly Val Leu Val Ile Asn Leu Leu Ser Arg Ser Ala Pro His
                100                     105                     110

<210> SEQ ID NO 288
<211> LENGTH: 110
<212> TYPE: PRT
<213> ORGANISM: Escherichia coli

<400> SEQUENCE: 288

Met Asn Pro Tyr Ile Tyr Leu Gly Gly Ala Ile Leu Ala Glu Val Ile
1                       5                       10                      15

Gly Thr Thr Leu Met Lys Phe Ser Glu Gly Phe Thr Arg Leu Trp Pro
                20                      25                      30

Ser Val Gly Thr Ile Ile Cys Tyr Cys Ala Ser Phe Trp Leu Leu Ala
            35                      40                      45

Gln Thr Leu Ala Tyr Ile Pro Thr Gly Ile Ala Tyr Ala Ile Trp Ser
            50                      55                      60

Gly Val Gly Ile Val Leu Ile Ser Leu Leu Ser Trp Gly Phe Phe Gly
65                      70                      75                      80

Gln Arg Leu Asp Leu Pro Ala Ile Ile Gly Met Met Leu Ile Cys Ala
                        85                      90                      95

Gly Val Leu Val Ile Asn Leu Leu Ser Arg Ser Ala Pro His
                100                     105                     110

<210> SEQ ID NO 289
<211> LENGTH: 110
<212> TYPE: PRT
<213> ORGANISM: Escherichia coli

<400> SEQUENCE: 289

Met Asn Pro Tyr Ile Tyr Leu Gly Gly Ala Ile Leu Ala Glu Val Ile
1               5                   10                  15

Gly Thr Thr Leu Met Lys Phe Ser Glu Gly Phe Thr Arg Leu Trp Pro
            20                  25                  30

Ser Val Gly Thr Ile Ile Cys Tyr Cys Ala Ser Phe Trp Leu Leu Ala
        35                  40                  45

Gln Thr Leu Ala Tyr Ile Pro Thr Gly Ile Ala Tyr Ala Ile Trp Ser
    50                  55                  60

Gly Val Gly Ile Val Leu Ile Ser Leu Ser Trp Gly Phe Phe Gly
65                  70                  75                  80

Gln Arg Leu Asp Leu Pro Ala Ile Ile Gly Met Met Leu Ile Cys Ala
                85                  90                  95

Gly Val Leu Val Ile Asn Leu Leu Ser Arg Ser Ala Pro His
            100                 105                 110

<210> SEQ ID NO 290
<211> LENGTH: 110
<212> TYPE: PRT
<213> ORGANISM: Escherichia coli

<400> SEQUENCE: 290

Met Asn Pro Tyr Ile Tyr Leu Gly Gly Ala Ile Leu Ala Glu Val Ile
1               5                   10                  15

Gly Thr Thr Leu Met Lys Phe Ser Glu Gly Phe Thr Arg Leu Trp Pro
            20                  25                  30

Ser Val Gly Thr Ile Ile Cys Tyr Cys Ala Ser Phe Trp Leu Leu Ala
        35                  40                  45

Gln Thr Leu Ala Tyr Ile Pro Thr Gly Ile Ala Tyr Ala Ile Trp Ser
    50                  55                  60

Gly Val Gly Ile Val Leu Ile Ser Leu Ser Trp Gly Phe Phe Gly
65                  70                  75                  80

Gln Arg Leu Asp Leu Pro Ala Ile Ile Gly Met Met Leu Ile Cys Ala
                85                  90                  95

Gly Val Leu Val Ile Asn Leu Leu Ser Arg Ser Ala Pro His
            100                 105                 110

<210> SEQ ID NO 291
<211> LENGTH: 110
<212> TYPE: PRT
<213> ORGANISM: Escherichia albertii

<400> SEQUENCE: 291

Met Asn Pro Tyr Ile Tyr Leu Gly Gly Ala Ile Leu Ala Glu Val Ile
1               5                   10                  15

Gly Thr Thr Leu Met Lys Phe Ser Glu Gly Phe Thr Arg Leu Trp Pro
            20                  25                  30

Ser Val Gly Thr Ile Ile Cys Tyr Cys Ala Ser Phe Trp Leu Leu Ala
        35                  40                  45

Gln Thr Leu Ala Tyr Ile Pro Thr Gly Ile Ala Asn Ala Ile Trp Ser
    50                  55                  60

Gly Val Gly Ile Val Leu Ile Ser Leu Ser Trp Gly Ile Phe Gly
65                  70                  75                  80

Gln Arg Leu Asp Leu Pro Ala Ile Ile Gly Met Met Leu Ile Cys Ala
                85                  90                  95

```
Gly Val Leu Val Ile Asn Leu Leu Ser Arg Ser Ala Thr His
            100                 105                 110

<210> SEQ ID NO 292
<211> LENGTH: 110
<212> TYPE: PRT
<213> ORGANISM: Shigella sp.

<400> SEQUENCE: 292

Met Asn Pro Tyr Ile Tyr Leu Gly Gly Ala Ile Leu Ala Glu Val Ile
1               5                   10                  15

Gly Thr Thr Leu Met Lys Phe Ser Glu Gly Phe Thr Arg Leu Trp Pro
            20                  25                  30

Ser Val Gly Thr Ile Ile Cys Tyr Cys Ala Ser Phe Trp Leu Leu Ala
        35                  40                  45

Gln Thr Leu Ala Tyr Ile Pro Thr Gly Ile Ala Tyr Gly Ile Trp Ser
    50                  55                  60

Gly Val Gly Ile Val Leu Ile Ser Leu Leu Trp Gly Phe Phe Gly
65                  70                  75                  80

Gln Arg Leu Asp Leu Pro Ala Ile Ile Gly Met Met Leu Ile Cys Ala
                85                  90                  95

Gly Val Leu Val Ile Asn Leu Leu Ser Arg Ser Thr Pro His
            100                 105                 110

<210> SEQ ID NO 293
<211> LENGTH: 110
<212> TYPE: PRT
<213> ORGANISM: Escherichia coli

<400> SEQUENCE: 293

Met Asn Pro Tyr Ile Tyr Leu Gly Gly Ala Ile Leu Ala Glu Val Ile
1               5                   10                  15

Gly Thr Thr Leu Met Lys Phe Ser Glu Gly Phe Thr Arg Leu Trp Pro
            20                  25                  30

Ser Val Gly Thr Ile Ile Cys Tyr Cys Ala Ser Phe Trp Leu Leu Ala
        35                  40                  45

Gln Thr Leu Ala Tyr Ile Pro Thr Gly Ile Ala Tyr Ala Ile Trp Ser
    50                  55                  60

Gly Val Gly Ile Val Leu Ile Ser Leu Leu Ser Trp Gly Phe Phe Gly
65                  70                  75                  80

Gln Arg Leu Asp Leu Pro Ala Ile Ile Gly Met Met Leu Ile Cys Ala
                85                  90                  95

Gly Val Leu Val Ile Asn Leu Leu Ser Arg Ser Thr Pro His
            100                 105                 110

<210> SEQ ID NO 294
<211> LENGTH: 110
<212> TYPE: PRT
<213> ORGANISM: Escherichia coli

<400> SEQUENCE: 294

Met Asn Pro Tyr Ile Tyr Leu Gly Gly Ala Ile Leu Ala Glu Val Ile
1               5                   10                  15

Gly Thr Thr Leu Met Lys Phe Ser Glu Gly Phe Thr Arg Leu Trp Pro
            20                  25                  30

Ser Val Gly Thr Ile Ile Cys Tyr Cys Ala Ser Phe Trp Leu Leu Ala
        35                  40                  45
```

Gln Thr Leu Ala Tyr Ile Pro Thr Gly Ile Ala Tyr Ala Ile Trp Ser
    50                  55                  60

Gly Val Gly Ile Val Leu Ile Ser Leu Leu Ser Trp Gly Phe Phe Gly
65                  70                  75                  80

Gln Arg Leu Asp Leu Pro Ala Ile Ile Gly Met Met Leu Ile Cys Ala
                85                  90                  95

Gly Val Leu Val Ile Asn Leu Leu Ser Arg Ser Ala Pro His
            100                 105                 110

<210> SEQ ID NO 295
<211> LENGTH: 110
<212> TYPE: PRT
<213> ORGANISM: Escherichia coli

<400> SEQUENCE: 295

Met Asn Pro Tyr Ile Tyr Leu Gly Gly Ala Ile Leu Ala Glu Val Ile
1               5                   10                  15

Gly Thr Thr Leu Met Lys Phe Ser Glu Gly Phe Thr Arg Leu Trp Pro
                20                  25                  30

Ser Val Gly Thr Ile Ile Cys Tyr Cys Ala Ser Phe Trp Leu Leu Ala
            35                  40                  45

Gln Thr Leu Ala Tyr Ile Pro Thr Gly Ile Ala Tyr Ala Ile Trp Ser
    50                  55                  60

Gly Val Gly Ile Val Leu Ile Ser Leu Leu Ser Trp Gly Phe Phe Gly
65                  70                  75                  80

Gln Arg Leu Asp Leu Pro Ala Ile Ile Gly Met Met Leu Ile Cys Ala
                85                  90                  95

Gly Val Leu Val Ile Asn Leu Leu Ser Arg Ser Ala Pro His
            100                 105                 110

<210> SEQ ID NO 296
<211> LENGTH: 110
<212> TYPE: PRT
<213> ORGANISM: Escherichia coli

<400> SEQUENCE: 296

Met Asn Pro Tyr Ile Tyr Leu Gly Gly Ala Ile Leu Ala Glu Val Ile
1               5                   10                  15

Gly Thr Thr Leu Met Lys Phe Ser Glu Gly Phe Thr Arg Leu Trp Pro
                20                  25                  30

Ser Val Gly Thr Ile Ile Cys Tyr Cys Ala Ser Phe Trp Leu Leu Ala
            35                  40                  45

Gln Thr Leu Ala Tyr Ile Pro Thr Gly Ile Ala Tyr Ala Ile Trp Ser
    50                  55                  60

Gly Val Gly Ile Val Leu Ile Ser Leu Leu Ser Trp Gly Leu Phe Gly
65                  70                  75                  80

Gln Arg Leu Asp Leu Pro Ala Ile Ile Gly Met Met Leu Ile Cys Ala
                85                  90                  95

Gly Val Leu Val Ile Asn Leu Leu Ser Arg Ser Thr Pro His
            100                 105                 110

<210> SEQ ID NO 297
<211> LENGTH: 110
<212> TYPE: PRT
<213> ORGANISM: Escherichia coli

<400> SEQUENCE: 297

Met Asn Pro Tyr Ile Tyr Leu Gly Gly Ala Ile Leu Ala Glu Val Ile
1               5                   10                  15

Gly Thr Thr Leu Met Lys Phe Ser Glu Gly Phe Thr Arg Leu Trp Pro
            20                  25                  30

Ser Val Gly Thr Ile Ile Cys Tyr Cys Ala Ser Phe Trp Leu Leu Ala
        35                  40                  45

Gln Thr Leu Ala Tyr Ile Pro Thr Gly Ile Ala Tyr Ala Ile Trp Ser
    50                  55                  60

Gly Val Gly Ile Val Leu Ile Ser Leu Leu Ser Trp Gly Phe Phe Gly
65                  70                  75                  80

Gln Arg Leu Asp Leu Pro Ala Ile Ile Gly Met Met Leu Ile Cys Ala
                85                  90                  95

Gly Val Leu Val Ile Asn Leu Leu Ser Arg Ser Ala Pro His
            100                 105                 110

<210> SEQ ID NO 298
<211> LENGTH: 110
<212> TYPE: PRT
<213> ORGANISM: Escherichia coli

<400> SEQUENCE: 298

Met Asn Pro Tyr Ile Tyr Leu Gly Gly Ala Ile Leu Ala Glu Val Ile
1               5                   10                  15

Gly Thr Thr Leu Met Lys Phe Ser Glu Gly Phe Thr Arg Leu Trp Pro
            20                  25                  30

Ser Val Gly Thr Ile Ile Cys Tyr Cys Ala Ser Phe Trp Leu Leu Ala
        35                  40                  45

Gln Thr Leu Ala Tyr Ile Pro Thr Gly Ile Ala Tyr Ala Ile Trp Ser
    50                  55                  60

Gly Val Gly Ile Val Leu Ile Ser Leu Leu Ser Trp Gly Phe Phe Gly
65                  70                  75                  80

Gln Arg Leu Asp Leu Pro Ala Ile Ile Gly Met Met Leu Ile Cys Ala
                85                  90                  95

Gly Val Leu Val Ile Asn Leu Leu Ser Arg Ser Thr Pro His
            100                 105                 110

<210> SEQ ID NO 299
<211> LENGTH: 110
<212> TYPE: PRT
<213> ORGANISM: Escherichia coli

<400> SEQUENCE: 299

Met Asn Pro Tyr Ile Tyr Leu Gly Gly Ala Ile Leu Ala Glu Val Ile
1               5                   10                  15

Gly Thr Thr Leu Met Lys Phe Ser Glu Gly Phe Thr Arg Leu Trp Pro
            20                  25                  30

Ser Val Gly Thr Ile Ile Cys Tyr Cys Ala Ser Phe Trp Leu Leu Ala
        35                  40                  45

Gln Thr Leu Ala Tyr Ile Pro Thr Gly Ile Ala Tyr Ala Ile Trp Ser
    50                  55                  60

Gly Val Gly Ile Val Leu Ile Ser Leu Leu Ser Trp Gly Phe Phe Gly
65                  70                  75                  80

Gln Arg Leu Asp Leu Pro Ala Ile Ile Gly Met Met Leu Ile Cys Ala
                85                  90                  95

Gly Val Leu Val Ile Asn Leu Leu Ser Arg Ser Thr Pro His
            100                 105                 110

<210> SEQ ID NO 300
<211> LENGTH: 110
<212> TYPE: PRT
<213> ORGANISM: Escherichia coli

<400> SEQUENCE: 300

Met Asn Pro Tyr Ile Tyr Leu Gly Gly Ala Ile Leu Ala Glu Val Ile
1               5                   10                  15

Gly Thr Thr Leu Met Lys Phe Ser Glu Gly Phe Thr Arg Leu Trp Pro
            20                  25                  30

Ser Val Gly Thr Ile Ile Cys Tyr Cys Ala Ser Phe Trp Leu Leu Ala
        35                  40                  45

Gln Thr Leu Ala Tyr Ile Pro Thr Gly Ile Ala Tyr Ala Ile Trp Ser
    50                  55                  60

Gly Val Gly Ile Val Leu Ile Ser Leu Leu Ser Trp Gly Phe Phe Gly
65                  70                  75                  80

Gln Arg Leu Asp Leu Pro Ala Ile Ile Gly Met Met Leu Ile Cys Ala
                85                  90                  95

Gly Val Leu Val Ile Asn Leu Leu Ser Arg Ser Thr Pro His
            100                 105                 110

<210> SEQ ID NO 301
<211> LENGTH: 110
<212> TYPE: PRT
<213> ORGANISM: Escherichia coli

<400> SEQUENCE: 301

Met Asn Pro Tyr Ile Tyr Leu Gly Gly Ala Ile Leu Ala Glu Val Ile
1               5                   10                  15

Gly Thr Thr Leu Met Lys Phe Ser Glu Gly Phe Thr Arg Leu Trp Pro
            20                  25                  30

Ser Val Gly Thr Ile Ile Cys Tyr Cys Ala Ser Phe Trp Leu Leu Ala
        35                  40                  45

Gln Thr Leu Ala Tyr Ile Pro Thr Gly Ile Ala Tyr Ala Ile Trp Ser
    50                  55                  60

Gly Val Gly Ile Val Leu Ile Ser Leu Leu Ser Trp Gly Phe Phe Gly
65                  70                  75                  80

Gln Arg Leu Asp Leu Pro Ala Ile Ile Gly Met Met Leu Ile Cys Ala
                85                  90                  95

Gly Val Leu Val Ile Asn Leu Leu Ser Arg Ser Ala Pro His
            100                 105                 110

<210> SEQ ID NO 302
<211> LENGTH: 110
<212> TYPE: PRT
<213> ORGANISM: Escherichia coli

<400> SEQUENCE: 302

Met Asn Pro Tyr Ile Tyr Leu Gly Gly Ala Ile Leu Ala Glu Val Ile
1               5                   10                  15

Gly Thr Thr Leu Met Lys Phe Ser Glu Gly Phe Thr Arg Leu Trp Pro
            20                  25                  30

Ser Val Gly Thr Ile Ile Cys Tyr Cys Ala Ser Phe Trp Leu Leu Ala
           35                  40                  45

Gln Thr Leu Ala Tyr Ile Pro Thr Gly Ile Ala Tyr Ala Ile Trp Ser
       50                  55                  60

Gly Val Gly Ile Val Leu Ile Ser Leu Leu Ser Trp Gly Phe Phe Gly
65                  70                  75                  80

Gln Arg Leu Asp Leu Pro Ala Ile Ile Gly Met Met Leu Ile Cys Ala
               85                  90                  95

Gly Val Leu Val Ile Asn Leu Leu Ser Arg Ser Ala Pro His
           100                 105                 110

<210> SEQ ID NO 303
<211> LENGTH: 110
<212> TYPE: PRT
<213> ORGANISM: Escherichia coli

<400> SEQUENCE: 303

Met Asn Pro Tyr Ile Tyr Leu Gly Gly Ala Ile Leu Ala Glu Val Ile
1               5                   10                  15

Gly Thr Thr Leu Met Lys Phe Ser Glu Gly Phe Thr Arg Leu Trp Pro
           20                  25                  30

Ser Val Gly Thr Ile Ile Cys Tyr Cys Ala Ser Phe Trp Leu Leu Ala
           35                  40                  45

Gln Thr Leu Ala Tyr Ile Pro Thr Gly Ile Ala Tyr Ala Ile Trp Ser
       50                  55                  60

Gly Val Gly Ile Val Leu Ile Ser Leu Leu Ser Trp Gly Leu Phe Gly
65                  70                  75                  80

Gln Arg Leu Asp Leu Pro Ala Ile Ile Gly Met Met Leu Ile Cys Ala
               85                  90                  95

Gly Val Leu Val Ile Asn Leu Leu Ser Arg Ser Thr Pro His
           100                 105                 110

<210> SEQ ID NO 304
<211> LENGTH: 110
<212> TYPE: PRT
<213> ORGANISM: Escherichia coli

<400> SEQUENCE: 304

Met Asn Pro Tyr Ile Tyr Leu Gly Gly Ala Ile Leu Ala Glu Val Ile
1               5                   10                  15

Gly Thr Thr Leu Met Lys Phe Ser Glu Gly Phe Thr Arg Leu Trp Pro
           20                  25                  30

Ser Val Gly Thr Ile Ile Cys Tyr Cys Ala Ser Phe Trp Leu Leu Ala
           35                  40                  45

Gln Thr Leu Ala Tyr Ile Pro Thr Gly Ile Ala Tyr Ala Ile Trp Ser
       50                  55                  60

Gly Val Gly Ile Val Leu Ile Ser Leu Leu Ser Trp Gly Phe Phe Gly
65                  70                  75                  80

Gln Arg Leu Asp Leu Pro Ala Ile Ile Gly Met Met Leu Ile Cys Ala
               85                  90                  95

Gly Val Leu Val Ile Asn Leu Leu Ser Arg Ser Ala Pro His
           100                 105                 110

<210> SEQ ID NO 305
<211> LENGTH: 110
<212> TYPE: PRT
<213> ORGANISM: Escherichia coli

<400> SEQUENCE: 305

Met Asn Pro Tyr Ile Tyr Leu Gly Gly Ala Ile Leu Ala Glu Val Ile
1               5                   10                  15

Gly Thr Thr Leu Met Lys Phe Ser Glu Gly Phe Thr Arg Leu Trp Pro
            20                  25                  30

Ser Val Gly Thr Ile Ile Cys Tyr Cys Ala Ser Phe Trp Leu Leu Ala
        35                  40                  45

Gln Thr Leu Ala Tyr Ile Pro Thr Gly Ile Ala Tyr Ala Ile Trp Ser
    50                  55                  60

Gly Val Gly Ile Val Leu Ile Ser Leu Ser Trp Gly Phe Phe Gly
65                  70                  75                  80

Gln Arg Leu Asp Leu Pro Ala Ile Ile Gly Met Met Leu Ile Cys Ala
                85                  90                  95

Gly Val Leu Val Ile Asn Leu Leu Ser Arg Ser Ala Pro His
            100                 105                 110

<210> SEQ ID NO 306
<211> LENGTH: 110
<212> TYPE: PRT
<213> ORGANISM: Escherichia coli

<400> SEQUENCE: 306

Met Asn Pro Tyr Ile Tyr Leu Gly Gly Ala Ile Leu Ala Glu Val Ile
1               5                   10                  15

Gly Thr Thr Leu Met Lys Phe Ser Glu Gly Phe Thr Arg Leu Trp Pro
            20                  25                  30

Ser Val Gly Thr Ile Ile Cys Tyr Cys Ala Ser Phe Trp Leu Leu Ala
        35                  40                  45

Gln Thr Leu Ala Tyr Ile Pro Thr Gly Ile Ala Tyr Ala Ile Trp Ser
    50                  55                  60

Gly Val Gly Ile Val Leu Ile Ser Leu Ser Trp Gly Phe Phe Gly
65                  70                  75                  80

Gln Arg Leu Asp Leu Pro Ala Ile Ile Gly Met Met Leu Ile Cys Ala
                85                  90                  95

Gly Val Leu Val Ile Asn Leu Leu Ser Arg Ser Ala Pro His
            100                 105                 110

<210> SEQ ID NO 307
<211> LENGTH: 110
<212> TYPE: PRT
<213> ORGANISM: Escherichia coli

<400> SEQUENCE: 307

Met Asn Pro Tyr Ile Tyr Leu Gly Gly Ala Ile Leu Ala Glu Val Ile
1               5                   10                  15

Gly Thr Thr Leu Met Lys Phe Ser Glu Gly Phe Thr Arg Leu Trp Pro
            20                  25                  30

Ser Val Gly Thr Ile Ile Cys Tyr Cys Ala Ser Phe Trp Leu Leu Ala
        35                  40                  45

Gln Thr Leu Ala Tyr Ile Pro Thr Gly Ile Ala Tyr Ala Ile Trp Ser
    50                  55                  60

Gly Val Gly Ile Val Leu Ile Ser Leu Ser Trp Gly Phe Phe Gly
65                  70                  75                  80

Gln Arg Leu Asp Leu Pro Ala Ile Ile Gly Met Met Leu Ile Cys Ala
                85                  90                  95

Gly Val Leu Val Ile Asn Leu Leu Ser Arg Ser Ala Pro His
            100                 105                 110

<210> SEQ ID NO 308
<211> LENGTH: 110
<212> TYPE: PRT
<213> ORGANISM: Escherichia coli

<400> SEQUENCE: 308

Met Asn Pro Tyr Ile Tyr Leu Gly Gly Ala Ile Leu Ala Glu Val Ile
1               5                   10                  15

Gly Thr Thr Leu Met Lys Phe Ser Glu Gly Phe Thr Arg Leu Trp Pro
            20                  25                  30

Ser Val Gly Thr Ile Ile Cys Tyr Cys Ala Ser Phe Trp Leu Leu Ala
        35                  40                  45

Gln Thr Leu Ala Tyr Ile Pro Thr Gly Ile Ala Tyr Ala Ile Trp Ser
    50                  55                  60

Gly Val Gly Ile Val Leu Ile Ser Leu Leu Ser Trp Gly Phe Phe Gly
65                  70                  75                  80

Gln Arg Leu Asp Leu Pro Ala Ile Ile Gly Met Met Leu Ile Cys Ala
                85                  90                  95

Gly Val Leu Val Ile Asn Leu Leu Ser Arg Ser Ala Pro His
            100                 105                 110

<210> SEQ ID NO 309
<211> LENGTH: 110
<212> TYPE: PRT
<213> ORGANISM: Escherichia coli

<400> SEQUENCE: 309

Met Asn Pro Tyr Ile Tyr Leu Gly Gly Ala Ile Leu Ala Glu Val Ile
1               5                   10                  15

Gly Thr Thr Leu Met Lys Phe Ser Glu Gly Phe Thr Arg Leu Trp Pro
            20                  25                  30

Ser Val Gly Thr Ile Ile Cys Tyr Cys Ala Ser Phe Trp Leu Leu Ala
        35                  40                  45

Gln Thr Leu Ala Tyr Ile Pro Thr Gly Ile Ala Tyr Ala Ile Trp Ser
    50                  55                  60

Gly Val Gly Ile Val Leu Ile Ser Leu Leu Ser Trp Gly Phe Phe Gly
65                  70                  75                  80

Gln Arg Leu Asp Leu Pro Ala Ile Ile Gly Met Met Leu Ile Cys Ala
                85                  90                  95

Gly Val Leu Val Ile Asn Leu Leu Ser Arg Ser Thr Pro His
            100                 105                 110

<210> SEQ ID NO 310
<211> LENGTH: 110
<212> TYPE: PRT
<213> ORGANISM: Escherichia coli

<400> SEQUENCE: 310

Met Asn Pro Tyr Ile Tyr Leu Gly Gly Ala Ile Leu Ala Glu Val Ile
1               5                   10                  15

Gly Thr Thr Leu Met Lys Phe Ser Glu Gly Phe Thr Arg Leu Trp Pro
            20                  25                  30

-continued

Ser Val Gly Thr Ile Ile Cys Tyr Cys Ala Ser Phe Trp Leu Leu Ala
         35                  40                  45

Gln Thr Leu Ala Tyr Ile Pro Thr Gly Ile Ala Tyr Ala Ile Trp Ser
     50                  55                  60

Gly Val Gly Ile Val Leu Ile Ser Leu Leu Ser Trp Gly Phe Phe Gly
 65                  70                  75                  80

Gln Arg Leu Asp Leu Pro Ala Ile Ile Gly Met Met Leu Ile Cys Ala
                 85                  90                  95

Gly Val Leu Val Ile Asn Leu Leu Ser Arg Ser Thr Pro His
            100                 105                 110

<210> SEQ ID NO 311
<211> LENGTH: 110
<212> TYPE: PRT
<213> ORGANISM: Escherichia coli

<400> SEQUENCE: 311

Met Asn Pro Tyr Ile Tyr Leu Gly Gly Ala Ile Leu Ala Glu Val Ile
 1               5                  10                  15

Gly Thr Thr Leu Met Lys Phe Ser Glu Gly Phe Thr Arg Leu Trp Pro
             20                  25                  30

Ser Val Gly Thr Ile Ile Cys Tyr Cys Ala Ser Phe Trp Leu Leu Ala
         35                  40                  45

Gln Thr Leu Ala Tyr Ile Pro Thr Gly Ile Ala Tyr Ala Ile Trp Ser
     50                  55                  60

Gly Val Gly Ile Val Leu Ile Ser Leu Leu Ser Trp Gly Phe Phe Gly
 65                  70                  75                  80

Gln Arg Leu Asp Leu Pro Ala Ile Ile Gly Met Met Leu Ile Cys Ala
                 85                  90                  95

Gly Val Leu Val Ile Asn Leu Leu Ser Arg Ser Ala Pro His
            100                 105                 110

<210> SEQ ID NO 312
<211> LENGTH: 110
<212> TYPE: PRT
<213> ORGANISM: Escherichia coli

<400> SEQUENCE: 312

Met Asn Pro Tyr Ile Tyr Leu Gly Gly Ala Ile Leu Ala Glu Val Ile
 1               5                  10                  15

Gly Thr Thr Leu Met Lys Phe Ser Glu Gly Phe Thr Arg Leu Trp Pro
             20                  25                  30

Ser Val Gly Thr Ile Ile Cys Tyr Cys Ala Ser Phe Trp Leu Leu Ala
         35                  40                  45

Gln Thr Leu Ala Tyr Ile Pro Thr Gly Ile Ala Tyr Ala Ile Trp Ser
     50                  55                  60

Gly Val Gly Ile Val Leu Ile Ser Leu Leu Ser Trp Gly Phe Phe Gly
 65                  70                  75                  80

Gln Arg Leu Asp Leu Pro Ala Ile Ile Gly Met Met Leu Ile Cys Ala
                 85                  90                  95

Gly Val Leu Val Ile Asn Leu Leu Ser Arg Ser Thr Pro His
            100                 105                 110

<210> SEQ ID NO 313
<211> LENGTH: 110
<212> TYPE: PRT
<213> ORGANISM: Escherichia coli

<400> SEQUENCE: 313

Met Asn Pro Tyr Ile Tyr Leu Gly Gly Ala Ile Leu Ala Glu Val Ile
1               5                   10                  15

Gly Thr Thr Leu Met Lys Phe Ser Glu Gly Phe Thr Arg Leu Trp Pro
            20                  25                  30

Ser Val Gly Thr Ile Ile Cys Tyr Cys Ala Ser Phe Trp Leu Leu Ala
        35                  40                  45

Gln Thr Leu Ala Tyr Ile Pro Thr Gly Ile Ala Tyr Gly Ile Trp Ser
    50                  55                  60

Gly Val Gly Ile Val Leu Ile Ser Leu Leu Trp Gly Phe Phe Gly
65                  70                  75                  80

Gln Arg Leu Asp Leu Pro Ala Ile Ile Gly Met Met Leu Ile Cys Ala
                85                  90                  95

Gly Val Leu Val Ile Asn Leu Leu Ser Arg Ser Thr Pro His
            100                 105                 110

<210> SEQ ID NO 314
<211> LENGTH: 110
<212> TYPE: PRT
<213> ORGANISM: Escherichia coli

<400> SEQUENCE: 314

Met Asn Pro Tyr Ile Tyr Leu Gly Gly Ala Ile Leu Ala Glu Val Ile
1               5                   10                  15

Gly Thr Thr Leu Met Lys Phe Ser Glu Gly Phe Thr Arg Leu Trp Pro
            20                  25                  30

Ser Val Gly Thr Ile Ile Cys Tyr Cys Ala Ser Phe Trp Leu Leu Ala
        35                  40                  45

Gln Thr Leu Ala Tyr Ile Pro Thr Gly Ile Ala Tyr Ala Ile Trp Ser
    50                  55                  60

Gly Val Gly Ile Val Leu Ile Ser Leu Leu Ser Arg Gly Phe Phe Gly
65                  70                  75                  80

Gln Arg Leu Asp Leu Pro Ala Ile Ile Gly Met Met Leu Ile Cys Ala
                85                  90                  95

Gly Val Leu Val Ile Asn Leu Leu Ser Arg Ser Ala Pro His
            100                 105                 110

<210> SEQ ID NO 315
<211> LENGTH: 110
<212> TYPE: PRT
<213> ORGANISM: Escherichia coli

<400> SEQUENCE: 315

Met Asn Pro Tyr Ile Tyr Leu Gly Gly Ala Ile Leu Ala Glu Val Ile
1               5                   10                  15

Gly Thr Thr Leu Met Lys Phe Ser Glu Gly Phe Thr Arg Leu Trp Pro
            20                  25                  30

Ser Ala Gly Thr Ile Ile Cys Tyr Cys Ala Ser Phe Trp Leu Leu Ala
        35                  40                  45

Gln Thr Leu Ala Tyr Ile Pro Thr Gly Ile Ala Tyr Ala Ile Trp Ser
    50                  55                  60

Gly Val Gly Ile Val Leu Ile Ser Leu Leu Ser Trp Gly Phe Phe Gly
65                  70                  75                  80

Gln Arg Leu Asp Leu Pro Ala Ile Ile Gly Met Met Leu Ile Cys Ala
                85                  90                  95

```
Gly Val Leu Val Ile Asn Leu Leu Ser Arg Ser Ala Pro His
            100                 105                 110
```

<210> SEQ ID NO 316
<211> LENGTH: 110
<212> TYPE: PRT
<213> ORGANISM: Escherichia coli

<400> SEQUENCE: 316

```
Met Asn Pro Tyr Ile Tyr Leu Gly Gly Ala Ile Leu Ala Glu Val Ile
1               5                   10                  15

Gly Thr Thr Leu Met Lys Phe Ser Glu Gly Phe Thr Arg Leu Trp Pro
            20                  25                  30

Ser Val Gly Thr Ile Ile Cys Tyr Cys Ala Ser Phe Trp Leu Leu Ala
        35                  40                  45

Gln Thr Leu Ala Tyr Ile Pro Thr Gly Ile Ala Tyr Ala Ile Trp Ser
    50                  55                  60

Gly Val Gly Ile Val Leu Ile Ser Leu Leu Ser Trp Gly Ile Phe Gly
65                  70                  75                  80

Gln Arg Leu Asp Leu Pro Ala Ile Ile Gly Met Met Leu Ile Cys Ala
                85                  90                  95

Gly Val Leu Val Ile Asn Leu Leu Ser Arg Ser Ala Thr His
            100                 105                 110
```

<210> SEQ ID NO 317
<211> LENGTH: 110
<212> TYPE: PRT
<213> ORGANISM: Escherichia coli

<400> SEQUENCE: 317

```
Met Asn Pro Tyr Ile Tyr Leu Gly Gly Ala Ile Leu Ala Glu Val Ile
1               5                   10                  15

Gly Thr Thr Leu Met Lys Phe Ser Glu Gly Phe Thr Arg Leu Trp Pro
            20                  25                  30

Ser Val Gly Thr Ile Ile Cys Tyr Cys Ala Ser Phe Trp Leu Leu Ala
        35                  40                  45

Gln Thr Leu Ala Tyr Ile Pro Thr Gly Ile Ala Tyr Ala Ile Trp Ser
    50                  55                  60

Gly Val Gly Ile Val Leu Ile Ser Leu Leu Ser Trp Gly Leu Phe Asp
65                  70                  75                  80

Gln Arg Leu Asp Leu Pro Ala Ile Ile Gly Met Met Leu Ile Cys Ala
                85                  90                  95

Gly Val Leu Val Ile Asn Leu Leu Ser Arg Ser Thr Pro His
            100                 105                 110
```

<210> SEQ ID NO 318
<211> LENGTH: 110
<212> TYPE: PRT
<213> ORGANISM: Escherichia coli

<400> SEQUENCE: 318

```
Met Asn Pro Tyr Ile Tyr Leu Gly Gly Ala Ile Leu Ala Glu Val Ile
1               5                   10                  15

Gly Thr Thr Leu Met Lys Phe Ser Glu Gly Phe Thr Arg Leu Trp Pro
            20                  25                  30
```

```
Ser Val Gly Thr Ile Ile Cys Tyr Cys Ala Ser Phe Trp Leu Leu Ala
        35                  40                  45

Gln Thr Leu Ala Tyr Ile Pro Thr Gly Ile Ala Tyr Ala Ile Trp Ser
    50                  55                  60

Gly Val Gly Ile Val Leu Ile Ser Leu Leu Ser Trp Gly Phe Phe Gly
65                  70                  75                  80

Gln Arg Leu Asp Leu Pro Ala Ile Ile Gly Met Met Leu Ile Cys Ala
                85                  90                  95

Gly Val Leu Val Ile Asn Leu Leu Ser Arg Ser Ala Pro His
            100                 105                 110

<210> SEQ ID NO 319
<211> LENGTH: 110
<212> TYPE: PRT
<213> ORGANISM: Escherichia coli

<400> SEQUENCE: 319

Met Asn Pro Tyr Ile Tyr Leu Gly Gly Ala Ile Leu Ala Glu Val Ile
1               5                   10                  15

Gly Thr Thr Leu Met Lys Phe Ser Glu Gly Phe Thr Arg Leu Trp Pro
            20                  25                  30

Ser Val Gly Thr Ile Ile Cys Tyr Cys Ala Ser Phe Trp Leu Leu Ala
        35                  40                  45

Gln Thr Leu Ala Tyr Ile Pro Thr Gly Ile Ala Tyr Ala Ile Trp Ser
    50                  55                  60

Gly Val Gly Ile Val Leu Ile Ser Leu Leu Ser Trp Gly Phe Phe Ser
65                  70                  75                  80

Gln Arg Leu Asp Leu Pro Ala Ile Ile Gly Met Met Leu Ile Cys Ala
                85                  90                  95

Gly Val Leu Val Ile Asn Leu Leu Ser Arg Ser Ala Pro His
            100                 105                 110

<210> SEQ ID NO 320
<211> LENGTH: 110
<212> TYPE: PRT
<213> ORGANISM: Escherichia coli

<400> SEQUENCE: 320

Met Asn Pro Tyr Ile Tyr Leu Gly Gly Ala Ile Leu Ala Glu Val Ile
1               5                   10                  15

Gly Thr Thr Leu Met Lys Phe Ser Glu Gly Phe Thr Arg Leu Trp Pro
            20                  25                  30

Ser Val Gly Thr Ile Ile Cys Tyr Cys Thr Ser Phe Trp Leu Leu Ala
        35                  40                  45

Gln Thr Leu Ala Tyr Ile Pro Thr Gly Ile Ala Tyr Ala Ile Trp Ser
    50                  55                  60

Gly Val Gly Ile Val Leu Ile Ser Leu Leu Ser Trp Gly Phe Phe Gly
65                  70                  75                  80

Gln Arg Leu Asp Leu Pro Ala Ile Ile Gly Met Met Leu Ile Cys Ala
                85                  90                  95

Gly Val Leu Val Ile Asn Leu Leu Ser Arg Ser Ala Pro His
            100                 105                 110

<210> SEQ ID NO 321
<211> LENGTH: 110
<212> TYPE: PRT
<213> ORGANISM: Escherichia coli
```

-continued

<400> SEQUENCE: 321

Met Asn Pro Tyr Ile Tyr Leu Gly Gly Ala Ile Leu Ala Glu Val Ile
1               5                   10                  15

Gly Thr Thr Leu Met Lys Tyr Ser Glu Gly Phe Thr Arg Leu Trp Pro
            20                  25                  30

Ser Val Gly Thr Ile Ile Cys Tyr Cys Ala Ser Phe Trp Leu Leu Ala
        35                  40                  45

Gln Thr Leu Ala Tyr Ile Pro Thr Gly Ile Ala Tyr Ala Ile Trp Ser
    50                  55                  60

Gly Val Gly Ile Val Leu Ile Ser Leu Leu Ser Trp Gly Phe Phe Gly
65                  70                  75                  80

Gln Arg Leu Asp Leu Pro Ala Ile Ile Gly Met Met Leu Ile Cys Ala
                85                  90                  95

Gly Val Leu Val Ile Asn Leu Leu Ser Arg Ser Ala Pro His
            100                 105                 110

<210> SEQ ID NO 322
<211> LENGTH: 110
<212> TYPE: PRT
<213> ORGANISM: Shigella flexneri

<400> SEQUENCE: 322

Met Asn Pro Tyr Ile Tyr Leu Gly Gly Ala Ile Leu Ala Glu Val Ile
1               5                   10                  15

Gly Thr Thr Leu Met Lys Phe Ser Glu Gly Phe Thr Arg Leu Trp Pro
            20                  25                  30

Ser Val Gly Thr Ile Ile Cys Tyr Cys Ala Ser Phe Trp Leu Leu Ala
        35                  40                  45

Gln Thr Leu Ala Tyr Ile Pro Thr Gly Ile Ala Tyr Ala Ile Trp Ser
    50                  55                  60

Gly Val Gly Ile Val Leu Ile Ser Leu Leu Ser Trp Gly Phe Phe Gly
65                  70                  75                  80

Gln Arg Leu Asp Leu Pro Ala Ile Ile Gly Met Met Leu Ile Cys Ala
                85                  90                  95

Gly Val Leu Val Ile Asn Leu Leu Ser Arg Ser Ala Pro His
            100                 105                 110

<210> SEQ ID NO 323
<211> LENGTH: 110
<212> TYPE: PRT
<213> ORGANISM: Escherichia coli

<400> SEQUENCE: 323

Met Asn Pro Tyr Ile Tyr Leu Gly Gly Ala Ile Leu Ala Glu Val Ile
1               5                   10                  15

Gly Thr Thr Leu Met Lys Phe Ser Glu Gly Phe Thr Arg Leu Trp Pro
            20                  25                  30

Ser Val Gly Thr Ile Ile Cys Tyr Cys Ala Ser Phe Trp Leu Leu Ala
        35                  40                  45

Gln Thr Leu Ala Tyr Ile Pro Thr Gly Ile Ala Tyr Ala Ile Trp Ser
    50                  55                  60

Gly Val Gly Ile Val Leu Ile Ser Leu Leu Ser Trp Gly Phe Phe Gly
65                  70                  75                  80

Gln Arg Leu Asp Leu Pro Ala Ile Ile Gly Met Met Leu Ile Cys Ala
                85                  90                  95

Gly Val Leu Val Ile Asn Leu Leu Ser Arg Ser Ala Pro His
            100                 105                 110

<210> SEQ ID NO 324
<211> LENGTH: 110
<212> TYPE: PRT
<213> ORGANISM: Shigella flexneri

<400> SEQUENCE: 324

Met Asn Pro Tyr Ile Tyr Leu Gly Gly Ala Ile Leu Ala Glu Val Ile
1               5                   10                  15

Gly Thr Thr Leu Met Lys Phe Ser Glu Gly Phe Thr Arg Leu Trp Pro
            20                  25                  30

Ser Val Gly Thr Ile Ile Cys Tyr Cys Ala Ser Phe Trp Leu Leu Ala
        35                  40                  45

Gln Thr Leu Ala Tyr Ile Pro Thr Gly Ile Ala Tyr Ala Ile Trp Ser
    50                  55                  60

Gly Val Gly Ile Val Leu Ile Ser Leu Leu Ser Trp Gly Phe Phe Gly
65                  70                  75                  80

Gln Arg Leu Asp Leu Pro Ala Ile Ile Gly Met Met Leu Ile Cys Ala
                85                  90                  95

Gly Val Leu Val Ile Asn Leu Leu Ser Arg Ser Ala Pro His
            100                 105                 110

<210> SEQ ID NO 325
<211> LENGTH: 110
<212> TYPE: PRT
<213> ORGANISM: Shigella flexneri

<400> SEQUENCE: 325

Met Asn Pro Tyr Ile Tyr Leu Gly Gly Ala Ile Leu Ala Glu Val Ile
1               5                   10                  15

Gly Thr Thr Leu Met Lys Phe Ser Glu Gly Phe Thr Arg Leu Trp Pro
            20                  25                  30

Ser Val Gly Thr Ile Ile Cys Tyr Cys Ala Ser Phe Trp Leu Leu Ala
        35                  40                  45

Gln Thr Leu Ala Tyr Ile Pro Thr Gly Ile Ala Tyr Ala Ile Trp Ser
    50                  55                  60

Gly Val Gly Ile Val Leu Ile Ser Leu Leu Ser Trp Gly Phe Phe Gly
65                  70                  75                  80

Gln Arg Leu Asp Leu Pro Ala Ile Ile Gly Met Met Leu Ile Cys Ala
                85                  90                  95

Gly Val Leu Val Ile Asn Leu Leu Ser Arg Ser Ala Pro His
            100                 105                 110

<210> SEQ ID NO 326
<211> LENGTH: 110
<212> TYPE: PRT
<213> ORGANISM: Escherichia coli

<400> SEQUENCE: 326

Met Asn Pro Tyr Ile Tyr Leu Gly Gly Ala Ile Leu Ala Glu Val Ile
1               5                   10                  15

Gly Thr Thr Leu Met Lys Phe Ser Glu Gly Phe Thr Arg Leu Trp Pro
            20                  25                  30

Ser Val Gly Thr Ile Ile Cys Tyr Cys Ala Ser Phe Trp Leu Leu Ala
            35                  40                  45

Gln Thr Leu Ala Tyr Ile Pro Thr Gly Ile Ala Tyr Ala Ile Trp Ser
        50                  55                  60

Gly Val Gly Ile Val Leu Ile Ser Leu Leu Ser Trp Gly Phe Phe Gly
65                  70                  75                  80

Gln Arg Leu Asp Leu Pro Ala Ile Ile Gly Met Met Leu Ile Cys Ala
                85                  90                  95

Gly Val Leu Val Ile Asn Leu Leu Ser Arg Ser Thr Pro His
            100                 105                 110

<210> SEQ ID NO 327
<211> LENGTH: 110
<212> TYPE: PRT
<213> ORGANISM: Escherichia coli

<400> SEQUENCE: 327

Met Asn Pro Tyr Ile Tyr Leu Gly Gly Ala Ile Leu Ala Glu Val Ile
1               5                   10                  15

Gly Thr Thr Leu Met Lys Phe Ser Glu Gly Phe Thr Arg Leu Trp Pro
            20                  25                  30

Ser Val Gly Thr Ile Ile Cys Tyr Cys Ala Ser Phe Trp Leu Leu Ala
            35                  40                  45

Gln Thr Leu Ala Tyr Ile Pro Thr Gly Ile Ala Tyr Ala Ile Trp Ser
        50                  55                  60

Gly Val Gly Ile Val Leu Ile Ser Leu Leu Ser Trp Gly Phe Phe Gly
65                  70                  75                  80

Gln Arg Leu Asp Leu Pro Ala Ile Ile Gly Met Met Leu Ile Cys Ala
                85                  90                  95

Gly Val Leu Val Ile Asn Leu Leu Ser Arg Ser Ala Pro His
            100                 105                 110

<210> SEQ ID NO 328
<211> LENGTH: 110
<212> TYPE: PRT
<213> ORGANISM: Escherichia coli

<400> SEQUENCE: 328

Met Asn Pro Tyr Ile Tyr Leu Gly Gly Ala Ile Leu Ala Glu Val Ile
1               5                   10                  15

Gly Thr Thr Leu Met Lys Phe Ser Glu Gly Phe Thr Arg Leu Trp Pro
            20                  25                  30

Ser Val Gly Thr Ile Ile Cys Tyr Cys Ala Ser Phe Trp Leu Leu Ala
            35                  40                  45

Gln Thr Leu Ala Tyr Ile Pro Thr Gly Ile Ala Tyr Ala Ile Trp Ser
        50                  55                  60

Gly Val Gly Ile Val Leu Ile Ser Leu Leu Ser Trp Gly Leu Phe Gly
65                  70                  75                  80

Gln Arg Leu Asp Leu Pro Ala Ile Ile Gly Met Met Leu Ile Cys Ala
                85                  90                  95

Gly Val Leu Val Ile Asn Leu Leu Ser Arg Ser Thr Pro His
            100                 105                 110

<210> SEQ ID NO 329
<211> LENGTH: 110
<212> TYPE: PRT
<213> ORGANISM: Shigella sonnei

<400> SEQUENCE: 329

Met Asn Pro Tyr Ile Tyr Leu Gly Gly Ala Ile Leu Ala Glu Val Ile
1               5                   10                  15

Gly Thr Thr Leu Met Lys Phe Ser Glu Gly Phe Thr Arg Leu Trp Pro
            20                  25                  30

Ser Val Gly Thr Ile Ile Cys Tyr Cys Ala Ser Phe Trp Leu Leu Ala
        35                  40                  45

Gln Thr Leu Ala Tyr Ile Pro Thr Gly Ile Ala Tyr Ala Ile Trp Ser
    50                  55                  60

Gly Val Gly Ile Val Leu Ile Ser Leu Ser Trp Gly Phe Phe Gly
65                  70                  75                  80

Gln Arg Leu Asp Leu Pro Ala Ile Ile Gly Met Met Leu Ile Cys Ala
                85                  90                  95

Gly Val Leu Val Ile Asn Leu Leu Ser Arg Ser Ala Pro His
            100                 105                 110

<210> SEQ ID NO 330
<211> LENGTH: 110
<212> TYPE: PRT
<213> ORGANISM: Escherichia coli

<400> SEQUENCE: 330

Met Asn Pro Tyr Ile Tyr Leu Gly Gly Ala Ile Leu Ala Glu Val Ile
1               5                   10                  15

Gly Thr Thr Leu Met Lys Phe Ser Glu Gly Phe Thr Arg Leu Trp Pro
            20                  25                  30

Ser Val Gly Thr Ile Ile Cys Tyr Cys Ala Ser Phe Trp Leu Leu Ala
        35                  40                  45

Gln Thr Leu Ala Tyr Ile Pro Thr Gly Ile Ala Tyr Ala Ile Trp Ser
    50                  55                  60

Gly Val Gly Ile Val Leu Ile Ser Leu Ser Trp Gly Phe Phe Gly
65                  70                  75                  80

Gln Arg Leu Asp Leu Pro Ala Ile Ile Gly Met Met Leu Ile Cys Ala
                85                  90                  95

Gly Val Leu Val Ile Asn Leu Leu Ser Arg Ser Ala Pro Asn
            100                 105                 110

<210> SEQ ID NO 331
<211> LENGTH: 110
<212> TYPE: PRT
<213> ORGANISM: Escherichia coli

<400> SEQUENCE: 331

Met Asn Pro Tyr Ile Tyr Leu Gly Gly Ala Ile Leu Ala Glu Val Ile
1               5                   10                  15

Gly Thr Thr Leu Met Lys Phe Ser Glu Gly Phe Thr Arg Leu Trp Pro
            20                  25                  30

Ser Val Gly Thr Ile Ile Cys Tyr Cys Ala Ser Phe Trp Leu Leu Ala
        35                  40                  45

Gln Thr Leu Ala Tyr Ile Pro Thr Gly Ile Ala Tyr Ala Ile Trp Ser
    50                  55                  60

Gly Val Gly Ile Val Leu Ile Ser Leu Ser Trp Gly Leu Phe Gly
65                  70                  75                  80

Gln Arg Leu Asp Leu Pro Ala Ile Ile Gly Met Met Leu Ile Cys Ala
                85                  90                  95

Gly Val Leu Val Ile Asn Leu Leu Ser Arg Ser Thr Pro His
            100                 105                 110

<210> SEQ ID NO 332
<211> LENGTH: 110
<212> TYPE: PRT
<213> ORGANISM: Escherichia coli

<400> SEQUENCE: 332

Met Asn Pro Tyr Ile Tyr Leu Gly Gly Ala Ile Leu Ala Glu Val Ile
1               5                   10                  15

Gly Thr Thr Leu Met Lys Phe Ser Glu Gly Phe Thr Arg Leu Trp Pro
            20                  25                  30

Ser Val Gly Thr Ile Ile Cys Tyr Cys Ala Ser Phe Trp Leu Leu Ala
        35                  40                  45

Gln Thr Leu Ala Tyr Ile Pro Thr Gly Ile Ala Tyr Ala Ile Trp Ser
    50                  55                  60

Gly Val Gly Ile Val Leu Ile Ser Leu Leu Ser Trp Gly Leu Phe Gly
65                  70                  75                  80

Gln Arg Leu Asp Leu Pro Ala Ile Ile Gly Met Met Leu Ile Cys Ala
                85                  90                  95

Gly Val Leu Val Ile Asn Leu Leu Ser Arg Ser Thr Pro His
            100                 105                 110

<210> SEQ ID NO 333
<211> LENGTH: 110
<212> TYPE: PRT
<213> ORGANISM: Escherichia coli

<400> SEQUENCE: 333

Met Asn Pro Tyr Ile Tyr Leu Gly Gly Ala Ile Leu Ala Glu Val Ile
1               5                   10                  15

Gly Thr Thr Leu Met Lys Phe Ser Glu Gly Phe Thr Arg Leu Trp Pro
            20                  25                  30

Ser Val Gly Thr Ile Ile Cys Tyr Cys Ala Ser Phe Trp Leu Leu Ala
        35                  40                  45

Gln Thr Leu Ala Tyr Ile Pro Thr Gly Ile Ala Tyr Ala Ile Trp Ser
    50                  55                  60

Gly Val Gly Ile Val Leu Ile Ser Leu Leu Ser Trp Gly Phe Phe Gly
65                  70                  75                  80

Gln Arg Leu Asp Leu Pro Ala Ile Ile Gly Met Met Leu Ile Cys Ala
                85                  90                  95

Gly Val Leu Val Ile Asn Leu Leu Ser Arg Ser Ala Pro His
            100                 105                 110

<210> SEQ ID NO 334
<211> LENGTH: 110
<212> TYPE: PRT
<213> ORGANISM: Escherichia coli

<400> SEQUENCE: 334

Met Asn Pro Tyr Ile Tyr Leu Gly Gly Ala Ile Leu Ala Glu Val Ile
1               5                   10                  15

Gly Thr Thr Leu Met Lys Phe Ser Glu Gly Phe Thr Arg Leu Trp Pro
            20                  25                  30

Ser Val Gly Thr Ile Ile Cys Tyr Cys Ala Ser Phe Trp Leu Leu Ala
            35                  40                  45

Gln Thr Leu Ala Tyr Ile Pro Thr Gly Ile Ala Tyr Ala Ile Trp Ser
    50                  55                  60

Gly Val Gly Ile Val Leu Ile Ser Leu Leu Ser Trp Gly Phe Phe Gly
65                  70                  75                  80

Gln Arg Leu Asp Leu Pro Ala Ile Ile Gly Met Met Leu Ile Cys Ala
                85                  90                  95

Gly Val Leu Val Ile Asn Leu Leu Ser Arg Ser Ala Pro His
            100                 105                 110

<210> SEQ ID NO 335
<211> LENGTH: 110
<212> TYPE: PRT
<213> ORGANISM: Escherichia coli

<400> SEQUENCE: 335

Met Asn Pro Tyr Ile Tyr Leu Gly Gly Ala Ile Leu Ala Glu Val Ile
1               5                   10                  15

Gly Thr Thr Leu Met Lys Phe Ser Glu Gly Phe Thr Arg Leu Trp Pro
            20                  25                  30

Ser Val Gly Thr Ile Ile Cys Tyr Cys Ala Ser Phe Trp Leu Leu Ala
            35                  40                  45

Gln Thr Leu Ala Tyr Ile Pro Thr Gly Ile Ala Tyr Ala Ile Trp Ser
    50                  55                  60

Gly Val Gly Ile Val Leu Ile Ser Leu Leu Ser Trp Gly Phe Phe Gly
65                  70                  75                  80

Gln Arg Leu Asp Leu Pro Ala Ile Ile Gly Met Met Leu Ile Cys Ala
                85                  90                  95

Gly Val Leu Val Ile Asn Leu Leu Ser Arg Ser Ala Pro His
            100                 105                 110

<210> SEQ ID NO 336
<211> LENGTH: 110
<212> TYPE: PRT
<213> ORGANISM: Escherichia albertii

<400> SEQUENCE: 336

Met Asn Pro Tyr Ile Tyr Leu Gly Gly Ala Ile Leu Ala Glu Val Ile
1               5                   10                  15

Gly Thr Thr Leu Met Lys Phe Ser Glu Gly Phe Thr Arg Leu Trp Pro
            20                  25                  30

Ser Val Gly Thr Ile Ile Cys Tyr Cys Thr Ser Phe Trp Leu Leu Ala
            35                  40                  45

Gln Thr Leu Ala Tyr Ile Pro Thr Gly Ile Ala Tyr Ala Ile Trp Ser
    50                  55                  60

Gly Val Gly Ile Val Leu Ile Ser Leu Leu Ser Trp Gly Ile Phe Gly
65                  70                  75                  80

Gln Arg Leu Asp Leu Pro Ala Ile Ile Gly Met Met Leu Ile Cys Ala
                85                  90                  95

Gly Val Leu Val Ile Asn Leu Leu Ser Arg Ser Ala Thr His
            100                 105                 110

<210> SEQ ID NO 337
<211> LENGTH: 110
<212> TYPE: PRT
<213> ORGANISM: Escherichia albertii

<400> SEQUENCE: 337

Met Asn Pro Tyr Ile Tyr Leu Gly Gly Ala Ile Leu Ala Glu Val Ile
1               5                   10                  15

Gly Thr Thr Leu Met Lys Phe Ser Glu Gly Phe Thr Arg Leu Trp Pro
            20                  25                  30

Ser Val Gly Thr Ile Ile Cys Tyr Cys Ala Ser Phe Trp Leu Leu Ala
        35                  40                  45

Gln Thr Leu Ala Tyr Ile Pro Thr Gly Ile Ala Tyr Ala Ile Trp Ser
    50                  55                  60

Gly Val Gly Ile Val Leu Ile Ser Leu Ser Trp Gly Ile Phe Gly
65                  70                  75                  80

Gln Arg Leu Asp Leu Pro Ala Ile Ile Gly Met Met Leu Ile Cys Ala
                85                  90                  95

Gly Val Leu Val Ile Asn Leu Leu Ser Arg Ser Ala Thr His
            100                 105                 110

<210> SEQ ID NO 338
<211> LENGTH: 110
<212> TYPE: PRT
<213> ORGANISM: Escherichia coli

<400> SEQUENCE: 338

Met Asn Pro Tyr Ile Tyr Leu Gly Gly Ala Ile Leu Ala Glu Val Ile
1               5                   10                  15

Gly Thr Thr Leu Met Lys Phe Ser Glu Gly Phe Thr Arg Leu Trp Pro
            20                  25                  30

Ser Val Gly Thr Ile Ile Cys Tyr Cys Ala Ser Phe Trp Leu Leu Ala
        35                  40                  45

Gln Thr Leu Ala Tyr Ile Pro Thr Gly Ile Ala Tyr Ala Ile Trp Ser
    50                  55                  60

Gly Val Gly Ile Val Leu Ile Ser Leu Ser Trp Gly Phe Phe Gly
65                  70                  75                  80

Gln Arg Leu Asp Leu Pro Ala Ile Ile Gly Met Met Leu Ile Cys Ala
                85                  90                  95

Gly Val Leu Val Ile Asn Leu Leu Ser Arg Ser Ala Pro His
            100                 105                 110

<210> SEQ ID NO 339
<211> LENGTH: 110
<212> TYPE: PRT
<213> ORGANISM: Escherichia coli

<400> SEQUENCE: 339

Met Asn Pro Tyr Ile Tyr Leu Gly Gly Ala Ile Leu Ala Glu Val Ile
1               5                   10                  15

Gly Thr Thr Leu Met Lys Phe Ser Glu Gly Phe Thr Arg Leu Trp Pro
            20                  25                  30

Ser Val Gly Thr Ile Ile Cys Tyr Cys Ala Ser Phe Trp Leu Leu Ala
        35                  40                  45

Gln Thr Leu Ala Tyr Ile Pro Thr Gly Ile Ala Tyr Ala Ile Trp Ser
    50                  55                  60

Gly Val Gly Ile Val Leu Ile Ser Leu Ser Trp Gly Phe Phe Gly
65                  70                  75                  80

Gln Arg Leu Asp Leu Pro Ala Ile Ile Gly Met Met Leu Ile Cys Ala
                85                  90                  95

Gly Val Leu Val Ile Asn Leu Leu Ser Arg Ser Ala Pro His
            100                 105                 110

<210> SEQ ID NO 340
<211> LENGTH: 110
<212> TYPE: PRT
<213> ORGANISM: Escherichia coli

<400> SEQUENCE: 340

Met Asn Pro Tyr Ile Tyr Leu Gly Gly Ala Ile Leu Ala Glu Val Ile
1               5                   10                  15

Gly Thr Thr Leu Met Lys Phe Ser Glu Gly Phe Thr Arg Leu Trp Pro
            20                  25                  30

Ser Val Gly Thr Ile Ile Cys Tyr Cys Ala Ser Phe Trp Leu Leu Ala
        35                  40                  45

Gln Thr Leu Ala Tyr Ile Pro Thr Gly Ile Ala Tyr Ala Ile Trp Ser
    50                  55                  60

Gly Val Gly Ile Val Leu Ile Ser Leu Leu Ser Trp Gly Phe Phe Gly
65                  70                  75                  80

Gln Arg Leu Asp Leu Pro Ala Ile Ile Gly Met Met Leu Ile Cys Ala
                85                  90                  95

Gly Val Leu Val Ile Asn Leu Leu Ser Arg Ser Thr Pro His
            100                 105                 110

<210> SEQ ID NO 341
<211> LENGTH: 110
<212> TYPE: PRT
<213> ORGANISM: Escherichia coli

<400> SEQUENCE: 341

Met Asn Pro Tyr Ile Tyr Leu Gly Gly Ala Ile Leu Ala Glu Val Ile
1               5                   10                  15

Gly Thr Thr Leu Met Lys Phe Ser Glu Gly Phe Thr Arg Leu Trp Pro
            20                  25                  30

Ser Val Gly Thr Ile Ile Cys Tyr Cys Ala Ser Phe Trp Leu Leu Ala
        35                  40                  45

Gln Thr Leu Ala Tyr Ile Pro Thr Gly Ile Ala Tyr Ala Ile Trp Ser
    50                  55                  60

Gly Val Gly Ile Val Leu Ile Ser Leu Leu Ser Trp Gly Phe Phe Gly
65                  70                  75                  80

Gln Arg Leu Asp Leu Pro Ala Ile Ile Gly Met Met Leu Ile Cys Ala
                85                  90                  95

Gly Val Leu Val Ile Asn Leu Leu Ser Arg Ser Ala Pro His
            100                 105                 110

<210> SEQ ID NO 342
<211> LENGTH: 110
<212> TYPE: PRT
<213> ORGANISM: Shigella sonnei

<400> SEQUENCE: 342

Met Asn Pro Tyr Ile Tyr Leu Gly Gly Ala Ile Leu Ala Glu Val Ile
1               5                   10                  15

Gly Thr Thr Leu Met Lys Phe Ser Glu Gly Phe Thr Arg Leu Trp Pro
            20                  25                  30

Ser Val Gly Thr Ile Ile Cys Tyr Cys Ala Ser Phe Trp Leu Leu Ala
        35                  40                  45

Gln Thr Leu Ala Tyr Ile Pro Thr Gly Ile Ala Tyr Ala Ile Trp Ser
    50                  55                  60

Gly Val Gly Ile Val Leu Ile Gly Leu Ser Trp Gly Phe Phe Gly
65                  70                  75                  80

Gln Arg Leu Asp Leu Pro Ala Ile Ile Gly Met Met Leu Ile Cys Ala
                85                  90                  95

Gly Val Leu Val Ile Asn Leu Leu Ser Arg Ser Ala Pro His
            100                 105                 110

<210> SEQ ID NO 343
<211> LENGTH: 110
<212> TYPE: PRT
<213> ORGANISM: Shigella sonnei

<400> SEQUENCE: 343

Met Asn Pro Tyr Ile Tyr Leu Gly Gly Ala Ile Leu Ala Glu Val Ile
1               5                   10                  15

Gly Thr Thr Leu Met Lys Phe Ser Glu Gly Phe Thr Arg Leu Trp Pro
            20                  25                  30

Ser Val Gly Thr Ile Ile Cys Tyr Cys Ala Ser Phe Trp Leu Leu Ala
        35                  40                  45

Gln Thr Leu Ala Tyr Ile Pro Lys Gly Ile Ala Tyr Ala Ile Trp Ser
    50                  55                  60

Gly Val Gly Ile Val Leu Ile Ser Leu Leu Ser Trp Gly Phe Phe Gly
65                  70                  75                  80

Gln Arg Leu Asp Leu Pro Ala Ile Ile Gly Met Met Leu Ile Cys Ala
                85                  90                  95

Gly Val Leu Val Ile Asn Leu Leu Ser Arg Ser Ala Pro His
            100                 105                 110

<210> SEQ ID NO 344
<211> LENGTH: 110
<212> TYPE: PRT
<213> ORGANISM: Shigella sonnei

<400> SEQUENCE: 344

Met Asn Pro Tyr Ile Tyr Leu Gly Gly Ala Ile Leu Ala Glu Val Ile
1               5                   10                  15

Gly Thr Thr Leu Met Lys Phe Ser Glu Gly Phe Thr Arg Leu Trp Pro
            20                  25                  30

Ser Val Gly Thr Ile Ile Cys Tyr Cys Thr Ser Phe Trp Leu Leu Ala
        35                  40                  45

Gln Thr Leu Ala Tyr Ile Pro Thr Gly Ile Ala Tyr Ala Ile Trp Ser
    50                  55                  60

Gly Val Gly Ile Val Leu Ile Ser Leu Leu Ser Trp Gly Phe Phe Gly
65                  70                  75                  80

Gln Arg Leu Asp Leu Pro Ala Ile Ile Gly Met Met Leu Ile Cys Ala
                85                  90                  95

Gly Val Leu Val Ile Asn Leu Leu Ser Arg Ser Ala Pro His
            100                 105                 110

<210> SEQ ID NO 345
<211> LENGTH: 110
<212> TYPE: PRT
<213> ORGANISM: Escherichia coli

<400> SEQUENCE: 345

Met Asn Pro Tyr Ile Tyr Leu Gly Gly Ala Ile Leu Ala Glu Val Ile
1               5                   10                  15

Gly Thr Thr Leu Met Lys Phe Ser Glu Gly Phe Thr Arg Leu Trp Pro
            20                  25                  30

Ser Val Gly Thr Ile Ile Cys Tyr Cys Ala Ser Phe Trp Leu Leu Ala
        35                  40                  45

Gln Thr Leu Ala Tyr Ile Pro Thr Gly Ile Ala Tyr Ala Ile Trp Ser
    50                  55                  60

Gly Val Gly Ile Val Leu Ile Ser Leu Ser Trp Gly Leu Phe Gly
65                  70                  75                  80

Gln Arg Leu Asp Leu Pro Ala Ile Ile Gly Met Met Leu Ile Cys Ala
                85                  90                  95

Gly Val Leu Val Ile Asn Leu Leu Ser Arg Ser Thr Pro His
            100                 105                 110

<210> SEQ ID NO 346
<211> LENGTH: 110
<212> TYPE: PRT
<213> ORGANISM: Escherichia coli

<400> SEQUENCE: 346

Met Asn Pro Tyr Ile Tyr Leu Gly Gly Ala Ile Leu Ala Glu Val Ile
1               5                   10                  15

Gly Thr Thr Leu Met Lys Phe Ser Glu Gly Phe Thr Arg Leu Trp Pro
            20                  25                  30

Ser Val Gly Thr Ile Ile Cys Tyr Cys Ala Ser Phe Trp Leu Leu Ala
        35                  40                  45

Gln Thr Leu Ala Tyr Ile Pro Thr Gly Ile Ala Tyr Ala Ile Trp Ser
    50                  55                  60

Gly Val Gly Ile Val Leu Ile Ser Leu Ser Trp Gly Phe Phe Gly
65                  70                  75                  80

Gln Arg Leu Asp Leu Pro Ala Ile Ile Gly Met Met Leu Ile Cys Ala
                85                  90                  95

Gly Val Leu Val Ile Asn Leu Leu Ser Arg Ser Ala Pro Asn
            100                 105                 110

<210> SEQ ID NO 347
<211> LENGTH: 110
<212> TYPE: PRT
<213> ORGANISM: Escherichia coli

<400> SEQUENCE: 347

Met Asn Pro Tyr Ile Tyr Leu Gly Gly Ala Ile Leu Ala Glu Val Ile
1               5                   10                  15

Gly Thr Thr Leu Met Lys Phe Ser Glu Gly Phe Thr Arg Leu Trp Pro
            20                  25                  30

Ser Val Gly Thr Ile Ile Cys Tyr Cys Ala Ser Phe Trp Leu Leu Ala
        35                  40                  45

Gln Thr Leu Ala Tyr Ile Pro Lys Gly Ile Ala Tyr Ala Ile Trp Ser
    50                  55                  60

Gly Val Gly Ile Val Leu Ile Ser Leu Ser Trp Gly Phe Phe Gly
65                  70                  75                  80

Gln Arg Leu Asp Leu Pro Ala Ile Ile Gly Met Met Leu Ile Cys Ala
                85                  90                  95

-continued

Gly Val Leu Val Ile Asn Leu Leu Ser Arg Ser Ala Pro His
            100                 105                 110

<210> SEQ ID NO 348
<211> LENGTH: 110
<212> TYPE: PRT
<213> ORGANISM: Escherichia coli

<400> SEQUENCE: 348

Met Asn Pro Tyr Ile Tyr Leu Gly Gly Ala Ile Leu Ala Glu Val Ile
1               5                   10                  15

Gly Thr Thr Leu Met Lys Phe Ser Glu Gly Phe Thr Arg Leu Trp Pro
            20                  25                  30

Ser Val Gly Thr Ile Ile Cys Tyr Cys Thr Ser Phe Trp Leu Leu Ala
        35                  40                  45

Gln Thr Leu Ala Tyr Ile Pro Thr Gly Ile Ala Tyr Ala Ile Trp Ser
    50                  55                  60

Gly Val Gly Ile Val Leu Ile Ser Leu Leu Ser Trp Gly Phe Phe Gly
65                  70                  75                  80

Gln Arg Leu Asp Leu Pro Ala Ile Ile Gly Met Met Leu Ile Cys Ala
                85                  90                  95

Gly Val Leu Val Ile Asn Leu Leu Ser Arg Ser Ala Pro His
            100                 105                 110

<210> SEQ ID NO 349
<211> LENGTH: 110
<212> TYPE: PRT
<213> ORGANISM: Shigella boydii

<400> SEQUENCE: 349

Met Asn Pro Tyr Ile Tyr Leu Gly Gly Ala Ile Leu Ala Glu Val Ile
1               5                   10                  15

Gly Thr Thr Leu Met Lys Phe Ser Glu Gly Phe Thr Arg Leu Trp Pro
            20                  25                  30

Ser Val Gly Thr Ile Ile Cys Tyr Cys Ala Ser Phe Trp Leu Leu Ala
        35                  40                  45

Gln Thr Leu Ala Tyr Ile Pro Thr Gly Ile Ala Tyr Ala Ile Trp Ser
    50                  55                  60

Gly Val Gly Ile Val Leu Ile Ser Leu Leu Ser Trp Gly Leu Phe Asp
65                  70                  75                  80

Gln Arg Leu Asp Leu Pro Ala Ile Ile Gly Met Met Leu Ile Cys Ala
                85                  90                  95

Gly Val Leu Val Ile Asn Leu Leu Ser Arg Ser Thr Pro His
            100                 105                 110

<210> SEQ ID NO 350
<211> LENGTH: 110
<212> TYPE: PRT
<213> ORGANISM: Shigella boydii

<400> SEQUENCE: 350

Met Asn Pro Tyr Ile Tyr Leu Gly Gly Ala Ile Leu Ala Glu Val Ile
1               5                   10                  15

Gly Thr Thr Leu Met Lys Phe Ser Glu Gly Phe Thr Arg Leu Trp Pro
            20                  25                  30

Ser Val Gly Thr Ile Ile Cys Tyr Cys Ala Ser Phe Trp Leu Leu Ala
        35                  40                  45

Gln Thr Leu Ala Tyr Ile Pro Thr Gly Ile Ala Tyr Ala Ile Trp Ser
50                  55                  60

Gly Val Gly Ile Val Leu Ile Ser Leu Leu Ser Trp Gly Phe Phe Gly
65                  70                  75                  80

Gln Arg Leu Asp Leu Pro Ala Ile Ile Gly Met Met Leu Ile Cys Ala
                85                  90                  95

Gly Val Leu Val Ile Asn Leu Leu Ser Arg Ser Ala Pro His
            100                 105                 110

<210> SEQ ID NO 351
<211> LENGTH: 110
<212> TYPE: PRT
<213> ORGANISM: Shigella flexneri

<400> SEQUENCE: 351

Met Asn Pro Tyr Ile Tyr Leu Gly Gly Ala Ile Leu Ala Glu Val Ile
1               5                   10                  15

Gly Thr Thr Leu Met Lys Phe Ser Glu Gly Phe Thr Arg Leu Trp Pro
            20                  25                  30

Ser Val Gly Thr Ile Ile Cys Tyr Cys Ala Ser Phe Trp Leu Leu Ala
        35                  40                  45

Gln Thr Leu Ala Tyr Ile Pro Thr Gly Ile Ala Tyr Ala Ile Trp Ser
50                  55                  60

Gly Val Gly Ile Val Leu Ile Ser Leu Leu Ser Trp Gly Phe Phe Gly
65                  70                  75                  80

Gln Arg Leu Asp Leu Pro Ala Ile Ile Gly Met Met Leu Ile Cys Ala
                85                  90                  95

Gly Val Leu Val Ile Asn Leu Leu Ser Arg Ser Ala Pro His
            100                 105                 110

<210> SEQ ID NO 352
<211> LENGTH: 117
<212> TYPE: PRT
<213> ORGANISM: Escherichia coli

<400> SEQUENCE: 352

Met Asn Arg Lys Glu Tyr Ala Met Asn Pro Tyr Ile Tyr Leu Gly Gly
1               5                   10                  15

Ala Ile Leu Ala Glu Val Ile Gly Thr Thr Leu Met Lys Phe Ser Glu
            20                  25                  30

Gly Phe Thr Arg Leu Trp Pro Ser Val Gly Thr Ile Ile Cys Tyr Cys
        35                  40                  45

Ala Ser Phe Trp Leu Leu Ala Gln Thr Leu Ala Tyr Ile Pro Thr Gly
50                  55                  60

Ile Ala Tyr Ala Ile Trp Ser Gly Val Gly Ile Val Leu Ile Ser Leu
65                  70                  75                  80

Leu Ser Trp Gly Phe Phe Gly Gln Arg Leu Asp Leu Pro Ala Ile Ile
                85                  90                  95

Gly Met Met Leu Ile Cys Ala Gly Val Leu Val Ile Asn Leu Leu Ser
            100                 105                 110

Arg Ser Ala Pro His
        115

<210> SEQ ID NO 353

<211> LENGTH: 117
<212> TYPE: PRT
<213> ORGANISM: Escherichia coli

<400> SEQUENCE: 353

Met Asn Arg Lys Glu Tyr Ala Met Asn Pro Tyr Ile Tyr Leu Gly Gly
1               5                   10                  15

Ala Ile Leu Ala Glu Val Ile Gly Thr Thr Leu Met Lys Phe Ser Glu
            20                  25                  30

Gly Phe Thr Arg Leu Trp Pro Ser Val Gly Thr Ile Ile Cys Tyr Cys
        35                  40                  45

Ala Ser Phe Trp Leu Leu Ala Gln Thr Leu Ala Tyr Ile Pro Thr Gly
    50                  55                  60

Ile Ala Tyr Ala Ile Trp Ser Gly Val Gly Ile Val Leu Ile Ser Leu
65                  70                  75                  80

Leu Ser Trp Gly Phe Phe Gly Gln Arg Leu Asp Leu Pro Ala Ile Ile
                85                  90                  95

Gly Met Met Leu Ile Cys Ala Gly Val Leu Val Ile Asn Leu Leu Ser
            100                 105                 110

Arg Ser Ala Pro His
        115

<210> SEQ ID NO 354
<211> LENGTH: 117
<212> TYPE: PRT
<213> ORGANISM: Escherichia coli

<400> SEQUENCE: 354

Met Asn Arg Lys Glu Tyr Ala Met Asn Pro Tyr Ile Tyr Leu Gly Gly
1               5                   10                  15

Ala Ile Leu Ala Glu Val Ile Gly Thr Thr Leu Met Lys Phe Ser Glu
            20                  25                  30

Gly Phe Thr Arg Leu Trp Pro Ser Val Gly Thr Ile Ile Cys Tyr Cys
        35                  40                  45

Ala Ser Phe Trp Leu Leu Ala Gln Thr Leu Ala Tyr Ile Pro Thr Gly
    50                  55                  60

Ile Ala Tyr Ala Ile Trp Ser Gly Val Gly Ile Val Leu Ile Ser Leu
65                  70                  75                  80

Leu Ser Trp Gly Phe Phe Gly Gln Arg Leu Asp Leu Pro Ala Ile Ile
                85                  90                  95

Gly Met Met Leu Ile Cys Ala Gly Val Leu Val Ile Asn Leu Leu Ser
            100                 105                 110

Arg Ser Ala Pro His
        115

<210> SEQ ID NO 355
<211> LENGTH: 117
<212> TYPE: PRT
<213> ORGANISM: Escherichia coli

<400> SEQUENCE: 355

Met Asn Arg Lys Glu Tyr Ala Met Asn Pro Tyr Ile Tyr Leu Gly Gly
1               5                   10                  15

Ala Ile Leu Ala Glu Val Ile Gly Thr Thr Leu Met Lys Phe Ser Glu
            20                  25                  30

Gly Phe Thr Arg Leu Trp Pro Ser Val Gly Thr Ile Ile Cys Tyr Cys
            35                  40                  45

Ala Ser Phe Trp Leu Leu Ala Gln Thr Leu Ala Tyr Ile Pro Thr Gly
     50                  55                  60

Ile Ala Tyr Ala Ile Trp Ser Gly Val Gly Ile Val Leu Ile Ser Leu
65                  70                  75                  80

Leu Ser Trp Gly Phe Phe Gly Gln Arg Leu Asp Leu Pro Ala Ile Ile
                85                  90                  95

Gly Met Met Leu Ile Cys Ala Gly Val Leu Val Ile Asn Leu Leu Ser
            100                 105                 110

Arg Ser Ala Pro His
        115

<210> SEQ ID NO 356
<211> LENGTH: 117
<212> TYPE: PRT
<213> ORGANISM: Escherichia coli

<400> SEQUENCE: 356

Met Asn Arg Lys Glu Tyr Ala Met Asn Pro Tyr Ile Tyr Leu Gly Gly
1               5                   10                  15

Ala Ile Leu Ala Glu Val Ile Gly Thr Thr Leu Met Lys Phe Ser Glu
            20                  25                  30

Gly Phe Thr Arg Leu Trp Pro Ser Val Gly Thr Ile Ile Cys Tyr Cys
            35                  40                  45

Ala Ser Phe Trp Leu Leu Ala Gln Thr Leu Ala Tyr Ile Pro Thr Gly
     50                  55                  60

Ile Ala Tyr Ala Ile Trp Ser Gly Val Gly Ile Val Leu Ile Ser Leu
65                  70                  75                  80

Leu Ser Trp Gly Phe Phe Gly Gln Arg Leu Asp Leu Pro Ala Ile Ile
                85                  90                  95

Gly Met Met Leu Ile Cys Ala Gly Val Leu Val Ile Asn Leu Leu Ser
            100                 105                 110

Arg Ser Ala Pro His
        115

<210> SEQ ID NO 357
<211> LENGTH: 117
<212> TYPE: PRT
<213> ORGANISM: Escherichia coli

<400> SEQUENCE: 357

Met Asn Arg Lys Glu Tyr Ala Met Asn Pro Tyr Ile Tyr Leu Gly Gly
1               5                   10                  15

Ala Ile Leu Ala Glu Val Ile Gly Thr Thr Leu Met Lys Phe Ser Glu
            20                  25                  30

Gly Phe Thr Arg Leu Trp Pro Ser Val Gly Thr Ile Ile Cys Tyr Cys
            35                  40                  45

Ala Ser Phe Trp Leu Leu Ala Gln Thr Leu Ala Tyr Ile Pro Thr Gly
     50                  55                  60

Ile Ala Tyr Ala Ile Trp Ser Gly Val Gly Ile Val Leu Ile Ser Leu
65                  70                  75                  80

Leu Ser Trp Gly Phe Phe Gly Gln Arg Leu Asp Leu Pro Ala Ile Ile
                85                  90                  95

Gly Met Met Leu Ile Cys Ala Gly Val Leu Val Ile Asn Leu Leu Ser
            100                 105                 110

Arg Ser Ala Pro His
        115

<210> SEQ ID NO 358
<211> LENGTH: 117
<212> TYPE: PRT
<213> ORGANISM: Escherichia coli

<400> SEQUENCE: 358

Met Asn Arg Lys Glu Tyr Ala Met Asn Pro Tyr Ile Tyr Leu Gly Gly
1               5                   10                  15

Ala Ile Leu Ala Glu Val Ile Gly Thr Thr Leu Met Lys Phe Ser Glu
            20                  25                  30

Gly Phe Thr Arg Leu Trp Pro Ser Val Gly Thr Ile Ile Cys Tyr Cys
        35                  40                  45

Ala Ser Phe Trp Leu Leu Ala Gln Thr Leu Ala Tyr Ile Pro Thr Gly
    50                  55                  60

Ile Ala Tyr Ala Ile Trp Ser Gly Val Gly Ile Val Leu Ile Ser Leu
65                  70                  75                  80

Leu Ser Trp Gly Phe Phe Gly Gln Arg Leu Asp Leu Pro Ala Ile Ile
                85                  90                  95

Gly Met Met Leu Ile Cys Ala Gly Val Leu Val Ile Asn Leu Leu Ser
            100                 105                 110

Arg Ser Ala Pro His
        115

<210> SEQ ID NO 359
<211> LENGTH: 117
<212> TYPE: PRT
<213> ORGANISM: Escherichia coli

<400> SEQUENCE: 359

Met Asn Arg Lys Glu Tyr Ala Met Asn Pro Tyr Ile Tyr Leu Gly Gly
1               5                   10                  15

Ala Ile Leu Ala Glu Val Ile Gly Thr Thr Leu Met Lys Phe Ser Glu
            20                  25                  30

Gly Phe Thr Arg Leu Trp Pro Ser Val Gly Thr Ile Ile Cys Tyr Cys
        35                  40                  45

Ala Ser Phe Trp Leu Leu Ala Gln Thr Leu Ala Tyr Ile Pro Thr Gly
    50                  55                  60

Ile Ala Tyr Ala Ile Trp Ser Gly Val Gly Ile Val Leu Ile Ser Leu
65                  70                  75                  80

Leu Ser Trp Gly Phe Phe Gly Gln Arg Leu Asp Leu Pro Ala Ile Ile
                85                  90                  95

Gly Met Met Leu Ile Cys Ala Gly Val Leu Val Ile Asn Leu Leu Ser
            100                 105                 110

Arg Ser Thr Pro His
        115

<210> SEQ ID NO 360
<211> LENGTH: 117
<212> TYPE: PRT
<213> ORGANISM: Escherichia coli

<400> SEQUENCE: 360

Met Asn Arg Lys Glu Tyr Ala Met Asn Pro Tyr Ile Tyr Leu Gly Gly
1               5                   10                  15

Ala Ile Leu Ala Glu Val Ile Gly Thr Thr Leu Met Lys Phe Ser Glu
            20                  25                  30

Gly Phe Thr Arg Leu Trp Pro Ser Val Gly Thr Ile Ile Cys Tyr Cys
            35                  40                  45

Ala Ser Phe Trp Leu Leu Ala Gln Thr Leu Ala Tyr Ile Pro Thr Gly
 50                  55                  60

Ile Ala Tyr Ala Ile Trp Ser Gly Val Gly Ile Val Leu Ile Ser Leu
 65                  70                  75                  80

Leu Ser Trp Gly Phe Phe Gly Gln Arg Leu Asp Leu Pro Ala Ile Ile
                85                  90                  95

Gly Met Met Leu Ile Cys Ala Gly Val Leu Val Ile Asn Leu Leu Ser
                100                 105                 110

Arg Ser Ala Pro His
        115

<210> SEQ ID NO 361
<211> LENGTH: 117
<212> TYPE: PRT
<213> ORGANISM: Escherichia coli

<400> SEQUENCE: 361

Met Asn Arg Lys Glu Tyr Ala Met Asn Pro Tyr Ile Tyr Leu Gly Gly
1               5                   10                  15

Ala Ile Leu Ala Glu Val Ile Gly Thr Thr Leu Met Lys Phe Ser Glu
            20                  25                  30

Gly Phe Thr Arg Leu Trp Pro Ser Val Gly Thr Ile Ile Cys Tyr Cys
            35                  40                  45

Ala Ser Phe Trp Leu Leu Ala Gln Thr Leu Ala Tyr Ile Pro Thr Gly
 50                  55                  60

Ile Ala Tyr Ala Ile Trp Ser Gly Val Gly Ile Val Leu Ile Ser Leu
 65                  70                  75                  80

Leu Ser Trp Gly Phe Phe Gly Gln Arg Leu Asp Leu Pro Ala Ile Ile
                85                  90                  95

Gly Met Met Leu Ile Cys Ala Gly Val Leu Val Ile Asn Leu Leu Ser
                100                 105                 110

Arg Ser Ala Pro His
        115

<210> SEQ ID NO 362
<211> LENGTH: 165
<212> TYPE: PRT
<213> ORGANISM: Escherichia coli

<400> SEQUENCE: 362

Met Asn Ser Phe Val Ser Leu Gly Phe Leu Leu Ile Ile Ile Val Pro
1               5                   10                  15

Ala Phe Ile Ser Cys His Ala Arg Ala Pro Trp Ile His Ile His Gln
            20                  25                  30

Asp Glu Asn Gly Glu Leu Cys Ser Asn Cys Ser Thr Ile Leu Ser Ser
            35                  40                  45

Met Asn Arg Lys Glu Tyr Ala Met Asn Pro Tyr Ile Tyr Leu Gly Gly
        50                  55                  60

Ala Ile Leu Ala Glu Val Ile Gly Thr Thr Leu Met Lys Phe Ser Glu
 65                  70                  75                  80

Gly Phe Thr Arg Leu Trp Pro Ser Val Gly Thr Ile Ile Cys Tyr Cys
                85                  90                  95

```
Ala Ser Phe Trp Leu Leu Ala Gln Thr Leu Ala Tyr Ile Pro Thr Gly
                100                 105                 110

Ile Ala Tyr Ala Ile Trp Ser Gly Val Gly Ile Val Leu Ile Ser Leu
            115                 120                 125

Leu Ser Trp Gly Phe Phe Gly Gln Arg Leu Asp Leu Pro Ala Ile Ile
130                 135                 140

Gly Met Met Leu Ile Cys Ala Gly Val Leu Val Ile Asn Leu Leu Ser
145                 150                 155                 160

Arg Ser Ala Pro His
                165

<210> SEQ ID NO 363
<211> LENGTH: 165
<212> TYPE: PRT
<213> ORGANISM: Shigella flexneri

<400> SEQUENCE: 363

Met Asn Ser Phe Val Ser Leu Gly Phe Leu Leu Ile Ile Ile Val Pro
1               5                   10                  15

Ala Phe Ile Ser Cys His Ala Arg Ala Pro Trp Ile His Ile His Gln
            20                  25                  30

Asp Glu Asn Gly Glu Leu Cys Ser Asn Cys Ser Thr Ile Leu Ser Ser
        35                  40                  45

Met Asn Arg Lys Glu Tyr Ala Met Asn Pro Tyr Ile Tyr Leu Gly Gly
    50                  55                  60

Ala Ile Leu Ala Glu Val Ile Gly Thr Thr Leu Met Lys Phe Ser Glu
65                  70                  75                  80

Gly Phe Thr Arg Leu Trp Pro Ser Val Gly Thr Ile Ile Cys Tyr Cys
                85                  90                  95

Ala Ser Phe Trp Leu Leu Ala Gln Thr Leu Ala Tyr Ile Pro Thr Gly
                100                 105                 110

Ile Ala Tyr Ala Ile Trp Ser Gly Val Gly Ile Val Leu Ile Ser Leu
            115                 120                 125

Leu Ser Trp Gly Phe Phe Gly Gln Arg Leu Asp Leu Pro Ala Ile Ile
130                 135                 140

Gly Met Met Leu Ile Cys Ala Gly Val Leu Val Ile Asn Leu Leu Ser
145                 150                 155                 160

Arg Ser Ala Pro His
                165

<210> SEQ ID NO 364
<211> LENGTH: 165
<212> TYPE: PRT
<213> ORGANISM: Escherichia coli

<400> SEQUENCE: 364

Met Asn Ser Phe Val Ser Leu Gly Phe Leu Leu Ile Ile Ile Val Pro
1               5                   10                  15

Ala Phe Ile Ser Cys His Ala Arg Ala Pro Trp Ile His Ile His Gln
            20                  25                  30

Asp Glu Asn Gly Glu Leu Cys Ser Asn Cys Ser Thr Ile Leu Ser Ser
        35                  40                  45

Met Asn Arg Lys Glu Tyr Ala Met Asn Pro Tyr Ile Tyr Leu Gly Gly
    50                  55                  60

Ala Ile Leu Ala Glu Val Ile Gly Thr Thr Leu Met Lys Phe Ser Glu
65                  70                  75                  80
```

```
Gly Phe Thr Arg Leu Trp Pro Ser Val Gly Thr Ile Ile Cys Tyr Cys
                85                  90                  95

Ala Ser Phe Trp Leu Leu Ala Gln Thr Leu Ala Tyr Ile Pro Thr Gly
            100                 105                 110

Ile Ala Tyr Ala Ile Trp Ser Gly Val Gly Ile Val Leu Ile Ser Leu
        115                 120                 125

Leu Ser Trp Gly Phe Phe Gly Gln Arg Leu Asp Leu Pro Ala Ile Ile
    130                 135                 140

Gly Met Met Leu Ile Cys Ala Gly Val Leu Val Ile Asn Leu Leu Ser
145                 150                 155                 160

Arg Ser Ala Pro His
                165

<210> SEQ ID NO 365
<211> LENGTH: 165
<212> TYPE: PRT
<213> ORGANISM: Shigella flexneri

<400> SEQUENCE: 365

Met Asn Ser Phe Val Ser Leu Gly Phe Leu Leu Ile Ile Ile Val Pro
1               5                   10                  15

Ala Phe Ile Ser Cys His Ala Arg Ala Pro Trp Ile His Ile His Gln
            20                  25                  30

Asp Glu Asn Gly Glu Leu Cys Ser Asn Cys Ser Thr Ile Leu Ser Ser
        35                  40                  45

Met Asn Arg Lys Glu Tyr Ala Met Asn Pro Tyr Ile Tyr Leu Gly Gly
    50                  55                  60

Ala Ile Leu Ala Glu Val Ile Gly Thr Thr Leu Met Lys Phe Ser Glu
65                  70                  75                  80

Gly Phe Thr Arg Leu Trp Pro Ser Val Gly Thr Ile Ile Cys Tyr Cys
                85                  90                  95

Ala Ser Phe Trp Leu Leu Ala Gln Thr Leu Ala Tyr Ile Pro Thr Gly
            100                 105                 110

Ile Ala Tyr Ala Ile Trp Ser Gly Val Gly Ile Val Leu Ile Ser Leu
        115                 120                 125

Leu Ser Trp Gly Phe Phe Gly Gln Arg Leu Asp Leu Pro Ala Ile Ile
    130                 135                 140

Gly Met Met Leu Ile Cys Ala Gly Val Leu Val Ile Asn Leu Leu Ser
145                 150                 155                 160

Arg Ser Ala Pro His
                165

<210> SEQ ID NO 366
<211> LENGTH: 165
<212> TYPE: PRT
<213> ORGANISM: Shigella sonnei

<400> SEQUENCE: 366

Met Asn Ser Phe Val Ser Leu Gly Phe Leu Leu Ile Ile Ile Val Pro
1               5                   10                  15

Ala Phe Ile Ser Cys His Ala Arg Ala Pro Trp Ile His Ile His Gln
            20                  25                  30

Asp Glu Asn Gly Glu Leu Cys Ser Asn Cys Ser Thr Ile Leu Ser Ser
        35                  40                  45

Met Asn Arg Lys Glu Tyr Ala Met Asn Pro Tyr Ile Tyr Leu Gly Gly
    50                  55                  60
```

Ala Ile Leu Ala Glu Val Ile Gly Thr Thr Leu Met Lys Phe Ser Glu
65                  70                  75                  80

Gly Phe Thr Arg Leu Trp Pro Ser Val Gly Thr Ile Ile Cys Tyr Cys
                85                  90                  95

Ala Ser Phe Trp Leu Leu Ala Gln Thr Leu Ala Tyr Ile Pro Thr Gly
            100                 105                 110

Ile Ala Tyr Ala Ile Trp Ser Gly Val Gly Ile Val Leu Ile Ser Leu
        115                 120                 125

Leu Ser Trp Gly Phe Phe Gly Gln Arg Leu Asp Leu Pro Ala Ile Ile
    130                 135                 140

Gly Met Met Leu Ile Cys Ala Gly Val Leu Val Ile Asn Leu Leu Ser
145                 150                 155                 160

Arg Ser Ala Pro His
                165

<210> SEQ ID NO 367
<211> LENGTH: 170
<212> TYPE: PRT
<213> ORGANISM: Escherichia coli

<400> SEQUENCE: 367

Met Leu Pro Gly Arg Val Asn Ser Phe Val Ser Leu Gly Phe Leu Leu
1               5                   10                  15

Ile Ile Ile Val Pro Ala Phe Ile Ser Cys His Ala Arg Ala Pro Trp
            20                  25                  30

Ile His Ile His Gln Asp Glu Asn Gly Glu Leu Cys Ser Asn Cys Ser
        35                  40                  45

Thr Ile Leu Ser Ser Met Asn Arg Lys Glu Tyr Ala Met Asn Pro Tyr
    50                  55                  60

Ile Tyr Leu Gly Gly Ala Ile Leu Ala Glu Val Ile Gly Thr Thr Leu
65                  70                  75                  80

Met Lys Phe Ser Glu Gly Phe Thr Arg Leu Trp Pro Ser Val Gly Thr
                85                  90                  95

Ile Ile Cys Tyr Cys Ala Ser Phe Trp Leu Leu Ala Gln Thr Leu Ala
            100                 105                 110

Tyr Ile Pro Thr Gly Ile Ala Tyr Ala Ile Trp Ser Gly Val Gly Ile
        115                 120                 125

Val Leu Ile Ser Leu Leu Ser Trp Gly Phe Phe Gly Gln Arg Leu Asp
    130                 135                 140

Leu Pro Ala Ile Ile Gly Met Met Leu Ile Cys Ala Gly Val Leu Val
145                 150                 155                 160

Ile Asn Leu Leu Ser Arg Ser Ala Pro His
                165                 170

<210> SEQ ID NO 368
<211> LENGTH: 170
<212> TYPE: PRT
<213> ORGANISM: Escherichia coli

<400> SEQUENCE: 368

Met Leu Pro Gly Arg Val Asn Ser Phe Val Ser Leu Gly Phe Leu Leu
1               5                   10                  15

Ile Ile Ile Val Pro Ala Phe Ile Ser Cys His Ala Arg Ala Pro Trp
            20                  25                  30

Ile His Ile His Gln Asp Glu Asn Gly Glu Leu Cys Ser Asn Cys Ser
        35                  40                  45

Thr Ile Leu Ser Ser Met Asn Arg Lys Glu Tyr Ala Met Asn Pro Tyr
          50                  55                  60

Ile Tyr Leu Gly Gly Ala Ile Leu Ala Glu Val Ile Gly Thr Thr Leu
 65                  70                  75                  80

Met Lys Phe Ser Glu Gly Phe Thr Arg Leu Trp Pro Ser Val Gly Thr
                 85                  90                  95

Ile Ile Cys Tyr Cys Ala Ser Phe Trp Leu Ala Gln Thr Leu Ala
                100                 105                 110

Tyr Ile Pro Thr Gly Ile Ala Tyr Ala Ile Trp Ser Gly Val Gly Ile
                115                 120                 125

Val Leu Ile Ser Leu Leu Ser Trp Gly Phe Phe Gly Gln Arg Leu Asp
        130                 135                 140

Leu Pro Ala Ile Ile Gly Met Met Leu Ile Cys Ala Gly Val Leu Val
145                 150                 155                 160

Ile Asn Leu Leu Ser Arg Ser Ala Pro His
                165                 170

<210> SEQ ID NO 369
<211> LENGTH: 170
<212> TYPE: PRT
<213> ORGANISM: Escherichia coli

<400> SEQUENCE: 369

Met Leu Ile Gly Arg Val Asn Ser Phe Val Ser Leu Gly Phe Leu Leu
 1               5                  10                  15

Ile Ile Ile Val Pro Ala Phe Ile Ser Cys His Ala Arg Ala Pro Trp
                 20                  25                  30

Ile His Ile His Gln Asp Glu Asn Gly Glu Leu Cys Ser Asn Cys Ser
            35                  40                  45

Thr Ile Leu Ser Ser Met Asn Arg Lys Glu Tyr Ala Met Asn Pro Tyr
          50                  55                  60

Ile Tyr Leu Gly Gly Ala Ile Leu Ala Glu Val Ile Gly Thr Thr Leu
 65                  70                  75                  80

Met Lys Phe Ser Glu Gly Phe Thr Arg Leu Trp Pro Ser Val Gly Thr
                 85                  90                  95

Ile Ile Cys Tyr Cys Ala Ser Phe Trp Leu Ala Gln Thr Leu Ala
                100                 105                 110

Tyr Ile Pro Thr Gly Ile Ala Tyr Ala Ile Trp Ser Gly Val Gly Ile
                115                 120                 125

Val Leu Ile Ser Leu Leu Ser Trp Gly Phe Phe Gly Gln Arg Leu Asp
        130                 135                 140

Leu Pro Ala Ile Ile Gly Met Met Leu Ile Cys Ala Gly Val Leu Val
145                 150                 155                 160

Ile Asn Leu Leu Ser Arg Ser Ala Pro His
                165                 170

<210> SEQ ID NO 370
<211> LENGTH: 170
<212> TYPE: PRT
<213> ORGANISM: Escherichia coli

<400> SEQUENCE: 370

Met Leu Pro Gly Arg Val Asn Ser Phe Val Ser Leu Gly Phe Leu Leu
 1               5                  10                  15

Ile Ile Ile Val Pro Ala Phe Ile Ser Cys His Ala Arg Ala Pro Trp
                 20                  25                  30

-continued

Ile His Ile His Gln Asp Glu Asn Gly Glu Leu Cys Ser Asn Cys Ser
         35                  40                  45

Thr Ile Leu Ser Ser Met Asn Arg Lys Glu Tyr Ala Met Asn Pro Tyr
 50                  55                  60

Ile Tyr Leu Gly Gly Ala Ile Leu Ala Glu Val Ile Gly Thr Thr Leu
 65                  70                  75                  80

Met Lys Phe Ser Glu Gly Phe Thr Arg Leu Trp Pro Ser Val Gly Thr
                 85                  90                  95

Ile Ile Cys Tyr Cys Ala Ser Phe Trp Leu Leu Ala Gln Thr Leu Ala
                100                 105                 110

Tyr Ile Pro Thr Gly Ile Ala Tyr Ala Ile Trp Ser Gly Val Gly Ile
            115                 120                 125

Val Leu Ile Ser Leu Leu Ser Trp Gly Phe Phe Gly Gln Arg Leu Asp
130                 135                 140

Leu Pro Ala Ile Ile Gly Met Met Leu Ile Cys Ala Gly Val Leu Val
145                 150                 155                 160

Ile Asn Leu Leu Ser Arg Ser Ala Pro His
                165                 170

<210> SEQ ID NO 371
<211> LENGTH: 170
<212> TYPE: PRT
<213> ORGANISM: Escherichia coli

<400> SEQUENCE: 371

Met Leu Pro Gly Arg Val Asn Ser Phe Val Ser Leu Gly Phe Leu Leu
 1               5                  10                  15

Ile Ile Ile Val Pro Ala Phe Ile Ser Cys His Ala Arg Ala Pro Trp
                 20                  25                  30

Ile His Ile His Gln Asp Glu Asn Gly Glu Leu Cys Ser Asn Cys Ser
         35                  40                  45

Thr Ile Leu Ser Ser Met Asn Arg Lys Glu Tyr Ala Met Asn Pro Tyr
 50                  55                  60

Ile Tyr Leu Gly Gly Ala Ile Leu Ala Glu Val Ile Gly Thr Thr Leu
 65                  70                  75                  80

Met Lys Phe Ser Glu Gly Phe Thr Arg Leu Trp Pro Ser Val Gly Thr
                 85                  90                  95

Ile Ile Cys Tyr Cys Ala Ser Phe Trp Leu Leu Ala Gln Thr Leu Ala
                100                 105                 110

Tyr Ile Pro Thr Gly Ile Ala Tyr Ala Ile Trp Ser Gly Val Gly Ile
            115                 120                 125

Val Leu Ile Ser Leu Leu Ser Trp Gly Phe Phe Gly Gln Arg Leu Asp
130                 135                 140

Leu Pro Ala Ile Ile Gly Met Met Leu Ile Cys Ala Gly Val Leu Val
145                 150                 155                 160

Ile Asn Leu Leu Ser Arg Ser Ala Pro His
                165                 170

<210> SEQ ID NO 372
<211> LENGTH: 170
<212> TYPE: PRT
<213> ORGANISM: Escherichia coli

<400> SEQUENCE: 372

Met Leu Pro Gly Arg Val Asn Ser Phe Val Ser Leu Gly Phe Leu Leu
 1               5                  10                  15

```
Ile Ile Ile Val Pro Ala Phe Ile Ser Cys His Ala Arg Ala Pro Trp
            20                  25                  30

Ile His Ile His Gln Asp Glu Asn Ser Glu Leu Cys Ser Asn Cys Ser
        35                  40                  45

Thr Ile Leu Ser Ser Met Asn Arg Lys Glu Tyr Ala Met Asn Pro Tyr
50                  55                  60

Ile Tyr Leu Gly Gly Ala Ile Leu Ala Glu Val Ile Gly Thr Thr Leu
65                  70                  75                  80

Met Lys Phe Ser Glu Gly Phe Thr Arg Leu Trp Pro Ser Val Gly Thr
                85                  90                  95

Ile Ile Cys Tyr Cys Ala Ser Phe Trp Leu Leu Ala Gln Thr Leu Ala
                100                 105                 110

Tyr Ile Pro Thr Gly Ile Ala Tyr Ala Ile Trp Ser Gly Val Gly Ile
            115                 120                 125

Val Leu Ile Ser Leu Leu Ser Trp Gly Phe Phe Gly Gln Arg Leu Asp
        130                 135                 140

Leu Pro Ala Ile Ile Gly Met Met Leu Ile Cys Ala Gly Val Leu Val
145                 150                 155                 160

Ile Asn Leu Leu Ser Arg Ser Ala Pro His
                165                 170

<210> SEQ ID NO 373
<211> LENGTH: 170
<212> TYPE: PRT
<213> ORGANISM: Escherichia coli

<400> SEQUENCE: 373

Met Leu Pro Gly Arg Val Asn Ser Phe Val Ser Leu Gly Phe Leu Leu
1               5                   10                  15

Ile Ile Ile Val Pro Ala Phe Ile Ser Cys His Ala Arg Ala Pro Trp
            20                  25                  30

Ile His Ile His Gln Asp Glu Asn Ser Glu Leu Cys Ser Asn Cys Ser
        35                  40                  45

Thr Ile Leu Ser Ser Met Asn Arg Lys Glu Tyr Ala Met Asn Pro Tyr
50                  55                  60

Ile Tyr Leu Gly Gly Ala Ile Leu Ala Glu Val Ile Gly Thr Thr Leu
65                  70                  75                  80

Met Lys Phe Ser Glu Gly Phe Thr Arg Leu Trp Pro Ser Val Gly Thr
                85                  90                  95

Ile Ile Cys Tyr Cys Ala Ser Phe Trp Leu Leu Ala Gln Thr Leu Ala
                100                 105                 110

Tyr Ile Pro Thr Gly Ile Ala Tyr Ala Ile Trp Ser Gly Val Gly Ile
            115                 120                 125

Val Leu Ile Ser Leu Leu Ser Trp Gly Phe Phe Gly Gln Arg Leu Asp
        130                 135                 140

Leu Pro Ala Ile Ile Gly Met Met Leu Ile Cys Ala Gly Val Leu Val
145                 150                 155                 160

Ile Asn Leu Leu Ser Arg Ser Ala Pro His
                165                 170

<210> SEQ ID NO 374
<211> LENGTH: 170
<212> TYPE: PRT
<213> ORGANISM: Escherichia coli
```

<400> SEQUENCE: 374

Met Leu Ile Gly Arg Val Asn Ser Phe Val Ser Leu Gly Phe Leu Leu
1               5                   10                  15

Ile Ile Ile Val Pro Ala Phe Ile Ser Cys His Ala Arg Ala Pro Trp
            20                  25                  30

Ile His Ile His Gln Asp Glu Asn Gly Glu Leu Cys Ser Asn Cys Ser
        35                  40                  45

Thr Ile Leu Ser Ser Met Asn Arg Lys Glu Tyr Ala Met Asn Pro Tyr
50                  55                  60

Ile Tyr Leu Gly Gly Ala Ile Leu Ala Glu Val Ile Gly Thr Thr Leu
65                  70                  75                  80

Met Lys Phe Ser Glu Gly Phe Thr Arg Leu Trp Pro Ser Val Gly Thr
                85                  90                  95

Ile Ile Cys Tyr Cys Ala Ser Phe Trp Leu Leu Ala Gln Thr Leu Ala
            100                 105                 110

Tyr Ile Pro Thr Gly Ile Ala Tyr Ala Ile Trp Ser Gly Val Gly Ile
        115                 120                 125

Val Leu Ile Ser Leu Leu Ser Trp Gly Phe Phe Gly Gln Arg Leu Asp
130                 135                 140

Leu Pro Ala Ile Ile Gly Met Met Leu Ile Cys Ala Gly Val Leu Val
145                 150                 155                 160

Ile Asn Leu Leu Ser Arg Ser Ala Pro His
                165                 170

<210> SEQ ID NO 375
<211> LENGTH: 110
<212> TYPE: PRT
<213> ORGANISM: Escherichia coli

<400> SEQUENCE: 375

Met Asn Pro Tyr Ile Tyr Leu Gly Gly Ala Ile Leu Ala Glu Val Ile
1               5                   10                  15

Gly Thr Thr Leu Met Lys Phe Ser Glu Gly Phe Thr Arg Leu Trp Pro
            20                  25                  30

Ser Val Gly Thr Ile Ile Cys Tyr Cys Ala Ser Phe Trp Leu Leu Ala
        35                  40                  45

Gln Thr Leu Ala Tyr Ile Pro Thr Gly Ile Ala Tyr Ala Ile Trp Ser
    50                  55                  60

Gly Val Gly Ile Val Leu Ile Ser Leu Leu Ser Trp Gly Phe Phe Gly
65                  70                  75                  80

Gln Arg Leu Asp Leu Pro Ala Val Ile Gly Met Met Leu Ile Cys Ala
                85                  90                  95

Gly Val Leu Val Ile Asn Leu Leu Ser Arg Ser Thr Pro His
            100                 105                 110

<210> SEQ ID NO 376
<211> LENGTH: 110
<212> TYPE: PRT
<213> ORGANISM: Escherichia coli

<400> SEQUENCE: 376

Met Asn Pro Tyr Ile Tyr Leu Gly Gly Ala Ile Leu Ala Glu Val Ile
1               5                   10                  15

Gly Thr Thr Leu Met Lys Phe Ser Glu Gly Phe Thr Arg Leu Trp Pro
            20                  25                  30

```
Ser Val Gly Thr Ile Ile Cys Tyr Cys Ala Ser Phe Trp Leu Leu Ala
        35                  40                  45

Gln Thr Leu Ala Tyr Ile Pro Thr Gly Ile Ala Tyr Ala Ile Trp Ser
    50                  55                  60

Gly Val Gly Ile Val Leu Ile Ser Leu Leu Ser Trp Gly Phe Phe Gly
65                  70                  75                  80

Gln Arg Leu Asp Leu Pro Ala Val Ile Gly Met Met Leu Ile Cys Ala
                85                  90                  95

Gly Val Leu Val Ile Asn Leu Leu Ser Arg Ser Thr Pro His
            100                 105                 110

<210> SEQ ID NO 377
<211> LENGTH: 110
<212> TYPE: PRT
<213> ORGANISM: Escherichia sp.

<400> SEQUENCE: 377

Met Asn Pro Tyr Ile Tyr Leu Gly Gly Ala Ile Leu Ala Glu Val Ile
1               5                   10                  15

Gly Thr Thr Leu Met Lys Phe Ser Glu Gly Phe Thr Arg Leu Trp Pro
            20                  25                  30

Ser Val Gly Thr Ile Ile Cys Tyr Cys Ala Ser Phe Trp Leu Leu Ala
        35                  40                  45

Gln Thr Leu Ala Tyr Ile Pro Thr Gly Ile Ala Tyr Ala Ile Trp Ser
    50                  55                  60

Gly Val Gly Ile Val Leu Ile Ser Leu Leu Ser Trp Gly Phe Phe Gly
65                  70                  75                  80

Gln Arg Leu Asp Leu Pro Ala Val Ile Gly Met Met Leu Ile Cys Ala
                85                  90                  95

Gly Val Leu Val Ile Asn Leu Leu Ser Arg Ser Thr Pro His
            100                 105                 110

<210> SEQ ID NO 378
<211> LENGTH: 110
<212> TYPE: PRT
<213> ORGANISM: Escherichia coli

<400> SEQUENCE: 378

Met Asn Pro Tyr Ile Tyr Leu Gly Gly Ala Ile Leu Ala Glu Val Ile
1               5                   10                  15

Gly Thr Thr Leu Met Lys Phe Ser Glu Gly Phe Thr Arg Leu Trp Pro
            20                  25                  30

Ser Val Gly Thr Ile Ile Cys Tyr Cys Ala Ser Phe Trp Leu Leu Ala
        35                  40                  45

Gln Thr Leu Ala Tyr Ile Pro Thr Gly Ile Ala Tyr Ala Ile Trp Ser
    50                  55                  60

Gly Val Gly Ile Val Leu Ile Ser Leu Leu Ser Trp Gly Phe Phe Gly
65                  70                  75                  80

Gln Arg Leu Asp Leu Pro Ala Val Ile Gly Met Met Leu Ile Cys Ala
                85                  90                  95

Gly Val Leu Val Ile Asn Leu Leu Ser Arg Ser Thr Pro His
            100                 105                 110

<210> SEQ ID NO 379
<211> LENGTH: 110
<212> TYPE: PRT
<213> ORGANISM: Escherichia coli
```

<400> SEQUENCE: 379

Met Asn Pro Tyr Ile Tyr Leu Gly Gly Ala Ile Leu Ala Glu Val Ile
1               5                   10                  15

Gly Thr Thr Leu Met Lys Phe Ser Glu Gly Phe Thr Arg Leu Trp Pro
            20                  25                  30

Ser Val Gly Thr Ile Ile Cys Tyr Cys Ala Ser Phe Trp Leu Leu Ala
        35                  40                  45

Gln Thr Leu Ala Tyr Ile Pro Thr Gly Ile Ala Tyr Ala Ile Trp Ser
    50                  55                  60

Gly Val Gly Ile Val Leu Ile Ser Leu Leu Ser Trp Gly Phe Phe Val
65                  70                  75                  80

Gln Arg Leu Asp Leu Pro Ala Val Ile Gly Met Met Leu Ile Cys Ala
                85                  90                  95

Gly Val Leu Val Ile Asn Leu Leu Ser Arg Ser Thr Pro His
            100                 105                 110

<210> SEQ ID NO 380
<211> LENGTH: 110
<212> TYPE: PRT
<213> ORGANISM: Escherichia coli

<400> SEQUENCE: 380

Met Asn Pro Tyr Ile Tyr Leu Gly Gly Ala Ile Leu Ala Glu Val Ile
1               5                   10                  15

Gly Thr Thr Leu Met Lys Phe Ser Glu Gly Phe Thr Arg Leu Trp Pro
            20                  25                  30

Ser Val Gly Thr Ile Ile Cys Tyr Cys Ala Ser Phe Trp Leu Leu Ala
        35                  40                  45

Gln Thr Leu Ala Tyr Ile Pro Thr Gly Ile Ala Tyr Ala Ile Trp Ser
    50                  55                  60

Gly Val Gly Ile Val Leu Ile Ser Leu Leu Ser Trp Gly Phe Phe Gly
65                  70                  75                  80

Gln Arg Leu Asp Leu Pro Ala Val Ile Gly Met Met Leu Ile Cys Ala
                85                  90                  95

Gly Val Leu Val Ile Asn Leu Leu Ser Arg Ser Thr Pro His
            100                 105                 110

<210> SEQ ID NO 381
<211> LENGTH: 110
<212> TYPE: PRT
<213> ORGANISM: Escherichia coli

<400> SEQUENCE: 381

Met Asn Pro Tyr Ile Tyr Leu Gly Gly Ala Ile Leu Ala Glu Val Ile
1               5                   10                  15

Gly Thr Thr Leu Met Lys Phe Ser Glu Gly Phe Thr Arg Leu Trp Pro
            20                  25                  30

Ser Val Gly Thr Ile Ile Cys Tyr Cys Ala Ser Phe Trp Leu Leu Ala
        35                  40                  45

Gln Thr Leu Ala Tyr Ile Pro Thr Gly Ile Ala Tyr Ala Ile Trp Ser
    50                  55                  60

Gly Val Gly Ile Val Leu Ile Ser Leu Leu Ser Trp Gly Phe Phe Gly
65                  70                  75                  80

Gln Arg Leu Asp Leu Pro Ala Val Ile Gly Met Met Leu Ile Cys Ala
                85                  90                  95

Gly Val Leu Val Ile Asn Leu Leu Ser Arg Ser Thr Pro His
            100                 105                 110

<210> SEQ ID NO 382
<211> LENGTH: 110
<212> TYPE: PRT
<213> ORGANISM: Escherichia coli

<400> SEQUENCE: 382

Met Asn Pro Tyr Ile Tyr Leu Gly Gly Ala Ile Leu Ala Glu Val Ile
1               5                   10                  15

Gly Thr Thr Leu Met Lys Phe Ser Glu Gly Phe Thr Arg Leu Trp Pro
            20                  25                  30

Ser Val Gly Thr Ile Ile Cys Tyr Cys Ala Ser Phe Trp Leu Leu Ala
        35                  40                  45

Gln Thr Leu Ala Tyr Ile Pro Thr Gly Ile Ala Tyr Ala Ile Trp Ser
    50                  55                  60

Gly Val Gly Ile Val Leu Ile Ser Leu Leu Ser Trp Gly Phe Phe Gly
65                  70                  75                  80

Gln Arg Leu Asp Leu Pro Ala Ile Ile Gly Met Met Leu Ile Cys Ser
                85                  90                  95

Gly Val Leu Val Ile Asn Leu Leu Ser Arg Ser Ala Pro His
            100                 105                 110

<210> SEQ ID NO 383
<211> LENGTH: 110
<212> TYPE: PRT
<213> ORGANISM: Escherichia coli

<400> SEQUENCE: 383

Met Asn Pro Tyr Ile Tyr Leu Gly Gly Ala Ile Leu Ala Glu Val Ile
1               5                   10                  15

Gly Thr Thr Leu Met Lys Phe Ser Glu Gly Phe Thr Arg Leu Trp Pro
            20                  25                  30

Ser Val Gly Thr Ile Ile Cys Tyr Cys Ala Ser Phe Trp Leu Leu Ala
        35                  40                  45

Gln Thr Leu Ala Tyr Ile Pro Thr Gly Ile Ala Tyr Ala Ile Trp Ser
    50                  55                  60

Gly Val Gly Ile Val Leu Ile Ser Leu Leu Ser Trp Gly Phe Phe Gly
65                  70                  75                  80

Gln Arg Leu Asp Leu Pro Ala Val Ile Gly Met Met Leu Ile Cys Ala
                85                  90                  95

Gly Val Leu Val Ile Asn Leu Leu Ser Arg Ser Thr Pro His
            100                 105                 110

<210> SEQ ID NO 384
<211> LENGTH: 110
<212> TYPE: PRT
<213> ORGANISM: Escherichia coli

<400> SEQUENCE: 384

Met Asn Pro Tyr Ile Tyr Leu Gly Gly Ala Ile Leu Ala Glu Val Ile
1               5                   10                  15

Gly Thr Thr Leu Met Lys Phe Ser Glu Gly Phe Thr Arg Leu Trp Pro
            20                  25                  30

```
Ser Val Gly Thr Ile Ile Cys Tyr Cys Ala Ser Phe Trp Leu Leu Ala
        35                  40                  45

Gln Thr Leu Ala Tyr Ile Pro Thr Gly Ile Ala Tyr Ala Ile Trp Ser
    50                  55                  60

Gly Val Gly Ile Val Leu Ile Ser Leu Leu Ser Trp Gly Phe Phe Gly
65                  70                  75                  80

Gln Arg Leu Asp Leu Pro Ala Val Ile Gly Met Met Leu Ile Cys Ala
                85                  90                  95

Gly Val Leu Val Ile Asn Leu Leu Ser Arg Ser Thr Pro His
                100                 105                 110

<210> SEQ ID NO 385
<211> LENGTH: 110
<212> TYPE: PRT
<213> ORGANISM: Escherichia coli

<400> SEQUENCE: 385

Met Asn Pro Tyr Ile Tyr Leu Gly Gly Ala Ile Leu Ala Glu Val Ile
1               5                   10                  15

Gly Thr Thr Leu Met Lys Phe Ser Glu Gly Phe Thr Arg Leu Trp Pro
            20                  25                  30

Ser Val Gly Thr Ile Ile Cys Tyr Cys Ala Ser Phe Trp Leu Leu Ala
        35                  40                  45

Gln Thr Leu Ala Tyr Ile Pro Thr Gly Ile Ala Tyr Ala Ile Trp Ser
    50                  55                  60

Gly Val Gly Ile Val Leu Ile Ser Leu Leu Ser Trp Gly Phe Phe Gly
65                  70                  75                  80

Gln Arg Leu Asp Met Pro Ala Ile Ile Gly Met Met Leu Ile Cys Ala
                85                  90                  95

Gly Val Leu Val Ile Asn Leu Leu Ser Arg Ser Thr Pro His
                100                 105                 110

<210> SEQ ID NO 386
<211> LENGTH: 110
<212> TYPE: PRT
<213> ORGANISM: Shigella flexneri

<400> SEQUENCE: 386

Met Asn Pro Tyr Ile Tyr Leu Gly Gly Ala Ile Leu Ala Glu Val Ile
1               5                   10                  15

Gly Thr Thr Leu Met Lys Phe Ser Glu Gly Phe Thr Arg Leu Trp Pro
            20                  25                  30

Ser Val Gly Thr Ile Ile Cys Tyr Cys Ala Ser Phe Trp Leu Leu Ala
        35                  40                  45

Gln Thr Leu Ala Tyr Ile Pro Thr Gly Ile Ala Tyr Ala Ile Trp Ser
    50                  55                  60

Gly Val Gly Ile Val Leu Ile Ser Leu Leu Ser Trp Gly Phe Phe Gly
65                  70                  75                  80

Gln Arg Leu Asp Leu Pro Ala Ile Ile Gly Met Met Leu Ile Cys Thr
                85                  90                  95

Gly Val Leu Val Ile Asn Leu Leu Ser Arg Ser Ala Pro His
                100                 105                 110

<210> SEQ ID NO 387
<211> LENGTH: 110
<212> TYPE: PRT
<213> ORGANISM: Escherichia albertii
```

-continued

```
<400> SEQUENCE: 387

Met Asn Pro Tyr Ile Tyr Leu Gly Gly Ala Ile Leu Ala Glu Val Ile
1               5                   10                  15

Gly Thr Thr Leu Met Lys Phe Ser Glu Gly Phe Thr Arg Leu Trp Pro
            20                  25                  30

Ser Val Gly Thr Ile Ile Cys Tyr Cys Ala Ser Phe Trp Leu Leu Ala
        35                  40                  45

Gln Thr Leu Ala Tyr Ile Pro Thr Gly Ile Ala Tyr Ala Ile Trp Ser
    50                  55                  60

Gly Val Gly Ile Val Leu Ile Ser Leu Leu Ser Trp Gly Ile Phe Gly
65                  70                  75                  80

Gln Arg Leu Asp Leu Pro Ala Ile Ile Gly Met Met Leu Ile Cys Ala
                85                  90                  95

Gly Val Leu Val Ile Asn Leu Phe Ser Arg Ser Ala Thr His
            100                 105                 110

<210> SEQ ID NO 388
<211> LENGTH: 110
<212> TYPE: PRT
<213> ORGANISM: Shigella sp.

<400> SEQUENCE: 388

Met Asn Pro Tyr Ile Tyr Leu Gly Gly Ala Ile Leu Ala Glu Val Ile
1               5                   10                  15

Gly Thr Thr Leu Met Lys Phe Ser Glu Gly Phe Thr Arg Leu Trp Pro
            20                  25                  30

Ser Val Gly Thr Ile Ile Cys Tyr Cys Ala Ser Phe Trp Leu Leu Ala
        35                  40                  45

Gln Thr Leu Ala Tyr Ile Pro Thr Gly Ile Ala Tyr Ala Ile Trp Ser
    50                  55                  60

Gly Val Gly Ile Val Leu Ile Ser Leu Leu Ser Trp Gly Phe Phe Gly
65                  70                  75                  80

Gln Arg Leu Asp Leu Ser Ala Ile Ile Gly Met Met Leu Ile Cys Ala
                85                  90                  95

Gly Val Leu Val Ile Asn Leu Leu Ser Arg Ser Ala Pro His
            100                 105                 110

<210> SEQ ID NO 389
<211> LENGTH: 110
<212> TYPE: PRT
<213> ORGANISM: Citrobacter sp.

<400> SEQUENCE: 389

Met Asn Thr Tyr Ile Tyr Leu Gly Ala Ala Ile Leu Ala Glu Val Thr
1               5                   10                  15

Gly Thr Thr Leu Met Lys Phe Thr Asp Gly Phe Thr Arg Leu Trp Pro
            20                  25                  30

Ser Val Gly Thr Ile Val Cys Tyr Cys Ala Ser Phe Trp Leu Leu Ser
        35                  40                  45

Gln Thr Leu Ala His Ile Pro Thr Gly Ile Ala Tyr Ala Ile Trp Ser
    50                  55                  60

Gly Val Gly Ile Val Leu Ile Ser Leu Leu Ala Trp Val Ile His Gly
65                  70                  75                  80
```

Gln Arg Leu Asp Leu Pro Ala Ile Ile Gly Met Ala Leu Ile Cys Ala
                85                  90                  95

Gly Val Leu Ile Ile Asn Leu Leu Ser Arg Ser Ala Val His
            100                 105                 110

<210> SEQ ID NO 390
<211> LENGTH: 110
<212> TYPE: PRT
<213> ORGANISM: Escherichia sp.

<400> SEQUENCE: 390

Met Asn Pro Tyr Ile Tyr Leu Gly Gly Ala Ile Phe Ala Glu Val Ile
1               5                   10                  15

Gly Thr Thr Leu Met Lys Tyr Ser Asp Gly Phe Thr Arg Leu Trp Pro
            20                  25                  30

Ser Val Gly Thr Ile Ile Cys Tyr Cys Ala Ser Phe Trp Leu Leu Ala
        35                  40                  45

Gln Thr Leu Ala Tyr Ile Pro Thr Gly Ile Ala Tyr Ala Ile Trp Ser
    50                  55                  60

Gly Val Gly Ile Val Leu Ile Ser Leu Leu Ser Trp Gly Phe Phe Gly
65                  70                  75                  80

Gln Arg Leu Asp Leu Pro Ala Ile Ile Gly Met Ile Leu Ile Cys Ala
                85                  90                  95

Gly Val Leu Val Ile Asn Leu Leu Ser Arg Ser Ala Pro His
            100                 105                 110

<210> SEQ ID NO 391
<211> LENGTH: 110
<212> TYPE: PRT
<213> ORGANISM: Escherichia sp.

<400> SEQUENCE: 391

Met Asn Pro Tyr Ile Tyr Leu Gly Gly Ala Ile Phe Ala Glu Val Ile
1               5                   10                  15

Gly Thr Thr Leu Met Lys Tyr Ser Asp Gly Phe Thr Arg Leu Trp Pro
            20                  25                  30

Ser Val Gly Thr Ile Ile Cys Tyr Cys Ala Ser Phe Trp Leu Leu Ala
        35                  40                  45

Gln Thr Leu Ala Tyr Ile Pro Thr Gly Ile Ala Tyr Ala Ile Trp Ser
    50                  55                  60

Gly Val Gly Ile Val Leu Ile Ser Leu Leu Phe Trp Gly Phe Phe Gly
65                  70                  75                  80

Gln Arg Leu Asp Leu Pro Ala Ile Ile Gly Met Ile Leu Ile Cys Ala
                85                  90                  95

Gly Val Leu Val Ile Asn Leu Leu Ser Arg Ser Ala Pro His
            100                 105                 110

<210> SEQ ID NO 392
<211> LENGTH: 110
<212> TYPE: PRT
<213> ORGANISM: Escherichia sp.

<400> SEQUENCE: 392

Met Asn Pro Tyr Ile Tyr Leu Gly Gly Ala Ile Phe Ala Glu Val Ile
1               5                   10                  15

Gly Thr Thr Leu Met Lys Tyr Ser Asp Gly Phe Thr Arg Leu Trp Pro
            20                  25                  30

```
Ser Val Gly Thr Ile Ile Cys Tyr Cys Ala Ser Phe Trp Leu Leu Ala
        35                  40                  45

Gln Thr Leu Ala Tyr Ile Pro Thr Gly Ile Ala Tyr Ala Ile Trp Ser
    50                  55                  60

Gly Val Gly Ile Val Leu Ile Ser Leu Leu Ser Trp Gly Phe Phe Gly
65                  70                  75                  80

Gln Arg Leu Asp Leu Pro Ala Ile Ile Gly Met Ile Leu Ile Cys Ala
                85                  90                  95

Gly Val Leu Val Ile Asn Leu Leu Ser Arg Ser Ala Pro His
                100                 105                 110

<210> SEQ ID NO 393
<211> LENGTH: 110
<212> TYPE: PRT
<213> ORGANISM: Escherichia sp.

<400> SEQUENCE: 393

Met Asn Pro Tyr Ile Tyr Leu Gly Gly Ala Ile Phe Ala Glu Val Ile
1               5                   10                  15

Gly Thr Thr Leu Met Lys Tyr Ser Asp Gly Phe Thr Arg Leu Trp Pro
                20                  25                  30

Ser Val Gly Thr Ile Ile Cys Tyr Cys Ala Ser Phe Trp Leu Leu Ala
        35                  40                  45

Gln Thr Leu Ala Tyr Ile Pro Thr Gly Ile Ala Tyr Ala Ile Trp Ser
    50                  55                  60

Gly Val Gly Ile Val Leu Ile Ser Leu Leu Ser Trp Gly Phe Phe Gly
65                  70                  75                  80

Gln Arg Leu Asp Leu Pro Ala Ile Ile Gly Met Ile Leu Ile Cys Ala
                85                  90                  95

Gly Val Leu Val Ile Asn Leu Leu Ser Arg Ser Ala Pro His
                100                 105                 110

<210> SEQ ID NO 394
<211> LENGTH: 110
<212> TYPE: PRT
<213> ORGANISM: Escherichia coli

<400> SEQUENCE: 394

Met Asn Pro Tyr Ile Tyr Leu Gly Gly Ala Ile Phe Ala Glu Val Ile
1               5                   10                  15

Gly Thr Thr Leu Met Lys Tyr Ser Asp Gly Phe Thr Arg Leu Trp Pro
                20                  25                  30

Ser Val Gly Thr Ile Ile Cys Tyr Cys Ala Ser Phe Trp Leu Leu Ala
        35                  40                  45

Gln Thr Leu Ala Tyr Ile Pro Thr Gly Ile Ala Tyr Ala Ile Trp Ser
    50                  55                  60

Gly Val Gly Ile Val Leu Ile Ser Leu Leu Ser Trp Gly Phe Phe Gly
65                  70                  75                  80

Gln Arg Leu Asp Leu Pro Ala Ile Ile Gly Met Ile Leu Ile Cys Ala
                85                  90                  95

Gly Val Leu Val Ile Asn Leu Leu Ser Arg Ser Ala Pro His
                100                 105                 110

<210> SEQ ID NO 395
<211> LENGTH: 111
<212> TYPE: PRT
<213> ORGANISM: Shigella sonnei
```

-continued

<400> SEQUENCE: 395

Met Asn Pro Tyr Ile Tyr Leu Gly Gly Ala Ile Leu Ala Glu Val Ile
1               5                   10                  15

Gly Thr Thr Leu Met Lys Phe Ser Glu Gly Phe Thr Arg Leu Trp Pro
            20                  25                  30

Ser Val Gly Thr Ile Ile Cys Tyr Cys Ala Ser Phe Trp Leu Leu Ala
        35                  40                  45

Gln Thr Leu Ala Tyr Ile Pro Thr Gly Ile Ala Tyr Ala Ile Trp Ser
    50                  55                  60

Gly Val Gly Ile Val Leu Ile Ser Leu Leu Ser Trp Gly Phe Phe Gly
65                  70                  75                  80

Gln Arg Leu Asp Leu Pro Ala Ile Ile Gly Met Met Leu Ile Cys Ala
                85                  90                  95

Gly Val Leu Val Ile Asn Leu Gly Asp Ala Ala Asn Leu Leu Ile
            100                 105                 110

<210> SEQ ID NO 396
<211> LENGTH: 86
<212> TYPE: PRT
<213> ORGANISM: Shigella sp.

<400> SEQUENCE: 396

Met Val Phe Ser Arg Leu Tyr Pro Ser Ile Val Val Ile Gly Tyr
1               5                   10                  15

Cys Leu Ser Phe Trp Ala Leu Ser Gln Val Val Arg Val Met Pro Leu
            20                  25                  30

Gly Ile Ala Tyr Ala Ile Trp Ser Gly Leu Gly Ile Val Leu Val Ser
        35                  40                  45

Val Ala Ala Val Phe Leu Tyr Gln Gln Lys Leu Asp Leu Pro Ala Ile
    50                  55                  60

Ile Gly Met Ser Leu Ile Ile Ala Gly Val Leu Val Ile Asn Leu Leu
65                  70                  75                  80

Ser Lys Ser Ala Ser His
                85

<210> SEQ ID NO 397
<211> LENGTH: 110
<212> TYPE: PRT
<213> ORGANISM: Shigella sp.

<400> SEQUENCE: 397

Met Asn Gly Leu Thr Tyr Leu Met Leu Ala Ile Ser Glu Val Ile
1               5                   10                  15

Ala Thr Thr Met Leu Lys Ala Ser Asp Gly Phe Ser Arg Leu Tyr Pro
            20                  25                  30

Ser Ile Val Val Ile Gly Tyr Cys Leu Ser Phe Trp Ala Leu Ser
        35                  40                  45

Gln Val Val Arg Val Met Pro Leu Gly Ile Ala Tyr Ala Ile Trp Ser
    50                  55                  60

Gly Leu Gly Ile Val Leu Val Ser Val Ala Ala Val Phe Leu Tyr Gln
65                  70                  75                  80

Gln Lys Leu Asp Leu Pro Ala Ile Ile Gly Met Ser Leu Ile Ile Ala
                85                  90                  95

Gly Val Leu Val Ile Asn Leu Leu Ser Lys Ser Ala Ser His
            100                 105                 110

```
<210> SEQ ID NO 398
<211> LENGTH: 110
<212> TYPE: PRT
<213> ORGANISM: Shigella sp.

<400> SEQUENCE: 398

Met Asn Gly Leu Thr Tyr Leu Met Leu Ala Ile Ile Ser Glu Val Ile
1               5                   10                  15

Ala Thr Thr Met Leu Lys Ala Ser Asp Gly Phe Ser Arg Leu Tyr Pro
            20                  25                  30

Ser Ile Val Val Ile Gly Tyr Cys Leu Ser Phe Trp Ala Leu Ser
        35                  40                  45

Gln Val Val Arg Val Met Pro Leu Gly Ile Ala Tyr Ala Ile Trp Ser
50                  55                  60

Gly Leu Gly Ile Val Leu Val Ser Val Ala Ala Val Phe Leu Tyr Gln
65                  70                  75                  80

Gln Lys Leu Asp Leu Pro Ala Ile Ile Gly Met Ser Leu Ile Ile Ala
            85                  90                  95

Gly Val Leu Val Ile Asn Leu Leu Ser Lys Ser Ala Ser His
        100                 105                 110

<210> SEQ ID NO 399
<211> LENGTH: 110
<212> TYPE: PRT
<213> ORGANISM: Serratia plymuthica

<400> SEQUENCE: 399

Met Ser Gly Phe Ile Tyr Leu Thr Met Ala Ile Val Ala Glu Val Ile
1               5                   10                  15

Ala Thr Thr Met Leu Lys Ala Ser Glu Gly Phe Thr Arg Leu Trp Pro
            20                  25                  30

Ser Leu Val Val Val Gly Tyr Ala Val Ala Phe Trp Gly Leu Ser
        35                  40                  45

Met Val Val Lys Thr Met Pro Leu Gly Ile Val Tyr Ala Ile Trp Ser
50                  55                  60

Gly Met Gly Ile Val Leu Val Ser Ile Ala Ala Val Phe Val Tyr Gln
65                  70                  75                  80

Gln Lys Leu Asp Leu Pro Ala Val Ile Gly Met Val Leu Ile Ile Ala
            85                  90                  95

Gly Val Leu Val Ile Asn Leu Leu Ser Lys Thr Ala Ala His
        100                 105                 110

<210> SEQ ID NO 400
<211> LENGTH: 110
<212> TYPE: PRT
<213> ORGANISM: Serratia plymuthica

<400> SEQUENCE: 400

Met Ser Gly Phe Ile Tyr Leu Thr Met Ala Ile Val Ala Glu Val Ile
1               5                   10                  15

Ala Thr Thr Met Leu Lys Ala Ser Glu Gly Phe Thr Arg Leu Trp Pro
            20                  25                  30

Ser Leu Val Val Val Gly Tyr Ala Val Ala Phe Trp Gly Leu Ser
        35                  40                  45

Met Val Val Lys Thr Met Pro Leu Gly Ile Val Tyr Ala Ile Trp Ser
50                  55                  60

Gly Met Gly Ile Val Leu Val Ser Ile Ala Ala Val Phe Val Tyr Gln
65                  70                  75                  80
```

Gln Lys Leu Asp Leu Pro Ala Val Ile Gly Met Val Leu Ile Ile Ala
            85                  90                  95

Gly Val Leu Val Ile Asn Leu Leu Ser Lys Thr Ala Ala His
            100                 105                 110

<210> SEQ ID NO 401
<211> LENGTH: 110
<212> TYPE: PRT
<213> ORGANISM: Proteus vulgaris

<400> SEQUENCE: 401

Met Asn Gly Leu Thr Tyr Leu Met Leu Ala Ile Ile Ser Glu Val Ile
1               5                   10                  15

Ala Thr Thr Met Leu Lys Ala Ser Glu Gly Phe Ser Arg Leu Tyr Pro
            20                  25                  30

Ser Ile Val Val Ile Gly Tyr Cys Phe Ser Phe Trp Ala Leu Ser
            35                  40                  45

Gln Val Val Arg Val Met Pro Leu Gly Ile Ala Tyr Ala Ile Trp Ser
    50                  55                  60

Gly Leu Gly Ile Val Leu Val Ser Val Ala Ala Val Phe Ile Tyr Gln
65                  70                  75                  80

Gln Lys Leu Asp Leu Pro Ala Ile Ile Gly Met Gly Leu Ile Ile Ala
            85                  90                  95

Gly Val Leu Val Ile Asn Leu Leu Ser Lys Ser Ala Ser His
            100                 105                 110

<210> SEQ ID NO 402
<211> LENGTH: 110
<212> TYPE: PRT
<213> ORGANISM: Proteus vulgaris

<400> SEQUENCE: 402

Met Asn Gly Leu Thr Tyr Leu Ile Leu Ala Ile Ile Ser Glu Val Ile
1               5                   10                  15

Ala Thr Thr Met Leu Lys Ala Ser Glu Gly Phe Ser Arg Leu Tyr Pro
            20                  25                  30

Ser Ile Ile Val Val Ile Gly Tyr Cys Phe Ser Phe Trp Ala Leu Ser
            35                  40                  45

Gln Val Val Lys Val Met Pro Leu Gly Ile Ala Tyr Ala Ile Trp Ser
    50                  55                  60

Gly Leu Gly Ile Val Ser Val Ser Val Ala Ala Val Phe Ile Tyr Gln
65                  70                  75                  80

Gln Lys Leu Asp Leu Pro Ala Ile Ile Gly Met Gly Leu Ile Ile Ala
            85                  90                  95

Gly Val Leu Val Ile Asn Leu Leu Ser Lys Ser Ala Ser His
            100                 105                 110

<210> SEQ ID NO 403
<211> LENGTH: 103
<212> TYPE: PRT
<213> ORGANISM: Proteus vulgaris

<400> SEQUENCE: 403

Met Leu Ala Ile Ile Ser Glu Val Ile Ala Thr Thr Met Leu Lys Ala
1               5                   10                  15

Ser Asp Gly Phe Ser Arg Leu Tyr Pro Ser Ile Val Val Ile Gly
            20                  25                  30

-continued

Tyr Cys Phe Ser Phe Trp Ala Leu Ser Gln Val Val Lys Val Met Pro
         35                  40                  45

Leu Gly Ile Ala Tyr Ala Ile Trp Ser Gly Leu Gly Ile Val Leu Val
 50                  55                  60

Ser Val Ala Ala Val Phe Leu Tyr Gln Gln Lys Leu Asp Leu Pro Ala
 65                  70                  75                  80

Ile Val Gly Met Thr Leu Ile Ile Ala Gly Val Leu Val Ile Asn Leu
                 85                  90                  95

Leu Ser Lys Ser Ala Ser His
                100

<210> SEQ ID NO 404
<211> LENGTH: 110
<212> TYPE: PRT
<213> ORGANISM: Proteus mirabilis

<400> SEQUENCE: 404

Met Asn Gly Leu Thr Tyr Leu Ile Leu Ala Ile Ile Ser Glu Val Ile
  1               5                  10                  15

Ala Thr Thr Val Leu Lys Ala Ser Asp Gly Phe Ser Arg Leu Tyr Pro
                 20                  25                  30

Ser Ile Val Val Val Gly Tyr Cys Phe Ser Phe Trp Ala Leu Ser
             35                  40                  45

Gln Val Val Lys Val Met Pro Leu Gly Ile Ala Tyr Ala Ile Trp Ser
 50                  55                  60

Gly Leu Gly Ile Val Leu Val Ser Val Ala Ala Val Phe Val Tyr Gln
 65                  70                  75                  80

Gln Lys Leu Asp Leu Pro Ala Ile Val Gly Met Thr Leu Ile Ile Ala
                 85                  90                  95

Gly Val Leu Val Ile Asn Leu Leu Ser Asn Ser Thr Ser His
                100                 105                 110

<210> SEQ ID NO 405
<211> LENGTH: 110
<212> TYPE: PRT
<213> ORGANISM: Proteus sp.

<400> SEQUENCE: 405

Met Asn Gly Leu Thr Tyr Leu Ile Leu Ala Ile Ile Ser Glu Val Ile
  1               5                  10                  15

Ala Thr Thr Val Leu Lys Ala Ser Asp Gly Phe Ser Arg Leu Tyr Pro
                 20                  25                  30

Ser Ile Val Val Val Gly Tyr Cys Phe Ser Phe Trp Ala Leu Ser
             35                  40                  45

Gln Val Val Lys Val Met Pro Leu Gly Ile Ala Tyr Ala Ile Trp Ser
 50                  55                  60

Gly Leu Gly Ile Val Leu Val Ser Val Ala Ala Val Phe Val Tyr Gln
 65                  70                  75                  80

Gln Lys Leu Asp Leu Pro Ala Ile Val Gly Met Thr Leu Ile Ile Ala
                 85                  90                  95

Gly Val Leu Val Ile Asn Leu Leu Ser Asn Ser Thr Ser His
                100                 105                 110

<210> SEQ ID NO 406
<211> LENGTH: 110
<212> TYPE: PRT
<213> ORGANISM: Proteus hauseri

<400> SEQUENCE: 406

Met Asn Gly Leu Thr Tyr Leu Met Leu Ala Ile Ile Ser Glu Val Ile
1               5                   10                  15

Ala Thr Thr Met Leu Lys Ala Ser Asp Gly Phe Ser Arg Leu Tyr Pro
            20                  25                  30

Ser Ile Val Val Ile Gly Tyr Cys Leu Ser Phe Trp Ala Leu Ser
        35                  40                  45

Gln Val Val Arg Val Met Pro Leu Gly Ile Ala Tyr Ala Ile Trp Ser
    50                  55                  60

Gly Leu Gly Ile Val Leu Val Ser Val Ala Ala Val Phe Leu Tyr Gln
65                  70                  75                  80

Gln Lys Leu Asp Leu Pro Ala Ile Val Gly Met Thr Leu Ile Ile Ala
                85                  90                  95

Gly Val Leu Val Ile Asn Leu Leu Ser Lys Ser Ala Ser His
            100                 105                 110

<210> SEQ ID NO 407
<211> LENGTH: 110
<212> TYPE: PRT
<213> ORGANISM: Proteus mirabilis

<400> SEQUENCE: 407

Met Asn Gly Leu Thr Tyr Leu Ile Leu Ala Ile Ile Ser Glu Val Ile
1               5                   10                  15

Ala Thr Thr Val Leu Lys Ala Ser Asp Gly Phe Ser Arg Leu Tyr Pro
            20                  25                  30

Ser Ile Val Val Val Gly Tyr Cys Phe Ser Phe Trp Ala Leu Ser
        35                  40                  45

Gln Val Val Lys Val Met Pro Leu Gly Ile Ala Tyr Ala Ile Trp Ser
    50                  55                  60

Gly Leu Gly Ile Val Leu Val Ser Val Ala Ala Val Phe Val Tyr Gln
65                  70                  75                  80

Gln Lys Leu Asp Leu Pro Ala Ile Val Gly Met Thr Leu Ile Ile Ala
                85                  90                  95

Gly Val Leu Val Ile Asn Leu Leu Ser Asn Ser Thr Ser His
            100                 105                 110

<210> SEQ ID NO 408
<211> LENGTH: 110
<212> TYPE: PRT
<213> ORGANISM: Proteus penneri

<400> SEQUENCE: 408

Met Asn Gly Leu Thr Tyr Leu Met Leu Ala Ile Ile Ser Glu Val Ile
1               5                   10                  15

Ala Thr Thr Met Leu Lys Ala Ser Asp Gly Phe Ser Arg Leu Tyr Pro
            20                  25                  30

Ser Ile Val Val Ile Gly Tyr Cys Phe Ser Phe Trp Ala Leu Ser
        35                  40                  45

Gln Val Val Lys Val Met Pro Leu Gly Ile Ala Tyr Ala Ile Trp Ser
    50                  55                  60

Gly Leu Gly Ile Val Leu Val Ser Val Ala Ala Val Phe Leu Tyr Gln
65                  70                  75                  80

-continued

Gln Lys Leu Asp Leu Pro Ala Ile Val Gly Met Thr Leu Ile Ile Ala
                85                  90                  95

Gly Val Leu Val Ile Asn Leu Leu Ser Lys Ser Ala Ser His
            100                 105                 110

<210> SEQ ID NO 409
<211> LENGTH: 110
<212> TYPE: PRT
<213> ORGANISM: Proteus mirabilis

<400> SEQUENCE: 409

Met Asn Gly Leu Thr Tyr Leu Ile Leu Ala Ile Ile Ser Glu Val Ile
1               5                   10                  15

Ala Thr Thr Val Leu Lys Ala Ser Asp Gly Phe Ser Arg Leu Tyr Pro
                20                  25                  30

Ser Ile Val Val Val Gly Tyr Cys Phe Ser Phe Trp Ala Leu Ser
            35                  40                  45

Gln Val Val Lys Val Met Pro Leu Gly Ile Ala Tyr Ala Ile Trp Ser
        50                  55                  60

Gly Leu Gly Ile Val Leu Val Ser Val Ala Ala Val Phe Val Tyr Gln
65                  70                  75                  80

Gln Lys Leu Asp Leu Pro Ala Ile Val Gly Met Thr Leu Ile Ile Ala
                85                  90                  95

Gly Val Leu Val Ile Asn Leu Leu Ser Asn Ser Thr Ala His
            100                 105                 110

<210> SEQ ID NO 410
<211> LENGTH: 110
<212> TYPE: PRT
<213> ORGANISM: Providencia rettgeri

<400> SEQUENCE: 410

Met Lys Gly Leu Ser Phe Leu Phe Ile Ser Ile Ala Glu Val Ile
1               5                   10                  15

Ala Thr Thr Thr Leu Lys Ala Ser Asp Gly Phe Ser Arg Phe Trp Pro
                20                  25                  30

Ser Leu Val Val Val Ile Gly Tyr Ala Val Ser Phe Trp Gly Leu Ser
            35                  40                  45

Gln Val Val Lys Val Met Pro Leu Gly Ile Ala Tyr Ala Ile Trp Ser
        50                  55                  60

Gly Leu Gly Ile Val Leu Val Ser Ile Ala Ala Ile Tyr Ile Tyr Asn
65                  70                  75                  80

Gln Lys Leu Asp Leu Pro Ala Ile Ile Gly Met Leu Phe Ile Ile Val
                85                  90                  95

Gly Val Leu Ile Ile Asn Leu Leu Ser Lys Ser Gly Thr His
            100                 105                 110

<210> SEQ ID NO 411
<211> LENGTH: 110
<212> TYPE: PRT
<213> ORGANISM: Providencia rustigianii

<400> SEQUENCE: 411

Met Lys Gly Leu Gly Phe Leu Leu Met Ser Ile Val Ala Glu Val Ile
1               5                   10                  15

Ala Thr Thr Thr Leu Lys Ala Ser Asp Gly Phe Ser Arg Phe Trp Pro
                20                  25                  30

```
Ser Leu Ile Val Val Ile Gly Tyr Ala Ile Ser Phe Trp Gly Leu Ser
         35                  40                  45

Gln Val Val Lys Val Met Pro Leu Gly Ile Ala Tyr Ala Ile Trp Ser
 50                  55                  60

Gly Leu Gly Ile Val Leu Val Ser Val Ala Ala Ile Tyr Ile Tyr Asn
 65                  70                  75                  80

Gln Lys Leu Asp Leu Pro Ala Ile Ile Gly Met Leu Leu Ile Ile Val
                 85                  90                  95

Gly Val Leu Ile Ile Asn Leu Phe Ser Lys Ser Gly Thr His
                100                 105                 110

<210> SEQ ID NO 412
<211> LENGTH: 124
<212> TYPE: PRT
<213> ORGANISM: Xenorhabdus thuongxuanensis

<400> SEQUENCE: 412

Met Lys Phe Ala Leu Ser Tyr Asn Phe Gly Leu Val Ser Asn Met Asn
 1               5                  10                  15

Val Trp Gly Tyr Leu Phe Ile Ala Ile Leu Ser Glu Val Ile Ala Thr
                 20                  25                  30

Thr Met Leu Lys Ser Ala Asp Gly Phe Thr Arg Leu Val Pro Ser Ile
         35                  40                  45

Ile Val Val Thr Gly Tyr Cys Leu Ser Phe Trp Ala Leu Ser Gln Val
 50                  55                  60

Val Lys Val Met Pro Leu Gly Ile Ala Tyr Ala Val Trp Ser Cys Leu
 65                  70                  75                  80

Gly Ile Val Leu Val Ser Ile Ala Gly Ile Phe Leu Tyr Gln Gln Lys
                 85                  90                  95

Leu Asp Leu Pro Ala Ile Ile Gly Ile Leu Leu Ile Ile Ala Gly Val
                100                 105                 110

Leu Val Ile Asn Leu Leu Ser Lys Ser Ala Gly His
        115                 120

<210> SEQ ID NO 413
<211> LENGTH: 131
<212> TYPE: PRT
<213> ORGANISM: Xenorhabdus doucetiae

<400> SEQUENCE: 413

Met Val Asn Trp Ala Val Phe Trp Lys Phe Gly Leu Ser Tyr His Leu
 1               5                  10                  15

Gly Leu Val Ser Asn Met Asn Val Trp Gly Tyr Leu Phe Ile Ala Ile
                 20                  25                  30

Leu Ser Glu Val Ile Ala Thr Thr Met Leu Lys Thr Ala Asp Gly Phe
         35                  40                  45

Thr Arg Leu Val Pro Ser Ile Val Val Leu Gly Tyr Cys Leu Ser
 50                  55                  60

Phe Trp Ala Leu Ser Gln Val Val Lys Thr Met Pro Leu Gly Ile Ala
 65                  70                  75                  80

Tyr Ala Val Trp Ser Cys Leu Gly Ile Val Leu Val Ser Ile Ala Gly
                 85                  90                  95

Ile Phe Leu Tyr Gln Gln Lys Leu Asp Leu Pro Ala Ile Ile Gly Ile
                100                 105                 110

Leu Leu Ile Ile Ala Gly Val Leu Val Ile Asn Leu Leu Ser Lys Ser
        115                 120                 125
```

Ala Gly His
    130

<210> SEQ ID NO 414
<211> LENGTH: 110
<212> TYPE: PRT
<213> ORGANISM: Enterobacter cancerogenus

<400> SEQUENCE: 414

Met Asn Thr Tyr Leu Phe Leu Gly Ile Ala Ile Val Ala Glu Val Ile
1               5                   10                  15

Gly Thr Thr Phe Met Lys Tyr Ser Glu Gly Phe Thr Arg Leu Trp Pro
            20                  25                  30

Ser Leu Ala Thr Leu Ile Cys Tyr Phe Ala Ala Phe Tyr Met Leu Ser
        35                  40                  45

Gln Thr Leu Ala His Ile Pro Thr Gly Val Ala Tyr Ala Ile Trp Ser
    50                  55                  60

Gly Ala Gly Ile Val Leu Ile Ser Leu Val Gly Trp Leu Val Ser Gly
65                  70                  75                  80

Gln Lys Leu Asp Leu Pro Ala Ile Ile Gly Met Ala Phe Ile Cys Ile
                85                  90                  95

Gly Val Leu Ile Ile Asn Val Leu Ser Lys Ser Gly Ala His
            100                 105                 110

<210> SEQ ID NO 415
<211> LENGTH: 110
<212> TYPE: PRT
<213> ORGANISM: Serratia plymuthica

<400> SEQUENCE: 415

Met Ser Gly Phe Ile Tyr Leu Thr Met Ala Ile Val Ala Glu Val Ile
1               5                   10                  15

Ala Thr Thr Met Leu Lys Ala Ser Glu Gly Phe Thr Arg Leu Trp Pro
            20                  25                  30

Ser Leu Ala Val Ile Val Gly Tyr Ala Val Ala Phe Trp Gly Leu Ser
        35                  40                  45

Met Val Val Lys Thr Met Pro Leu Gly Ile Val Tyr Ala Ile Trp Ser
    50                  55                  60

Gly Met Gly Ile Val Leu Val Ser Ile Ala Ala Val Phe Val Tyr Gln
65                  70                  75                  80

Gln Lys Leu Asp Leu Pro Ala Val Ile Gly Met Gly Leu Ile Ile Ala
                85                  90                  95

Gly Val Leu Val Ile Asn Leu Leu Ser Lys Thr Ala Ala His
            100                 105                 110

<210> SEQ ID NO 416
<211> LENGTH: 110
<212> TYPE: PRT
<213> ORGANISM: Serratia fonticola

<400> SEQUENCE: 416

Met Thr Ala Phe Ile Tyr Leu Ala Met Ala Ile Ile Ala Glu Val Ile
1               5                   10                  15

Ala Thr Thr Leu Leu Lys Ala Ser Glu Gly Phe Thr Arg Leu Trp Pro
            20                  25                  30

```
Ser Val Phe Val Leu Gly Tyr Ala Val Ala Phe Trp Gly Leu Ser
        35                  40                  45
Met Val Val Lys Thr Met Pro Leu Gly Ile Val Tyr Ala Ile Trp Ser
 50                  55                  60
Gly Leu Gly Ile Val Leu Val Ser Ile Ala Ala Val Phe Ile Tyr Gln
 65                  70                  75                  80
Gln Lys Leu Asp Leu Pro Ala Val Ile Gly Met Gly Leu Ile Ile Ala
                85                  90                  95
Gly Val Leu Val Ile Asn Leu Leu Ser Lys Ser Ala Gly His
                100                 105                 110

<210> SEQ ID NO 417
<211> LENGTH: 110
<212> TYPE: PRT
<213> ORGANISM: Escherichia vulneris

<400> SEQUENCE: 417

Met His Ala Tyr Val His Leu Gly Ile Ala Ile Val Ala Glu Val Ile
 1               5                  10                  15
Gly Thr Thr Leu Met Arg Tyr Ser Glu Gly Phe Thr Lys Leu Trp Pro
                20                  25                  30
Thr Val Ala Thr Leu Gly Cys Tyr Ala Val Ala Phe Trp Phe Leu Ser
        35                  40                  45
Gln Thr Leu Gln Tyr Ile Pro Thr Gly Ile Ala Tyr Ala Ile Trp Ser
 50                  55                  60
Gly Val Gly Ile Val Leu Ile Ser Ala Ala Gly Trp Ile Phe Ser Gly
 65                  70                  75                  80
Gln Lys Leu Asp Leu Pro Ala Ile Gly Gly Met Ala Leu Ile Cys Ala
                85                  90                  95
Gly Val Leu Val Ile Asn Leu Phe Ser Lys Ser Val Ala His
                100                 105                 110

<210> SEQ ID NO 418
<211> LENGTH: 106
<212> TYPE: PRT
<213> ORGANISM: Serratia rubidaea

<400> SEQUENCE: 418

Met Tyr Leu Thr Met Ala Ile Ile Ala Glu Val Ile Ala Thr Thr Met
 1               5                  10                  15
Leu Lys Ala Ser Glu Gly Phe Thr Arg Leu Trp Pro Ser Leu Val Val
                20                  25                  30
Val Leu Gly Tyr Gly Val Ala Phe Trp Gly Leu Ser Met Val Val Lys
        35                  40                  45
Ser Met Pro Leu Gly Ile Val Tyr Ala Ile Trp Ser Gly Met Gly Val
 50                  55                  60
Val Leu Val Ser Ile Ala Ala Val Phe Ile Tyr Asn Gln Lys Leu Asp
 65                  70                  75                  80
Trp Pro Ala Ile Ile Gly Met Gly Leu Ile Val Ala Gly Val Leu Val
                85                  90                  95
Ile Asn Leu Leu Ser Lys Thr Ser Ala His
                100                 105

<210> SEQ ID NO 419
<211> LENGTH: 110
<212> TYPE: PRT
<213> ORGANISM: Serratia marcescens
```

<400> SEQUENCE: 419

```
Met Thr Gly Leu Met Tyr Leu Thr Met Ala Ile Ile Ala Glu Val Ile
1               5                   10                  15

Ala Thr Thr Met Leu Lys Ala Ser Glu Gly Phe Thr Arg Leu Trp Pro
            20                  25                  30

Ser Leu Val Val Leu Gly Tyr Gly Val Ala Phe Trp Gly Leu Ser
        35                  40                  45

Met Val Val Lys Ser Met Pro Leu Gly Ile Val Tyr Ala Ile Trp Ser
    50                  55                  60

Gly Met Gly Val Val Leu Val Ser Ile Ala Ala Val Phe Ile Tyr Asn
65                  70                  75                  80

Gln Lys Leu Asp Trp Pro Ala Ile Ile Gly Met Gly Leu Ile Val Ala
                85                  90                  95

Gly Val Leu Val Ile Asn Leu Leu Ser Lys Thr Ser Ala His
            100                 105                 110
```

<210> SEQ ID NO 420
<211> LENGTH: 110
<212> TYPE: PRT
<213> ORGANISM: Serratia marcescens

<400> SEQUENCE: 420

```
Met Ser Gly Phe Met Tyr Leu Thr Met Ala Ile Val Ala Glu Val Ile
1               5                   10                  15

Ala Thr Thr Met Leu Lys Ala Ser Glu Gly Phe Thr Arg Leu Trp Pro
            20                  25                  30

Ser Leu Leu Val Val Leu Gly Tyr Gly Val Ala Phe Trp Gly Leu Ser
        35                  40                  45

Met Val Val Lys Ser Met Pro Leu Gly Ile Val Tyr Ala Ile Trp Ser
    50                  55                  60

Gly Met Gly Ile Val Leu Val Ser Val Ala Ala Val Phe Val Tyr Gln
65                  70                  75                  80

Gln Lys Leu Asp Trp Pro Ala Ile Ile Gly Met Gly Leu Ile Ile Ala
                85                  90                  95

Gly Val Leu Val Ile Asn Leu Leu Ser Lys Ala Ser Val His
            100                 105                 110
```

<210> SEQ ID NO 421
<211> LENGTH: 110
<212> TYPE: PRT
<213> ORGANISM: Serratia odorifera

<400> SEQUENCE: 421

```
Met Asn Gly Phe Ile Tyr Leu Thr Met Ala Ile Ile Ala Glu Val Ile
1               5                   10                  15

Ala Thr Thr Met Leu Lys Ala Ser Glu Gly Phe Thr Arg Leu Trp Pro
            20                  25                  30

Ser Leu Val Val Val Gly Tyr Gly Val Ala Phe Trp Gly Leu Ser
        35                  40                  45

Met Val Val Lys Thr Met Pro Leu Gly Ile Val Tyr Ala Ile Trp Ser
    50                  55                  60

Gly Met Gly Ile Val Leu Val Ser Ile Ala Ala Val Phe Val Tyr Asn
65                  70                  75                  80

Gln Lys Leu Asp Trp Pro Ala Ile Ile Gly Met Gly Leu Ile Ile Ala
                85                  90                  95
```

Gly Val Leu Val Ile Asn Leu Leu Ser Lys Thr Ser Ala His
            100                 105                 110

<210> SEQ ID NO 422
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Any crosslinked amino acid
<220> FEATURE:
<221> NAME/KEY: MISC_FEATURE
<222> LOCATION: (4)..(11)
<223> OTHER INFORMATION: Crosslink between residues
<220> FEATURE:
<221> NAME/KEY: MOD_RES
<222> LOCATION: (11)..(11)
<223> OTHER INFORMATION: Any crosslinked amino acid

<400> SEQUENCE: 422

Asp Leu Pro Xaa Ile Ile Gly Met Met Leu Xaa Cys Ala Gly Val Leu
1               5                   10                  15

Ile Ile Asn Leu Leu Ser
            20

<210> SEQ ID NO 423
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: Any crosslinked amino acid
<220> FEATURE:
<221> NAME/KEY: MISC_FEATURE
<222> LOCATION: (5)..(12)
<223> OTHER INFORMATION: Crosslink between residues
<220> FEATURE:
<221> NAME/KEY: MOD_RES
<222> LOCATION: (12)..(12)
<223> OTHER INFORMATION: Any crosslinked amino acid

<400> SEQUENCE: 423

Asp Leu Pro Ala Xaa Ile Gly Met Met Leu Ile Xaa Ala Gly Val Leu
1               5                   10                  15

Ile Ile Asn Leu Leu Ser
            20

<210> SEQ ID NO 424
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Any crosslinked amino acid
<220> FEATURE:
<221> NAME/KEY: MISC_FEATURE
<222> LOCATION: (6)..(13)
<223> OTHER INFORMATION: Crosslink between residues
<220> FEATURE:
<221> NAME/KEY: MOD_RES
<222> LOCATION: (13)..(13)
<223> OTHER INFORMATION: Any crosslinked amino acid

<400> SEQUENCE: 424

Asp Leu Pro Ala Ile Xaa Gly Met Met Leu Ile Cys Xaa Gly Val Leu
1               5                   10                  15

Ile Ile Asn Leu Leu Ser
            20

<210> SEQ ID NO 425
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (9)..(9)
<223> OTHER INFORMATION: Any crosslinked amino acid
<220> FEATURE:
<221> NAME/KEY: MISC_FEATURE
<222> LOCATION: (9)..(16)
<223> OTHER INFORMATION: Crosslink between residues
<220> FEATURE:
<221> NAME/KEY: MOD_RES
<222> LOCATION: (16)..(16)
<223> OTHER INFORMATION: Any crosslinked amino acid

<400> SEQUENCE: 425

Asp Leu Pro Ala Ile Ile Gly Met Xaa Leu Ile Cys Ala Gly Val Xaa
1               5                   10                  15

Ile Ile Asn Leu Leu Ser
            20

<210> SEQ ID NO 426
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Any crosslinked amino acid
<220> FEATURE:
<221> NAME/KEY: MISC_FEATURE
<222> LOCATION: (4)..(11)
<223> OTHER INFORMATION: Crosslink between residues
<220> FEATURE:
<221> NAME/KEY: MOD_RES
<222> LOCATION: (11)..(11)
<223> OTHER INFORMATION: Any crosslinked amino acid

<400> SEQUENCE: 426

Asp Leu Pro Xaa Ile Ile Gly Met Met Leu Xaa Ser Ala Gly Val Leu
1               5                   10                  15

Ile Ile Asn Leu Leu Ser
            20

<210> SEQ ID NO 427
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES

```
<222> LOCATION: (6)..(6)
<223> OTHER INFORMATION: Any crosslinked amino acid
<220> FEATURE:
<221> NAME/KEY: MISC_FEATURE
<222> LOCATION: (6)..(13)
<223> OTHER INFORMATION: Crosslink between residues
<220> FEATURE:
<221> NAME/KEY: MOD_RES
<222> LOCATION: (13)..(13)
<223> OTHER INFORMATION: Any crosslinked amino acid

<400> SEQUENCE: 427

Asp Leu Pro Ala Ile Xaa Gly Met Met Leu Ile Ser Xaa Gly Val Leu
1               5                   10                  15

Ile Ile Asn Leu Leu Ser
            20

<210> SEQ ID NO 428
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (9)..(9)
<223> OTHER INFORMATION: Any crosslinked amino acid
<220> FEATURE:
<221> NAME/KEY: MISC_FEATURE
<222> LOCATION: (9)..(16)
<223> OTHER INFORMATION: Crosslink between residues
<220> FEATURE:
<221> NAME/KEY: MOD_RES
<222> LOCATION: (16)..(16)
<223> OTHER INFORMATION: Any crosslinked amino acid

<400> SEQUENCE: 428

Asp Leu Pro Ala Ile Ile Gly Met Xaa Leu Ile Ser Ala Gly Val Xaa
1               5                   10                  15

Ile Ile Asn Leu Leu Ser
            20

<210> SEQ ID NO 429
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(4)
<223> OTHER INFORMATION: Sarcosine
<220> FEATURE:
<221> NAME/KEY: MOD_RES
<222> LOCATION: (8)..(8)
<223> OTHER INFORMATION: Any crosslinked amino acid
<220> FEATURE:
<221> NAME/KEY: MISC_FEATURE
<222> LOCATION: (8)..(15)
<223> OTHER INFORMATION: Crosslink between residues
<220> FEATURE:
<221> NAME/KEY: MOD_RES
<222> LOCATION: (15)..(15)
<223> OTHER INFORMATION: Any crosslinked amino acid
```

```
<400> SEQUENCE: 429

Ala Xaa Xaa Xaa Asp Leu Pro Xaa Ile Ile Gly Met Met Leu Xaa Cys
1               5                   10                  15

Ala Gly Val Leu Ile Ile Asn Leu Leu Ser Lys Lys Lys
            20                  25

<210> SEQ ID NO 430
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(4)
<223> OTHER INFORMATION: Sarcosine
<220> FEATURE:
<221> NAME/KEY: MOD_RES
<222> LOCATION: (9)..(9)
<223> OTHER INFORMATION: Any crosslinked amino acid
<220> FEATURE:
<221> NAME/KEY: MISC_FEATURE
<222> LOCATION: (9)..(16)
<223> OTHER INFORMATION: Crosslink between residues
<220> FEATURE:
<221> NAME/KEY: MOD_RES
<222> LOCATION: (16)..(16)
<223> OTHER INFORMATION: Any crosslinked amino acid

<400> SEQUENCE: 430

Ala Xaa Xaa Xaa Asp Leu Pro Ala Xaa Ile Gly Met Met Leu Ile Xaa
1               5                   10                  15

Ala Gly Val Leu Ile Ile Asn Leu Leu Ser Lys Lys Lys
            20                  25

<210> SEQ ID NO 431
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(4)
<223> OTHER INFORMATION: Sarcosine
<220> FEATURE:
<221> NAME/KEY: MOD_RES
<222> LOCATION: (10)..(10)
<223> OTHER INFORMATION: Any crosslinked amino acid
<220> FEATURE:
<221> NAME/KEY: MISC_FEATURE
<222> LOCATION: (10)..(17)
<223> OTHER INFORMATION: Crosslink between residues
<220> FEATURE:
<221> NAME/KEY: MOD_RES
<222> LOCATION: (17)..(17)
<223> OTHER INFORMATION: Any crosslinked amino acid

<400> SEQUENCE: 431

Ala Xaa Xaa Xaa Asp Leu Pro Ala Ile Xaa Gly Met Met Leu Ile Cys
1               5                   10                  15

Xaa Gly Val Leu Ile Ile Asn Leu Leu Ser Lys Lys Lys
            20                  25

<210> SEQ ID NO 432
<211> LENGTH: 31
<212> TYPE: PRT
```

<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(4)
<223> OTHER INFORMATION: Sarcosine
<220> FEATURE:
<221> NAME/KEY: MOD_RES
<222> LOCATION: (13)..(13)
<223> OTHER INFORMATION: Any crosslinked amino acid
<220> FEATURE:
<221> NAME/KEY: MISC_FEATURE
<222> LOCATION: (13)..(20)
<223> OTHER INFORMATION: Crosslink between residues
<220> FEATURE:
<221> NAME/KEY: MOD_RES
<222> LOCATION: (20)..(20)
<223> OTHER INFORMATION: Any crosslinked amino acid

<400> SEQUENCE: 432

Ala Xaa Xaa Xaa Asp Leu Pro Ala Ile Ile Gly Met Xaa Leu Ile Cys
1               5                   10                  15

Ala Gly Val Xaa Ile Ile Asn Leu Leu Ser Lys Lys Lys Lys Lys
            20                  25                  30

<210> SEQ ID NO 433
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(4)
<223> OTHER INFORMATION: Sarcosine
<220> FEATURE:
<221> NAME/KEY: MOD_RES
<222> LOCATION: (8)..(8)
<223> OTHER INFORMATION: Any crosslinked amino acid
<220> FEATURE:
<221> NAME/KEY: MISC_FEATURE
<222> LOCATION: (8)..(15)
<223> OTHER INFORMATION: Crosslink between residues
<220> FEATURE:
<221> NAME/KEY: MOD_RES
<222> LOCATION: (15)..(15)
<223> OTHER INFORMATION: Any crosslinked amino acid

<400> SEQUENCE: 433

Ala Xaa Xaa Xaa Asp Leu Pro Xaa Ile Ile Gly Met Met Leu Xaa Ser
1               5                   10                  15

Ala Gly Val Leu Ile Ile Asn Leu Leu Ser Lys Lys Lys
            20                  25

<210> SEQ ID NO 434
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(4)
<223> OTHER INFORMATION: Sarcosine
<220> FEATURE:
<221> NAME/KEY: MOD_RES
<222> LOCATION: (10)..(10)
<223> OTHER INFORMATION: Any crosslinked amino acid
<220> FEATURE:

```
<221> NAME/KEY: MISC_FEATURE
<222> LOCATION: (10)..(17)
<223> OTHER INFORMATION: Crosslink between residues
<220> FEATURE:
<221> NAME/KEY: MOD_RES
<222> LOCATION: (17)..(17)
<223> OTHER INFORMATION: Any crosslinked amino acid

<400> SEQUENCE: 434

Ala Xaa Xaa Xaa Asp Leu Pro Ala Ile Xaa Gly Met Met Leu Ile Ser
 1               5                  10                  15

Xaa Gly Val Leu Ile Ile Asn Leu Leu Ser Lys Lys Lys
            20                  25

<210> SEQ ID NO 435
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(4)
<223> OTHER INFORMATION: Sarcosine
<220> FEATURE:
<221> NAME/KEY: MOD_RES
<222> LOCATION: (13)..(13)
<223> OTHER INFORMATION: Any crosslinked amino acid
<220> FEATURE:
<221> NAME/KEY: MISC_FEATURE
<222> LOCATION: (13)..(20)
<223> OTHER INFORMATION: Crosslink between residues
<220> FEATURE:
<221> NAME/KEY: MOD_RES
<222> LOCATION: (20)..(20)
<223> OTHER INFORMATION: Any crosslinked amino acid

<400> SEQUENCE: 435

Ala Xaa Xaa Xaa Asp Leu Pro Ala Ile Ile Gly Met Xaa Leu Ile Ser
 1               5                  10                  15

Ala Gly Val Xaa Ile Ile Asn Leu Leu Ser Lys Lys Lys Lys Lys
            20                  25                  30

<210> SEQ ID NO 436
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 436

Ile Ile Asn Lys Lys Ser
 1               5

<210> SEQ ID NO 437
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 437

Cys Ala Gly Val Leu Ile Ile Asn Lys Lys Ser
 1               5                  10

<210> SEQ ID NO 438
```

```
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 438

Asp Leu Pro Ala Ile Ile Gly Met
1               5

<210> SEQ ID NO 439
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (10)..(14)
<223> OTHER INFORMATION: Hydrocarbon staple between residues

<400> SEQUENCE: 439

Lys Lys Lys Lys Lys Lys Ala Gly Phe Ala Ala Trp Ala Ala Phe Gly
1               5                   10                  15

Ala
```

STABILIZED POLYPEPTIDES AND USES THEREOF

CROSS-REFERENCE TO RELATED APPLICATIONS

This application is a U.S. National Stage application under 35 U.S.C. 371 of PCT/US2019/012291, filed on Jan. 4, 2019, which claims the benefit of U.S. Provisional Patent Application No. 62/613,994, filed on Jan. 5, 2018, and also claims the benefit of U.S. Provisional Patent Application No. 62/714,464, filed on Aug. 3, 2018, each of which are incorporated herein by reference in their entireties.

GOVERNMENT INTEREST

This invention was made with government support under grant AI111416 awarded by the National Institutes of Health. The government has certain rights in the invention.

BACKGROUND OF THE INVENTION

Multidrug resistance poses serious challenges for the treatment of many infectious diseases. A common mechanism by which multidrug resistance is conferred to bacteria is based on the active efflux of a wide range of cytotoxic compounds by transmembrane pumps. Some of these systems utilize supplier proteins, such as multidrug transporter EmrE in *E. coli*, which transport compounds into the periplasm from the cytoplasm. The various suppliers have overlapping specificities, and collectively form a multidrug resistance network of proteins that renders bacteria effectively immune to a broad range of compounds. The small multidrug resistance family of membrane bound transporters is ubiquitous in bacteria. Accordingly, compounds capable of inhibiting these transporters could be useful in the treatment of bacterial infections.

SUMMARY OF THE INVENTION

The present invention features polypeptides which inhibit dimerization of small multidrug resistance transporters containing a stabilized α-helix, and the use of such polypeptides in the treatment of bacterial infections.

Accordingly, in an aspect, the invention features a polypeptide, or a pharmaceutically acceptable salt thereof, including a stabilized α-helix, wherein the polypeptide includes the structure of Formula I:

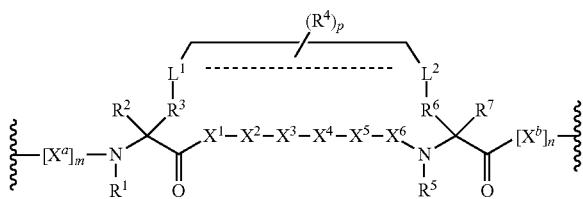

Formula I wherein the dotted line represents an optional double bond;
m is 1, 2, 3, 4, 5, or 6;
n is 6-m;
p is 0, 1, or 2;
each of $[X^a]_m$, $[X^b]_n$, and $X^1$—$X^6$ consist of consecutive amino acids of an α-helix of a monomer of a small multidrug resistance transporter (e.g., an α-helix of any one of SEQ ID NOs: 1-421), or conservative substitutions thereof;

$R^1$ and $R^5$ are, independently, hydrogen, optionally substituted acyl, or optionally substituted $C_1$-$C_6$ alkyl;

$R^2$ and $R^7$ are, independently, optionally substituted $C_1$-$C_6$ alkyl, optionally substituted $C_1$-$C_6$ alkenyl, optionally substituted $C_1$-$C_6$ alkynyl, optionally substituted $C_1$-$C_6$ heteroalkyl, optionally substituted $C_3$-$C_6$ carbocyclyl, or optionally substituted $C_2$-$C_9$ heterocyclyl;

$R^3$ and $R^6$ are, independently, optionally substituted $C_1$-$C_6$ alkylene, optionally substituted $C_1$-$C_6$ heteroalkylene, optionally substituted $C_3$-$C_6$ carbocyclyl, or optionally substituted $C_2$-$C_9$ heterocyclyl, or $R^1$ and $R^3$ or $R^5$ and $R^6$ combine with the atoms to which they are attached to form an optionally substituted $C_5$-$C_6$ heterocyclyl;

$L^1$ and $L^2$ are, independently, absent, optionally substituted $C_1$-$C_6$ alkylene, or —C(=O)O$R^{L1}$—, wherein each $R^{L1}$ is, independently, an optionally substituted $C_1$-$C_6$ alkyl; and each $R^4$ is, independently, optionally substituted $C_1$-$C_6$ alkyl, optionally substituted $C_1$-$C_6$ heteroalkyl, optionally substituted $C_5$-$C_{10}$ alkyl, wherein the polypeptide binds to the monomer of a small multidrug resistance transporter.

In some embodiments, the structure of Formula I includes the sequence of an α-helix of a monomer of a small multidrug resistance transporter (e.g., an α-helix of any one of SEQ ID NOs: 1-421) in which two of the amino acids are replaced with a cross-link.

In some embodiments, $R^2$ is optionally substituted $C_1$-$C_6$ alkyl (e.g., methyl). In some embodiments, $R^7$ is optionally substituted $C_1$-$C_6$ alkyl (e.g., methyl). In some embodiments, $R^1$ is hydrogen. In some embodiments, $R^5$ is hydrogen. In some embodiments, p is 0. In some embodiments, $R^6$ is optionally substituted $C_1$-$C_6$ alkylene (e.g., methylene). In some embodiments, $R^3$ is optionally substituted $C_1$-$C_6$ alkylene (e.g., methylene). In some embodiments, $L^1$ is optionally substituted $C_1$-$C_6$ alkylene (e.g., pentylene). In some embodiments, $L^2$ is optionally substituted $C_1$-$C_6$ alkylene (e.g., ethylene). In some embodiments, the dotted line represents a double bond.

In some embodiments, $X^1$ is glycine, alanine, valine, leucine, or isoleucine; $X^2$ is glycine, alanine, valine, leucine, or isoleucine; $X^3$ is glycine, alanine, valine, leucine, or isoleucine; $X^4$ is serine, cysteine, selenocysteine, threonine, or methionine; $X^5$ is serine, cysteine, selenocysteine, threonine, or methionine; and/or $X^6$ is histidine, lysine, or arginine.

In some embodiments, $X^1$ is glycine, alanine, valine, leucine, or isoleucine; $X^2$ is glycine, alanine, valine, leucine, or isoleucine; $X^3$ is serine, cysteine, selenocysteine, threonine, or methionine; $X^4$ is serine, cysteine, selenocysteine, threonine, or methionine; $X^5$ is histidine, lysine, or arginine, and/or $X^6$ is glycine, alanine, valine, leucine, or isoleucine.

In some embodiments, $X^1$ is glycine, alanine, valine, leucine, or isoleucine; $X^2$ is serine, cysteine, selenocysteine, threonine, or methionine; $X^3$ is serine, cysteine, selenocysteine, threonine, or methionine; $X^4$ is histidine, lysine, or arginine; $X^5$ is glycine, alanine, valine, leucine, or isoleucine; and/or $X^6$ is serine, cysteine, selenocysteine, threonine, or methionine.

In some embodiments, $X^1$ is histidine, lysine, or arginine; $X^2$ is glycine, alanine, valine, leucine, or isoleucine; $X^3$ is serine, cysteine, selenocysteine, threonine, or methionine; $X^4$ is glycine, alanine, valine, leucine, or isoleucine; $X^5$ is glycine, alanine, valine, leucine, or isoleucine; and/or $X^6$ is glycine, alanine, valine, leucine, or isoleucine.

In some embodiments, $[X^b]_n$ includes the sequence lysine-lysine-serine, or conservative substitutions thereof. In some embodiments, $[X^b]_n$ includes the sequence isoleucine-isoleucine-asparagine-lysine-lysine-serine (SEQ ID NO: 436), or conservative substitutions thereof. In some embodiments, $X^1$-$X^6$ or $[X^b]_n$ includes the sequence cysteine-alanine-glycine, or conservative substitutions thereof. In some embodiments, $[X^b]_n$ includes the sequence cysteine-alanine-glycine-valine-leucine-isoleucine-isoleucine-asparagine-lysine-lysine-serine (SEQ ID NO: 437), or conservative substitutions thereof. In some embodiments, $[X^a]_m$ includes the sequence Aspartic acid-leucine-proline, or conservative substitutions thereof. In some embodiments, $[X^a]_m$ includes the sequence Aspartic acid-leucine-proline-alanine-isoleucine-isoleucine-glycine-methionine (SEQ ID NO: 438), or conservative substitutions thereof.

In some embodiments, the polypeptide includes the structure:

(SEQ ID NO: 422)

(SEQ ID NO: 423)

(SEQ ID NO: 424)

(SEQ ID NO: 425)

In some embodiments, the polypeptide includes the structure:

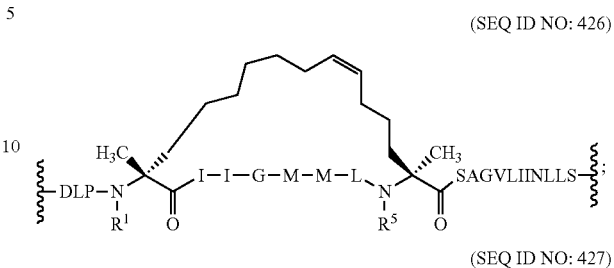

(SEQ ID NO: 426)

(SEQ ID NO: 427)

(SEQ ID NO: 428)

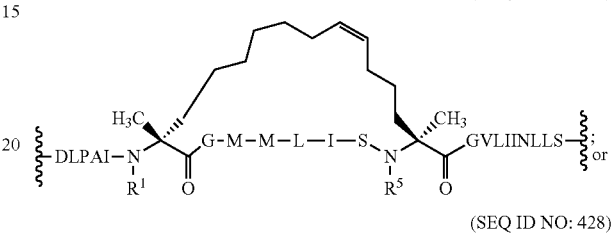

In some embodiments, the polypeptide consists of the structure:

(SEQ ID NO: 422)

(SEQ ID NO: 423)

(SEQ ID NO: 424)

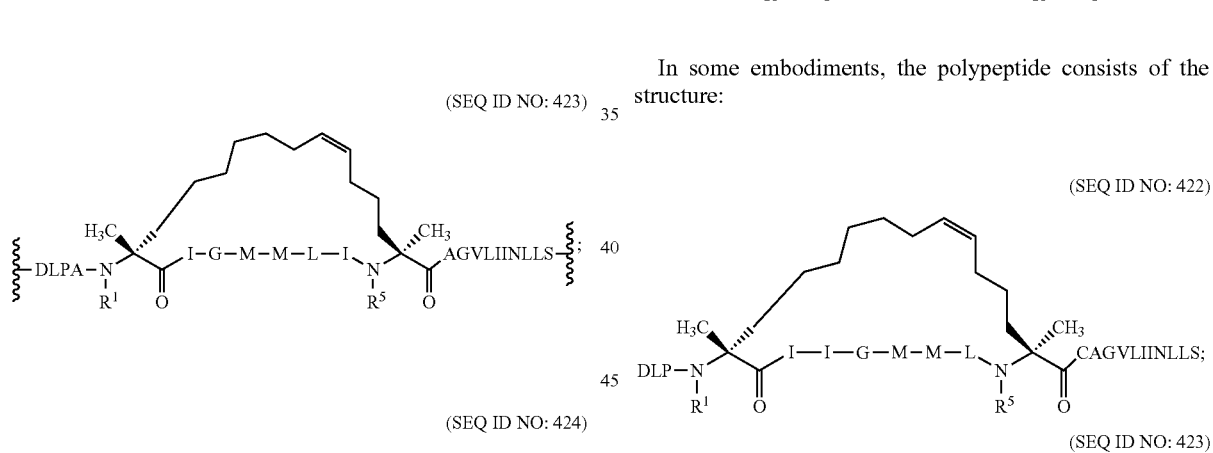

(SEQ ID NO: 425)

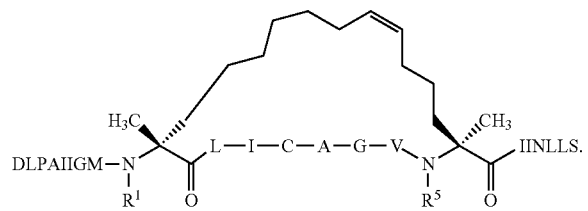

In some embodiments, the polypeptide consists of the structure:

(SEQ ID NO: 426)

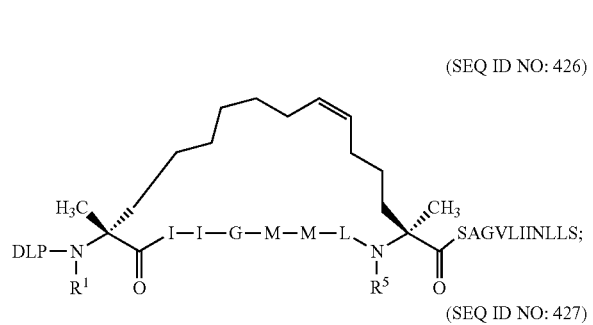

(SEQ ID NO: 427)

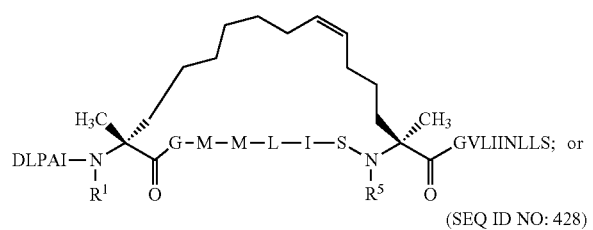

(SEQ ID NO: 428)

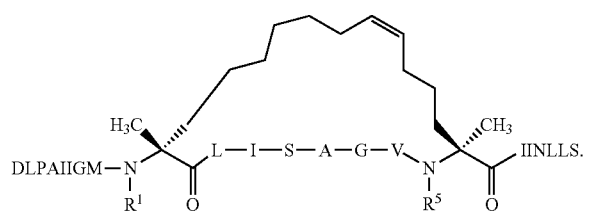

In some embodiments, the polypeptide includes a solubility tag (e.g., one or more lysine residues or a sarcosine-containing tag) at the N- and/or C-terminus. In some embodiments, the polypeptide is acetylated at the N-terminus. In some embodiments, the polypeptide is amidated at the C-terminus. In some embodiments, the polypeptide includes a solubility tag including at least one lysine (e.g., at least two, at least three, at least four, at least five) at the C-terminus. In some embodiments, the polypeptide includes (e.g., at the N-terminus) the structure:

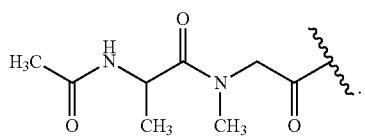

In some embodiments, the polypeptide includes (e.g., at the C-terminus) the structure:

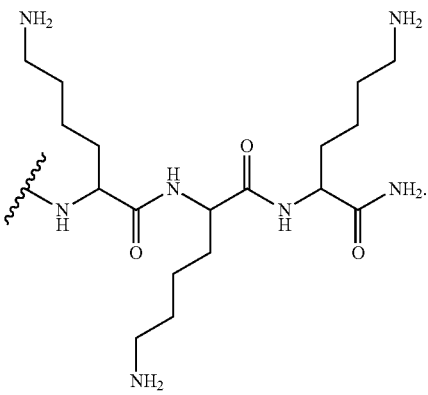 [SMILES: *NC(CCCCN)C(=O)NC(CCCCN)C(=O)NC(CCCCN)C(N)=O]

In some embodiments, the polypeptide consists of the structure:

(SEQ ID NO: 429)

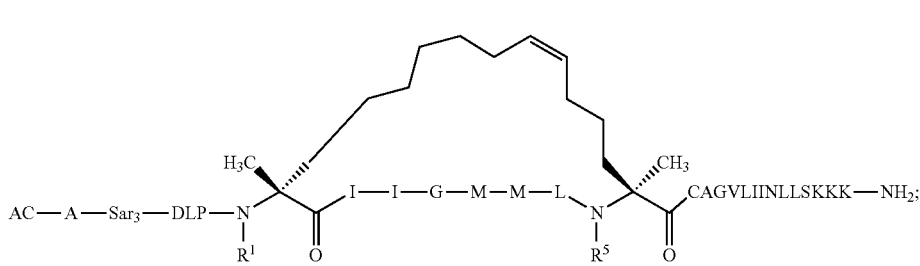

(SEQ ID NO: 430)

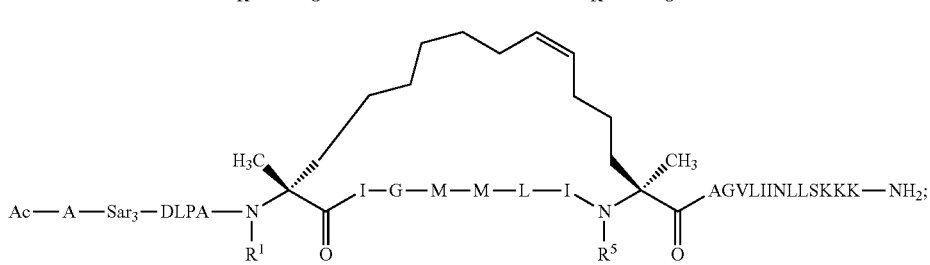

(SEQ ID NO: 431)

Ac—A—Sar₃—DLPAI—N(R¹)—[staple]—G—M—M—L—I—C—N(R⁵)—[staple]—GVLIINLLSKKK—NH₂; or (SEQ ID NO: 432)

Ac—A—Sar₃—DLPAIIGM—N(R¹)—[staple]—L—I—C—A—G—V—N(R⁵)—[staple]—IINLLSKKKKK—NH₂.

In some embodiments, the polypeptide consists of the structure:

(SEQ ID NO: 433)

Ac—A—Sar₃—DLPA—N(R¹)—[staple]—I—I—G—M—M—L—N(R⁵)—[staple]—SAGVLIINLLSKKK—NH₂;

(SEQ ID NO: 434)

Ac—A—Sar₃—DLPAI—N(R¹)—[staple]—G—M—M—L—I—S—N(R⁵)—[staple]—GVLIINLLSKKK—NH₂; or (SEQ ID NO: 435)

Ac—A—Sar₃—DLPAIIGM—N(R¹)—[staple]—L—I—S—A—G—V—N(R⁵)—[staple]—IINLLSKKKKK—NH₂.

In another aspect, the invention features a pharmaceutical composition including any of the foregoing polypeptides and a pharmaceutically acceptable carrier.

In another aspect, the invention features a method of reducing efflux in a bacterial cell, the method including contacting the cell with any of the foregoing polypeptides or pharmaceutical compositions. In some embodiments, the bacterial cell is a gram-negative bacteria (e.g., *E. coli, P. aeruginosa, B. pertussis,* or *N. meningitides*). In some embodiments, the bacterial cell is a gram-positive bacteria (e.g., *S. aureus* or *B. anthracis*).

In another aspect, the invention features a method of treating a bacterial infection in a subject in need thereof, the method including administering any of the foregoing polypeptides or pharmaceutical compositions. In some embodiments, the bacterial infection includes bacteria which are resistant to one or more antibacterial agents or the bacterial infection has failed to respond to treatment with one or more antibacterial agents. In some embodiments, the bacterial infection includes bacteria which express one or more small molecule resistance membrane-bound transporters. In some embodiments, the method further includes administering one or more antibacterial agents (e.g., ampicillin, erythromycin, or tetracycline). In some embodiments, the one or more antibacterial agents is a β-lactam antibiotic, a cephalosporin antibiotic, a carbapenem antibiotic, a polymyxin antibiotic, a rifamycin antibiotic, a lipiarycin antibiotic, a quinolone antibiotic, a sulfonamide antibiotic, a macrolide antibiotic, a lincosamide antibiotic, a tetracycline antibiotic, an aminoglycoside antibiotic, a cyclic lipopeptide antibiotic, a glycylcycline antibiotic, an oxazolidinone antibiotic, or a combination thereof. In some embodiments, the one or more antibacterial agent and any of the foregoing polypeptides or pharmaceutical compositions are administered within 28 days of each other (e.g., within 21, 14, 10, 7, 5, 4, 3, 2, or 1 days) or within 24 hours (e.g., 12, 6, 3, 2, or 1 hours; or concomitantly) each in an amount that together are effective to treat the subject.

BRIEF DESCRIPTION OF THE DRAWINGS

FIG. 1A is a CD spectrum of polypeptides of the invention in micelles. FIG. 1B is a CD spectrum of polypeptides of the invention in lipid bilayers.

DETAILED DESCRIPTION

Figure 1A:
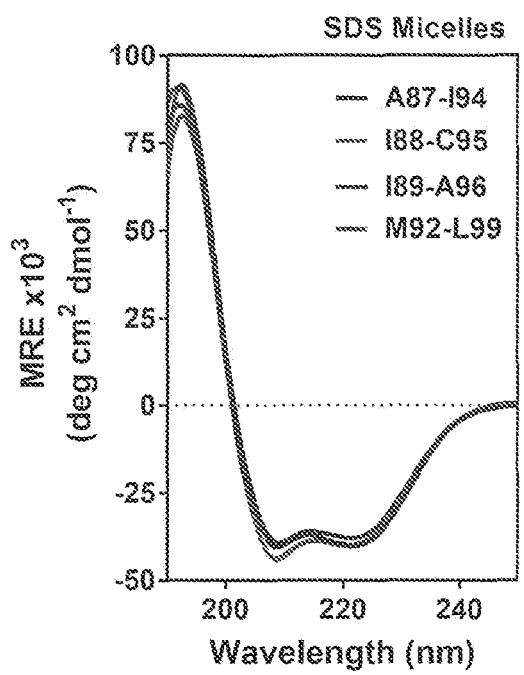
FIGS. 1A and 1B are CD spectra of polypeptides of the invention.

Peptide stapling and stitching is a synthetic strategy known to increase helix stabilization, in which adjacent or subsequent turns of an α-helix are cross-linked by a macrocyclic bridge. See, e.g., Kim et al., *Nat. Protoc.* (2011) 6:761-771. This incorporated staple can enforce the bioactive α-helical conformation of a synthetic peptide and confer on it increased target affinity, robust cell penetration, and/or extended in vivo half-life. The present invention features polypeptides which inhibit dimerization of small multidrug resistance transporters including a stabilized α-helix, and the use of such polypeptides in the treatment of bacterial infections.

Polypeptides

Exemplary polypeptides of the invention comprise the structure of Formula I:

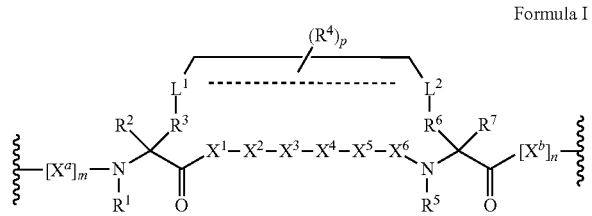

Formula I wherein the dotted line represents an optional double bond;
m is 1, 2, 3, 4, 5, or 6;
n is 6-m;
p is 0, 1, or 2;
each of $[X^a]_m$, $[X^b]_n$, and $X^1$-$X^6$ consist of consecutive amino acids of an α-helix of a monomer of a small multidrug resistance transporter, or conservative substitutions thereof;

$R^1$ and $R^5$ are, independently, hydrogen, optionally substituted acyl, or optionally substituted $C_1$-$C_6$ alkyl;

$R^2$ and $R^7$ are, independently, optionally substituted $C_1$-$C_6$ alkyl, optionally substituted $C_1$-$C_6$ alkenyl, optionally substituted $C_1$-$C_6$ alkynyl, optionally substituted $C_1$-$C_6$ heteroalkyl, optionally substituted $C_3$-$C_6$ carbocyclyl, or optionally substituted $C_2$-$C_9$ heterocyclyl;

$R^3$ and $R^6$ are, independently, optionally substituted $C_1$-$C_6$ alkylene, optionally substituted $C_1$-$C_6$ heteroalkylene, optionally substituted $C_3$-$C_6$ carbocyclyl, or optionally substituted $C_2$-$C_9$ heterocyclyl, or $R^1$ and $R^3$ or $R^5$ and $R^6$ combine with the atoms to which they are attached to form an optionally substituted $C_5$-$C_6$ heterocyclyl;

$L^1$ and $L^2$ are, independently, absent, optionally substituted $C_1$-$C_6$ alkylene, or —C(=O)OR$^{L1}$—, wherein each $R^{L1}$ is, independently, an optionally substituted $C_1$-$C_6$ alkyl; and each $R^4$ is, independently, optionally substituted $C_1$-$C_6$ alkyl, optionally substituted $C_1$-$C_6$ heteroalkyl, optionally substituted $C_5$-$C_{10}$ alkyl, wherein the polypeptide binds to the monomer of a small multidrug resistance transporter.

Peptide Staples

Groups $R^2$, $R^3$, $R^6$, $R^7$, $L^1$, and $L^2$

As generally defined above, $R^2$ is substituted or unsubstituted alkyl; substituted or unsubstituted alkenyl; substituted or unsubstituted alkynyl; substituted or unsubstituted heteroalkyl; substituted or unsubstituted carbocyclyl; substituted or unsubstituted heterocyclyl. In certain embodiments, $R^2$ is substituted or unsubstituted $C_{1-10}$alkyl. In certain embodiments, $R^2$ is substituted methyl. In certain embodiments, $R^2$ is unsubstituted methyl. In certain embodiments, $R^2$ is substituted ethyl. In certain embodiments, $R^2$ is unsubstituted ethyl. In certain embodiments, $R^2$ is substituted n-propyl. In certain embodiments, $R^2$ is unsubstituted n-propyl. In certain embodiments, $R^2$ is substituted iso-propyl. In certain embodiments, $R^2$ is unsubstituted iso-propyl. In certain embodiments, $R^2$ is substituted or unsubstituted heteroalkyl. In certain embodiments, $R^2$ is substituted or unsubstituted heteroalkyl with at least one nitrogen. In certain embodiments, $R^2$ is unsubstituted heteroalkyl containing at least one nitrogen. In certain embodiments, $R^2$ is substituted heteroalkyl containing at least one nitrogen.

As generally defined above, $R^3$ is substituted or unsubstituted alkylene; substituted or unsubstituted heteroalkylene; substituted or unsubstituted carbocyclylene; or substituted or unsubstituted heterocyclylene; or optionally $R^2$, $R^3$ and the carbon to which $R^2$ and $R^3$ are attached are joined to form a ring. In certain embodiments, $R^3$ is substituted or unsubstituted alkylene. In certain embodiments, $R^3$ is substituted or unsubstituted alkylene. In certain embodiments, $R^3$ is substituted $C_{1-10}$ alkylene. In certain embodiments, $R^3$ is unsubstituted $C_{1-10}$ alkylene. In certain embodiments, $R^3$ is substituted or unsubstituted heteroalkylene. In certain embodiments, $R^3$ is substituted heteroalkylene. In certain embodiments, $R^3$ is unsubstituted heteroalkylene. In certain embodiments, $R^3$ is substituted or unsubstituted heteroalkylene containing at least one nitrogen. In certain embodiments, $R^3$ is —(CH$_2$)$_j$—Y$_1$—, wherein j is an integer between 0 and 10, inclusive; and Y$_1$ is a bond, —CR$^8$R$^9$— or —NR$^{10}$—, wherein each of R$^8$ and R$^9$ is independently hydrogen, halogen, or $C_{1-6}$ alkyl; and R$^{10}$ is hydrogen; acyl; optionally substituted $C_{1-6}$ alkyl; or an amino protecting group. In certain embodiments, $R^3$ is —(CH$_2$)$_j$—. In certain embodiments, $R^3$ is —(CH$_2$)$_j$—NR$^1$—. In certain embodiments, $R^3$ is —(CH$_2$)$_j$—NH—. In certain embodiments, $R^3$ is —(CH$_2$)$_{j+1}$—. In certain embodiments, j is 0. In certain embodiments, j is 1. In certain embodiments, j is 2. In certain embodiments, j is 3. In certain embodiments, j is 4. In certain embodiments, j is 5. In certain embodiments, j is 6. In certain embodiments, j is 7. In certain embodiments, j is 8. In certain embodiments, j is 9. In certain embodiments, j is 10.

As generally defined above, each instance of $R^{10}$ is, independently, hydrogen; acyl; optionally substituted $C_{1-6}$ alkyl; or an amino protecting group. In certain embodiments, $R^{10}$ is hydrogen. In certain embodiments, $R^{10}$ is acyl; optionally substituted $C_{1-6}$ alkyl; or an amino protecting group. In certain embodiments, $R^{10}$ is acyl or optionally substituted $C_{1-6}$ alkyl. In certain embodiments, $R^{10}$ is substituted or unsubstituted alkyl. In certain embodiments, $R^{10}$ is substituted or unsubstituted $C_{1-6}$ alkyl. In certain embodiments, $R^{10}$ is unsubstituted $C_{1-6}$ alkyl. In certain embodiments, $R^{10}$ is methyl, ethyl, or propyl. In certain embodiments, $R^{10}$ is acyl. In certain embodiments, $R^{10}$ is acetyl (—C(=O)CH$_3$). In certain embodiments, $R^{10}$ is an amino protecting group. In certain embodiments, $R^{10}$ is TBS, TBPS, Bn, BOC, Cbz, Fmoc, trifluoroacetyl, triphenylmethyl, or Ts.

In certain embodiments, at least one instance of $R^2$ and $R^3$ together with the carbon atom to which they are attached, are joined to form a ring. In this instance, in certain embodiments, the ring formed by $R^2$ and $R^3$ together with the carbon atom to which they are attached is substituted or unsubstituted $C_{3-6}$ carbocyclyl or heterocyclyl. In certain embodiments, the ring formed by $R^2$ and $R^3$ together with the carbon atom to which they are attached is substituted or unsubstituted $C_{3-6}$ carbocyclyl. In certain embodiments, the ring formed by $R^2$ and $R^3$ together with the carbon atom to which they are attached is substituted or unsubstituted $C_{3-6}$ heterocyclyl. In certain embodiments, the ring formed by $R^2$ and $R^3$ together with the carbon atom to which they are attached is substituted or unsubstituted $C_{3-6}$ heterocyclyl containing at least one O, N, or S atom. In certain embodiments, the ring formed by $R^2$ and $R^3$ together with the carbon atom to which they are attached is substituted or unsubstituted $C_{3-6}$ heterocyclyl containing at least one nitrogen atom. In certain embodiments, the ring formed by $R^2$ and $R^3$ together with the carbon atom to which they are attached is substituted or unsubstituted $C_{3-6}$ heterocyclyl containing one nitrogen atom. In certain embodiments, the ring formed by $R^2$ and $R^3$ together with the carbon atom to which they are attached is unsubstituted $C_{3-6}$ heterocyclyl containing one nitrogen atom.

In certain embodiments, $R^2$, $R^3$, and the carbon to which $R^2$ and $R^3$ are attached are joined to form a ring. In certain embodiments, the ring formed by $R^2$, $R^3$, and the carbon to which $R^2$ and $R^3$ are attached is of the formula:

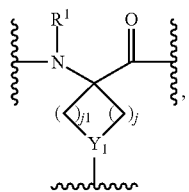

wherein $Y_1$ is —CR$^8$— or —N—, each of j and j1 is independently 0, 1, 2, 3, 4, 5, or 6. In certain embodiments, j1 is zero, and the ring formed by $R^2$, $R^3$ and the carbon to which $R^2$ and $R^3$ are attached is of the formula:

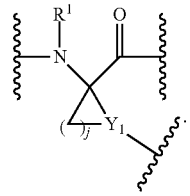

In certain embodiments, j is 0 and $Y_1$ is directly linked to the alpha-carbon of the amino acid. In certain embodiments, the ring formed by $R^2$, $R^3$ and the carbon to which $R^2$ and $R^3$ are attached is of the formula:

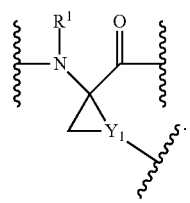

In certain embodiments, the ring formed by $R^2$, $R^3$ and the carbon to which $R^2$ and $R^3$ are attached is of the formula:

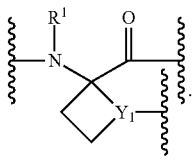

In certain embodiments, the ring formed by $R^2$, $R^3$ and the carbon to which $R^2$ and $R^3$ are attached is of the formula:

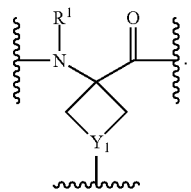

In certain embodiments, the ring formed by $R^2$, $R^3$ and the carbon to which $R^2$ and $R^3$ are attached is of the formula:

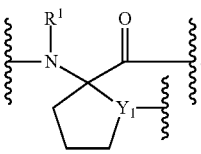

In certain embodiments, the ring formed by $R^2$, $R^3$ and the carbon to which $R^2$ and $R^3$ are attached is of the formula:

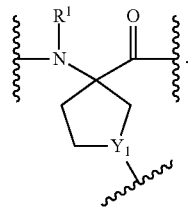

In certain embodiments, the ring formed by $R^2$, $R^3$ and the carbon to which $R^2$ and $R^3$ are attached is of the formula:

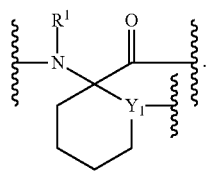

In certain embodiments, the ring formed by $R^{2a}$, $R^{3a}$ and the carbon to which $R^2$ and $R^3$ are attached is of the formula:

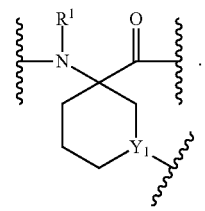

In certain embodiments, the ring formed by $R^2$, $R^3$ and the carbon to which $R^2$ and $R^3$ are attached is of the formula:

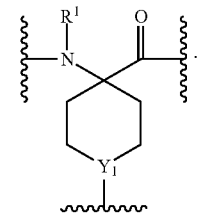

In certain embodiments, the ring formed by $R^2$, $R^3$ and the carbon to which $R^2$ and $R^3$ are attached is of the formula:

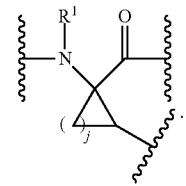

In certain embodiments, the ring formed by $R^2$, $R^3$ and the carbon to which $R^2$ and $R^3$ are attached is of the formula:

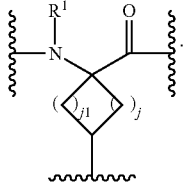

In certain embodiments, the ring formed by $R^{2a}$, $R^{3a}$ and the carbon to which $R^{2a}$ and $R^{3a}$ are attached is of the formula:

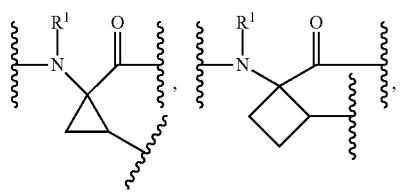

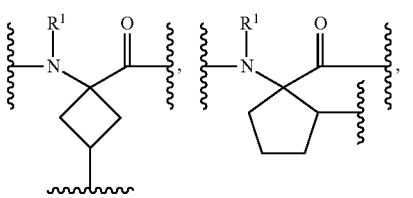

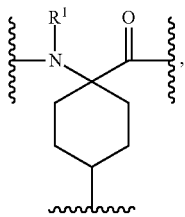

or stereoisomers thereof.

In certain embodiments, the ring formed by $R^{2a}$, $R^{3a}$ and the carbon to which $R^{2a}$ and $R^{3a}$ are attached is of the formula:

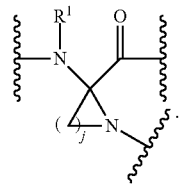

In certain embodiments, the ring formed by $R^{2a}$, $R^{3a}$ and the carbon to which $R^{2a}$ and $R^{3a}$ are attached is of the formula:

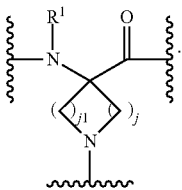

In certain embodiments, the ring formed by $R^{2a}$, $R^{3a}$ and the carbon to which $R^{2a}$ and $R^{3a}$ are attached is of the formula:

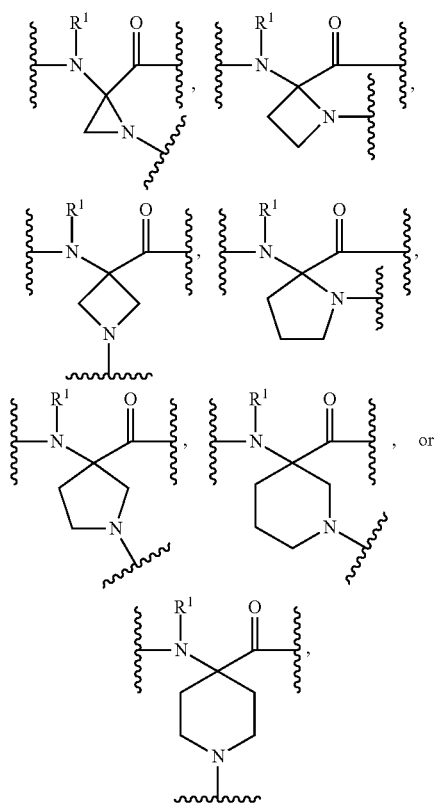

or stereoisomers thereof.

As used herein, each of j and j1 is independently an integer between 1 and 10, inclusive. In some embodiments, j is 1. In some embodiments, j is 2. In some embodiments, j is 3. In some embodiments, j is 4. In some embodiments, j is 5. In some embodiments, j is 6. In some embodiments, j is 7. In some embodiments, j is 8. In some embodiments, j is 9. In some embodiments, j is 10. In some embodiments, j1 is 1. In some embodiments, j1 is 2. In some embodiments, j1 is 3. In some embodiments, j1 is 4. In some embodiments, j1 is 5. In some embodiments, j1 is 6. In some embodiments, j1 is 7. In some embodiments, j1 is 8. In some embodiments, j1 is 9. In some embodiments, j1 is 10.

In some embodiments, $R^2$, $R^3$ and the carbon to which $R^2$ and $R^3$ are attached are not joined to form a ring. In this instance, $R^3$ is substituted or unsubstituted alkylene, substituted or unsubstituted alkenylene, substituted or unsubstituted alkynylene, substituted or unsubstituted heteroalkylene, or substituted or unsubstituted heterocyclylene. In some embodiments, $R^3$ is substituted or unsubstituted alkylene. In some embodiments, $R^3$ is substituted $C_{1-10}$ alkylene. In some embodiments, $R^3$ is —$(CH_2)_j$—, wherein j is an integer between 0 and 10, inclusive.

In some embodiments, $R^2$, $R^3$ and the carbon to which $R^2$ and $R^3$ are attached are not joined to form a ring. In this instance, $R^2$ is substituted or unsubstituted alkyl, substituted or unsubstituted alkenyl, substituted or unsubstituted alkynyl, substituted or unsubstituted heteroalkyl, or substituted or unsubstituted heterocyclyl. In some embodiments, $R^2$ is substituted or unsubstituted $C_{1-10}$ alkyl. In some embodiments, $R^2$ is substituted methyl. In some embodiments, $R^2$ is unsubstituted methyl. In some embodiments, $R^2$ is substituted ethyl. In some embodiments, $R^2$ is unsubstituted ethyl. In some embodiments, $R^2$ is substituted or unsubstituted $C_{2-6}$ alkyl.

As generally described above, $R^3$ is substituted or unsubstituted alkylene; substituted or unsubstituted heteroalkylene; substituted or unsubstituted carbocyclylene; or substituted or unsubstituted heterocyclylene; or optionally $R^6$, $R^7$ and the carbon to which $R^6$ and $R^7$ are attached are joined to form a ring. In some embodiments, $R^6$ is substituted or unsubstituted $C_{1-10}$ alkylene. In some embodiments, $R^6$ is substituted $C_{1-10}$ alkylene. In some embodiments, $R^6$ is unsubstituted $C_{1-10}$ alkylene. In some embodiments, $R^6$ is substituted or unsubstituted heteroalkylene. In some embodiments, $R^6$ is substituted heteroalkylene. In some embodiments, $R^6$ is unsubstituted heteroalkylene. In some embodiments, $R^6$ is substituted or unsubstituted heteroalkylene with at least one nitrogen. In some embodiments, $R^6$ is —$(CH_2)_k$—$Y_2$—, wherein k is an integer between 0 and 10, inclusive, and $Y_2$ is a bond, —$CR^8R^9$—, or —$NR^{10}$—, wherein $R^8$, $R^9$ and $R^{10}$ are as defined herein. In some embodiments, $R^6$ is —$(CH_2)_k$—. In some embodiments, $R^6$ is —$(CH_2)_k$—$NR^{10}$—. In some embodiments, $R^6$ is —$(CH_2)_k$—NH—. In some embodiments, $R^6$ is —$(CH_2)_{k+1}$—. In some embodiments, k is 0. In some embodiments, k is 1. In some embodiments, k is 2. In some embodiments, k is 3. In some embodiments, k is 4. In some embodiments, k is 5. In some embodiments, k is 6. In some embodiments, k is 7. In some embodiments, k is 8. In some embodiments, k is 9. In some embodiments, k is 10.

As generally described above, $R^7$ is substituted or unsubstituted alkyl; substituted or unsubstituted alkenyl; substituted or unsubstituted alkynyl; substituted or unsubstituted heteroalkyl; substituted or unsubstituted carbocyclyl; or substituted or unsubstituted heterocyclyl. In some embodiments, $R^7$ is substituted or unsubstituted $C_{1-10}$ alkyl. In some embodiments, $R^7$ is substituted or unsubstituted heteroalkyl. In some embodiments, $R^7$ is substituted or unsubstituted heteroalkyl with at least one nitrogen atom. In some embodiments, $R^7$ is unsubstituted heteroalkyl with at least one nitrogen atom. In some embodiments, $R^7$ is substituted heteroalkyl with at least one nitrogen atom.

In some embodiments, for at least one instance, $R^6$, $R^7$ and the carbon to which $R^6$ and $R^7$ are attached are joined to form a ring. In this instance, in some embodiments, the ring formed by $R^6$ and $R^7$ together with the carbon atom to which they are attached is substituted or unsubstituted $C_{3-6}$ carbocyclyl or heterocyclyl. In some embodiments, the ring formed by $R^6$ and $R^7$ together with the carbon atom to which they are attached is substituted or unsubstituted $C_{3-6}$ carbocyclyl. In some embodiments, the ring formed by $R^6$ and $R^7$ together with the carbon atom to which they are attached is substituted or unsubstituted $C_{3-6}$ heterocyclyl. In some embodiments, the ring formed by $R^6$ and $R^7$ together with the carbon atom to which they are attached is substituted or unsubstituted $C_{3-6}$ heterocyclyl with at least one O, N, or S atom. In some embodiments, the ring formed by $R^6$ and $R^7$ together with the carbon atom to which they are attached is substituted or unsubstituted $C_{3-6}$ heterocyclyl with at least one N. In some embodiments, the ring formed by $R^6$ and $R^7$ together with the carbon atom to which they are attached is substituted or unsubstituted $C_{3-6}$ heterocyclyl with one N. In some embodiments, the ring formed by $R^6$ and $R^7$ together with the carbon atom to which they are attached is unsubstituted $C_{3-6}$ heterocyclyl with one N.

In some embodiments, the ring formed by $R^6$, $R^7$ and the carbon to which $R^6$ and $R^7$ are attached is of the formulae:

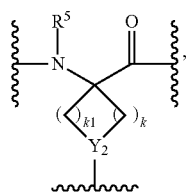

wherein $Y_2$ is $-CR^8-$ or $-N-$; k is 0, or an integer from 1 to 10, inclusive; and k1 is an integer from 1 to 10, inclusive. In some embodiments, k1 is zero, and the ring formed by $R^6$, $R^7$ and the carbon to which $R^6$ and $R^7$ are attached is of the formula:

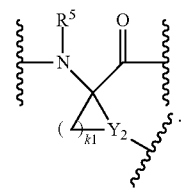

In some embodiments, the ring formed by $R^2$, $R^{3b}$ and the carbon to which $R^2$ and $R^{3b}$ are attached is of the formula:

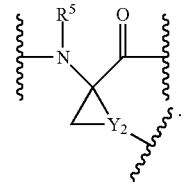

In some embodiments, the ring formed by $R^6$, $R^7$ and the carbon to which $R^6$ and $R^7$ are attached is of the formula:

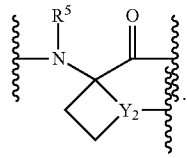

In some embodiments, the ring formed by $R^2$, $R^{3b}$ and the carbon to which $R^2$ and $R^{3b}$ are attached is of the formula:

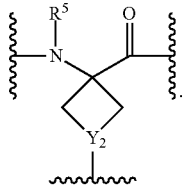

In some embodiments, the ring formed by $R^6$, $R^7$ and the carbon to which $R^6$ and $R^7$ are attached is of the formula:

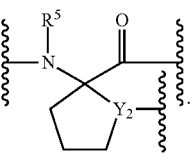

In some embodiments, the ring formed by $R^6$, $R^7$ and the carbon to which $R^6$ and $R^7$ are attached is of the formula:

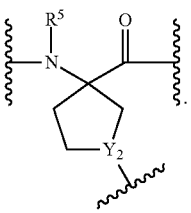

In some embodiments, the ring formed by $R^6$, $R^7$ and the carbon to which $R^6$ and $R^7$ are attached is of the formula:

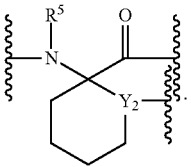

In some embodiments, the ring formed by $R^6$, $R^7$ and the carbon to which $R^6$ and $R^7$ are attached is of the formula:

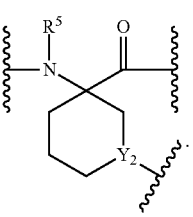

In some embodiments, the ring formed by $R^6$, $R^7$ and the carbon to which $R^6$ and $R^7$ are attached is of the formula:

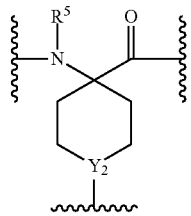

In some embodiments, the ring formed by $R^6$, $R^7$ and the carbon to which $R^6$ and $R^7$ are attached is of the formula:

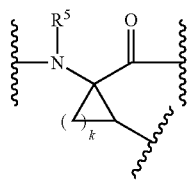

In some embodiments, the ring formed by $R^6$, $R^7$ and the carbon to which $R^6$ and $R^7$ are attached is of the formula:

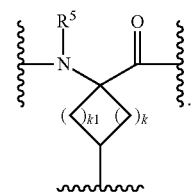

In some embodiments, the ring formed by $R^6$, $R^7$ and the carbon to which $R^6$ and $R^7$ are attached is of the formula:

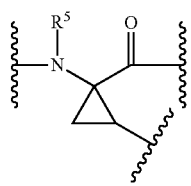

In some embodiments, the ring formed by $R^6$, $R^7$ and the carbon to which $R^6$ and $R^7$ are attached is of the formula:

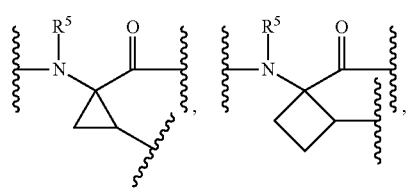

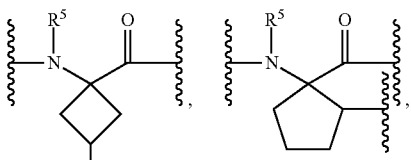

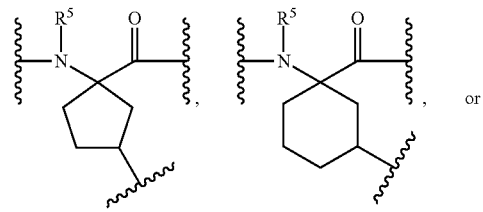

, or

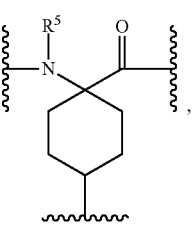

or stereoisomers thereof. In some embodiments, the ring formed by $R^6$, $R^7$ and the carbon to which $R^6$ and $R^7$ are attached is of the formula:

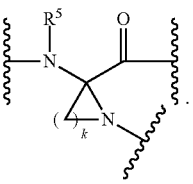

In some embodiments, the ring formed by $R^6$, $R^7$ and the carbon to which $R^6$ and $R^7$ are attached is of the formula:

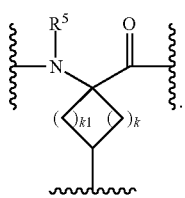

In some embodiments, the ring formed by $R^6$, $R^7$ and the carbon to which $R^6$ and $R^7$ are attached is of the formula:

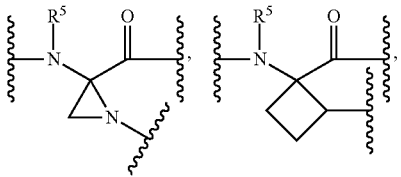

-continued

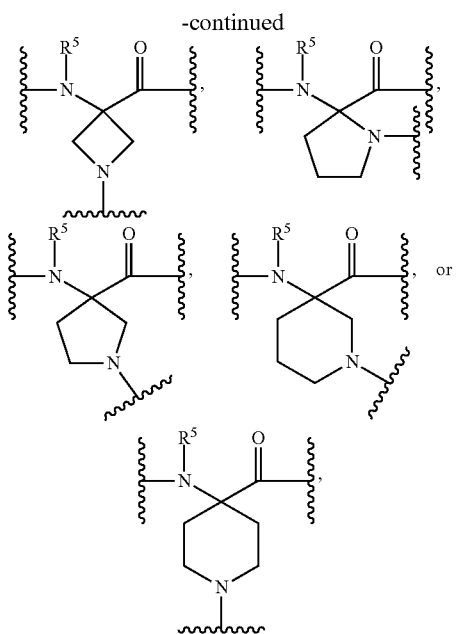

or stereoisomers thereof. thereof.

As used herein, k is an integer between 0 and 10, inclusive; and k1 is an integer between 1 and 10, inclusive. In some embodiments, k is 0. In some embodiments, k is 1. In some embodiments, k is 2. In some embodiments, k is 3. In some embodiments, k is 4. In some embodiments, k is 5. In some embodiments, k is 6. In some embodiments, k is 7. In some embodiments, k is 8. In some embodiments, k is 9. In some embodiments, k is 10. In some embodiments, k1 is 1. In some embodiments, k1 is 2. In some embodiments, k1 is 3. In some embodiments, k1 is 4. In some embodiments, k1 is 5. In some embodiments, k1 is 6. In some embodiments, k1 is 7. In some embodiments, k1 is 8. In some embodiments, k1 is 9. In some embodiments, k1 is 10.

In some embodiments, $R^6$, $R^7$ and the carbon to which $R^6$ and $R^7$ are attached are not joined to form a ring. In this instance, $R^6$ is substituted or unsubstituted alkylene, substituted or unsubstituted alkenylene, substituted or unsubstituted alkynylene, substituted or unsubstituted heteroalkylene, or substituted or unsubstituted heterocyclylene. In some embodiments, $R^6$ is substituted or unsubstituted alkylene. In some embodiments, $R^6$ is substituted $C_{1-10}$ alkylene. In some embodiments, $R^6$ is $-(CH_2)_k-$, wherein k is as defined above.

In some embodiments, $R^6$, $R^7$ and the carbon to which $R^6$ and $R^7$ are attached are not joined to form a ring. In this instance, in some embodiments, $R^7$ is substituted or unsubstituted $C_{1-10}$ alkyl, substituted or unsubstituted alkenyl, substituted or unsubstituted alkynyl, substituted or unsubstituted heteroalkyl, or substituted or unsubstituted heterocyclyl. In some embodiments, $R^7$ is substituted or unsubstituted $C_{1-10}$ alkyl. In some embodiments, $R^7$ is substituted methyl. In some embodiments, $R^7$ is unsubstituted methyl. In some embodiments, $R^7$ is substituted ethyl. In some embodiments, $R^7$ is unsubstituted ethyl. In some embodiments, $R^7$ is substituted or unsubstituted $C_{2-6}$ alkyl.

In some embodiments, for at least one instance, $R^2$, $R^3$, and the carbon to which $R^2$ and $R^3$ are attached are not joined to form a ring, and $R^6$, $R^7$, and the carbon to which $R^6$ and $R^7$ are attached are not joined form a ring. In some embodiments, $R^2$, $R^3$ and the carbon to which $R^2$ and $R^3$ are attached are not joined to form a ring, and $R^6$, $R^7$ and the carbon to which $R^6$ and $R^7$ are attached are joined form a ring. In some embodiments, $R^2$, $R^3$ and the carbon to which $R^2$ and $R^3$ are attached are joined to form a ring, and $R^6$, $R^7$ and the carbon to which $R^6$ and $R^7$ are attached are not joined form a ring. In some embodiments, for at least one instance, $R^2$, $R^3$ and the carbon to which $R^2$ and $R^3$ are attached are joined to form a ring, and $R^6$, $R^7$ and the carbon to which $R^6$ and $R^7$ are attached are joined form a ring.

In some embodiments, each instance of $R^3$ and $R^6$ are the same. In some embodiments, each instance of $R^3$ and $R^6$ are different.

As generally described above, $L_1$ is a bond, substituted or unsubstituted $C_{1-10}$ alkylene, or $-C(=O)OR^{L1}-$, wherein $R^{L1}$ is optionally substituted $C_{1-10}$ alkylene. In some embodiments, $L_1$ is substituted or unsubstituted alkylene. In some embodiments, $L_1$ is substituted $C_{1-10}$ alkylene. In some embodiments, $L_1$ is $-(CH_2)_g-$, wherein g is 0 or an integer between 1 and 10. In some embodiments, g is 0, and $L_1$ is a bond. In some embodiments, g is 1. In some embodiments, g is 2. In some embodiments, g is 3. In some embodiments, g is 4. In some embodiments, g is 5. In some embodiments, g is 6. In some embodiments, g is 7. In some embodiments, g is 8. In some embodiments, g is 9. In some embodiments, g is 10. In some embodiments, $R^{L1}$ is substituted $C_{1-10}$ alkylene. In some embodiments, $R^{L1}$ is $-C(=O)O(CH_2)_{g1}-$, wherein g1 is an integer between 1 and 10 inclusive. In some embodiments, g1 is 1. In some embodiments, g1 is 2. In some embodiments, g1 is 3. In some embodiments, g1 is 4. In some embodiments, g1 is 5. In some embodiments, g1 is 6. In some embodiments, g1 is 7. In some embodiments, g1 is 8. In some embodiments, g1 is 9. In some embodiments, g1 is 10.

As generally described above, $L_2$ is a bond, substituted or unsubstituted $C_{1-10}$ alkylene, or $-C(=O)OR^{L2}-$, wherein $R^{L2}$ is optionally substituted $C_{1-10}$ alkylene. In some embodiments, $L_2$ is substituted or unsubstituted alkylene. In some embodiments, $L_2$ is substituted $C_{1-10}$ alkylene. In some embodiments, $L_2$ is $-(CH_2)_h-$, wherein h is 0 or an integer between 1 and 10 inclusive. In some embodiments, h is 0, and $L_2$ is a bond. In some embodiments, h is 1. In some embodiments, h is 2. In some embodiments, h is 3. In some embodiments, h is 4. In some embodiments, h is 5. In some embodiments, h is 6. In some embodiments, h is 7. In some embodiments, h is 8. In some embodiments, h is 9. In some embodiments, h is 10. In some embodiments, $R^{L2}$ is substituted $C_{1-10}$ alkylene. In some embodiments, $R^{L2}$ is $-C(=O)O(CH_2)_{h1}-$, wherein h1 is an integer between 1 and 10 inclusive. In some embodiments, h1 is 1. In some embodiments, h1 is 2. In some embodiments, h1 is 3. In some embodiments, h1 is 4. In some embodiments, h1 is 5. In some embodiments, h1 is 6. In some embodiments, h1 is 7. In some embodiments, h1 is 8. In some embodiments, h1 is 9. In some embodiments, h1 is 10.

In some embodiments, each instance of $L_1$ and $L_2$ is the same. In some embodiments, each instance of $L_1$ and $L_2$ is different.

Group $R^1$ and $R^5$

As generally defined above, $R^1$ and $R^5$ are, independently, hydrogen; acyl; optionally substituted $C_{1-6}$ alkyl; or an amino protecting group.

In some embodiments, $R^1$ is hydrogen. In some embodiments, $R^1$ is acyl; optionally substituted $C_{1-6}$ alkyl; or an amino protecting group. In some embodiments, $R^1$ is acyl or optionally substituted $C_{1-6}$ alkyl.

In some embodiments, $R^1$ is substituted or unsubstituted alkyl. In some embodiments, $R^1$ is substituted or unsubstituted $C_{1-6}$ alkyl. In some embodiments, $R^1$ is unsubstituted $C_{1-6}$ alkyl. In some embodiments, $R^1$ is methyl, ethyl, or propyl.

In some embodiments, $R^1$ is acyl. In some embodiments, $R^1$ is acetyl (—C(═O)CH$_3$).

In some embodiments, $R^1$ is an amino protecting group. In some embodiments, $R^{a1}$ is TBS, TBPS, Bn, BOC, Cbz, Fmoc, trifluoroacetyl, triphenylmethyl, or Ts.

In some embodiments, $R^5$ is hydrogen. In some embodiments, $R^5$ is acyl; optionally substituted $C_{1-6}$ alkyl; or an amino protecting group. In some embodiments, $R^5$ is acyl or optionally substituted $C_{1-6}$alkyl.

In some embodiments, $R^5$ is substituted or unsubstituted alkyl. In some embodiments, $R^5$ is substituted or unsubstituted $C_{1-6}$ alkyl. In some embodiments, $R^5$ is unsubstituted $C_{1-6}$ alkyl. In some embodiments, $R^5$ is methyl, ethyl, or propyl.

In some embodiments, $R^5$ is acyl. In some embodiments, $R^5$ is acetyl (—C(═O)CH$_3$).

In some embodiments, $R^5$ is an amino protecting group. In some embodiments, $R^5$ is TBS, TBPS, Bn, BOC, Cbz, Fmoc, trifluoroacetyl, triphenylmethyl, or Ts.

In some embodiments, $R^1$ and $R^5$ are, independently, hydrogen, $C_{1-6}$alkyl (e.g., methyl), or acyl. In some embodiments, $R^1$ and $R^5$ are hydrogen.

In some embodiments, $R^1$ and $R^5$ are, independently, hydrogen, optionally substituted $C_{1-6}$alkyl (e.g., methyl), or acyl. In some embodiments, $R^1$ and $R^5$ are, independently, hydrogen, methyl, or acetyl. In some embodiments, $R^1$ and $R^5$ are, independently, hydrogen or methyl. In some embodiments, $R^1$ and $R^5$ are hydrogen. In some embodiments, $R^1$ and $R^5$ are methyl.

Groups ======, $R^4$ and P

As generally defined above, ====== represents a single bond or a double bond. In some embodiments, ====== is a single bond. In some embodiments, ====== is a double bond.

As generally defined above, each instance of $R^4$ is independently hydrogen; optionally substituted aliphatic; optionally substituted heteroaliphatic; substituted or unsubstituted aryl; optionally substituted heteroaryl; acyl; optionally substituted hydroxyl; optionally substituted thiol; optionally substituted amino; azido; cyano; isocyano; halo; or nitro.

As generally defined above, p is 0, 1, or 2.

In some embodiments, each instance of p is 0, and thus each instance of $R^4$ is absent to provide an unsubstituted crosslink. In some embodiments at least one instance of p is 1, and thus at least one instance of $R^4$ is a non-hydrogen substituent.

In some embodiments, after stapling of an inventive polypeptide, the method further comprises additional synthetic modification of the unsaturated staple or stitch of the cross-linked peptides. Any chemical or biological modification to the stapled or stitched polypeptide may be made. In some embodiments, the modifications are carried out on the Alloc moiety of a polypeptide. In some embodiments, the modifications extrude $CO_2$ from the Alloc moiety from the stapled peptides. In some embodiments, the $CO_2$ extrusion is carried out in the presence of a palladium catalyst. In some embodiments, the $CO_2$ extrusion is carried out in the presence of Pd(PPh$_3$)$_4$. In some embodiments, the modification comprises alkylation on the amide group of the staple or stitch.

In some embodiments, additional modifications of the stapled or stitched peptides include reduction, oxidation, and nucleophilic or electrophilic additions to the double bond provided from a metathesis reaction to provide a synthetically modified polypeptide. Other modifications may include conjugation of a stapled polypeptide, or a synthetically modifying the stapled polypeptide with a therapeutically active agent, label, or diagnostic agent anywhere on the stapled polypeptide scaffold, e.g., such as at the N-terminus of the stapled polypeptide, the C-terminus of the stapled polypeptide, on an amino acid side chain of the stapled polypeptide, or at one or more modified or unmodified stapled sites (i.e., to a staple). Such modification may be useful in delivery of the peptide or therapeutically active agent to a cell, tissue, or organ. Such modifications may, in some embodiments, allow for targeting to a particular type of cell or tissue.

The staples or stitches of the polypeptide may further comprise additional synthetic modification(s). Any chemical or biological modification may be made. In some embodiments, the staple or stitch has an Alloc group. In some embodiments, the modifications are carried out on the Alloc moiety of a polypeptide. In some embodiments, the modifications extrude $CO_2$ from the Alloc moiety from the stapled peptides. In some embodiments, the $CO_2$ extrusion is carried out in the presence of a palladium catalyst. In some embodiments, the $CO_2$ extrusion is carried out in the presence of Pd(PPh$_3$)$_4$. In some embodiments, such modifications include reduction, oxidation, and nucleophilic or electrophilic additions to the double bond provided from a metathesis reaction of the cross-link to provide a synthetically modified stapled or stitched polypeptide. One of ordinary skill in the art will appreciate that a wide variety of conditions may be employed to promote such transformations, therefore, a wide variety of conditions are envisioned; see generally, *March's Advanced Organic Chemistry: Reactions, Mechanisms, and Structure*, M. B. Smith and J. March, 5$^{th}$ Edition, John Wiley & Sons, 2001; *Advanced Organic Chemistry, Part B: Reactions and Synthesis*, Carey and Sundberg, 3$^{rd}$ Edition, Plenum Press, New York, 1993; and *Comprehensive Organic Transformations*, R. C. Larock, 2$^{nd}$ Edition, John Wiley & Sons, 1999, the entirety of each of which is hereby incorporated herein by reference. In other embodiments, the staple(s) of the polypeptide are not further modified.

In some embodiments, the staple or stitch has a double bond. In some embodiments, the modifications are carried out on the double bond of the stapled or stitched polypeptide. Exemplary conditions may be any reagent reactive with a double bond. In some embodiments, the reagent is able to react with a double bond, for example, via a hydrogenation, osmylation, hydroxylation (mono- or di-), amination, halogenation, cycloaddition (e.g., cyclopropanation, aziridination, epoxidation), oxy-mercuration, and/or a hydroboronation reaction, to provide a functionalized single bond. As one of ordinary skill in the art will clearly recognize, these above-described transformations will introduce functionalities compatible with the particular stabilized structures and the desired biological interactions; such functionalities include, but are not limited to, hydrogen; substituted or unsubstituted aliphatic; substituted or unsubstituted heteroaliphatic; substituted or unsubstituted aryl; substituted or unsubstituted heteroaryl; acyl; substituted or unsubstituted hydroxyl; substituted or unsubstituted amino; substituted or unsubstituted thiol; halo; cyano; nitro; azido; imino; oxo; and thiooxo.

Other modifications may further include conjugation of the stapled or stitched polypeptide, or a synthetically modified stapled or stitched polypeptide, with a biologically active agent, label, targeting moiety, diagnostic agent, anywhere on the polypeptide scaffold, e.g., such as at the N-terminus of the polypeptide, the C-terminus of the polypeptide, on an amino acid side chain of the polypeptide, or at one or more modified or unmodified stapled sites. Such modification may be useful in delivery of the peptide or biologically active agent to a cell, tissue, or organ. Such modifications may allow for targeting of the stabilized polypeptide to a particular type of cell or tissue. Conjugation of an agent (e.g., a label, a diagnostic agent, a biologically active agent, a targeting moiety) to the stapled polypeptide may be achieved in a variety of different ways. The agent may be covalently conjugated, directly or indirectly, to the polypeptide at the site of stapling, or to the N-terminus or the C-terminus of the polypeptide. Alternatively, the agent may be noncovalently conjugated, directly or indirectly, to the polypeptide at the site of stapling, or to the N-terminus or the C-terminus of the polypeptide, or any other site on the polypeptide. Indirect covalent conjugation is by means of one or more covalent bonds. Indirect non-covalent conjugation is by means of one or more non-covalent interactions. Conjugation may also be via a combination of non-covalent and covalent interactions. The agent may also be conjugated to the polypeptide through a linker. Any number of covalent bonds may be used in the conjugation of a biologically active agent and/or diagnostic agent to the inventive polypeptide of the present invention. Such bonds include amide linkages, ester linkages, disulfide linkages, carbon-carbon bonds, carbamate linkages, carbonate linkages, urea linkages, hydrazide linkages, and the like. In some embodiments, the bond is cleavable under physiological conditions (e.g., enzymatically cleavable, cleavable at a high or low pH, with heat, light, ultrasound, x-ray, etc.). However, in some embodiments, the bond is not cleavable.

In some embodiments, the additional modification is PEGylation. The PEGylation of the stapled or stitched polypeptide can be carried out using any of the PEGylation reactions known in the art. Such reactions are described, for example, in the following references: Francis et al., (1992), Focus on Growth Factors 3: 4-10; European Patent Nos. 0 154 316 and 0 401 384; and U.S. Pat. No. 4,179,337. For example, PEGylation can be carried out via an acylation reaction or an alkylation reaction with a reactive polyethylene glycol molecule (or an analogous reactive water-soluble polymer) as described herein. For the acylation reactions, a selected polymer should have a single reactive ester group. For reductive alkylation, a selected polymer should have a single reactive aldehyde group. A reactive aldehyde is, for example, polyethylene glycol propionaldehyde, which is water stable, or mono $C_{1-10}$ alkoxy or aryloxy derivatives thereof (see, e.g., U.S. Pat. No. 5,252,714).

The stapled peptides of the invention may be synthesized using methods known in the art, e.g., general methods of preparing the stapled or stitched peptides and addition modifications are described in U.S. Pat. Nos. 7,192,713; 7,723,469; 7,786,072; 8,198,405; 8,324,428; 8,592,377; 8,796,418, 8,889,632, 8,895,699, 9,074,009, 9,273,099, 9,556,227; 9,617,309; U.S. Patent Application Publication Nos: 2010-0184645; 2010-0168388; 2010-0081611; 2009-0176964; 2009-0149630; 2006-0008848; 2014-0296160; 2014-162339; 2014-0011979; 2015-0239937, 2015-119951; 2016-0024153; 2016-0215036; 2016-0244494; 2017-0240604; 2017-0066799; PCT Application Publication Nos: WO 2010/011313; WO 2008/121767; WO 2008/095063; WO 2008/061192; WO2014/055564; and WO 2005/044839, as well as PCT Application No. PCT/US2014/025544; the synthetic methods of which are incorporated by references herein.

Small Multidrug Resistance Transporters

The polypeptides of the invention include sequences of small multidrug resistance transporters of which two amino acids have been replaced with a cross-link. In some embodiments, the α-helix which is stabilized to produce the polypeptides of the invention is:

```
DLPAIIGMMLICAGVLIINLLS    (SEQ ID NO: 1)
```

Exemplary sequences of small multidrug resistance transporters which include an α-helix include:

```
Multidrug transporter EmrE (Escherichia coli
(strain K12)):
                                 (SEQ ID NO: 2)
MNPYIYLGGAILAEVIGTTLMKFSEGFTRDWPSVGTIICYCASFWLLAQT

LAYIPTGIAYAIWSGVGIVLISLLSWGFFGQRLDLPAIIGMMLICAGVLI

INLLSRSTPH

Antiseptic-resistance protein (Escherichia coli):
                                 (SEQ ID NO: 3)
MKGWLFLVIAIVGEVIATSALKSSEGFTKLAPSAVVIIGYGIAFYFLSLV

LKSIPVGVAYAVWSGLGVVIITAIAWLLHGQKLDAEGFVGMGLIIAAFLL

ARSPSWKSLRRPTPW

Multidrug SMR transporter (Escherichia coli):
                                 (SEQ ID NO: 4)
MNPYIYLGGAILAEVIGTTLMKFSEGFTRLWPSVGTIICYCASFWLLAQT

LAYIPTGIAYAIWSGVGIVLISLLSWGFFGQRLDLPAIIGMMLICAGVLV

INLLSRSAPH

EmrE (Mycobacterium tuberculosis):
                                 (SEQ ID NO: 5)
MYIRTQGEVLTYFPLCAIAAEAAATSLFKGSFGDFRVCSPGHDGAITAMP

SVLAASRIRSS

EmrE protein (Mycobacterium orygis):
                                 (SEQ ID NO: 6)
MIYLYLLCAIFAEVVATSLLKSTEGFTRLWPTVGCLVGYGIAFALLALSI

SHGMQTDVAYALWSAIGTAAIVLVAVLFLGSPISVMKVVGVGLIVVGVVT

LNLAGAH

Ethidium bromide resistance protein (Enterobacter
cloacae):
                                 (SEQ ID NO: 7)
MKGWLFLVIAIVGEVIATSALKSSEGFTKLAPSAVVIIGYGIAFYFLSLV

LKSIPVGVAYAVWSGLGVVIITAIAWLLHGQKLDAWGFVGMGLIIAAFLL

ARSPSWKSLRRPTPW

Orf3/QacEdelta1 fusion protein (Klebsiella
pneumoniae):
                                 (SEQ ID NO: 8)
MKGWLFLVIAIVGEVIATSALKSSEGFTKLAPSAVVIIGYGIAFYFLSLV

LKSIPVGVAYAVWSGLGVVIITAIAWLLHGQKLDAWGFVGMGLIIAAFLL

ARSPSWKSLRRPTPW

Antiseptic-resistance protein (Escherichia coli):
                                 (SEQ ID NO: 9)
MKGWLFLVIAIVGEVIATSALKSSEGFTKLAPSAVVIIGYGIAFYFLSLV

LKSIPVGVAYAVWSGLGVVIITAIAWLLHGQKLDAWGFVGMGLIIAAFLL

ARSPSWKSLRRPTPW
```

Ethidium bromide resistance protein (*Pseudomonas aeruginosa*):
(SEQ ID NO: 10)
MKGWLFLVIAIVGEVIATSALKSSEGFTKLAPSAVVIIGYGIAFYFLSLV

LKSIPVGVAYAVWSGLGVVITTAIAWLLHGQKLDAWGFVGMGLIIAAFLL

ARSPSWKSLRRPTPW

Multidrug transporter (*Providencia rettgeri*):
(SEQ ID NO: 11)
MKGWLELVTAIVGEVIATSALKSSEGFTKLAPSAVVIIGYGTAFYFLSLV

LKSIPVGVAYAVWSGLGVVIITAIAWLLHGQKLDAWGFVGMGLIIAAFLL

ARSPSWKSLRRPTPW

Multidrug DMT transporter (*Pseudomonas citronellolis*):
(SEQ ID NO: 12)
MPGYLYLAIAIVAEVIATASLKSVKGLSTPLPLLLVIVGYAISFWMLTLV

VRSIPVGIAYAIWAGLGIVLVSVAALVLYQQKLDAPALLGMGLIVSGVVV

IQLFSGSVSH

Methyl viologen resistance protein C (*Pseudomonas aeruginosa*):
(SEQ ID NO: 13)
MTNYLYLAIAIAAEVVATTSLKAVAGFSKPLPLLLVVGGYVLAFSMLVLV

MRTLPVGVVYAIWSGLGIVLVSLVAMPVYGQRLDPAALLGIGLIIAGVLV

IQLFSRASGH

Methyl viologen resistance protein C (*Pseudomonas aeruginosa*):
(SEQ ID NO: 14)
MNPYIYLAAAIVLEVIATSLLKASDGMSRLWPTVGALVGYGLCFYLLSVT

MKSVPTGIAYAIWSGVGIVLISLIGLVVFKQRLDAPALIGIGLICAGVLV

INLFSRSSAH

Membrane transport protein (*Bordetella pertussis*):
(SEQ ID NO: 15)
MNSWIHLSMAIVAEIIATSALKSSEGFTRLLPSLVTVAGYAIAFYFLALT

LRVIPVGVAYAIWSGVGIVLISLVGALLFKQHLDLPAIIGIALILAGVVV

MNVFSKSVGH

Membrane transport protein (*Bordetella pertussis*):
(SEQ ID NO: 16)
MAGYAIAFYFTALTLRVIPVGVAYAIWSGVGIVLISLVGALLFKQHLDLP

AIIGIALILAGVVMNVFSKSVGH

Membrane transport protein (*Bordetella pertussis*):
(SEQ ID NO: 17)
MGVAYAIWSGVGIVLISLVGALLFKQHLDLPAIIGIALILAGVVVMNVFS

KSVGK

Ethidium bromide-methyl viologen resistance protein EmrE (*Neisseria meningitidis* serogroup B):
(SEQ ID NO: 18)
MPLATAYAIWAGVGINLTALVSVVFFGEKADFIGIVSIGLILLGVVLLNT

MSHMSGH

Quaternary ammonium compound-resistance protein, small multidrug resistance protein family (*Bacillus cereus* var. anthracis (strain C1)):
(SEQ ID NO: 19)
MKNKAWL -continued Multidrug transporter EmrE (*Escherichia coli* (strain K12)):
(SEQ ID NO: 25)
MNPYIYLGGAILAEVIGTTLMKFSEGFTRLWPSVGTIICYCASFWLLAQTLAYIPTGIAYAIWSGVGIVLIS

LLSWGFFGQRLDLPAIIGMMLICAGVLIINLLSRSTPH

Hypothetical phage protein (*Escherichia coli* (strain SE11)):
(SEQ ID NO: 26)
MNPYIYLGGAILAEVIGTTLMKFSEGFTRLWPSVGTIICYCASFWLLAQTLAYIPTGIAYAIWSGVGIVLIS

LLSWGFFGQRLDLPAIIGMMLICAGVLVINLLSRSTPH

Multidrug transporter EmrE (*Escherichia coli* H591):
(SEQ ID NO: 27)
MNPYIYLGGAILAEVIGTTLMKFSEGFTRLWPSVGTIICYCASFWLLAQTLAYIPTGIAYAIWSGVGIVLIS

LLSWGFFGQRLDLPAIIGMMLICAGVLVINLLSRSTPH

Multidrug transporter EmrE (*Escherichia coli* KTE75):
(SEQ ID NO: 28)
MNPYIYLGGAILAEVIGTTLMKFSEGFTRLWPSVGTIICYCASFWLLAQTLAYIPTGIAYAIWSGVGIVLIS

LLSWGFFGQRLDLPAIIGMMLICAGVLVINLLSRSTPH

Multidrug transporter EmrE (*Escherichia coli* B088):
(SEQ ID NO: 29)
MNPYIYLGGAILAEVIGTTLMKFSEGFTRLWPSVGTIICYCASFWLLAQTLAYIPTGIAYAIWSGVGIVLIS

LLSWGFFGQRLDLPAIIGMMLICAGVLVINLLSRSTPH

EmrE protein (*Escherichia coli* (strain 55989/EAEC)):
(SEQ ID NO: 30)
MNPYIYLGGAILAEVIGTTLMKFSEGFTRLWPSVGTIICYCASFWLLAQTLAYIPTGIAYAIWSGVGIVLIS

LLSWGFFGQRLDLPAIIGMMLICAGVLVINLLSRSTPH

Multidrug transporter EmrE (*Escherichia coli* 2-427-07_S4_C3):
(SEQ ID NO: 31)
MNPYIYLGGAILAEVIGTTLMKFSEGFTRLWPSVGTIICYCASFWLLAQTLAYIPTGIAYAIWSGVGIVLIS

LLSWGFFGQRLDLPAIIGMMLICAGVLVINLLSRSTPH

Multidrug transporter EmrE (*Escherichia coli* 4.0967):
(SEQ ID NO: 32)
MNPYIYLGGAILAEVIGTTLMKFSEGFTRLWPSVGTIICYCASFWLLAQTLAYIPTGIAYAIWSGVGIVLIS

LLSWGFFGQRLDLPAIIGMMLICAGVLVINLLSRSTPH

Multidrug transporter EmrE (*Escherichia coli* 3-267-03_S4_C1):
(SEQ ID NO: 33)
MNPYIYLGGAILAEVIGTTLMKFSEGFTRLWPSVGTIICYCASFWLLAQTLAYIPTGIAYAIWSGVGIVLIS

LLSWGFFGQRLDLPAIIGMMLICAGVLVINLLSRSTPH

Multidrug transporter (*Escherichia coli* O146:H21 str. 2010C-3325):
(SEQ ID NO: 34)
MNPYIYLGGAILAEVIGTTLMKFSEGFTRLWPSVGTIICYCASFWLLAQTLAYIPTGIAYAIWSGVGIVLIS

LLSWGFFGQRLDLPAIIGMMLICAGVLVINLLSRSTPH

Multidrug transporter EmrE (*Escherichia coli* MS 145-7):
(SEQ ID NO: 35)
MNPYIYLGGAILAEVIGTTLMKFSEGFTRLWPSVGTIICYCASFWLLAQTLAYIPTGIAYAIWSGVGIVLIS

LLSWGFFGQRLDLPAIIGMMLICAGVLVINLLSRSTPH

Multidrug transporter EmrE (*Escherichia coli* 2-011-08_S1_C1):
(SEQ ID NO: 36)
MNPYIYLGGAILAEVIGTTLMKFSEGFTRLWPSVGTIICYCASFWLLAQTLAYIPTGIAYAIWSGVGIVLIS

LLSWGFFGQRLDLPAIIGMMLICAGVLVINLLSRSTPH

Multidrug transporter EmrE (*Escherichia coli* KTE66):
(SEQ ID NO: 37)
MNPYIYLGGAILAEVIGTTLMKFSEGFTRLWPSVGTIICYCASFWLLAQTLAYIPTGIAYAIWSGVGIVLIS

LLSWGFFGQRLDLPAIIGMMLICAGVLVINLLSRSTPH

-continued

Multidrug transporter EmrE (*Escherichia coli* B185):
(SEQ ID NO: 38)
MNPYIYLGGAILAEVIGTTLMKFSEGFTRLWPSVGTIICYCASFWLLAQTLAYIPTGIAYAIWSGVGIVLIS

LLSWGFFGQRLDLPAIIGMMLICAGVLVINLLSRSTPH

EmrE protein (*Escherichia coli* O139:H28 (strain E24377A/ETEC)):
(SEQ ID NO: 39)
MNPYIYLGGAILAEVIGTTLMKFSEGFTRLWPSVGTIICYCASFWLLAQTLAYIPTGIAYAIWSGVGIVLIS

LLSWGFFGQRLDLPAIIGMMLICAGVLVINLLSRSTPH

Multidrug transporter EmrE (*Escherichia coli* 1-392-07_S4_C3):
(SEQ ID NO: 40)
MNPYIYLGGAILAEVIGTTLMKFSEGFTRLWPSVGTIICYCASFWLLAQTLAYIPTGIAYAIWSGVGIVLIS

LLSWGFFGQRLDLPAIIGMMLICAGVLVINLLSRSTPH

Multidrug transporter EmrE (*Escherichia coli* 1-392-07_S4_C1):
(SEQ ID NO: 41)
MNPYIYLGGAILAEVIGTTLMKFSEGFTRLWPSVGTIICYCASFWLLAQTLAYIPTGIAYAIWSGVGIVLIS

LLSWGFFGQRLDLPAIIGMMLICAGVLVINLLSRSTPH

Multidrug transporter EmrE (*Escherichia coli* UMEA 3718-1):
(SEQ ID NO: 42)
MNPYIYLGGAILAEVIGTTLMKFSEGFTRLWPSVGTIICYCASFWLLAQTLAYIPTGIAYAIWSGVGIVLIS

LLSWGFFGQRLDLPAIIGMMLICAGVLVINLLSRSTPH

Multidrug SMR transporter (*Escherichia coli*):
(SEQ ID NO: 43)
MNPYIYLGGAILAEVIGTTLMKFSEGFTRLWPSVGTIICYCASFWLLAQTLAYIPTGIAYAIWSGVGIVLIS

LLSWGFFGQRLDLPAIIGMMLICAGVLVINLLSRSTPH

Multidrug resistance protein DLP12 prophage (*Escherichia coli* NCCP15648):
(SEQ ID NO: 44)
MNPYIYLGGAILAEVIGTTLMKFSEGFTRLWPSVGTIICYCASFWLLAQTLAYIPTGIAYAIWSGVGIVLIS

LLSWGFFGQRLDLPAIIGMMLICAGVLVINLLSRSTPH

Multidrug efflux protein (*Escherichia coli* O83:H1 (strain NRG 857C/AIEC)):
(SEQ ID NO: 45)
MNRKEYAMNPYIYLGGAILAEVIGTTLMKFSEGFTRLWPSVGTIICYCASFWLLAQTLAYIPTGIAYAIWSG

VGIVLISLLSWGFFGQRLDLPAIIGMMLICAGVLVINLLSRSTPH

Multidrug SMR transporter (*Escherichia coli* O157):
(SEQ ID NO: 46)
MNPYIYLGGAILAEVIGTTLMKFSEGFTRLWPSVGTIICYCASFWLLAQTLAYIPTGIAYAIWSGVGIVLIS

LLSWGFFGQRLDLPAVIGMMLICAGVLVINLLSRSTPH

Multidrug transporter EmrE (*Escherichia coli* KTE100):
(SEQ ID NO: 47)
MNPYIYLGGAILAEVIGTTLMKFSEGFTRLWPSVGTIICYCASFWLLAQTLAYIPTGIAYAIWSGVGIVLIS

LLSWGFFGQRLDLPAVIGMMLICAGVLVINLLSRSTPH

Multidrug transporter EmrE (*Escherichia sp.* KTE159):
(SEQ ID NO: 48)
MNPYIYLGGAILAEVIGTTLMKFSEGFTRLWPSVGTIICYCASFWLLAQTLAYIPTGIAYAIWSGVGIVLIS

LLSWGFFGQRLDLPAVIGMMLICAGVLVINLLSRSTPH

Multidrug efflux protein (*Escherichia coli* Xuzhou21):
(SEQ ID NO: 49)
MNPYIYLGGAILAEVIGTTLMKFSEGFTRLWPSVGTIICYCASFWLLAQTLAYIPTGIAYAIWSGVGIVLIS

LLSWGFFGQRLDLPAVIGMMLICAGVLVINLLSRSTPH

Ethidium bromide-methyl viologen resistance protein EmrE (*Escherichia coli* O157:H7 str. SS52):
(SEQ ID NO: 50)
MNPYIYLGGAILAEVIGTTLMKFSEGFTRLWPSVGTIICYCASFWLLAQTLAYIPTGIAYAIWSGVGIVLIS

LLSWGFFGQRLDLPAVIGMMLICAGVLVINLLSRSTPH

-continued

EmrE protein (*Escherichia coli* O157:H7 (strain EC869)):
(SEQ ID NO: 51)
MNPYIYLGGAILAEVIGTTLMKFSEGFTRLWPSVGTIICYCASFWLLAQTLAYIPTGIAYAIWSGVGIVLIS

LLSWGFFGQRLDLPAVIGMMLICAGVLVINLLSRSTPH

Multidrug SMR transporter (*Escherichia coli*):
(SEQ ID NO: 52)
MNPYIYLGGAILAEVIGTTLMKFSEGFTRLWPSVGTIICYCASFWLLAQTLAYIPTGIAYAIWSGVGIVLIS

LLSWGFFGQRLDLPAVIGMMLICAGVLVINLLSRSTPH

Integral membrane drug resistance protein EmrE (*Escherichia coli* O157:H7):
(SEQ ID NO: 53)
MNPYIYLGGAILAEVIGTTLMKFSEGFTRLWPSVGTIICYCASFWLLAQTLAYIPTGIAYAIWSGVGIVLIS

LLSWGFFGQRLDLPAVIGMMLICAGVLVINLLSRSTPH

Multidrug transporter EmrE (*Escherichia coli*):
(SEQ ID NO: 54)
MNPYIYLGGAILAEVIGTTLMKFSEGFTRLWPSVGTIICYCASFWLLAQTLAYIPTGIAYAIWSGVGIVLIS

LLSWGFFGQRLDLPAIIGMMLICAGVLVINLLSRSTPH

Multidrug transporter EmrE (*Escherichia coli* HVH 70 (4-2963531)):
(SEQ ID NO: 55)
MNPYIYLGGAILAEVIGTTLMKFSEGFTRLWPSVGTIICYCASFWLLAQTLAYIPTGIAYAIWSGVGIVLIS

LLSWGFFGQRLDLPAIIGMMLICAGVLVINLLSRSTPH

Multidrug transporter EmrE (*Escherichia coli* (strain UMEA 3162-1)):
(SEQ ID NO: 56)
MNPYIYLGGAILAEVIGTTLMKFSEGFTRLWPSVGTIICYCASFWLLAQTLAYIPTGIAYAIWSGVGIVLIS

LLSWGFFGQRLDLPAIIGMMLICAGVLVINLLSRSTPH

Multidrug transporter EmrE (*Escherichia coli* 2-005-03_S4_C3):
(SEQ ID NO: 57)
MNPYIYLGGAILAEVIGTTLMKFSEGFTRLWPSVGTIICYCASFWLLAQTLAYIPTGIAYAIWSGVGIVLIS

LLSWGFFGQRLDLPAIIGMMLICAGVLVINLLSRSTPH

Multidrug transporter EmrE (*Escherichia coli* H420):
(SEQ ID NO: 58)
MNPYIYLGGAILAEVIGTTLMKFSEGFTRLWPSVGTIICYCASFWLLAQTLAYIPTGIAYAIWSGVGIVLIS

LLSWGFFGQRLDLPAIIGMMLICAGVLVINLLSRSTPH

Multidrug transporter EmrE (*Escherichia coli* DEC6A):
(SEQ ID NO: 59)
MNPYIYLGGAILAEVIGTTLMKFSEGFTRLWPSVGTIICYCASFWLLAQTLAYIPTGIAYAIWSGVGIVLIS

LLSWGFFGQRLDLPAIIGMMLICAGVLVINLLSRSTPH

Multidrug transporter EmrE (*Escherichia coli* 97.0246):
(SEQ ID NO: 60)
MNPYIYLGGAILAEVIGTTLMKFSEGFTRLWPSVGTIICYCASFWLLAQTLAYIPTGIAYAIWSGVGIVLIS

LLSWGFFGQRLDLPAIIGMMLICAGVLVINLLSRSTPH

Multidrug efflux protein (*Escherichia coli* O104:H4 (strain 2011C-3493)):
(SEQ ID NO: 61)
MNPYIYLGGAILAEVIGTTLMKFSEGFTRLWPSVGTIICYCASFWLLAQTLAYIPTGIAYAIWSGVGIVLIS

LLSWGFFGQRLDLPAIIGMMLICAGVLVINLLSRSTPH

Multidrug efflux protein (*Escherichia coli* O111:H8 str. CVM9634):
(SEQ ID NO: 62)
MNPYIYLGGAILAEVIGTTLMKFSEGFTRLWPSVGTIICYCASFWLLAQTLAYIPTGIAYAIWSGVGIVLIS

LLSWGFFGQRLDLPAIIGMMLICAGVLVINLLSRSTPH

Multidrug transporter EmrE (*Escherichia coli* KTE73):
(SEQ ID NO: 63)
MNPYIYLGGAILAEVIGTTLMKFSEGFTRLWPSVGTIICYCASFWLLAQTLAYIPTGIAYAIWSGVGIVLIS

LLSWGFFGQRLDLPAIIGMMLICAGVLVINLLSRSTPH

-continued

Multidrug transporter EmrE (*Escherichia coli* HVH 70 (4-2963531)):
(SEQ ID NO: 64)
MNPYIYLGGAILAEVIGTTLMKFSEGFTRLWPSVGTIICYCASFWLLAQTLAYIPTGIAYAIWSGVGIVLIS

LLSWGFFGQRLDLPAIIGMMLICAGVLVINLLSRSTPH

Multidrug transporter EmrE (*Escherichia coli* UMNK88):
(SEQ ID NO: 65)
MNPYIYLGGAILAEVIGTTLMKFSEGFTRLWPSVGTIICYCASFWLLAQTLAYIPTGIAYAIWSGVGIVLIS

LLSWGFFGQRLDLPAIIGMMLICAGVLVINLLSRSTPH

Multidrug transporter (*Escherichia fergusonii*):
(SEQ ID NO: 66)
MNPYIYLGGAILAEVIGTTLMKFSEGFTRLWPSVGTIICYCASFWLLAQTLAYIPTGIAYAIWSGVGIVLIS

LLSWGFFGQRLDLPAIIGMMLICAGVLVINLLSRSTPH

Multidrug transporter EmrE (*Escherichia coli* B088):
(SEQ ID NO: 67)
MNPYIYLGGAILAEVIGTTLMKFSEGFTRLWPSVGTIICYCASFWLLAQTLAYIPTGIAYAIWSGVGIVLIS

LLSWGFFGQRLDLPAIIGMMLICAGVLVINLLSRSTPH

Ethidium bromide-methyl viologen resistance protein EmrE
(*Escherichia coli* ISC7):
(SEQ ID NO: 68)
MNPYIYLGGAILAEVIGTTLMKFSEGFTRLWPSVGTIICYCASFWLLAQTLAYIPTGIAYAIWSGVGIVLIS

LLSWGFFGQRLDLPAIIGMMLICAGVLVINLLSRSTPH

Multidrug transporter EmrE (*Escherichia coli* TA054):
(SEQ ID NO: 69)
MNPYIYLGGAILAEVIGTTLMKFSEGFTRLWPSVGTIICYCASFWLLAQTLAYIPTGIAYAIWSGVGIVLIS

LLSWGFFGQRLDLPAIIGMMLICAGVLVINLLSRSTPH

Multidrug transporter (*Escherichia coli* ATCC BAA-2209):
(SEQ ID NO: 70)
MNPYIYLGGAILAEVIGTTLMKFSEGFTRLWPSVGTIICYCASFWLLAQTLAYIPTGIAYAIWSGVGIVLIS

LLSWGFFGQRLDLPAIIGMMLICAGVLVINLLSRSTPH

Multidrug transporter EmrE (*Escherichia* sp. KTE114):
(SEQ ID NO: 71)
MNPYIYLGGAILAEVIGTTLMKFSEGFTRLWPSVGTIICYCASFWLLAQTLAYIPTGIAYAIWSGVGIVLIS

LLSWGFFGQRLDLPAIIGMMLICAGVLVINLLSRSTPH

Multidrug transporter EmrE (*Escherichia coli* HVH 25 (4-5851939)):
(SEQ ID NO: 72)
MNPYIYLGGAILAEVIGTTLMKFSEGFTRLWPSVGTIICYCASFWLLAQTLAYIPTGIAYAIWSGVGIVLIS

LLSWGFFGQRLDLPAIIGMMLICAGVLVINLLSRSTPH

Multidrug transporter EmrE (*Escherichia coli* H461):
(SEQ ID NO: 73)
MNPYIYLGGAILAEVIGTTLMKFSEGFTRLWPSVGTIICYCASFWLLAQTLAYIPTGIAYAIWSGVGIVLIS

LLSWGFFGQRLDLPAIIGMMLICAGVLVINLLSRSTPH

Multidrug transporter EmrE (*Escherichia coli* M718):
(SEQ ID NO: 74)
MNPYIYLGGAILAEVIGTTLMKFSEGFTRLWPSVGTIICYCASFWLLAQTLAYIPTGIAYAIWSGVGIVLIS

LLSWGFFGQRLDLPAIIGMMLICAGVLVINLLSRSTPH

Methyl viologen resistance protein C (*Achromobacter* sp.):
(SEQ ID NO: 75)
MNPYIYLGGAILAEVIGTTLMKFSEGFTRLWPSVGTIICYCASFWLLAQTLAYIPTGIAYAIWSGVGIVLIS

LLSWGFFGQRLDLPAIIGMMLICAGVLVINLLSRSTPH

Multidrug transporter EmrE (*Escherichia coli* KOEGE 71 (186a)):
(SEQ ID NO: 76)
MNPYIYLGGAILAEVIGTTLMKFSEGFTRLWPSVGTIICYCASFWLLAQTLAYIPTGIAYAIWSGVGIVLIS

LLSWGFFGQRLDLPAIIGMMLICAGVLVINLLSRSTPH

-continued

Multidrug transporter EmrE (*Escherichia coli* 2-427-07_S4_C3):
(SEQ ID NO: 77)
MNPYIYLGGAILAEVIGTTLMKFSEGFTRLWPSVGTIICYCASFWLLAQTLAYIPTGIAYAIWSGVGIVLIS

LLSWGFFGQRLDLPAIIGMMLICAGVLVINLLSRSTPH

Multidrug transporter (*Escherichia coli* O111:NM sir. K6722):
(SEQ ID NO: 78)
MNPYIYLGGAILAEVIGTTLMKFSEGFTRLWPSVGTIICYCASFWLLAQTLAYIPTGIAYAIWSGVGIVLIS

LLSWGFFGQRLDLPAIIGMMLICAGVLVINLLSRSTPH

Quaternary ammonium transporter (*Escherichia coli* APEC O2-211):
(SEQ ID NO: 79)
MNPYIYLGGAILAEVIGTTLMKFSEGFTRLWPSVGTIICYCASFWLLAQTLAYIPTGIAYAIWSGVGIVLIS

LLSWGFFGQRLDLPAIIGMMLICAGVLVINLLSRSTPH

Multidrug transporter EmrE (*Escherichia coli* KTE21):
(SEQ ID NO: 80)
MNPYIYLGGAILAEVIGTTLMKFSEGFTRLWPSVGTIICYCASFWLLAQTLAYIPTGIAYAIWSGVGIVLIS

LLSWGFFGQRLDLPAIIGMMLICAGVLVINLLSRSTPH

Multidrug resistance protein (*Escherichia coli* (strain ATCC 9637/CCM
2024/DSM 1116/NCIMB 8666/NRRL B-766/W)):
(SEQ ID NO: 81)
MNPYIYLGGAILAEVIGTTLMKFSEGFTRLWPSVGTIICYCASFWLLAQTLAYIPTGIAYAIWSGVGIVLIS

LLSWGFFGQRLDLPAIIGMMLICAGVLVINLLSRSTPH

Multidrug transporter EmrE (*Escherichia coli* 2-177-06_S3_C3):
(SEQ ID NO: 82)
MNPYIYLGGAILAEVIGTTLMKFSEGFTRLWPSVGTIICYCASFWLLAQTLAYIPTGIAYAIWSGVGIVLIS

LLSWGFFGQRLDLPAIIGMMLICAGVLVINLLSRSTPH

Multidrug transporter EmrE (*Escherichia coli* 3-267-03_S4_C1):
(SEQ ID NO: 83)
MNPYIYLGGAILAEVIGTTLMKFSEGFTRLWPSVGTIICYCASFWLLAQTLAYIPTGIAYAIWSGVGIVLIS

LLSWGFFGQRLDLPAIIGMMLICAGVLVINLLSRSTPH

Multidrug transporter EmrE (*Escherichia coli* HVH 50 (4-2593475)):
(SEQ ID NO: 84)
MNPYIYLGGAILAEVIGTTLMKFSEGFTRLWPSVGTIICYCASFWLLAQTLAYIPTGIAYAIWSGVGIVLIS

LLSWGFFGQRLDLPAIIGMMLICAGVLVINLLSRSTPH

Multidrug transporter EmrE (*Escherichia coli* 1.2264):
(SEQ ID NO: 85)
MNPYIYLGGAILAEVIGTTLMKFSEGFTRLWPSVGTIICYCASFWLLAQTLAYIPTGIAYAIWSGVGIVLIS

LLSWGFFGQRLDLPAIIGMMLICAGVLVINLLSRSTPH

Multidrug transporter EmrE (*Shigella flexneri* K-227):
(SEQ ID NO: 86)
MNPYIYLGGAILAEVIGTTLMKFSEGFTRLWPSVGTIICYCASFWLLAQTLAYIPTGIAYAIWSGVGIVLIS

LLSWGFFGQRLDLPAIIGMMLICAGVLVINLLSRSTPH

Multidrug transporter EmrE (*Shigella fiexneri* 2a sir. 301):
(SEQ ID NO: 87)
MNPYIYLGGAILAEVIGTTLMKFSEGFTRLWPSVGTIICYCASFWLLAQTLAYIPTGIAYAIWSGVGIVLIS

LLSWGFFGQRLDLPAIIGMMLICAGVLVINLLSRSTPH

Methylviologen resistance (*Shigella sunnier* (strain Ss046)):
(SEQ ID NO: 88)
MNPYIYLGGAILAEVIGTTLMKFSEGFTRLWPSVGTIICYCASFWLLAQTLAYIPTGIAYAIWSGVGIVLIS

LLSWGFFGQRLDLPAIIGMMLICAGVLVINLLSRSTPH

Multidrug transporter (*Escherichia coli* O174:H8 sir. 04-3038):
(SEQ ID NO: 89)
MNPYIYLGGAILAEVIGTTLMKFSEGFTRLWPSVGTIICYCASFWLLAQTLAYIPTGIAYAIWSGVGIVLIS

LLSWGFFGQRLDLPAIIGMMLICAGVLVINLLSRSTPH

-continued

Multidrug transporter EmrE (*Escherichia coli* KTE108):
(SEQ ID NO: 90)
MNPYIYLGGAILAEVIGTTLMKFSEGFTRLWPSVGTIICYCASFWLLAQTLAYIPTGIAYAIWSGVGIVLIS

LLSWGFFGQRLDLPAIIGMMLICAGVLVINLLSRSTPH

Methylviologen resistance (*Escherichia coli* G3/10):
(SEQ ID NO: 91)
MNPYIYLGGAILAEVIGTTLMKFSEGFTRLWPSVGTIICYCASFWLLAQTLAYIPTGIAYAIWSGVGIVLIS

LLSWGFFGQRLDLPAIIGMMLICAGVLVINLLSRSTPH

Small Multidrug Resistance protein (*Escherichia coli* TW10509):
(SEQ ID NO: 92)
MNPYIYLGGAILAEVIGTTLMKFSEGFTRLWPSVGTIICYCASFWLLAQTLAYIPTGIAYAIWSGVGIVLIS

LLSWGFFGQRLDLPAIIGMMLICAGVLVINLLSRSTPH

Multidrug transporter EmrE (*Escherichia coli* 4.0522):
(SEQ ID NO: 93)
MNPYIYLGGAILAEVIGTTLMKFSEGFTRLWPSVGTIICYCASFWLLAQTLAYIPTGIAYAIWSGVGIVLIS

LLSWGFFGQRLDLPAIIGMMLICAGVLVINLLSRSTPH

Integral membrane drug resistance protein EmrE (*Escherichia coli*
O111:H- (strain 11128/EHEC)):
(SEQ ID NO: 94)
MNPYIYLGGAILAEVIGTTLMKFSEGFTRLWPSVGTIICYCASFWLLAQTLAYIPTGIAYAIWSGVGIVLIS

LLSWGFFGQRLDLPAIIGMMLICAGVLVINLLSRSTPH

Multidrug transporter EmrE (*Escherichia coli* KTE20):
(SEQ ID NO: 95)
MNPYIYLGGAILAEVIGTTLMKFSEGFTRLWPSVGTIICYCASFWLLAQTLAYIPTGIAYAIWSGVGIVLIS

LLSWGFFGQRLDLPAIIGMMLICAGVLVINLLSRSTPH

Multidrug transporter EmrE (*Escherichia coli* 2-005-03_S4_C2):
(SEQ ID NO: 96)
MNPYIYLGGAILAEVIGTTLMKFSEGFTRLWPSVGTIICYCASFWLLAQTLAYIPTGIAYAIWSGVGIVLIS

LLSWGFFGQRLDLPAIIGMMLICAGVLVINLLSRSTPH

Multidrug transporter EmrE (*Escherichia coli* M605):
(SEQ ID NO: 97)
MNPYIYLGGAILAEVIGTTLMKFSEGFTRLWPSVGTIICYCASFWLLAQTLAYIPTGIAYAIWSGVGIVLIS

LLSWGFFGQRLDLPAIIGMMLICAGVLVINLLSRSTPH

Multidrug transporter EmrE (*Escherichia coli* TA447):
(SEQ ID NO: 98)
MNPYIYLGGAILAEVIGTTLMKFSEGFTRLWPSVGTIICYCASFWLLAQTLAYIPTGIAYAIWSGVGIVLIS

LLSWGFFGQRLDLPAIIGMMLICAGVLVINLLSRSTPH

Multidrug SMR transporter (*Escherichia coli* O104:H4):
(SEQ ID NO: 99)
MNPYIYLGGAILAEVIGTTLMKFSEGFTRLWPSVGTIICYCASFWLLAQTLAYIPTGIAYAIWSGVGIVLIS

LLSWGFFGQRLDLPAIIGMMLICAGVLVINLLSRSTPH

Multidrug transporter EmrE (*Escherichia coli* UMEA 3212-1):
(SEQ ID NO: 100)
MNPYIYLGGAILAEVIGTTLMKFSEGFTRLWPSVGTIICYCASFWLLAQTLAYIPTGIAYAIWSGVGIVLIS

LLSWGFFGQRLDLPAIIGMMLICAGVLVINLLSRSTPH

Multidrug transporter EmrE (*Escherichia coli* 2-177-06_S3_C2):
(SEQ ID NO: 101)
MNPYIYLGGAILAEVIGTTLMKFSEGFTRLWPSVGTIICYCASFWLLAQTLAYIPTGIAYAIWSGVGIVLIS

LLSWGFFGQRLDLPAIIGMMLICAGVLVINLLSRSTPH

Multidrug transporter EmrE (*Escherichia coli* 99.0741):
(SEQ ID NO: 102)
MNPYIYLGGAILAEVIGTTLMKFSEGFTRLWPSVGTIICYCASFWLLAQTLAYIPTGIAYAIWSGVGIVLIS

LLSWGFFGQRLDLPAIIGMMLICAGVLVINLLSRSTPH

-continued

Multidrug transporter EmrE (*Escherichia coli* UMEA 3323-1):
(SEQ ID NO: 103)
MNPYIYLGGAILAEVIGTTLMKFSEGFTRLWPSVGTIICYCASFWLLAQTLAYIPTGIAYAIWSGVGIVLIS
LLSWGFFGQRLDLPAIIGMMLICAGVLVINLLSRSTPH Multidrug transporter EmrE (*Escherichia coli* KTE10):
(SEQ ID NO: 104)
MNPYIYLGGAILAEVIGTTLMKFSEGFTRLWPSVGTIICYCASFWLLAQTLAYIPTGIAYAIWSGVGIVLIS
LLSWGFFGQRLDLPAIIGMMLICAGVLVINLLSRSTPH Multidrug transporter EmrE (*Escherichia coli* KTE182):
(SEQ ID NO: 105)
MNPYIYLGGAILAEVIGTTLMKFSEGFTRLWPSVGTIICYCASFWLLAQTLAYIPTGIAYAIWSGVGIVLIS
LLSWGFFGQRLDLPAIIGMMLICAGVLVINLLSRSTPH Multidrug transporter EmrE (*Escherichia coli* H386):
(SEQ ID NO: 106)
MNPYIYLGGAILAEVIGTTLMKFSEGFTRLWPSVGTIICYCASFWLLAQTLAYIPTGIAYAIWSGVGIVLIS
LLSWGFFGQRLDLPAIIGMMLICAGVLVINLLSRSTPH Multidrug efflux protein (*Escherichia coli* O83:H1 (strain NRG 857C/AIEC)):
(SEQ ID NO: 107)
MNPYIYLGGAILAEVIGTTLMKFSEGFTRLWPSVGTIICYCASFWLLAQTLAYIPTGIAYAIWSGVGIVLIS
LLSWGFFGQRLDLPAIIGMMLICAGVLVINLLSRSTPH Multidrug transporter EmrE (*Escherichia coli* 1-392-07_S4_C3):
(SEQ ID NO: 108)
MNPYIYLGGAILAEVIGTTLMKFSEGFTRLWPSVGTIICYCASFWLLAQTLAYIPTGIAYAIWSGVGIVLIS
LLSWGFFGQRLDLPAIIGMMLICAGVLVINLLSRSTPH Multidrug transporter EmrE (*Escherichia coli* 1-392-07_S4_C1):
(SEQ ID NO: 109)
MNPYIYLGGAILAEVIGTTLMKFSEGFTRLWPSVGTIICYCASFWLLAQTLAYIPTGIAYAIWSGVGIVLIS
LLSWGFFGQRLDLPAIIGMMLICAGVLVINLLSRSTPH Multidrug transporter EmrE (*Escherichia coli* 1-176-05_S3_C2):
(SEQ ID NO: 110)
MNPYIYLGGAILAEVIGTTLMKFSEGFTRLWPSVGTIICYCASFWLLAQTLAYIPTGIAYAIWSGVGIVLIS
LLSWGFFGQRLDLPAIIGMMLICAGVLVINLLSRSTPH Multidrug transporter (*Escherichia coli* O25b:H4-ST131):
(SEQ ID NO: 111)
MNPYIYLGGAILAEVIGTTLMKFSEGFTRLWPSVGTIICYCASFWLLAQTLAYIPTGIAYAIWSGVGIVLIS
LLSWGFFGQRLDLPAIIGMMLICAGVLVINLLSRSTPH Multidrug transporter EmrE (*Shigella fiexneri* VA-6):
(SEQ ID NO: 112)
MNPYIYLGGAILAEVIGTTLMKFSEGFTRLWPSVGTIICYCASFWLLAQTLAYIPTGIAYAIWSGVGIVLIS
LLSWGFFGQRLDLPAIIGMMLICAGVLVINLLSRSTPH Multidrug transporter EmrE (*Escherichia coli* H736):
(SEQ ID NO: 113)
MNPYIYLGGAILAEVIGTTLMKFSEGFTRLWPSVGTIICYCASFWLLAQTLAYIPTGIAYAIWSGVGIVLIS
LLSWGFFGQRLDLPAIIGMMLICAGVLVINLLSRSTPH Multidrug SMR transporter (*Shigella flexneri* 4c):
(SEQ ID NO: 114)
MNPYIYLGGAILAEVIGTTLMKFSEGFTRLWPSVGTIICYCASFWLLAQTLAYIPTGIAYAIWSGVGIVLIS
LLSWGFFGQRLDLPAIIGMMLICAGVLVINLLSRSTPH Multidrug SMR transporter (*Shigella flexneri*):
(SEQ ID NO: 115)
MNPYIYLGGAILAEVIGTTLMKFSEGFTRLWPSVGTIICYCASFWLLAQTLAYIPTGIAYAIWSGVGIVLIS
LLSWGFFGQRLDLPAIIGMMLICAGVLVINLLSRSTPH -continued Multidrug SMR transporter (*Escherichia coli*):
(SEQ ID NO: 116)
MNPYIYLGGAILAEVIGTTLMKFSEGFTRLWPSVGTIICYCASFWLLAQTLAYIPTGIAYAIWSGVGIVLIS
LLSWGFFGQRLDLPAIIGMMLICAGVLVINLLSRSTPH Multidrug SMR transporter (*Shigella sonnei*):
(SEQ ID NO: 117)
MNPYIYLGGAILAEVIGTTLMKFSEGFTRLWPSVGTIICYCASFWLLAQTLAYIPTGIAYAIWSGVGIVLIS
LLSWGFFGQRLDLPAIIGMMLICAGVLVINLLSRSTPH Multidrug transporter EmrE (*Escherichia coli* H605):
(SEQ ID NO: 118)
MNPYIYLGGAILAEVIGTTLMKFSEGFTRLWPSVGTIICYCASFWLLAQTLAYIPTGIAYAIWSGVGIVLIS
LLSWGFFGQRLDLPAIIGMMLICAGVLVINLLSRSTPH Quaternary ammonium transporter (*Escherichia coli* APEC O18):
(SEQ ID NO: 119)
MNPYIYLGGAILAEVIGTTLMKFSEGFTRLWPSVGTIICYCASFWLLAQTLAYIPTGIAYAIWSGVGIVLIS
LLSWGFFGQRLDLPAIIGMMLICAGVLVINLLSRSTPH Multidrug transporter (*Escherichia coli* N40513):
(SEQ ID NO: 120)
MNPYIYLGGAILAEVIGTTLMKFSEGFTRLWPSVGTIICYCASFWLLAQTLAYIPTGIAYAIWSGVGIVLIS
LLSWGFFGQRLDLPAIIGMMLICAGVLVINLLSRSTPH Multidrug transporter (*Escherichia coli* N40607):
(SEQ ID NO: 121)
MNPYIYLGGAILAEVIGTTLMKFSEGFTRLWPSVGTIICYCASFWLLAQTLAYIPTGIAYAIWSGVGIVLIS
LLSWGFFGQRLDLPAIIGMMLICAGVLVINLLSRSTPH Multidrug resistance protein DLP12 prophage (*Escherichia coli* NCCP15648):
(SEQ ID NO: 122)
MNPYIYLGGAILAEVIGTTLMKFSEGFTRLWPSVGTIICYCASFWLLAQTLAYIPTGIAYAIWSGVGIVLIS
LLSWGFFGQRLDLPAIIGMMLICAGVLVINLLSRSTPH Multidrug transporter (*Escherichia coli* N36254PS):
(SEQ ID NO: 123)
MNPYIYLGGAILAEVIGTTLMKFSEGFTRLWPSVGTIICYCASFWLLAQTLAYIPTGIAYAIWSGVGIVLIS
LLSWGFFGQRLDLPAIIGMMLICAGVLVINLLSRSTPH Multidrug SMR transporter (*Shigella boydii*):
(SEQ ID NO: 124)
MNPYIYLGGAILAEVIGTTLMKFSEGFTRLWPSVGTIICYCASFWLLAQTLAYIPTGIAYAIWSGVGIVLIS
LLSWGFFGQRLDLPAIIGMMLICAGVLVINLLSRSTPH Multidrug SMR transporter (*Shigella fiexneri* 1a):
(SEQ ID NO: 125)
MNPYIYLGGAILAEVIGTTLMKFSEGFTRLWPSVGTIICYCASFWLLAQTLAYIPTGIAYAIWSGVGIVLIS
LLSWGFFGQRLDLPAIIGMMLICAGVLVINLLSRSTPH Multidrug transporter EmrE (*Escherichia coli* MS 84-1):
(SEQ ID NO: 126)
MNRKEYAMNPYIYLGGAILAEVIGTTLMKFSEGFTRLWPSVGTIICYCASFWLLAQTLAYIPTGIAYAIWSG
VGIVLISLLSWGFFGQRLDLPAIIGMMLICAGVLVINLLSRSAPH Multidrug transporter EmrE (*Escherichia coli* MS 124-1):
(SEQ ID NO: 127)
MNRKEYAMNPYIYLGGAILAEVIGTTLMKFSEGFTRLWPSVGTIICYCASFWLLAQTLAYIPTGIAYAIWSG
VGIVLISLLSWGFFGQRLDLPAIIGMMLICAGVLVINLLSRSAPH Multidrug transporter EmrE (*Escherichia coli* 110957):
(SEQ ID NO: 128)
MNRKEYAMNPYIYLGGAILAEVIGTTLMKFSEGFTRLWPSVGTIICYCASFWLLAQTLAYIPTGIAYAIWSG
VGIVLISLLSWGFFGQRLDLPAIIGMMLICAGVLVINLLSRSAPH -continued Multidrug transporter EmrE (*Escherichia coli* MS 85-1):

(SEQ ID NO: 129)
MNRKEYAMNPYIYLGGAILAEVIGTTLMKFSEGFTRLWPSVGTIICYCASFWLLAQTLAYIPTGIAYAIWSG

VGIVLISLLSWGFFGQRLDLPAIIGMMLICAGVLVINLLSRSAPH

Multidrug transporter EmrE (*Escherichia coli* MS 117-3):

(SEQ ID NO: 130)
MNRKEYAMNPYIYLGGAILAEVIGTTLMKFSEGFTRLWPSVGTIICYCASFWLLAQTLAYIPTGIAYAIWSG

VGIVLISLLSWGFFGQRLDLPAIIGMMLICAGVLVINLLSRSAPH

Multidrug transporter EmrE (*Escherichia coli* 909945-2):

(SEQ ID NO: 131)
MNRKEYAMNPYIYLGGAILAEVIGTTLMKFSEGFTRLWPSVGTIICYCASFWLLAQTLAYIPTGIAYAIWSG

VGIVLISLLSWGFFGQRLDLPAIIGMMLICAGVLVINLLSRSAPH

Multidrug transporter EmrE (*Escherichia coli* 113290):

(SEQ ID NO: 132)
MNRKEYAMNPYIYLGGAILAEVIGTTLMKFSEGFTRLWPSVGTIICYCASFWLLAQTLAYIPTGIAYAIWSG

VGIVLISLLSWGFFGQRLDLPAIIGMMLICAGVLVINLLSRSAPH

Multidrug transporter EmrE (*Escherichia coli* MS 115-1):

(SEQ ID NO: 133)
MNRKEYAMNPYIYLGGAILAEVIGTTLMKFSEGFTRLWPSVGTIICYCASFWLLAQTLAYIPTGIAYAIWSG

VGIVLISLLSWGFFGQRLDLPAIIGMMLICAGVLVINLLSRSAPH

Multidrug transporter EmrE (*Escherichia coli* (strain MS 21-1)):

(SEQ ID NO: 134)
MNRKEYAMNPYIYLGGAILAEVIGTTLMKFSEGFTRLWPSVGTIICYCASFWLLAQTLAYIPTGIAYAIWSG

VGIVLISLLSWGFFGQRLDLPAIIGMMLICAGVLVINLLSRSAPH

Multidrug transporter EmrE (*Escherichia* sp. KTE52):

(SEQ ID NO: 135)
MNPYIYLGGAILAEVIGTTLMKFSEGFTRLWPSVGTIICYCASFWLLAQTLAYIPTGIAYAIWSGVGIVLIS

LLSWGLFGQRLDLPAIIGMMLICAGVLVINLLSRSTPH

Uncharacterized protein (*Escherichia fergusonii* ECD227):

(SEQ ID NO: 136)
MNPYIYLGGAILAEVIGTTLMKFSEGFTRLWPSVGTIICYCASFWLLAQTLAYIPTGIAYAIWSGVGIVLIS

LLSWGLFGQRLDLPAIIGMMLICAGVLVINLLSRSTPH

EmrE SMR transporter (*Escherichia coli* O55:H7 (strain CB9615/EPEC)):

(SEQ ID NO: 137)
MNPYIYLGGAILAEVIGTTLMKFSEGFTRLWPSVGTIICYCASFWLLAQTLAYIPTGIAYAIWSGVGIVLIS

LLSWGLFGQRLDLPAIIGMMLICAGVLVINLLSRSTPH

SMR family multidrug resistance protein (*Klebsiella oxytoca*):

(SEQ ID NO: 138)
MNPYIYLGGAILAEVIGTTLMKFSEGFTRLWPSVGTIICYCASFWLLAQTLAYIPTGIAYAIWSGVGIVLIS

LLSWGLFGQRLDLPAIIGMMLICAGVLVINLLSRSTPH

Multidrug transporter (*Escherichia coli* O128:H2 str. 2011C-3317):

(SEQ ID NO: 139)
MNPYIYLGGAILAEVIGTTLMKFSEGFTRLWPSVGTIICYCASFWLLAQTLAYIPTGIAYAIWSGVGIVLIS

LLSWGLFGQRLDLPAIIGMMLICAGVLVINLLSRSTPH

Multidrug efflux protein (*Escherichia coli* O157:H7 str. SS52):

(SEQ ID NO: 140)
MNPYIYLGGAILAEVIGTTLMKFSEGFTRLWPSVGTIICYCASFWLLAQTLAYIPTGIAYAIWSGVGIVLIS

LLSWGLFGQRLDLPAIIGMMLICAGVLVINLLSRSTPH

Multidrug transporter EmrE (*Escherichia coli* 97.0259):

(SEQ ID NO: 141)
MNPYIYLGGAILAEVIGTTLMKFSEGFTRLWPSVGTIICYCASFWLLAQTLAYIPTGIAYAIWSGVGIVLIS

LLSWGLFGQRLDLPAIIGMMLICAGVLVINLLSRSTPH

-continued

Multidrug transporter EmrE (*Escherichia coli* 9.0111):
(SEQ ID NO: 142)
MNPYIYLGGAILAEVIGTTLMKFSEGFTRLWPSVGTIICYCASFWLLAQTLAYIPTGIAYAIWSGVGIVLIS

LLSWGLFGQRLDLPAIIGMMLICAGVLVINLLSRSTPH

Multidrug SMR transporter (*Escherichia coli*):
(SEQ ID NO: 143)
MNPYIYLGGAILAEVIGTTLMKFSEGFTRLWPSVGTIICYCASFWLLAQTLAYIPTGIAYAIWSGVGIVLIS

LLSWGLFGQRLDLPAIIGMMLICAGVLVINLLSRSTPH

Multidrug transporter (*Escherichia coli* N37139PS):
(SEQ ID NO: 144)
MNPYIYLGGAILAEVIGTTLMKFSEGFTRLWPSVGTIICYCASFWLLAQTLAYIPTGIAYAIWSGVGIVLIS

LLSWGLFGQRLDLPAIIGMMLICAGVLVINLLSRSTPH

Multidrug transporter (*Escherichia coli* N36410PS):
(SEQ ID NO: 145)
MNPYIYLGGAILAEVIGTTLMKFSEGFTRLWPSVGTIICYCASFWLLAQTLAYIPTGIAYAIWSGVGIVLIS

LLSWGLFGQRLDLPAIIGMMLICAGVLVINLLSRSTPH

Multidrug transporter (*Escherichia coli* N37122PS):
(SEQ ID NO: 146)
MNPYIYLGGAILAEVIGTTLMKFSEGFTRLWPSVGTIICYCASFWLLAQTLAYIPTGIAYAIWSGVGIVLIS

LLSWGLFGQRLDLPAIIGMMLICAGVLVINLLSRSTPH

Multidrug transporter EmrE (*Escherichia* sp. KTE31):
(SEQ ID NO: 147)
MNPYIYLGGAILAEVIGTTLMKFSEGFTRLWPSVGTIICYCASFWLLAQTLAYIPTGIAYAIWSGVGIVLIS

LLSWGLFGQRLDLPAIIGMMLICAGVLVINLLSRSTPH

Multidrug SMR transporter (*Escherichia coli*):
(SEQ ID NO: 148)
MNPYIYLGGAILAEVIGTTLMKFSEGFTRLWPSVGTIICYCASFWLLAQTLAYIPTGIAYAIWSGVGIVLIS

LLSWGLFGQRLDLPAIIGMMLICAGVLVINLLSRSTPH

Multidrug transporter EmrE (*Escherichia coli* KTE33):
(SEQ ID NO: 149)
MNPYIYLGGAILAEVIGTTLMKFSEGFTRLWPSVGTIICYCASFWLLAQTLAYIPTGIAYAIWSGVGIVLIS

LLSWGLFGQRLDLPAIIGMMLICAGVLVINLLSRSTPH

Multidrug transporter EmrE (*Shigella flexneri* 2850-71):
(SEQ ID NO: 150)
MNPYIYLGGAILAEVIGTTLMKFSEGFTRLWPSVGTIICYCASFWLLAQTLAYIPTGIAYAIWSGVGIVLIS

LLSWGLFGQRLDLPAIIGMMLICAGVLVINLLSRSTPH

Multidrug transporter EmrE (*Escherichia* sp. KTE11):
(SEQ ID NO: 151)
MNPYIYLGGAILAEVIGTTLMKFSEGFTRLWPSVGTIICYCASFWLLAQTLAYIPTGIAYAIWSGVGIVLIS

LLSWGLFGQRLDLPAIIGMMLICAGVLVINLLSRSTPH

Multidrug transporter EmrE (*Escherichia* sp. KTE52):
(SEQ ID NO: 152)
MNPYIYLGGAILAEVIGTTLMKFSEGFTRLWPSVGTIICYCASFWLLAQTLAYIPTGIAYAIWSGVGIVLIS

LLSWGLFGQRLDLPAIIGMMLICAGVLVINLLSRSTPH

Multidrug transporter EmrE (*Escherichia* sp. KTE96):
(SEQ ID NO: 153)
MNPYIYLGGAILAEVIGTTLMKFSEGFTRLWPSVGTIICYCASFWLLAQTLAYIPTGIAYAIWSGVGIVLIS

LLSWGLFGQRLDLPAIIGMMLICAGVLVINLLSRSTPH

Multidrug transporter EmrE (*Escherichia* sp. KTE159):
(SEQ ID NO: 154)
MNPYIYLGGAILAEVIGTTLMKFSEGFTRLWPSVGTIICYCASFWLLAQTLAYIPTGIAYAIWSGVGIVLIS

LLSWGLFGQRLDLPAIIGMMLICAGVLVINLLSRSTPH

-continued

QacE family quaternary ammonium compound efflux SMR transporter
(*Escherichia coli*):
(SEQ ID NO: 155)
MNPYIYLGGAILAEVIGTTLMKFSEGFTRLWPSVGTIICYCASFWLLAQTLAYIPTGIAYAIWSGVGIVLIS

LLSWGLFGQRLDLPAIIGMMLICAGVLVINLLSRSTPH

Multidrug SMR transporter (*Escherichia coli*):
(SEQ ID NO: 156)
MNPYIYLGGAILAEVIGTTLMKFSEGFTRLWPSVGTIICYCASFWLLAQTLAYIPTGIAYAIWSGVGIVLIS

LLSWGLFGQRLDLPAIIGMMLICAGVLVINLLSRSTPH

Multidrug SMR transporter (*Shigella sonnei*):
(SEQ ID NO: 157)
MNPYIYLGGAILAEVIGTTLMKFSEGFTRLWPSVGTIICYCASFWLLAQTLAYIPTGIAYAIWSGVGIVLIS

LLSWGLFGQRLDLPAIIGMMLICAGVLVINLLSRSTPH

Multidrug SMR transporter (*Shigella sonnei*):
(SEQ ID NO: 158)
MNPYIYLGGAILAEVIGTTLMKFSEGFTRLWPSVGTIICYCASFWLLAQTLAYIPTGIAYAIWSGVGIVLIS

LLSWGLFGQRLDLPAIIGMMLICAGVLVINLLSRSTPH

Multidrug transporter EmrE (*Escherichia coli* E1118):
(SEQ ID NO: 159)
MNPYIYLGGAILAEVIGTTLMKFSEGFTRLWPSVGTIICYCASFWLLAQTLAYIPTGIAYAIWSGVGIVLIS

LLSWGLFGQRLDLPAIIGMMLICAGVLVINLLSRSTPH

Multidrug transporter EmrE (*Escherichia coli* KTE108):
(SEQ ID NO: 160)
MNPYIYLGGAILAEVIGTTLMKESEGFTRLWPSVGTIICYCASFWLLAQTLAYIPTGIAYAIWSGVGIVLIS

LLSWGFFVQRLDLPAVIGMMLICAGVLVINLLSRSTPH

Multidrug transporter (*Shigella* sp. RAMC 28760):
(SEQ ID NO: 161)
MNPYIYLGGAILAEVIGTTLMKFSEGFTRLWPSVGTIICYCASFWLLAQTLAYIPTGIAYGIWSGVGIVLIS

LLLWGFFGQRLDLPAIIGMMLICAGVLVINLLSRSTPH

Multidrug SMR transporter (*Escherichia coli* BL21-DE3)
(SEQ ID NO: 162)
MNPYIYLGGAILAEVIGTTLMKFSEGFTRLWPSVGTIICYCASFWLLAWLAYIPTGIAYGIWSGVGIVLIS

LLLWGFFGQRLDLPAIIGMMLICAGVLVINLLSRSTPH

Multidrug transporter (*Escherichia coli* SE11)
(SEQ ID NO: 163)
MNSFVSLGFLLIIIVPAFISCHARAPWIHIHQDENGELCSNCSTILSSMNRKEYAMNPYIYLGGAILAEVIG

TTLMKFSEGFTRLWPSVGTIICYCASFWLLAQTLAYIPTGIAYAIWSGVGIVLISLLSWGFFGQRLDLPAII

GMMLICAGVLVINLLSRSAPH

Methylviologen transporter EmrE (*Shigella flexneri* strain 8401)
(SEQ ID NO: 164)
MNSFVSLGFLLIIIVPAFISCHARAPWIHIHQDENGELCSNCSTILSSMNRKEYAMNPYIYLGGAILAEVIG

TTLMKFSEGFTRLWPSVGTIICYCASFWLLAQTLAYIPTGIAYAIWSGVGIVLISLLSWGFFGQRLDLPAII

GMMLICAGVLVINLLSRSAPH

Multidrug transporter EmrE (*Escherichia coli* O1:K1)
(SEQ ID NO: 165)
MNSFVSLGFLLIIIVPAFISCHARAPWIHIHQDENGELCSNCSTILSSMNRKEYAMNPYIYLGGAILAEVIG

TTLMKFSEGFTRLWPSVGTIICYCASFWLLAQTLAYIPTGIAYAIWSGVGIVLISLLSWGFFGQRLDLPAII

GMMLICAGVLVINLLSRSAPH

Multidrug transporter EmrE (*Shigella flexneri* strain 2002017)
(SEQ ID NO: 166)
MNSFVSLGFLLIIIVPAFISCHARAPWIHIHQDENGELCSNCSTILSSMNRKEYAMNPYIYLGGAILAEVIG

TTLMKFSEGFTRLWPSVGTIICYCASFWLLAQTLAYIPTGIAYAIWSGVGIVLISLLSWGFFGQRLDLPAII

GMMLICAGVLVINLLSRSAPH

-continued

Multidrug transporter EmrE (*Shigella sonnei*)
(SEQ ID NO: 167)
MNSFVSLGFLLIIIVPAFISCHARAPWIHIHQDENGELCSNCSTILSSMNRKEYAMNPYIYLGGAILAEVIG

TTLMKFSEGFTRLWPSVGTIICYCASFWLLAQTLAYIPTGIAYAIWSGVGIVLISLLSWGFFGQRLDLPAII

GMMLICAGVLVINLLSRSAPH

Multidrug transporter EmrE (*Escherichia coli* O45:K1)
(SEQ ID NO: 168)
MLPGRVNSFVSLGFLLIIIVPAFISCHARAPWIHIHQDENGELCSNCSTILSSMNRKEYAMNPYIYLGGAIL

AEVIGTTLMKFSEGFTRLWPSVGTIICYCASFWLLAQTLAYIPTGIAYAIWSGVGIVLISLLSWGFFGQRLD

LPAIIGMMLICAGVLVINLLSRSAPH

Multidrug transporter EmrE (*Escherichia coli* strain 55989)
(SEQ ID NO: 169)
MLPGRVNSFVSLGFLLIIIVPAFISCHARAPWIHIHQDENGELCSNCSTILSSMNRKEYAMNPYIYLGGAIL

AEVIGTTLMKFSEGFTRLWPSVGTIICYCASFWLLAQTLAYIPTGIAYAIWSGVGIVLISLLSWGFFGQRLD

LPAIIGMMLICAGVLVINLLSRSAPH

Multidrug transporter EmrE (*Escherichia coli* O8 strain ED1a)
(SEQ ID NO: 170)
MLPGRVNSFVSLGFLLIIIVPAFISCHARAPWIHIHQDENGELCSNCSTILSSMNRKEYAMNPYIYLGGAIL

AEVIGTTLMKFSEGFTRLWPSVGTIICYCASFWLLAQTLAYIPTGIAYAIWSGVGIVLISLLSWGFFGQRLD

LPAIIGMMLICAGVLVINLLSRSAPH

Multidrug transporter EmrE (*Escherichia coli* strain UT189/UPEC)
(SEQ ID NO: 171)
MLPGRVNSFVSLGFLLIIIVPAFISCHARAPWIHIHQDENGELCSNCSTILSSMNRKEYAMNPYIYLGGAIL

AEVIGTTLMKFSEGFTRLWPSVGTIICYCASFWLLAQTLAYIPTGIAYAIWSGVGIVLISLLSWGFFGQRLD

LPAIIGMMLICAGVLVINLLSRSAPH

Multidrug transporter EmrE (*Escheriehia coli* O6:H1 strain CFT073)
(SEQ ID NO: 172)
MLPGRVNSFVSLGFLLIIIVPAFISCHARAPWIHIHQDENGELCSNCSTILSSMNRKEYAMNPYIYLGGAIL

AEVIGTTLMKFSEGFTRLWPSVGTIICYCASFWLLAQTLAYIPTGIAYAIWSGVGIVLISLLSWGFFGQRLD

LPAIIGMMLICAGVLVINLLSRSAPH

Multidrug transporter EmrE (*Escherichia coli* O25b:H4)
(SEQ ID NO: 173)
MLPGRVNSFVSLGFLLIIIVPAFISCHARAPWIHIHQDENGELCSNCSTILSSMNRKEYAMNPYIYLGGAIL

AEVIGTTLMKFSEGFTRLWPSVGTIICYCASFWLLAQTLAYIPTGIAYAIWSGVGIVLISLLSWGFFGQRLD

LPAIIGMMLICAGVLVINLLSRSAPH

Multidrug transporter EmrE (*Escherichia coli* O25b:H4-ST131)
(SEQ ID NO: 174)
MLPGRVNSFVSLGFLLIIIVPAFISCHARAPWIHIHQDENGELCSNCSTILSSMNRKEYAMNPYIYLGGAIL

AEVIGTTLMKFSEGFTRLWPSVGTIICYCASFWLLAQTLAYIPTGIAYAIWSGVGIVLISLLSWGFFGQRLD

LPAIIGMMLICAGVLVINLLSRSAPH

Multidrug transporter EmrE (*Escherichia coli* TW10598)
(SEQ ID NO: 175)
MLPGRVNSFVSLGFLLIIIVPAFISCHARAPWIHIHQDENGELCSNCSTILSSMNRKEYAMNPYIYLGGAIL

AEVIGTTLMKFSEGFTRLWPSVGTIICYCASFWLLAQTLAYIPTGIAYAIWSGVGIVLISLLSWGFFGQRLD

LPAIIGMMLICAGVLVINLLSRSAPH

Multidrug transporter EmrE (*Escherichia coli* 1.2741)
(SEQ ID NO: 176)
MNPYIYLGGAILAEVIGTTLMKFSEGFTRLWPSVGTIICYCASFWLLAQTLAYIPTGIAYAIWSGVGIVLIS

LLSWGFFSQRLDLPAIIGMMLICAGVLVINLLSRSAPH

-continued

Multidrug SMR transporter (*Escherichia coli* M863)
(SEQ ID NO: 177)
MNPYIYLGGAILAEVIGTTLMKFSEGFTRLWPSVGTIICYCASFWLLAQTLAYIPTGIAYAIWSGVGIVLIS

LLSWGFFSQRLDLPAIIGMMLICAGVLVINLLSRSAPH

Multidrug SMR transporter (*Escherichia coli*)
(SEQ ID NO: 178)
MNPYIYLGGAILAEVIGTTLMKFSEGFTRLWPSVGTIICYCASFWLLAQTLAYIPTGIAYAIWSGVGIVLIS

LLSWGFFSQRLDLPAIIGMMLICAGVLVINLLSRSAPH

Multidrug SMR transporter (*Shigella sonnei*)
(SEQ ID NO: 179)
MNPYIYLGGAILAEVIGTTLMKFSEGFTRLWPSVGTIICYCASFWLLAQTLAYIPTGIAYAIWSGVGIVLIS

LLSWGFFSQRLDLPAIIGMMLICAGVLVINLLSRSAPH

Multidrug SMR transporter (*Escherichia coli*)
(SEQ ID NO: 180)
MNPYIYLGGAILAEVIGTTLMKFSEGFTRLWPSVGTIICYCASFWLLAQTLAYIPTGIAYAIWSGVGIVLIS

LLSWGFFSQRLDLPAIIGMMLICAGVLVINLLSRSAPH

Multidrug transporter EmrE (*Escherichia coli* DORA_B_14)
(SEQ ID NO: 181)
MNPYIYLGGAILAEVIGTTLMKFSEGFTRLWPSVGTIICYCASFWLLAQTLAYIPTGIAYAIWSGVGIVLIS

LLSWGFFSQRLDLPAIIGMMLICAGVLVINLLSRSAPH

Multidrug transporter EmrE (*Escherichia coli*)
(SEQ ID NO: 182)
MNPYIYLGGAILAEVIGTTLMKFSEGFTRLWPSVGTIICYCASFWLLAQTLAYIPTGIAYAIWSGVGIVLIS

LLSWGFFSQRLDLPAIIGMMLICAGVLVINLLSRSAPH

Multidrug transporter EmrE (*Escherichia coli* 908573)
(SEQ ID NO: 183)
MNPYIYLGGAILAEVIGTTLMKFSEGFTRLWPSVGTIICYCASFWLLAQTLAYIPTGIAYAIWSGVGIVLIS

LLSWGFFSQRLDLPAIIGMMLICAGVLVINLLSRSAPH

Multidrug SMR transporter (*Shigella* sp. FC2928)
(SEQ ID NO: 184)
MNPYIYLGGAILAEVIGTTLMKFSEGFTRLWPSVGTIICYCASFWLLAQTLAYIPTGIAYAIWSGVGIVLIS

LLSWGFFSQRLDLPAIIGMMLICAGVLVINLLSRSAPH

Multidrug transporter EmrE (*Escherichia coli* HVH 41)
(SEQ ID NO: 185)
MNPYIYLGGAILAEVIGTTLMKFSEGFTRLWPSVGTIICYCASFWLLAQTLAYIPTGIAYAIWSGVGIVLIS

LLSWGFFSQRLDLPAIIGMMLICAGVLVINLLSRSAPH

QacE quaternary ammonium compound efflux SMR transporter
(*Escherichia coli*)
(SEQ ID NO: 186)
MNPYIYLGGAILAEVIGTTLMKFSEGFTRLWPSVGTIICYCASFWLLAQTLAYIPTGIAYAIWSGVGIVLIS

LLSWGFFSQRLDLPAIIGMMLICAGVLVINLLSRSAPH

Multidrug SMR transporter (*Shigella boydii*)
(SEQ ID NO: 187)
MNPYIYLGGAILAEVIGTTLMKFSEGFTRLWPSVGTIICYCASFWLLAQTLAYIPTGIAYAIWSGVGIVLIS

LLSWGFFSQRLDLPAIIGMMLICAGVLVINLLSRSAPH

Multidrug SMR transporter (*Shigella dysenteriae*)
(SEQ ID NO: 188)
MNPYIYLGGAILAEVIGTTLMKFSEGFTRLWPSVGTIICYCASFWLLAQTLAYIPTGIAYAIWSGVGIVLIS

LLSWGFFSQRLDLPAIIGMMLICAGVLVINLLSRSAPH

Multidrug transporter EmrE (*Shigella dysenteriae*)
(SEQ ID NO: 189)
MNPYIYLGGAILAEVIGTTLMKFSEGFTRLWPSVGTIICYCASFWLLAQTLAYIPTGIAYAIWSGVGIVLIS

LLSWGFFSQRLDLPAIIGMMLICAGVLVINLLSRSAPH

```
Multidrug transporter EmrE (Escherichia sp. KTE11)
                                                             (SEQ ID NO: 190)
MNPYIYLGGAILAEVIGTTLMKFSEGFTRLWPSVGTIICYCASFWLLAQTLAYIPTGIAYAIWSGVGIVLIS

LLSWGFFSQRLDLPAIIGMMLICAGVLVINLLSRSAPH

Multidrug transporter EmrE (Escherichia aibertii B156)
                                                             (SEQ ID NO: 191)
MNPYIYLGGAILAEVIGTTLMKFSEGFTRLWPSVGTIICYCASFWLLAQTLAYIPTGIAYAIWSGVGIVLIS

LLSWGFFSQRLDLPAIIGMMLICAGVLVINLLSRSATH

Multidrug transporter EmrE (Escherichia sp. KTE96)
                                                             (SEQ ID NO: 192)
MNPYIYLGGAILAEVIGTTLMKFSEGFTRLWPSVGTIICYCASFWLLAQTLAYIPTGIAYAIWSGVGIVLIS

LLSWGFFSQRLDLPAIIGMMLICAGVLVINLLSRSAPH

Multidrug transporter EmrE (Escherichia sp, KTE159)
                                                             (SEQ ID NO: 193)
MNPYIYLGGAILAEVIGTTLMKFSEGFTRLWPSVGTIICYCASFWLLAQTLAYIPTGIAYAIWSGVGIVLIS

LLSWGFFSQRLDLPAIIGMMLICAGVLVINLLSRSAPH

Multidrug SMR transporter (Escherichia coli)
                                                             (SEQ ID NO: 194)
MNPYIYLGGAILAEVIGTTLMKFSEGFTRLWPSVGTIICYCASFWLLAQTLAYIPTGIAYAIWSGVGIVLIS

LLSWGFFSQRLDLPAIIGMMLICAGVLVINLLSRSAPH

Multidrug transporter EmrE (Escherichia coli)
                                                             (SEQ ID NO: 195)
MNPYIYLGGAILAEVIGTTLMKFSEGFTRLWPSVGTIICYCASFWLLAQTLAYIPTGIAYAIWSGVGIVLIS

LLSWGFFSQRLDLPAIIGMMLICAGVLVINLLSRSATH

Multidrug transporter EmrE (Escherichia albertii)
                                                             (SEQ ID NO: 196)
MNPYIYLGGAILAEVIGTTLMKFSEGFTRLWPSVGTIICYCASFWLLAQTLAYIPTGIAYAIWSGVGIVLIS

LLSWGFFSQRLDLPAIIGMMLICAGVLVINLLSRSATH

Multidrug transporter EmrE (Escherichia coli E1118)
                                                             (SEQ ID NO: 197)
MNPYIYLGGAILAEVIGTTLMKFSEGFTRLWPSVGTIICYCASFWLLAQTLAYIPTGIAYAIWSGVGIVLIS

LLSWGFFSQRLDLPAIIGMMLICAGVLVINLLSRSAPH

Ethidium bromide-methyl vioiogen transporter EmrE (Escherichia aibertii
KF1)
                                                             (SEQ ID NO: 198)
MNPYIYLGGAILAEVIGTTLMKFSEGFTRLWPSVGTIICYCASFWLLAQTLAYIPTGIAYAIWSGVGIVLIS

LLSWGFFSQRLDLPAIIGMMLICAGVLVINLLSRSATH

Multidrug transporter EmrE (Escherichia albertii)
                                                             (SEQ ID NO: 199)
MNPYIYLGGAILAEVIGTTLMKFSEGFTRLWPSVGTIICYCASFWLLAQTLAYIPTGIAYAIWSGVGIVLIS

LLSWGFFSQRLDLPAIIGMMLICAGVLVINLLSRSATH

Multidrug transporter EmrE (Escherichia sp. KTE52)
                                                             (SEQ ID NO: 200)
MNPYIYLGGAILAEVIGTTLMKFSEGFTRLWPSVGTIICYCASFWLLAQTLAYIPTGIAYAIWSGVGIVLIS

LLSWGFFSQRLDLPAIIGMMLICAGVLVINLLSRSAPH

Multidrug transporter EmrE (Escherichia aibertii strain TW07627)
                                                             (SEQ ID NO: 201)
MNPYIYLGGAILAEVIGTTLMKFSEGFTRLWPSVGTIICYCASFWLLAQTLAYIPTGIANAIWSGVGIVLIS

LLSWGIFGQRLDLPAIIGMMLICAGVLVINLLSRSATH

Multidrug transporter EmrE (Shigella sonnei)
                                                             (SEQ ID NO: 202)
MNPYIYLGGAILAEVIGTTLMKFSEGFTRLWPSVGTIICYCASFWLLAQTLAYIPTGIAYAIWSGVGIVLIS

LLSWGFFGQRLDLPAIIGMMLICAGVLVNLGDAANLLI
```

-continued

Multidrug transporter EmrE (*Shigella flexneri* 5a strain M90T)

(SEQ ID NO: 203)
MNSFVSLGFLLIIIVPAFISCHARAPWIHIHQDENGELCSNCSTILSSMNRKEYAMNPYIYLGGAILAEVIG

TTLMKFSEGFTRLWPSVGTIICYCASFWLLAQTLAYIPTGIAYAIWSGVGIVLISLLSWGFFGQRLDLPAII

GMMLICAYYG

Multidrug transporter EmrE (*Citrobacter* sp. MGH106)

(SEQ ID NO: 204)
MNTYIYLGAAILAEVTGTTLMKFTDGFTRLWPSVGTIVCYCASFWLLSQTLAHIPTGIAYAIWSGVGIVLIS

LLAWVIHGQRLDLPAIIGMALICAGVLIINLLSRSAVH

Multidrug SMR transporter (*Escherichia coli*)

(SEQ ID NO: 205)
MNPYIYLGGAILAEVIGTTLMKFSEGFTRLWPSAGTIICYCASFWLLAQTLAYIPTGIAYAIWSGVGIVLIS

LLSWGFFGQRLDLPAIIDTVMACKFFPGPVSR

Multidrug SMR transporter (*Paenibacillus* sp. VT-16-81)

(SEQ ID NO: 206)
MNPYIYLGGAILAEVIGTTLMKFSEGFTRLWPSVGTIICYCASFWLLAQTLAYIPTGIAYAIWSGVGIVLIS

LLSWGFFGQR

Ethidium bromide-methyl vioiogen EmrE transporter (*Kiebsiella pneumoniae*)

(SEQ ID NO: 207)
MNPYIYLGGAILAEVIGTTLMKFSEGFTRLWPSVGTIICYCASFWLLAQTLAYIPTGIAYGIWSGVGIVLIS

LLSWGFFLPTAGPASHYRHDVDLCRCVGY

Multidrug SMR transporter (*Shigella sonnei*)

(SEQ ID NO: 208)
MNPYIYLGGAILAEVIGTTLMKFSEGFTRLWPSVGTIICYCASFWELAQTLAYIPTGIAYAIWSGVRYCPD

Multidrug transporter EmrE (*Escheriehia coli*)

(SEQ ID NO: 209)
MNPYIYLGGAILAEVIGTTLMKFSEGFTRLWPSVGTIICYCASFWLLAQTLAYIPTGIAYAIWYMRTFISCK

R

Further exemplary polypeptides which include an α-helix include polypeptides which include a sequence at least 80% identical to PAIIGMMLICAG (SEQ ID NO: 210):

Multidrug transporter EmrE (*Escherichia coli* O104:H4 strain 2011C-3493)

(SEQ ID NO: 211)
MNRKEYAMNPYIYLGGAILAEVIGTTLMKFSEGFTRLWPSVGTIICYCASFWLLAQTLAYIPTGIAYAIWYM

RTFISCKR

Membrane transporters of cations (*Fundulus heteroclitus*)

(SEQ ID NO: 212)
MNPYIYLGGAILAEVIGTTLMKFSEGFTRLWPSVGTIICYCASFWLLAQTLAYIPTGIAYAIWSGVGIVLIS

LLSWGFFGQRLDLPAIIGMMLICAGVLIINLLSRSTPH

Multidrug transporter EmrE (*Escherichia coli* 2.3916)

(SEQ ID NO: 213)
MNPYIYLGGAILAEVIGTTLMKFSEGFTRLWPSVGTIICYCASFWLLAQTLAYIPTGIAYAIWSGVGIVLIS

LLSWGFFGQRLDLPAIIGMMLICAGVLIINLLSRSTPH

Multidrug transporter EmrE (*Escherichia coli* UMNF18)

(SEQ ID NO: 214)
MNPYIYLGGAILAEVIGTTLMKFSEGFTRLWPSVGTIICYCASFWLLAQTLAYIPTGIAYAIWSGVGIVLIS

LLSWGFFGQRLDLPAIIGMMLICAGVLIINLLSRSTPH

-continued

QacE family quaternary ammonium compound efflux SMR transporter
(*Escherichia coli*)
(SEQ ID NO: 215)
MNPYIYLGGAILAEVIGTTLMKFSEGFTRLWPSVGTIICYCASFWLLAQTLAYIPTGIAYAIWSGVGIVLIS

LLSWGFFGQRLDLPAIIGMMLICAGVLIINLLSRSTPH

Multidrug transporter EmrE (*Escherichia coli* strain K12)
(SEQ ID NO: 216)
MNPYIYLGGAILAEVIGTTLMKFSEGFTRLWPSVGTIICYCASFWLLAQTLAYIPTGIAYAIWSGVGIVLIS

LLSWGFFGQRLDLPAIIGMMLICAGVLIINLLSRSTPH

Multidrug SMR transporter (*Shigella sonnei*)
(SEQ ID NO: 217)
MLSGQSGIVLISLLSWGFFGQRLDLPAIIGMMLICAGVLVINLLSRSTPH Multidrug transporter EmrE (*Escherichia coli* strain UMEA 3162-1)
(SEQ ID NO: 218)
MNPYIYLGGAILAEVIGTTLMKFSEGFTRLWPSVGTIICYCASFWLLAQTLAYIPTGIAYAIWSGVGIVLIS

LLSWGFFGQRLDLPAIIGMMLICAGVLIINLLSRSAPH

Multidrug transporter EmrE (*Escherichia* sp. KTE11)
(SEQ ID NO: 219)
MNPYIYLGGAILAEVIGTTLMKFSEGFTRLWPSVGTIICYCASFWLLAQTLAYIPTGIAYAIWSGVGIVLIS

LLSWGFFGQRLDLPAIIGMMLICAGVLVINLLSRSAPH

Multidrug transporter EmrE (*Escherichia* sp. KTE52)
(SEQ ID NO: 220)
MNPYIYLGGAILAEVIGTTLMKFSEGFTRLWPSVGTIICYCASFWLLAQTLAYIPTGIAYAIWSGVGIVLIS

LLSWGFFGQRLDLPAIIGMMLICAGVLVINLLSRSAPH

Multidrug transporter EmrE (*Escherichia* sp. KTE52)
(SEQ ID NO: 221)
MNPYIYLGGAILAEVIGTTLMKFSEGFTRLWPSVGTIICYCASFWLLAQTLAYIPTGIAYAIWSGVGIVLIS

LLSWGFFGQRLDLPAIIGMMLICAGVLVINLLSRSTPH

MuLtidrug SMR transporter (*Escherichia coli* strain SE11)
(SEQ ID NO: 222)
MNPYIYLGGAILAEVIGTTLMKFSEGFTRLWPSVGTIICYCASFWLLAQTLAYIPTGIAYAIWSGVGIVLIS

LLSWGFFGQRLDLPAIIGMMLICAGVLVINLLSRSTPH

Multidrug transporter EmrE (*Escherichia coli* 2-005-03_S4_C3)
(SEQ ID NO: 223)
MNPYIYLGGAILAEVIGTTLMKFSEGFTRLWPSVGTIICYCASFWLLAQTLAYIPTGIAYAIWSGVGIVLIS

LLSWGFFGQRLDLPAIIGMMLICAGVLVINLLSRSAPH

Multidrug transporter EmrE (*Escherichia coli* H420)
(SEQ ID NO: 224)
MNPYIYLGGAILAEVIGTTLMKFSEGFTRLWPSVGTIICYCASFWLLAQTLAYIPTGIAYAIWSGVGIVLIS

LLSWGFFGQRLDLPAIIGMMLICAGVLVINLLSRSAPH

Multidrug transporter EmrE (*Escherichia coli* DEC6A)
(SEQ ID NO: 225)
MNPYIYLGGAILAEVIGTTLMKFSEGFTRLWPSVGTIICYCASFWLLAQTLAYIPTGIAYAIWSGVGIVLIS

LLSWGFFGQRLDLPAIIGMMLICAGVLVINLLSRSAPH

Multidrug transporter EmrE (*Escherichia coli* 97.0246)
(SEQ ID NO: 226)
MNPYIYLGGAILAEVIGTTLMKFSEGFTRLWPSVGTIICYCASFWLLAQTLAYIPTGIAYAIWSGVGIVLIS

LLSWGFFGQRLDLPAIIGMMLICAGVLVINLLSRSAPH

Multidrug transporter EmrE (*Escherichia coli* O104:H4 strain 2011C-3493)
(SEQ ID NO: 227)
MNPYIYLGGAILAEVIGTTLMKFSEGFTRLWPSVGTIICYCASFWLLAQTLAYIPTGIAYAIWSGVGIVLIS

LLSWGFFGQRLDLPAIIGMMLICAGVLVINLLSRSAPH

-continued

Multidrug transporter EmrE (*Escherichia coli* H591)
(SEQ ID NO: 228)
MNPYIYLGGAILAEVIGTTLMKFSEGFTRLWPSVGTIICYCASFWLLAQTLAYIPTGIAYAIWSGVGIVLIS

LLSWGFFGQRLDLPAIIGMMLICAGVLVINLLSRSTPH

Multidrug SMR transporter (*Escheriehia fergusonii* ECD227)
(SEQ ID NO: 229)
MNPYIYLGGAILAEVIGTTLMKFSEGFTRLWPSVGTIICYCASFWLLAQTLAYIPTGIAYAIWSGVGIVLIS

LLSWGFFGQRLDLPAIIGMMLICAGVLVINLLSRSTPH

Multidrug transporter EmrE (*Escherichia coli* O111:H8 str. CVM9634)
(SEQ ID NO: 230)
MNPYIYLGGAILAEVIGTTLMKFSEGFTRLWPSVGTIICYCASFWLLAQTLAYIPTGIAYAIWSGVGIVLIS

LLSWGFFGQRLDLPAIIGMMLICAGVLVINLLSRSAPH

Multidrug transporter EmrE (*Escherichia coli* O55:H7 strain CB9615/EPEC)
(SEQ ID NO: 231)
MNPYIYLGGAILAEVIGTTLMKFSEGFTRLWPSVGTIICYCASFWLLAQTLAYIPTGIAYAIWSGVGIVLIS

LLSWGFFGQRLDLPAIIGMMLICAGVLVINLLSRSTPH

Multidrug transporter EmrE (*Escherichia coli* KTE73)
(SEQ ID NO: 232)
MNPYIYLGGAILAEVIGTTLMKFSEGFTRLWPSVGTIICYCASFWLLAQTLAYIPTGIAYAIWSGVGIVLIS

LLSWGFFGQRLDLPAIIGMMLICAGVLVINLLSRSAPH

Multidrug transporter EmrE (*Escheriehia coli* KTE75)
(SEQ ID NO: 233)
MNPYIYLGGAILAEVIGTTLMKFSEGFTRLWPSVGTIICYCASFWLLAQTLAYIPTGIAYAIWSGVGIVLIS

LLSWGFFGQRLDLPAIIGMMLICAGVLVINLLSRSTPH

Multidrug transporter EmrE (*Escherichia coli* HVH 70 4-2963531)
(SEQ ID NO: 234)
MNPYIYLGGAILAEVIGTTLMKFSEGFTRLWPSVGTIICYCASFWLLAQTLAYIPTGIAYAIWSGVGIVLIS

LLSWGFFGQRLDLPAIIGMMLICAGVLVINLLSRSAPH

Multidrug transporter EmrE (*Klebsiella oxytoca*)
(SEQ ID NO: 235)
MNPYIYLGGAILAEVIGTTLMKFSEGFTRLWPSVGTIICYCASFWLLAQTLAYIPTGIAYAIWSGVGIVLIS

LLSWGFFGQRLDLPAIIGMMLICAGVLVINLLSRSTPH

Multidrug transporter EmrE (Escherichia coli HVH 70 4-2963531)
(SEQ ID NO: 236)
MNPYIYLGGAILAEVIGTTLMKFSEGFTRLWPSVGTIICYCASFWLLAQTLAYIPTGIAYAIWSGVGIVLIS

LLSWGFFGQRLDLPAIIGMMLICAGVLVINLLSRSTPH

Multidrug transporter EmrE (*Escherichia coli* 1.2741)
(SEQ ID NO: 237)
MNPYIYLGGAILAEVIGTTLMKFSEGFTRLWPSVGTIICYCASFWLLAQTLAYIPTGIAYAIWSGVGIVLIS

LLSWGFFGQRLDLPAIIGMMLICAGVLVINLLSRSAPH

Multidrug transporter EmrE (*Escherichia coli* UMNK88)
(SEQ ID NO: 238)
MNPYIYLGGAILAEVIGTTLMKFSEGFTRLWPSVGTIICYCASFWLLAQTLAYIPTGIAYAIWSGVGIVLIS

LLSWGFFGQRLDLPAIIGMMLICAGVLVINLLSRSAPH

Multidrug SMR transporter (*Escherichia fergusonii*)
(SEQ ID NO: 239)
MNPYIYLGGAILAEVIGTTLMKFSEGFTRLWPSVGTIICYCASFWLLAQTLAYIPTGIAYAIWSGVGIVLIS

LLSWGFFGQRLDLPAIIGMMLICAGVLVINLLSRSAPH

Multidrug transporter EmrE (*Escherichia coli* B088)
(SEQ ID NO: 240)
MNPYIYLGGAILAEVIGTTLMKFSEGFTRLWPSVGTIICYCASFWLLAQTLAYIPTGIAYAIWSGVGIVLIS

LLSWGFFGQRLDLPAIIGMMLICAGVLVINLLSRSTPH

-continued

Multidrug transporter EmrE (*Escherichia coli* B088)
(SEQ ID NO: 241)
MNPYIYLGGAILAEVIGTTLMKFSEGFTRLWPSVGTIICYCASFWLLAQTLAYIPTGIAYAIWSGVGIVLIS
LLSWGFFGQRLDLPAIIGMMLICAGVLVINLLSRSAPH Multidrug transporter EmrE (*Escherichia coli* strain 55989/EAEC)
(SEQ ID NO: 242)
MNPYIYLGGAILAEVIGTTLMKFSEGFTRLWPSVGTIICYCASFWLLAQTLAYIPTGIAYAIWSGVGIVLIS
LLSWGFFGQRLDLPAIIGMMLICAGVLVINLLSRSTPH Ethidium bromide-methyl viologen transporter EmrE (*Escherichia coli* ISC7)
(SEQ ID NO: 243)
MNPYIYLGGAILAEVIGTTLMKFSEGFTRLWPSVGTIICYCASFWLLAQTLAYIPTGIAYAIWSGVGIVLIS
LLSWGFFGQRLDLPAIIGMMLICAGVLVINLLSRSAPH Multidrug transporter EmrE (*Escherichla coli* TA054)
(SEQ ID NO: 244)
MNPYIYLGGAILAEVIGTTLMKFSEGFTRLWPSVGTIICYCASFWLLAQTLAYIPTGIAYAIWSGVGIVLIS
LLSWGFFGQRLDLPAIIGMMLICAGVLVINLLSRSAPH Multidrug transporter EmrE (*Escherichia coli* ATCC BAA-2209)
(SEQ ID NO: 245)
MNPYIYLGGAILAEVIGTTLMKFSEGFTRLWPSVGTIICYCASFWLLAQTLAYIPTGIAYAIWSGVGIVLIS
LLSWGFFGQRLDLPAIIGMMLICAGVLVINLLSRSAPH Multidrug transporter EmrE (*Escherichia albertii* B156)
(SEQ ID NO: 246)
MNPYIYLGGAILAEVIGTTLMKFSEGFTRLWPSVGTIICYCASFWLLAQTLAYIPTGIAYAIWSGVGIVLIS
LLSWGFFGQRLDLPAIIGMMLICAGVLVINLLSRSAPH Multidrug transporter EmrE (*Escherichia sp*, KTE96)
(SEQ ID NO: 247)
MNPYIYLGGAILAEVIGTTLMKFSEGFTRLWPSVGTIICYCASFWLLAQTLAYIPTGIAYAIWSGVGIVLIS
LLSWGFFGQRLDLPAIIGMMLICAGVLVINLLSRSAPH Multidrug transporter EmrE (*Escherichia sp*. KTE114)
(SEQ ID NO: 248)
MNPYIYLGGAILAEVIGTTLMKFSEGFTRLWPSVGTIICYCASFWLLAQTLAYIPTGIAYAIWSGVGIVLIS
LLSWGFFGQRLDLPAIIGMMLICAGVLVINLLSRSAPH Multidrug transporter EmrE (*Escherichia coli* HVH 25 4-5851939)
(SEQ ID NO: 249)
MNPYIYLGGAILAEVIGTTLMKFSEGFTRLWPSVGTIICYCASFWLLAQTLAYIPTGIAYAIWSGVGIVLIS
LLSWGFFGQRLDLPAIIGMMLICAGVLVINLLSRSAPH Multidrug transporter EmrE (*Escherichia coli* H461)
(SEQ ID NO: 250)
MNPYIYLGGAILAEVIGTTLMKFSEGFTRLWPSVGTIICYCASFWLLAQTLAYIPTGIAYAIWSGVGIVLIS
LLSWGFFGQRLDLPAIIGMMLICAGVLVINLLSRSAPH Multidrug transporter EmrE (*Escherichia coli* M718)
(SEQ ID NO: 251)
MNPYIYLGGAILAEVIGTTLMKFSEGFTRLWPSVGTIICYCASFWLLAQTLAYIPTGIAYAIWSGVGIVLIS
LLSWGFFGQRLDLPAIIGMMLICAGVLVINLLSRSAPH Methyl viologen transporter EmrE (Achromobacter sp.)
(SEQ ID NO: 252)
MNPYIYLGGAILAEVIGTTLMKFSEGFTRLWPSVGTIICYCASFWLLAQTLAYIPTGIAYAIWSGVGIVLIS
LLSWGFFGQRLDLPAIIGMMLICAGVLVINLLSRSAPH Multidrug transporter EmrE (*Escherichla coli* 2-427-07_S4_C3)
(SEQ ID NO: 253)
MNPYIYLGGAILAEVIGTTLMKFSEGFTRLWPSVGTIICYCASFWLLAQTLAYIPTGIAYAIWSGVGIVLIS
LLSWGFFGQRLDLPAIIGMMLICAGVLVINLLSRSTPH -continued Multidrug transporter EmrE (*Escherichia coli* KOEGE 71 186a)
(SEQ ID NO: 254)
MNPYIYLGGAILAEVIGTTLMKFSEGFTRLWPSVGTIICYCASFWLLAQTLAYIPTGIAYAIWSGVGIVLIS
LLSWGFFGQRLDLPAIIGMMLICAGVLVINLLSRSAPH Multidrug transporter EmrE (*Escherichia coli* 2-427-07_S4_C3)
(SEQ ID NO: 255)
MNPYIYLGGAILAEVIGTTLMKFSEGFTRLWPSVGTIICYCASFWLLAQTLAYIPTGIAYAIWSGVGIVLIS
LLSWGFFGQRLDLPAIIGMMLICAGVLVINLLSRSAPH Multidrug SMR transporter (*Escherichia coli* O111:NM strain K6722)
(SEQ ID NO: 256)
MNPYIYLGGAILAEVIGTTLMKFSEGFTRLWPSVGTIICYCASFWLLAQTLAYIPTGIAYAIWSGVGIVLIS
LLSWGFFGQRLDLPAIIGMMLICAGVLVINLLSRSAPH Quaternary ammonium transporter (*Escherichia coli* APEC O2-211)
(SEQ ID NO: 257)
MNPYIYLGGAILAEVIGTTLMKFSEGFTRLWPSVGTIICYCASFWLLAQTLAYIPTGIAYAIWSGVGIVLIS
LLSWGFFGQRLDLPAIIGMMLICAGVLVINLLSRSAPH Multidrug transporter EmrE (*Escherichia coli* KTE21)
(SEQ ID NO: 258)
MNPYIYLGGAILAEVIGTTLMKFSEGFTRLWPSVGTIICYCASFWLLAQTLAYIPTGIAYAIWSGVGIVLIS
LLSWGFFGQRLDLPAIIGMMLICAGVLVINLLSRSAPH Multidrug SMR transporter (*Escherichia coli* O128:H2 strain 2011C-3317)
(SEQ ID NO: 259)
MNPYIYLGGAILAEVIGTTLMKFSEGFTRLWPSVGTIICYCASFWLLAQTLAYIPTGIAYAIWSGVGIVLIS
LLSWGFFGQRLDLPAIIGMMLICAGVLVINLLSRSTPH Multidrug SMR transporter (*Shigella dysenteriae*)
(SEQ ID NO: 260)
MNPYIYLGGAILAEVIGTTLMKFSEGFTRLWPSVGTIICYCASFWLLAQTLAYIPTGIAYAIWSGVGIVLIS
LLSWGFFGQRLDLPAIIGMMLICAGVLVINLLSRSAPH Multidrug transporter EmrE (*Escherichia coli* 4.0967)
(SEQ ID NO: 261)
MNPYIYLGGAILAEVIGTTLMKFSEGFTRLWPSVGTIICYCASFWLLAQTLAYIPTGIAYAIWSGVGIVLIS
LLSWGFFGQRLDLPAIIGMMLICAGVLVINLLSRSTPH Multidrug transporter EmrE (*Escherichia* sp. KTE159)
(SEQ ID NO: 262)
MNPYIYLGGAILAEVIGTTLMKFSEGFTRLWPSVGTIICYCASFWLLAQTLAYIPTGIAYAIWSGVGIVLIS
LLSWGFFGQRLDLPAIIGMMLICAGVLVINLLSRSAPH Multidrug transporter EmrE (*Escherichia coli* strain ATCC 9637)
(SEQ ID NO: 263)
MNPYIYLGGAILAEVIGTTLMKFSEGFTRLWPSVGTIICYCASFWLLAQTLAYIPTGIAYAIWSGVGIVLIS
LLSWGFFGQRLDLPAIIGMMLICAGVLVINLLSRSAPH Multidrug transporter EmrE (*Escheriehia coli* 3-267-03_S4_C1)
(SEQ ID NO: 264)
MNPYIYLGGAILAEVIGTTLMKFSEGFTRLWPSVGTIICYCASFWLLAQTLAYIPTGIAYAIWSGVGIVLIS
LLSWGFFGQRLDLPAIIGMMLICAGVLVINLLSRSTPH Multidrug transporter EmrE (*Escherichia coli* 2-177-06_S3_C3)
(SEQ ID NO: 265)
MNPYIYLGGAILAEVIGTTLMKFSEGFTRLWPSVGTIICYCASFWLLAQTLAYIPTGIAYAIWSGVGIVLIS
LLSWGFFGQRLDLPAIIGMMLICAGVLVINLLSRSAPH Multidrug transporter EmrE (*Escherichia coli* 3-267-03_S4_C1)
(SEQ ID NO: 266)
MNPYIYLGGAILAEVIGTTLMKFSEGFTRLWPSVGTIICYCASFWLLAQTLAYIPTGIAYAIWSGVGIVLIS
LLSWGFFGQRLDLPAIIGMMLICAGVLVINLLSRSAPH -continued Multidrug transporter EmrE (*Escherichia coli* HVH 50 4-2593475)
(SEQ ID NO: 267)
MNPYIYLGGAILAEVIGTTLMKFSEGFTRLWPSVGTIICYCASFWLLAQTLAYIPTGIAYAIWSGVGIVLIS

LLSWGFFGQRLDLPAIIGMMLICAGVLVINLLSRSAPH

Multidrug transporter EmrE (*Escherichia coli* 1.2264)
(SEQ ID NO: 268)
MNPYIYLGGAILAEVIGTTLMKFSEGFTRLWPSVGTIICYCASFWLLAQTLAYIPTGIAYAIWSGVGIVLIS

LLSWGFFGQRLDLPAIIGMMLICAGVLVINLLSRSSPH

Multidrug transporter EmrE (*Shigella flexneri* K-227)
(SEQ ID NO: 269)
MNPYIYLGGAILAEVIGTTLMKFSEGFTRLWPSVGTIICYCASFWLLAQTLAYIPTGIAYAIWSGVGIVLIS

LLSWGFFGQRLDLPAIIGMMLICAGVLVINLLSRSSPH

Multidrug SMR transporter (*Escherichia coli* O146:H21 strain 2010C-3325)
(SEQ ID NO: 270)
MNPYIYLGGAILAEVIGTTLMKFSEGFTRLWPSVGTIICYCASFWLLAQTLAYIPTGIAYAIWSGVGIVLIS

LLSWGFFGQRLDLPAIIGMMLICAGVLVINLLSRSTPH

Multidrug transporter EmrE (*Shigelia flexneri* 2a strain 301)
(SEQ ID NO: 271)
MNPYIYLGGAILAEVIGTTLMKFSEGFTRLWPSVGTIICYCASFWLLAQTLAYIPTGIAYAIWSGVGIVLIS

LLSWGFFGQRLDLPAIIGMMLICAGVLVINLLSRSAPH

Methylviologen resistance transporter EmrE (*Shigella sonnei* strain Ss046)
(SEQ ID NO: 272)
MNPYIYLGGAILAEVIGTTLMKFSEGFTRLWPSVGTIICYCASFWLLAQTLAYIPTGIAYAIWSGVGIVLIS

LLSWGFFGQRLDLPAIIGMMLICAGVLVINLLSRSAPH

Multidrug SMR transporter (*Escherichia coli* O174:H8 strain 04-3038)
(SEQ ID NO: 273)
MNPYIYLGGAILAEVIGTTLMKFSEGFTRLWPSVGTIICYCASFWLLAQTLAYIPTGIAYAIWSGVGIVLIS

LLSWGFFGQRLDLPAIIGMMLICAGVLVINLLSRSAPH

Multidrug transporter EmrE (*Escherichia coli* KTE108)
(SEQ ID NO: 274)
MNPYIYLGGAILAEVIGTTLMKFSEGFTRLWPSVGTIICYCASFWLLAQTLAYIPTGIAYAIWSGVGIVLIS

LLSWGFFGQRLDLPAIIGMMLICAGVLVINLLSRSAPH

Multidrug transporter EmrE (*Escherichia coli* O157:H7 strain SS52)
(SEQ ID NO: 275)
MNPYIYLGGAILAEVIGTTLMKFSEGFTRLWPSVGTIICYCASFWLLAQTLAYIPTGIAYAIWSGVGIVLIS

LLSWGFFGQRLDLPAIIGMMLICAGVLVINLLSRSTPH

Multidrug transporter EmrE (*Escherichia coli* MS 145-7)
(SEQ ID NO: 276)
MNPYIYLGGAILAEVIGTTLMKFSEGFTRLWPSVGTIICYCASFWLLAQTLAYIPTGIAYAIWSGVGIVLIS

LLSWGFFGQRLDLPAIIGMMLICAGVLVINLLSRSTPH

Multidrug transporter EmrE (*Shigella dysenteriae* 225-75)
(SEQ ID NO: 277)
MNPYIYLGGAILAEVIGTTLMKFSEGFTRLWPSVGTIICYCASFWLLAQTLAYIPTGIAYAIWSGVGIVLIS

LLSWGFFGQRLDLPAIIGMMLICAGVLVINLLSRSAPH

Multidrug transporter EmrE (*Escherichia coli* 908573)
(SEQ ID NO: 278)
MNPYIYLGGAILAEVIGTTLMKFSEGFTRLWPSVGTIICYCASFWLLAQTLAYIPTGIAYAIWSGVGIVLIS

LLSWGFFGQRLDLPAIIGMMLICAGVLVINLLSRSTPH

Methylviologen transporter (*Escherichia coli* G3/10)
(SEQ ID NO: 279)
MNPYIYLGGAILAEVIGTTLMKFSEGFTRLWPSVGTIICYCASFWLLAQTLAYIPTGIAYAIWSGVGIVLIS

LLSWGFFGQRLDLPAIIGMMLICAGVLVINLLSRSAPH

-continued

Multidrug transporter EmrE (*Escherichia coli* HVH 41 4-2677849)
(SEQ ID NO: 280)
MNPYIYLGGAILAEVIGTTLMKFSEGFTRLWPSVGTIICYCASFWLLAQTLAYIPTGIAYAIWSGVGIVLIS

LLSWGLFDQRLDLPAIIGMMLICAGVLVINLLSRSTPH

Multidrug SMR transporter (*Escherichia coli* M863)
(SEQ ID NO: 281)
MNPYIYLGGAILAEVIGTTLMKFSEGFTRLWPSVGTIICYCASFWLLAQTLAYIPTGIAYAIWSGVGIVLIS

LLSWGFFGQRLDLPAIIGMMLICAGVLVINLLSRSAPH

Multidrug SMR transporter (*Escherichia coli* TW10509)
(SEQ ID NO: 282)
MNPYIYLGGAILAEVIGTTLMKFSEGFTRLWPSVGTIICYCASFWLLAQTLAYIPTGIAYAIWSGVGIVLIS

LLSWGFFGQRLDLPAIIGMMLICAGVLVINLLSRSAPH

Multidrug transporter EmrE (*Escherichia coli* 4.0522)
(SEQ ID NO: 283)
MNPYIYLGGAILAEVIGTTLMKFSEGFTRLWPSVGTIICYCASFWLLAQTLAYIPTGIAYAIWSGVGIVLIS

LLSWGFFGQRLDLPAIIGMMLICAGVLVINLLSRSAPH

Multidrug transporter EmrE (*Escherichia coli* O111:H- strain 11128/EHEC)
(SEQ ID NO: 284)
MNPYIYLGGAILAEVIGTTLMKFSEGFTRLWPSVGTIICYCASFWLLAQTLAYIPTGIAYAIWSGVGIVLIS

LLSWGFFGQRLDLPAIIGMMLICAGVLVINLLSRSAPH

Multidrug transporter EmrE (*Escherichia coli* KTE20)
(SEQ ID NO: 285)
MNPYIYLGGAILAEVIGTTLMKFSEGFTRLWPSVGTIICYCASFWLLAQTLAYIPTGIAYAIWSGVGIVLIS

LLSWGFFGQRLDLPAIIGMMLICAGVLVINLLSRSAPH

Multidrug transporter EmrE (*Escherichia coli* 2-005-03_S4_C2)
(SEQ ID NO: 286)
MNPYIYLGGAILAEVIGTTLMKFSEGFTRLWPSVGTIICYCASFWLLAQTLAYIPTGIAYAIWSGVGIVLIS

LLSWGFFGQRLDLPAIIGMMLICAGVLVINLLSRSAPH

Multidrug transporter EmrE (*Escherichia sp.* KTE31)
(SEQ ID NO: 287)
MNPYIYLGGAILAEVIGTTLMKFSEGFTRLWPSVGTIICYCASFWLLAQTLAYIPTGIAYAIWSGVGIVLIS

LLSWGFFGQRLDLPAIIGMMLICAGVLVINLLSRSAPH

Multidrug transporter EmrE (*Escherichia coli* M605)
(SEQ ID NO: 288)
MNPYIYLGGAILAEVIGTTLMKFSEGFTRLWPSVGTIICYCASFWLLAQTLAYIPTGIAYAIWSGVGIVLIS

LLSWGFFGQRLDLPAIIGMMLICAGVLVINLLSRSAPH

Multidrug transporter EmrE (*Escherichia coli* TA447)
(SEQ ID NO: 289)
MNPYIYLGGAILAEVIGTTLMKFSEGFTRLWPSVGTIICYCASFWLLAQTLAYIPTGIAYAIWSGVGIVLIS

LLSWGFFGQRLDLPAIIGMMLICAGVLVINLLSRSAPH

Multidrug SMR transporter (*Escherichia coli* O104:H4)
(SEQ ID NO: 290)
MNPYIYLGGAILAEVIGTTLMKFSEGFTRLWPSVGTIICYCASFWLLAQTLAYIPTGIAYAIWSGVGIVLIS

LLSWGFFGQRLDLPAIIGMMLICAGVLVINLLSRSAPH

Multidrug transporter EmrE (*Escherichia albertii* strain TW07627)
(SEQ ID NO: 291)
MNPYIYLGGAILAEVIGTTLMKFSEGFTRLWPSVGTIICYCASFWLLAQTLAYIPTGIAYAIWSGVGIVLIS

LLSWGFFGQRLDLPAIIGMMLICAGVLVINLLSRSAPH

Multidrug SMR transporter (*Shigella* sp. PAMC 28760)
(SEQ ID NO: 292)
MNPYIYLGGAILAEVIGTTLMKFSEGFTRLWPSVGTIICYCASFWLLAQTLAYIPTGIAYAIWSGVGIVLIS

LLLWGFFGQRLDLPAIIGMMLICAGVLVINLLSRSTPH

-continued

Multidrug transporter EmrE (*Escherichia coli* 2-011-08_S1_C1)
(SEQ ID NO: 293)
MNPYIYLGGAILAEVIGTTLMKFSEGFTRLWPSVGTIICYCASFWLLAQTLAYIPTGIAYAIWSGVGIVLIS

LLSWGFFGQRLDLPAIIGMMLICAGVLVINLLSRSTPH

Multidrug transporter EmrE (*Escherichia coli* UMEA 3212-1)
(SEQ ID NO: 294)
MNPYIYLGGAILAEVIGTTLMKFSEGFTRLWPSVGTIICYCASFWLLAQTLAYIPTGIAYAIWSGVGIVLIS

LLSWGFFGQRLDLPAIIGMMLICAGVLVINLLSRSAPH

Multidrug transporter EmrE (*Escherichia coli* 2-177-06_S3_C2)
(SEQ ID NO: 295)
MNPYIYLGGAILAEVIGTTLMKFSEGFTRLWPSVGTIICYCASFWLLAQTLAYIPTGIAYAIWSGVGIVLIS

LLSWGFFGQRLDLPAIIGMMLICAGVLVINLLSRSAPH

Multidrug transporter EmrE (*Escherichia coli* 97.0259)
(SEQ ID NO: 296)
MNPYIYLGGAILAEVIGTTLMKFSEGFTRLWPSVGTIICYCASFWLLAQTLAYIPTGIAYAIWSGVGIVLIS

LLSWGFFGQRLDLPAIIGMMLICAGVLVINLLSRSAPH

Multidrug transporter EmrE (*Escherichia coli* 99.0741)
(SEQ ID NO: 297)
MNPYIYLGGAILAEVIGTTLMKFSEGFTRLWPSVGTIICYCASFWLLAQTLAYIPTGIAYAIWSGVGIVLIS

LLSWGFFGQRLDLPAIIGMMLICAGVLVINLLSRSAPH

Multidrug transporter EmrE (*Escherichia coli* KTE66)
(SEQ ID NO: 298)
MNPYIYLGGAILAEVIGTTLMKFSEGFTRLWPSVGTIICYCASFWLLAQTLAYIPTGIAYAIWSGVGIVLIS

LLSWGFFGQRLDLPAIIGMMLICAGVLVINLLSRSTPH

Multidrug transporter EmrE (*Escherichia coli* B185)
(SEQ ID NO: 299)
MNPYIYLGGAILAEVIGTTLMKFSEGFTRLWPSVGTIICYCASFWLLAQTLAYIPTGIAYAIWSGVGIVLIS

LLSWGFFGQRLDLPAIIGMMLICAGVLVINLLSRSTPH

Multidrug transporter EmrE (*Escherichia coli* O139:H28 strain E24377A/ETEC)
(SEQ ID NO: 300)
MNPYIYLGGAILAEVIGTTLMKFSEGFTRLWPSVGTIICYCASFWLLAQTLAYIPTGIAYAIWSGVGIVLIS

LLSWGFFGQRLDLPAIIGMMLICAGVLVINLLSRSTPH

Multidrug transporter EmrE (*Escherichia coli* UMEA 3323-1)
(SEQ ID NO: 301)
MNPYIYLGGAILAEVIGTTLMKFSEGFTRLWPSVGTIICYCASFWLLAQTLAYIPTGIAYAIWSGVGIVLIS

LLSWGFFGQRLDLPAIIGMMLICAGVLVINLLSRSAPH

Multidrug transporter EmrE (*Escherichia coli* KTE10)
(SEQ ID NO: 302)
MNPYIYLGGAILAEVIGTTLMKFSEGFTRLWPSVGTIICYCASFWLLAQTLAYIPTGIAYAIWSGVGIVLIS

LLSWGFFGQRLDLPAIIGMMLICAGVLVINLLSRSAPH

Multidrug transporter EmrE (*Escheriehia coli* 9.0111)
(SEQ ID NO: 303)
MNPYIYLGGAILAEVIGTTLMKFSEGFTRLWPSVGTIICYCASFWLLAQTLAYIPTGIAYAIWSGVGIVLIS

LLSWGFFGQRLDLPAIIGMMLICAGVLVINLLSRSTPH

Multidrug transporter EmrE (*Escherichia coli* KTE182)
(SEQ ID NO: 304)
MNPYIYLGGAILAEVIGTTLMKFSEGFTRLWPSVGTIICYCASFWLLAQTLAYIPTGIAYAIWSGVGIVLIS

LLSWGFFGQRLDLPAIIGMMLICAGVLVINLLSRSAPH

Multidrug transporter EmrE (*Escherichia coli* H386)
(SEQ ID NO: 305)
MNPYIYLGGAILAEVIGTTLMKFSEGFTRLWPSVGTIICYCASFWLLAQTLAYIPTGIAYAIWSGVGIVLIS

LLSWGFFGQRLDLPAIIGMMLICAGVLVINLLSRSAPH

Multidrug transporter EmrE (*Escherichia coli* O83:H1 strain NRG 857C/AIEC)
(SEQ ID NO: 306)
MNPYIYLGGAILAEVIGTTLMKFSEGFTRLWPSVGTIICYCASFWLLAQTLAYIPTGIAYAIWSGVGIVLIS

LLSWGFFGQRLDLPAIIGMMLICAGVLVINLLSRSAPH

Multidrug transporter EmrE (*Escherichia coli* 1-392-07_S4_C3)
(SEQ ID NO: 307)
MNPYIYLGGAILAEVIGTTLMKFSEGFTRLWPSVGTIICYCASFWLLAQTLAYIPTGIAYAIWSGVGIVLIS

LLSWGFFGQRLDLPAIIGMMLICAGVLVINLLSRSAPH

Multidrug transporter EmrE (*Escherichia coli* 1-392-07_S4_C1)
(SEQ ID NO: 308)
MNPYIYLGGAILAEVIGTTLMKFSEGFTRLWPSVGTIICYCASFWLLAQTLAYIPTGIAYAIWSGVGIVLIS

LLSWGFFGQRLDLPAIIGMMLICAGVLVINLLSRSAPH

Multidrug transporter EmrE (*Escherichia coli* 1-392-07_S4_C3)
(SEQ ID NO: 309)
MNPYIYLGGAILAEVIGTTLMKFSEGFTRLWPSVGTIICYCASFWLLAQTLAYIPTGIAYAIWSGVGIVLIS

LLSWGFFGQRLDLPAIIGMMLICAGVLVINLLSRSTPH

Multidrug transporter EmrE (*Escherichia coli* 1-392-07_S4_C1)
(SEQ ID NO: 310)
MNPYIYLGGAILAEVIGTTLMKFSEGFTRLWPSVGTIICYCASFWLLAQTLAYIPTGIAYAIWSGVGIVLIS

LLSWGFFGQRLDLPAIIGMMLICAGVLVINLLSRSTPH

Multidrug transporter EmrE (*Escherichia coli* 1-176-05_S3_C2)
(SEQ ID NO: 311)
MNPYIYLGGAILAEVIGTTLMKFSEGFTRLWPSVGTIICYCASFWLLAQTLAYIPTGIAYAIWSGVGIVLIS

LLSWGFFGQRLDLPAIIGMMLICAGVLVINLLSRSAPH

Multidrug transporter EmrE (*Escherichia coli* UMEA 3718-1)
(SEQ ID NO: 312)
MNPYIYLGGAILAEVIGTTLMKFSEGFTRLWPSVGTIICYCASFWLLAQTLAYIPTGIAYAIWSGVGIVLIS

LLSWGFFGQRLDLPAIIGMMLICAGVLVINLLSRSTPH

Multidrug SMR transporter (*Escherichia coli* strain B/BL21-DE3)
(SEQ ID NO: 313)
MNPYIYLGGAILAEVIGTTLMKFSEGFTRLWPSVGTIICYCASFWLLAQTLAYIPTGIAYAIWSGVGIVLIS

LLSWGFFGQRLDLPAIIGMMLICAGVLVINLLSRSTPH

Multidrug SMR transporter (*Escherichia coli*)
(SEQ ID NO: 314)
MNPYIYLGGAILAEVIGTTLMKFSEGFTRLWPSVGTIICYCASFWLLAQTLAYIPTGIAYAIWSGVGIVLIS

LLSWGFFGQRLDLPAIIGMMLICAGVLVINLLSRSAPH

QacE family quaternary ammonium compound efflux SMR transporter
(*Escherichia coli*)
(SEQ ID NO: 315)
MNPYIYLGGAILAEVIGTTLMKFSEGFTRLWPSVGTIICYCASFWLLAQTLAYIPTGIAYAIWSGVGIVLIS

LLSWGFFGQRLDLPAIIGMMLICAGVLVINLLSRSAPH

Multidrug transporter EmrE (*Escherichia coli*)
(SEQ ID NO: 316)
MNPYIYLGGAILAEVIGTTLMKFSEGFTRLWPSVGTIICYCASFWLLAQTLAYIPTGIAYAIWSGVGIVLIS

LLSWGFFGQRLDLPAIIGMMLICAGVLVINLLSRSAPH

QacE family quaternary ammonium compound efflux SMR transporter
(*Escherichia coli*)
(SEQ ID NO: 317)
MNPYIYLGGAILAEVIGTTLMKFSEGFTRLWPSVGTIICYCASFWLLAQTLAYIPTGIAYAIWSGVGIVLIS

LLSWGFFGQRLDLPAIIGMMLICAGVLVINLLSRSTPH

Multidrug SMR transporter (*Escherichia coli* O25b:H4-ST131)
(SEQ ID NO: 318)
MNPYIYLGGAILAEVIGTTLMKFSEGFTRLWPSVGTIICYCASFWLLAQTLAYIPTGIAYAIWSGVGIVLIS

LLSWGFFGQRLDLPAIIGMMLICAGVLVINLLSRSAPH

-continued

Multidrug SMR transporter (*Escherichia coli*)

(SEQ ID NO: 319)

MNPYIYLGGAILAEVIGTTLMKFSEGFTRLWPSVGTIICYCASFWLLAQTLAYIPTGIAYAIWSGVGIVLIS

LLSWGFFGQRLDLPAIIGMMLICAGVLVINLLSRSAPH

Multidrug SMR transporter (*Escherichia coli*)

(SEQ ID NO: 320)

MNPYIYLGGAILAEVIGTTLMKFSEGFTRLWPSVGTIICYCASFWLLAQTLAYIPTGIAYAIWSGVGIVLIS

LLSWGFFGQRLDLPAIIGMMLICAGVLVINLLSRSAPH

Multidrug transporter EmrE (*Escherichia coli* KTE33)

(SEQ ID NO: 321)

MNPYIYLGGAILAEVIGTTLMKFSEGFTRLWPSVGTIICYCASFWLLAQTLAYIPTGIAYAIWSGVGIVLIS

LLSWGFFGQRLDLPAIIGMMLICAGVLVINLLSRSAPH

Multidrug transporter EmrE (*Shigella flexneri* VA-6)

(SEQ ID NO: 322)

MNPYIYLGGAILAEVIGTTLMKFSEGFTRLWPSVGTIICYCASFWLLAQTLAYIPTGIAYAIWSGVGIVLIS

LLSWGFFGQRLDLPAIIGMMLICAGVLVINLLSRSAPH

Multidrug transporter EmrE (*Escherichia coli* H736)

(SEQ ID NO: 323)

MNPYIYLGGAILAEVIGTTLMKFSEGFTRLWPSVGTIICYCASFWLLAQTLAYIPTGIAYAIWSGVGIVLIS

LLSWGFFGQRLDLPAIIGMMLICAGVLVINLLSRSAPH

Multidrug SMR transporter (*Shigella flexneri* 4c)

(SEQ ID NO: 324)

MNPYIYLGGAILAEVIGTTLMKFSEGFTRLWPSVGTIICYCASFWLLAQTLAYIPTGIAYAIWSGVGIVLIS

LLSWGFFGQRLDLPAIIGMMLICAGVLVINLLSRSAPH

Multidrug SMR transporter (*Shigella flexneri*)

(SEQ ID NO: 325)

MNPYIYLGGAILAEVIGTTLMKFSEGFTRLWPSVGTIICYCASFWLLAQTLAYIPTGIAYAIWSGVGIVLIS

LLSWGFFGQRLDLPAIIGMMLICAGVLVINLLSRSAPH

Multidrug SMR transporter (*Escherichia coli*)

(SEQ ID NO: 326)

MNPYIYLGGAILAEVIGTTLMKFSEGFTRLWPSVGTIICYCASFWLLAQTLAYIPTGIAYAIWSGVGIVLIS

LLSWGFFGQRLDLPAIIGMMLICAGVLVINLLSRSTPH

Multidrug transporter EmrE (*Escherichia coli*)

(SEQ ID NO: 327)

MNPYIYLGGAILAEVIGTTLMKFSEGFTRLWPSVGTIICYCASFWLLAQTLAYIPTGIAYAIWSGVGIVLIS

LLSWGFFGQRLDLPAIIGMMLICAGVLVINLLSRSAPH

Multidrug transporter EmrE (*Escherichia coli*)

(SEQ ID NO: 328)

MNPYIYLGGAILAEVIGTTLMKFSEGFTRLWPSVGTIICYCASFWLLAQTLAYIPTGIAYAIWSGVGIVLIS

LLSWGFFGQRLDLPAIIGMMLICAGVLVINLLSRSTPH

Multidrug transporter EmrE (*Shigella sonnei*)

(SEQ ID NO: 329)

MNPYIYLGGAILAEVIGTTLMKFSEGFTRLWPSVGTIICYCASFWLLAQTLAYIPTGIAYAIWSGVGIVLIS

LLSWGFFGQRLDLPAIIGMMLICAGVLVINLLSRSAPH

Multidrug transporter EmrE (*Escherichia coli* DORA_B_14)

(SEQ ID NO: 330)

MNPYIYLGGAILAEVIGTTLMKFSEGFTRLWPSVGTIICYCASFWLLAQTLAYIPTGIAYAIWSGVGIVLIS

LLSWGFFGQRLDLPAIIGMMLICAGVLVINLLSRSAPN

Multidrug SMR transporter (*Escherichia coli* N37139PS)

(SEQ ID NO: 331)

MNPYIYLGGAILAEVIGTTLMKFSEGFTRLWPSVGTIICYCASFWLLAQTLAYIPTGIAYAIWSGVGIVLIS

LLSWGFFGQRLDLPAIIGMMLICAGVLVINLLSRSTPH

-continued

Multidrug transporter EmrE (*Escherichia coli* N36410PS)
(SEQ ID NO: 332)
MNPYIYLGGAILAEVIGTTLMKFSEGFTRLWPSVGTIICYCASFWLLAQTLAYIPTGIAYAIWSGVGIVLIS
LLSWGFFGQRLDLPAIIGMMLICAGVLVINLLSRSTPH Multidrug transporter EmrE (*Escherichia coli* H605)
(SEQ ID NO: 333)
MNPYIYLGGAILAEVIGTTLMKFSEGFTRLWPSVGTIICYCASFWLLAQTLAYIPTGIAYAIWSGVGIVLIS
LLSWGFFGQRLDLPAIIGMMLICAGVLVINLLSRSAPH Quaternary ammonium transporter (*Escherichia coli* APEC O18)
(SEQ ID NO: 334)
MNPYIYLGGAILAEVIGTTLMKFSEGFTRLWPSVGTIICYCASFWLLAQTLAYIPTGIAYAIWSGVGIVLIS
LLSWGFFGQRLDLPAIIGMMLICAGVLVINLLSRSAPH Multidrug transporter EmrE (*Escherichia coli* N40513)
(SEQ ID NO: 335)
MNPYIYLGGAILAEVIGTTLMKFSEGFTRLWPSVGTIICYCASFWLLAQTLAYIPTGIAYAIWSGVGIVLIS
LLSWGFFGQRLDLPAIIGMMLICAGVLVINLLSRSAPH Multidrug transporter EmrE (*Escherichia albertii*)
(SEQ ID NO: 336)
MNPYIYLGGAILAEVIGTTLMKFSEGFTRLWPSVGTIICYCASFWLLAQTLAYIPTGIAYAIWSGVGIVLIS
LLSWGFFGQRLDLPAIIGMMLICAGVLVINLLSRSAPH Multidrug transporter EmrE (Escherichia albertii)
(SEQ ID NO: 337)
MNPYIYLGGAILAEVIGTTLMKFSEGFTRLWPSVGTIICYCASFWLLAQTLAYIPTGIAYAIWSGVGIVLIS
LLSWGFFGQRLDLPAIIGMMLICAGVLVINLLSRSAPH Multidrug transporter EmrE (*Escherichia coli* N40607)
(SEQ ID NO: 338)
MNPYIYLGGAILAEVIGTTLMKFSEGFTRLWPSVGTIICYCASFWLLAQTLAYIPTGIAYAIWSGVGIVLIS
LLSWGFFGQRLDLPAIIGMMLICAGVLVINLLSRSAPH Multidrug SMR transporter (*Escherichia coli* NCCP15648)
(SEQ ID NO: 339)
MNPYIYLGGAILAEVIGTTLMKFSEGFTRLWPSVGTIICYCASFWLLAQTLAYIPTGIAYAIWSGVGIVLIS
LLSWGFFGQRLDLPAIIGMMLICAGVLVINLLSRSAPH Multidrug SMR transporter (*Escherichia coli* NCCP15648)
(SEQ ID NO: 340)
MNPYIYLGGAILAEVIGTTLMKFSEGFTRLWPSVGTIICYCASFWLLAQTLAYIPTGIAYAIWSGVGIVLIS
LLSWGFFGQRLDLPAIIGMMLICAGVLVINLLSRSTPH Multidrug transporter EmrE (*Escherichia coli* N36254PS)
(SEQ ID NO: 341)
MNPYIYLGGAILAEVIGTTLMKFSEGFTRLWPSVGTIICYCASFWLLAQTLAYIPTGIAYAIWSGVGIVLIS
LLSWGFFGQRLDLPAIIGMMLICAGVLVINLLSRSAPH Multidrug SMR transporter (*Shigella sonnei*)
(SEQ ID NO: 342)
MNPYIYLGGAILAEVIGTTLMKFSEGFTRLWPSVGTIICYCASFWLLAQTLAYIPTGIAYAIWSGVGIVLIS
LLSWGFFGQRLDLPAIIGMMLICAGVLVINLLSRSAPH Multidrug SMR transporter (*Shigella sonnei*)
(SEQ ID NO: 343)
MNPYIYLGGAILAEVIGTTLMKFSEGFTRLWPSVGTIICYCASFWLLAQTLAYIPTGIAYAIWSGVGIVLIS
LLSWGFFGQRLDLPAIIGMMLICAGVLVINLLSRSAPH Multidrug SMR transporter (*Shigella sonnei*)
(SEQ ID NO: 344)
MNPYIYLGGAILAEVIGTTLMKFSEGFTRLWPSVGTIICYCASFWLLAQTLAYIPTGIAYAIWSGVGIVLIS
LLSWGFFGQRLDLPAIIGMMLICAGVLVINLLSRSAPH -continued Multidrug transporter EmrE (*Escherichia coli* N37122PS)
(SEQ ID NO: 345)
MNPYIYLGGAILAEVIGTTLMKFSEGFTRLWPSVGTIICYCASFWLLAQTLAYIPTGIAYAIWSGVGIVLIS
LLSWGFFGQRLDLPAIIGMMLICAGVLVINLLSRSTPH Multidrug transporter EmrE (*Escherichia coli*)
(SEQ ID NO: 346)
MNPYIYLGGAILAEVIGTTLMKFSEGFTRLWPSVGTIICYCASFWLLAQTLAYIPTGIAYAIWSGVGIVLIS
LLSWGFFGQRLDLPAIIGMMLICAGVLVINLLSRSAPN Multidrug SMR transporter (*Escherichia coli*)
(SEQ ID NO: 347)
MNPYIYLGGAILAEVIGTTLMKFSEGFTRLWPSVGTIICYCASFWLLAQTLAYIPTGIAYAIWSGVGIVLIS
LLSWGFFGQRLDLPAIIGMMLICAGVLVINLLSRSAPH Multidrug transporter EmrE (*Escherichia coli* E1118)
(SEQ ID NO: 348)
MNPYIYLGGAILAEVIGTTLMKFSEGFTRLWPSVGTIICYCASFWLLAQTLAYIPTGIAYAIWSGVGIVLIS
LLSWGFFGQRLDLPAIIGMMLICAGVLVINLLSRSAPH Multidrug SMR transporter (*Shigella boydii*)
(SEQ ID NO: 349)
MNPYIYLGGAILAEVIGTTLMKFSEGFTRLWPSVGTIICYCASFWLLAQTLAYIPTGIAYAIWSGVGIVLIS
LLSWGFFGQRLDLPAIIGMMLICAGVLVINLLSRSTPH Multidrug SMR transporter (*Shigella boydii*)
(SEQ ID NO: 350)
MNPYIYLGGAILAEVIGTTLMKFSEGFTRLWPSVGTIICYCASFWLLAQTLAYIPTGIAYAIWSGVGIVLIS
LLSWGFFGQRLDLPAIIGMMLICAGVLVINLLSRSAPH Multidrug SMR transporter (*Shigella flexneri* 1a)
(SEQ ID NO: 351)
MNPYIYLGGAILAEVIGTTLMKFSEGFTRLWPSVGTIICYCASFWLLAQTLAYIPTGIAYAIWSGVGIVLIS
LLSWGFFGQRLDLPAIIGMMLICAGVLVINLLSRSAPH Multidrug transporter EmrE (*Escherichia coli* MS 84-1)
(SEQ ID NO: 352)
MNRKEYAMNPYIYLGGAILAEVIGTTLMKFSEGFTRLWPSVGTIICYCASFWLLAQTLAYIPTGIAYAIWSG
VGIVLISLLSWGFFGQRLDLPAIIGMMLICAGVLVINLLSRSAPH Multidrug transporter EmrE (*Escherichia coli* MS 124-1)
(SEQ ID NO: 353)
MNRKEYAMNPYIYLGGAILAEVIGTTLMKFSEGFTRLWPSVGTIICYCASFWLLAQTLAYIPTGIAYAIWSG
VGIVLISLLSWGFFGQRLDLPAIIGMMLICAGVLVINLLSRSAPH Multidrug transporter EmrE (*Escherichia coli* 110957)
(SEQ ID NO: 354)
MNRKEYAMNPYIYLGGAILAEVIGTTLMKFSEGFTRLWPSVGTIICYCASFWLLAQTLAYIPTGIAYAIWSG
VGIVLISLLSWGFFGQRLDLPAIIGMMLICAGVLVINLLSRSAPH Multidrug transporter EmrE (*Escherichia coli* MS 85-1)
(SEQ ID NO: 355)
MNRKEYAMNPYIYLGGAILAEVIGTTLMKFSEGFTRLWPSVGTIICYCASFWLLAQTLAYIPTGIAYAIWSG
VGIVLISLLSWGFFGQRLDLPAIIGMMLICAGVLVINLLSRSAPH Multidrug transporter EmrE (*Escherichia coli* MS 117-3)
(SEQ ID NO: 356)
MNRKEYAMNPYIYLGGAILAEVIGTTLMKFSEGFTRLWPSVGTIICYCASFWLLAQTLAYIPTGIAYAIWSG
VGIVLISLLSWGFFGQRLDLPAIIGMMLICAGVLVINLLSRSAPH Multidrug transporter EmrE (*Escherichia coli* 909945-2)
(SEQ ID NO: 357)
MNRKEYAMNPYIYLGGAILAEVIGTTLMKFSEGFTRLWPSVGTIICYCASFWLLAQTLAYIPTGIAYAIWSG
VGIVLISLLSWGFFGQRLDLPAIIGMMLICAGVLVINLLSRSAPH -continued Multidrug transporter EmrE (*Escherichia coli* 113290)
(SEQ ID NO: 358)
MNRKEYAMNPYIYLGGAILAEVIGTTLMKFSEGFTRLWPSVGTIICYCASFWLLAQTLAYIPTGIAYAIWSG

VGIVLISLLSWGFFGQRLDLPAIIGMMLICAGVLVINLLSRSAPH

Multidrug transporter EmrE (*Escherichia coli* O83:H1 strain NRG 857C/AIEC)
(SEQ ID NO: 359)
MNRKEYAMNPYIYLGGAILAEVIGTTLMKFSEGFTRLWPSVGTIICYCASFWLLAQTLAYIPTGIAYAIWSG

VGIVLISLLSWGFFGQRLDLPAIIGMMLICAGVLVINLLSRSAPH

Multidrug transporter EmrE (*Escherichia coli* MS 115-1)
(SEQ ID NO: 360)
MNRKEYAMNPYIYLGGAILAEVIGTTLMKFSEGFTRLWPSVGTIICYCASFWLLAQTLAYIPTGIAYAIWSG

VGIVLISLLSWGFFGQRLDLPAIIGMMLICAGVLVINLLSRSAPH

Multidrug transporter EmrE (*Escherichia coli* strain MS 21-1)
(SEQ ID NO: 361)
MNRKEYAMNPYIYLGGAILAEVIGTTLMKFSEGFTRLWPSVGTIICYCASFWLLAQTLAYIPTGIAYAIWSG

VGIVLISLLSWGFFGQRLDLPAIIGMMLICAGVLVINLLSRSAPH

Multidrug SMR transporter (*Escherichia coli* strain SE11)
(SEQ ID NO: 362)
MNSFVSLGFLLIIIVPAFISCHARAPWIHIHQDENGELCSNCSTILSSMNRKEYAMNPYIYLGGAILAEVIG

TTLMKFSEGFTRLWPSVGTIICYCASFWLLAQTLAYIPTGIAYAIWSGVGIVLISLLSWGFFGQRLDLPAII

GMMLICAGVLVINLLSRSAPH

Methylviologen resistance transporter EmrE (*Shigella flexneri* serotype
5b strain 8401)
(SEQ ID NO: 363)
MNSFVSLGFLLIIIVPAFISCHARAPWIHIHQDENGELCSNCSTILSSMNRKEYAMNPYIYLGGAILAEVIG

TTLMKFSEGFTRLWPSVGTIICYCASFWLLAQTLAYIPTGIAYAIWSGVGIVLISLLSWGFFGQRLDLPAII

GMMLICAGVLVINLLSRSAPH

Multidrug transporter EmrE (*Escherichia coli* O1:K1/APEC)
(SEQ ID NO: 364)
MNSFVSLGFLLIIIVPAFISCHARAPWIHIHQDENGELCSNCSTILSSMNRKEYAMNPYIYLGGAILAEVIG

TTLMKFSEGFTRLWPSVGTIICYCASFWLLAQTLAYIPTGIAYAIWSGVGIVLISLLSWGFFGQRLDLPAII

GMMLICAGVLVINLLSRSAPH

Multidrug transporter EmrE (*Shigella flexneri* serotype X strain 2002017)
(SEQ ID NO: 365)
MNSFVSLGFLLIIIVPAFISCHARAPWIHIHQDENGELCSNCSTILSSMNRKEYAMNPYIYLGGAILAEVIG

TTLMKFSEGFTRLWPSVGTIICYCASFWLLAQTLAYIPTGIAYAIWSGVGIVLISLLSWGFFGQRLDLPAII

GMMLICAGVLVINLLSRSAPH

Multidrug transporter EmrE (*Shigella sonnei*)
(SEQ ID NO: 366)
MNSFVSLGFLLIIIVPAFISCHARAPWIHIHQDENGELCSNCSTILSSMNRKEYAMNPYIYLGGAILAEVIG

TTLMKFSEGFTRLWPSVGTIICYCASFWLLAQTLAYIPTGIAYAIWSGVGIVLISLLSWGFFGQRLDLPAII

GMMLICAGVLVINLLSRSAPH

Multidrug transporter EmrE (*Escherichia coli* O45:K1 strain S88/ExPEC)
(SEQ ID NO: 367)
MLPGRVNSFVSLGFLLIIIVPAFISCHARAPWIHIHQDENGELCSNCSTILSSMNRKEYAMNPYIYLGGAIL

AEVIGTTLMKFSEGFTRLWPSVGTIICYCASFWLLAQTLAYIPTGIAYAIWSGVGIVLISLLSWGFFGQRLD

LPAIIGMMLICAGVLVINLLSRSAPH

Multidrug transporter EmrE (*Escherichia coli* strain 55989/EAEC)
(SEQ ID NO: 368)
MLPGRVNSFVSLGFLLIIIVPAFISCHARAPWIHIHQDENGELCSNCSTILSSMNRKEYAMNPYIYLGGAIL

AEVIGTTLMKFSEGFTRLWPSVGTIICYCASFWLLAQTLAYIPTGIAYAIWSGVGIVLISLLSWGFFGQRLD

LPAIIGMMLICAGVLVINLLSRSAPH

Multidrug transporter EmrE (*Escherichia coli* O81 strain ED1a)
(SEQ ID NO: 369)
MLPGRVNSFVSLGFLLIIIVPAFISCHARAPWIHIHQDENGELCSNCSTILSSMNRKEYAMNPYIYLGGAIL

AEVIGTTLMKFSEGFTRLWPSVGTIICYCASFWLLAQTLAYIPTGIAYAIWSGVGIVLISLLSWGFFGQRLD

LPAIIGMMLICAGVLVINLLSRSAPH

Multidrug transporter EmrE (*Escherichia coli* strain UTI89/UPEC)
(SEQ ID NO: 370)
MLPGRVNSFVSLGFLLIIIVPAFISCHARAPWIHIHQDENGELCSNCSTILSSMNRKEYAMNPYIYLGGAIL

AEVIGTTLMKFSEGFTRLWPSVGTIICYCASFWLLAQTLAYIPTGIAYAIWSGVGIVLISLLSWGFFGQRLD

LPAIIGMMLICAGVLVINLLSRSAPH

Multidrug transporter EmrE (*Escherichia coli* O6:H1 strain CFT073)
(SEQ ID NO: 371)
MLPGRVNSFVSLGFLLIIIVPAFISCHARAPWIHIHQDENGELCSNCSTILSSMNRKEYAMNPYIYLGGAIL

AEVIGTTLMKFSEGFTRLWPSVGTIICYCASFWLLAQTLAYIPTGIAYAIWSGVGIVLISLLSWGFFGQRLD

LPAIIGMMLICAGVLVINLLSRSAPH

Multidrug transporter EmrE (*Escherichia coli* O25b:H4)
(SEQ ID NO: 372)
MLPGRVNSFVSLGFLLIIIVPAFISCHARAPWIHIHQDENGELCSNCSTILSSMNRKEYAMNPYIYLGGAIL

AEVIGTTLMKFSEGFTRLWPSVGTIICYCASFWLLAQTLAYIPTGIAYAIWSGVGIVLISLLSWGFFGQRLD

LPAIIGMMLICAGVLVINLLSRSAPH

Multidrug transporter EntrE (*Escherichia coli* O25b:H4-ST131)
(SEQ ID NO: 373)
MLPGRVNSFVSLGFLLIIIVPAFISCHARAPWIHIHQDENGELCSNCSTILSSMNRKEYAMNPYIYLGGAIL

AEVIGTTLMKFSEGFTRLWPSVGTIICYCASFWLLAQTLAYIPTGIAYAIWSGVGIVLISLLSWGFFGQRLD

LPAIIGMMLICAGVLVINLLSRSAPH

Multidrug transporter EmrE (*Escherichia coli* TW10598)
(SEQ ID NO: 374)
MLPGRVNSFVSLGFLLIIIVPAFISCHARAPWIHIHQDENGELCSNCSTILSSMNRKEYAMNPYIYLGGAIL

AEVIGTTLMKFSEGFTRLWPSVGTIICYCASFWLLAQTLAYIPTGIAYAIWSGVGIVLISLLSWGFFGQRLD

LPAIIGMMLICAGVLVINLLSRSAPH

Multidrug SMR transporter (*Escherichia coli* O157)
(SEQ ID NO: 375)
MNPYIYLGGAILAEVIGTTLMKFSEGPTRLWPSVGTIICYCASFWLLAQTLAYIPTGIAYAIWSGVGIVLIS

LLSWGFFGQRLDLPAVIGMMLICAGVLVINLLSRSTPH

Multidrug transporter EntrE (*Escherichia coli* KTE100)
(SEQ ID NO: 376)
MNPYIYLGGAILAEVIGTTLMKFSEGPTRLWPSVGTIICYCASFWLLAQTLAYIPTGIAYAIWSGVGIVLIS

LLSWGFFGQRLDLPAVIGMMLICAGVLVINLLSRSTPH

Multidrug transporter EntrE (*Escherichia* sp. KTE159)
(SEQ ID NO: 377)
MNPYIYLGGAILAEVIGTTLMKFSEGPTRLWPSVGTIICYCASFWLLAQTLAYIPTGIAYAIWSGVGIVLIS

LLSWGFFGQRLDLPAVIGMMLICAGVLVINLLSRSTPH

Multidrug transporter EmrE (*Escherichia coli* Xuzhou21)
(SEQ ID NO: 378)
MNPYIYLGGAILAEVIGTTLMKFSEGPTRLWPSVGTIICYCASFWLLAQTLAYIPTGIAYAIWSGVGIVLIS

LLSWGFFGQRLDLPAVIGMMLICAGVLVINLLSRSTPH

Multidrug transporter EmrE (*Escheriehia coli* KTE108)
(SEQ ID NO: 379)
MNPYIYLGGAILAEVIGTTLMKFSEGPTRLWPSVGTIICYCASFWLLAQTLAYIPTGIAYAIWSGVGIVLIS

LLSWGFFGQRLDLPAVIGMMLICAGVLVINLLSRSTPH

-continued

Ethidium bromide-methyl viologen transporter EmrE (*Escherichia coli* O157:H7 strain SS52)

(SEQ ID NO: 380)
MNPYIYLGGAILAEVIGTTLMKFSEGPTRLWPSVGTIICYCASFWLLAQTLAYIPTGIAYAIWSGVGIVLIS
LLSWGFFGQRLDLPAVIGMMLICAGVLVINLLSRSTPH

Multidrug transporter EmrE (*Escherichia coli* O157:H7 strain EC869)

(SEQ ID NO: 381)
MNPYIYLGGAILAEVIGTTLMKFSEGPTRLWPSVGTIICYCASFWLLAQTLAYIPTGIAYAIWSGVGIVLIS
LLSWGFFGQRLDLPAVIGMMLICAGVLVINLLSRSTPH

Multidrug SMR transporter (*Escherichia coli*)

(SEQ ID NO: 382)
MNPYIYEGGAILAEVIGTTLMKFSEGFTRLWPSVGTIICYCASFWLLAQTLAYIPTGIAYAIWSGVGIVLIS
LLSWGEFGQRLDLPAIIGMMTJCSGVLVINLLSRSAPH

Multidrug SMR transporter (*Escherichia coli*)

(SEQ ID NO: 383)
MNPYIYLGGAILAEVIGTTLMKFSEGPTRLWPSVGTIICYCASFWLLAQTLAYIPTGIAYAIWSGVGIVLIS
LLSWGFFGQRLDLPAVIGMMLICAGVLVINLLSRSTPH

Multidrug transporter EmrE (*Escherichia coli* O157:H7)

(SEQ ID NO: 384)
MNPYIYLGGAILAEVIGTTLMKFSEGPTRLWPSVGTIICYCASFWLLAQTLAYIPTGIAYAIWSGVGIVLIS
LLSWGFFGQRLDLPAVIGMMLICAGVLVINLLSRSTPH

Multidrug transporter EmrE (*Escherichia coli*)

(SEQ ID NO: 385)
MNPYIYLGGAILAEVIGTTLMKFSEGPTRLWPSVGTIICYCASFWLLAQTLAYIPTGIAYAIWSGVGIVLIS
LLSWGFFGQRLDLPAIIGMMLICAGVLVINLLSRSTPH

Multidrug transporter EmrE (*Shigella flexneri* 2850-71)

(SEQ ID NO: 386)
MNPYIYLGGAILAEVIGTTLMKFSEGPTRLWPSVGTIICYCASFWLLAQTLAYIPTGIAYAIWSGVGIVLIS
LLSWGFFGQRLDLPAIIGMMLICTGVLVINLLSRSTPH

Ethidium bromide-methyl viologen transporter EmrE (*Escherichia albertii* KF1)

(SEQ ID NO: 387)
MNPYIYLGGAILAEVIGTTLMKFSEGPTRLWPSVGTIICYCASFWLLAQTLAYIPTGIAYAIWSGVGIVLIS
LLSWGIFGQRLDLPAIIGMMLICAGVLVINLFSRSAPH

Multidrug SMR transporter (*Shigella* sp. FC2928)

(SEQ ID NO: 388)
MNPYIYLGGAILAEVIGTTLMKFSEGPTRLWPSVGTIICYCASFWLLAQTLAYIPTGIAYAIWSGVGIVLIS
LLSWGFFGQRLDLSAIIGMMLICAGVLVINLLSRSAPH

Multidrug transporter EmrE (Citrobacter sp. MGH106)

(SEQ ID NO: 389)
MNTYIYLGAAILAEVTGTTLMKFTDGFTRLWPSVGTIVCYCASFWLLSQTLAHIPTGIAYAIWSGVGIVLIS
LLAWVIHGQRLDLPAIIGMALICAGVLIINLLSRSAVH

Multidrug transporter EmrE (*Escherichia* sp. KTE11)

(SEQ ID NO: 390)
MNPYIYLGGAIFAEVIGTTLMKFSDGFTRLWPSVGTIICYCASFWLLAQTLAYIPTGIAYAIWSGVGIVLIS
LLSWGFFGQRLDLPAIIGMILICAGVLVINLLSRSAPH

Multidrug transporter EmrE (*Escherichia* sp. KTE52)

(SEQ ID NO: 391)
MNPYIYLGGAIFAEVIGTTLMKFSDGFTRLWPSVGTIICYCASFWLLAQTLAYIPTGIAYAIWSGVGIVLIS
LLFWGFFGQRLDLPAIIGMILICAGVLVINLLSRSAPH

Multidrug transporter EmrE (*Escherichia* sp. KTE96)

(SEQ ID NO: 392)
MNPYIYLGGAIFAEVIGTTLMKFSEGPTRLWPSVGTIICYCASFWLLAQTLAYIPTGIAYAIWSGVGIVLIS
LLSWGFFGQRLDLPAIIGMILICAGVLVINLLSRSAPH

-continued

Multidrug transporter EmrE (*Escherichia* sp. KTE159)
(SEQ ID NO: 393)
MNPYIYLGGAIFAEVIGTTLMKYSDGFTRLWPSVGTIICYCASFWLLAQTLAYIPTGIAYAIWSGVGIVLIS

LLSWGFFGQRLDLPAIIGMILICAGVLVINLLSRSAPH

Multidrug transporter EmrE (*Escherichia coli* E1118)
(SEQ ID NO: 394)
MNPYIYLGGAIFAEVIGTTLMKYSDGFTRLWPSVGTIICYCASFWLLAQTLAYIPTGIAYAIWSGVGIVLIS

LLSWGFFGQRLDLPAIIGMILICAGVLVINLLSRSAPH

Multidrug transporter EmrE (*Shigella sonnei*)
(SEQ ID NO: 395)
MNPYIYLGGAILAEVIGTTLMKFSEGFTRLWPSVGTIICYCASFWLLAQTLAYIPTGIAYAIWSGVGIVLIS

LLSWGFFGQRLDLPAIIGMMLICAGVLVINLGDAANLLI

Multidrug DMT transporter (*Shigella* sp. FC1967)
(SEQ ID NO: 396)
MVFSRLYPSIVVVIGYCLSFWALSQVVRVMPLGIAYAIWSGLGIVLVSVAAVFLYQQKLDLPAIIGMSLIIA

GVLVINLLSKSASH

Multidrug DMT transporter (*Shigella* sp. FC130)
(SEQ ID NO: 397)
MNGLTYLMLAIISEVIATTMLKASDGFSRLYPSIVVVIGYCLSFWALSQVVRVMPLGIAYAIWSGLGIVLVS

VAAVFLYQQKLDLPAIIGMSLIIAGVLVINLLSKSASH

Multidrug DMT transporter (*Shigella* sp. FC1655)
(SEQ ID NO: 398)
MNGLTYLMLAIISEVIATTMLKASDGFSRLYPSIVVVIGYCLSFWALSQVVRVMPLGIAYAIWSGLGIVLVS

VAAVFLYQQKLDLPAIIGMSLIIAGVLVINLLSKSASH

Multidrug transporter EmrE (*Serratia plymuthica* 4Rx13)
(SEQ ID NO: 399)
MSGFIYLTMAIVAEVIATTMLKASEGFTRLWPSLVVVVGYAVAFWGLSMVVKTMPLGIVYAIWSGMGIVLVS

IAAVFVYQQKLDLPAVIGMVLIIAGVLVINLLSKTAAH

Multidrug DMT transporter (*Serratia plymuthica* S13)
(SEQ ID NO: 400)
MSGFIYLTMAIVAEVIATTMLKASEGFTRLWPSLVVVVGYAVAFWGLSMVVKTMPLGIVYAIWSGMGIVLVS

IAAVFVYQQKLDLPAVIGMVLIIAGVLVINLLSKTAAH

Multidrug transporter EmrE (*Proteus vulgaris*)
(SEQ ID NO: 401)
MNGLTYLMLAIISEVIATTMLKASEGFSRLYPSIVVVIGYCFSFWALSQVVRVMPLGIAYAIWSGLGIVLVS

VAAVFIYQQKLDLPAIIGMGLIIAGVLVINLLSKSASH

Multidrug transporter EmrE (*Proteus vulgaris*)
(SEQ ID NO: 402)
MNGLTYLMLAIISEVIATTMLKASEGFSRLYPSIVVVIGYCFSFWALSQVVRVMPLGIAYAIWSGLGIVLVS

VAAVFIYQQKLDLPAIIGMGLIIAGVLVINLLSKSASH

Multidrug transporter EmrE (*Proteus vulgaris*)
(SEQ ID NO: 403)
MLAIISEVIATTMLKAEDGESRLYPSIVVVIGYCFSFWALSQVVKVMPLGIAYAIWEGLGIVLVSVAAVFLY

QQKLDLPAIVGMTLIIAGVLVINLLSKSASH

Multidrug transporter EmrE (*Proteus mirabilis* ATCC 29906)
(SEQ ID NO: 404)
MNGLTYLILTIISEVIATTVLKASDGGSRLYPSIVVVVGYCFSFWALSQVVKVMPLGIAYAIWSGLGIVLVS

VAAVFVYQQKLDLPAIVGMTLIIAGVLVINLLSNSTSH

Multidrug DMT transporter (*Proteus* sp. HMSC14B05)
(SEQ ID NO: 405)
MNGLTYLILTIISEVIATTVLKASDGGSRLYPSIVVVVGYCFSFWALSQVVKVMPLGIAYAIWSGLGIVLVS

VAAVFVYQQKLDLPAIVGMTLIIAGVLVINLLSNSTSH

```
Methyl yiologen transporter EmrE (Proteus hsuseri ZMd44)
                                                              (SEQ ID NO: 406)
MNGLTYLMLAIISEVIATTMLKASDGFSRLYPSIVVVIGYCLSFWALSQVVRVMPLGIAYAIWSGLGIVLVS

VAAVFLYQQKLDLPAIVGMTLIIAGVLVINLLSKSASH

Methyl viologen transporter EmrE (Proteus mirabilis strain HI4320)
                                                              (SEQ ID NO: 407)
MNGLTYLILAIISEVIATTVLKASDGFSRLYPSIVVVVGYCFSFWALSQVVKVMPLGIAYAIWSGLGIVLVS

VAAVFVYQQKLDLPAIVGMTLIIAGVLVINLLSNSTSH

Multidrug SMR transporter (Proteus penneri ATCC 35198)
                                                              (SEQ ID NO: 408)
MNGLTYLMLAIISEVIATTMLKASDGFSRLYPSIVVVIGYCFSFWALSQVVKVMPLGIAYAIWSGLGIVLVS

VAAVFLYQQKLDLPAIVGMTLIIAGVLVINLLSKSASH

Multidrug DMT transporter (Proteus mirabilis)
                                                              (SEQ ID NO: 409)
MNGLTYLILAIISEVIATTVLKASDGFSRLYPSIVVVVGYCFSFWALSQVVKVMPLGIAYAIWSGLGIVLVS

VAAVFVYQQKLDLPAIVGMTLIIAGVLVINLLSNSTAH

Multidrug transporter EmrE (Providencia rettgeri)
                                                              (SEQ ID NO: 410)
MKGLSFLFISIIAEVIATTTLKASDGFSRFWPSLVVVIGYAVSFWGLSQVVKVMPLGIAYAIWSGLGIVLVS

IAAIYIYNQKLDLPAIIGMLFIIVGVLIINLLSKSGTH

Multidrug SMR transporter (Providencia rustigianii DSM 4541)
                                                              (SEQ ID NO: 411)
MKGLGFLLMSIVAEVIATTTLKASDGFSRFWPSLIVVTGYATSFWGLSQVVKVMPLGIAYAIWSGLGIVLVS

VAAIYIYNQKLDLPAIIGMLLIIVGVLIINLFSKSGTH

Multidrug SMR transporter (Xenorhabdus thuongxuanensis)
                                                              (SEQ ID NO: 412)
MKFALSYNFGLVSNMNVWGYLFIAILSEVIATTMLKSADGFTRLVPSIIVVTGYCLSFWALSQVVKVMPLGI

AYAVWSCLGIVLVSIAGIFLYQQKLDLPAIIGILLIIAGVLVINLLSKSAGH

Multidrug transporter EmrE (Xenorhabdus doucetiae)
                                                              (SEQ ID NO: 413)
MVNWAVFWKFGLSYHLGLVSNMNVWGYLFIAILSEVIATTMLKTADGFTRLVPSIVVVLGYCLSFWALSQVV

KTMPLGIAYAVWSCLGIVLVSIAGIFLYQQKLDLPAIIGILLIIAGVLVINLLSKSAGH

Multidrug SMR transporter (Enterobacter cancerogenus)
                                                              (SEQ ID NO: 414)
MNTYLFLGIAIVAEVIGTTFMKYSEGFTRLWPSLATLICYFAAFYMLSQTLAHIPTGVAYAIWSGAGIVLIS

LVGWLVSGQKLDLPAIIGMAFICIGVLIINVLSKSGAH

Multidrug transporter EmrE (Serratia plymuthica PRI-2C)
                                                              (SEQ ID NO: 415)
MSGFIYLTMAIVAEVIATTMLKASEGFTRLWPSLAVIVGYAVAFWGLSMVVKTMPLGIVYAIWSGMGIVLVS

IAAVFVYQQKLDLPAVIGMGLIIAGVLVINLLSKTAAH

Ethidium bromide-methyl viologen transporter EmrE (Serratia fonticola
AU-P3(3))
                                                              (SEQ ID NO: 416)
MTAFIYLAMAIIAEVIATTLLKASEGFTRLWPSVFVVLGYAVAFWGLSMVVKTMPLGIVYAIWSGLGIVLVS

IAAVFIYQQKLDLPAVIGMGLIIAGVLVINLLSKSAGH

Multidrug transporter EmrE (Escherichia vulneris NBRC 102420)
                                                              (SEQ ID NO: 417)
MHAYVHLGIAIVAEVIGTTLMRYSEGFTKLWPTVATLGCYAVAFWFLSQTLQYIPTGIAYAIWSGVGIVLIS

AAGWIFSGQKLDLPAIGGMALICAGVLVINLFSKSVAH

Ethidium bromide-methyl viologen transporter EmrE (Serratia rubidaea)
                                                              (SEQ ID NO: 418)
MYLTMAIIAEVIATTMLKASEGFTRLWPSLVVVLGYGVAFWGLSMVVKSMPLGIVYAIWSGMGVVLVSIAAV

FIYNQKLDWPAIIGMGLIVAGVLVINLLSKTSAH
```

-continued

Cation/cationic drug transporter (*Serratia marcescens* FGI94)
(SEQ ID NO: 419)
MTGLMYLTMAIIAEVIATTMLKASEGFTRLWPSLVVVLGYGVAFWGLSMVVKSMPLGIVYAIWSGMGVVLVS

IAAVFIYNQKLDWPAIIGMGLIVAGVLVINLLSKTSAH

Multidrug DMT transporter (*Serratia marcescens*)
(SEQ ID NO: 420)
MSGFMYLTMAIVAEVIATTMLKASEGFTRLWPSLLVVLGYGVAFWGLSMVVKSMPLGIVYAIWSGMGIVLVS

VAAVFVYQQKLDWPAIIGMGLIIAGVLVINLLSKASVH

Multidrug transporter EmrE (*Serratia odorifera* DSM 4582)
(SEQ ID NO: 421)
MNGFIYLTMAIIAEVIATTMLKASEGFTREWPSLVVVVGYGVAFWGLSMVVKTMPLGIVYAIWSGMGIVLVS

IAAVFVYNQKLDWPAIIGMGLIIAGVLVINLLSKTSAH

Methods of Treatment

This invention describes peptides and methods of use for the treatment of bacterial infections. Pathogenic bacterial strains may become resistant to various treatments by developing a resistance to certain pharmaceutical agents. The resistance is conferred by small multidrug resistance (SMR) membrane-bound transporters. SMRs are a family of ubiquitous transporters in bacteria (e.g., *M. tuberculosis, P. aeruginosa, B. pertussis, N. meningitis, B. anthracis*, and *S. aureus*) that efflux a wide range of cytotoxic compounds through transmembrane pumps. SMRs include, for example, EmrE transporters and various quaternary ammonium compound (QAC) transporters. In an attempt to treat a bacterial infection, one might administer an antibiotic agent to combat the infection. However, an SMR transporter effluxes the antibiotic agent before it can kill the infection, thus conferring resistance to the antibiotic. Therefore, to effectively treat a drug resistant bacterial infection, one may need to inhibit one or more SMRs.

The peptides of the invention described herein include a C-terminal polypeptide of any one of an SMR transporter. SMRs exist as obligate dimers in their active form, with each monomer a ~110 residue four helix-bundle. The C-terminal polypeptide inhibits the dimerization of the SMR, thus preventing it from oligomerizing into its active state and reducing (e.g., by about 1%, 2%, 3%, 4%, 5%, 6%, 7%, 8%, 9%, 10%, 20%, 30%, 40%, 50%, 60%, 70%, 80%, 90%, 95%, 97%, 99%, or about 100%) or completely eliminating its ability to efflux the antibiotic. Following administration of the peptide, one could then administer an antibiotic agent, to which the bacteria is now sensitive, in order to effectively treat the infection. Following treatment with a peptide of the invention with or without an antibiotic agent, the size of the bacterial infection, the bacterial load, or the total number of bacterial cells is reduced (e.g., by about 1%, 2%, 3%, 4%, 5%, 6%, 7%, 8%, 9%, 10%, 20%, 30%, 40%, 50%, 60%, 70%, 80%, 90%, 95%, 97%, 99%, or about 100%) or completely eliminated relative to its initial size.

The polypeptides of the invention may be able to treat bacterial infections by preventing efflux of antibacterial agents administered in combination with a polypeptide of the invention. In some embodiments, the bacterial infection includes bacteria which express one or more small molecule resistance membrane-bound transporters.

"Antibacterial agents," also known as antibiotics, as used herein refer to agents used in the treatment and prevention of bacterial infections. Antibacterial agents include agents which kill the bacteria, known as "bactericidal agents" and agents which inhibit bacterial growth, known as "bacteriostatic agents." Antibacterial agents are generally classed based on their mechanism of action, chemical structure, or spectrum of activity. Some antibacterial agents useful in combination with the polypeptides of the invention include (i) agents which target the bacteria cell wall (e.g., β-lactam antibiotics, cephalosporin antibiotics, carbapenem antibiotics), (ii) agents which target the cell membrane (e.g., polymyxin antibiotics), (iii) agents that interfere with bacterial enzymes (e.g., rifamycin antibiotics, lipiarmycin antibiotics, quinolone antibiotics, sulfonamide antibiotics), or (iv) agents which inhibit protein synthesis (e.g., macrolide antibiotics, lincosamide antibiotics, tetracycline antibiotics, aminoglycoside antibiotics).

In some embodiments, the method further includes administering one or more antibacterial agents (e.g., ampicillin, erythromycin, or tetracycline). In some embodiments, the one or more antibacterial agents is a β-lactam antibiotic such as a penicillin antibiotic (e.g., amoxicillin, ampicillin, bacampicillin, carbenicillin, cloxacillin, dicloxacillin, flucloxacillin, mexlocillin, nafcillin, oxacillin, penicillin G, penicillin V, piperacillin, pivampicillin, pivmecillinam, ticarcillin), a cephalosporin antibiotic (e.g., cefacetrile, cefadroxil, cephalexin, cefaloglycin, cefalonium, cefaloridine, cefalotin, cefapirin, cefatrizine, cefazaflur, cefazedone, cefazolin, cefradine, cefroxadine, ceftezole, cefaclor, cefamandole, cefmetazole, cefonicd, cefotetan, cefoxitin, cefprozil, cefuroxime, cefuzonam, cefcapene, cefdaloxime, cefdinir, cefditoren, cefetamet, cefixime, cefmenoxime, cefodizime, cefotaxime, cefpimizole, cefpodoxime, cefteram, ceftibuten, ceftioflur, ceftiolene, ceftizoxime, ceftriaxone, cefoperazone, ceftazidime, cefclidine, cefepime, cefluprenam, cefoselis, cefozopran, cefpirome, cefquinome, ceftobiprole, ceftaroline, cefaclomezine, cefaloram, cefaparole, cefcanel, cefedrolor, cefempidone, cefetrizole, cefivitril, cefmatilen, cefmepidium, cefovecin, cefoxazole, cefrotil, cefsumide, cefuracetime, ceftioxide), a monobactam antibiotic (e.g., aztreonam), or a carbapenem antibiotic (e.g., imipenem, doripenem, ertapenem, meropenem), a polymyxin antibiotic (e.g., polymyxin B), a rifamycin antibiotic (e.g., rifampin, rifabutin, rifapentine, rifalazil), a lipiarycin antibiotic, a quinolone antibiotic (e.g., flumequine, nalidixic add, oxolinic acid, piromidic add, pipemidic acid, rosoxacin, ciprofloxacin, enoxacin, lomefloxacin, nadifloxacin, norfloxacin, ofloxacin, pefloxacin, rufloxacin, balofloxacin, gatifloxacin, grepafloxacin, levofloxacin, moxifloxacin, pazufloxacin, sparfloxacin, temafloxacin, tosufloxacin, besifloxacin, delafloxacin, clinafloxacin, gemifloxacin, prulifloxacin, sitafloxacin, trovafloxacin), a fluoroquinolone antibiotic (e.g., delafloxacin), a sulfonamide antibiotic (e.g., sulfamethizole, sulfamethoxazole, trimethoprim-sulfamethoxazole), a macrolide antibiotic (e.g., fidaxomicin, azithromycin, erythromycin, clarithromycin, roxithromycin, dirithromycin, telithromycin), a lincosamide antibiotic (e.g., clindamycin, lincomycin), a tetracycline antibiotic (e.g., demeclocycline, doxycycline, minocycline, oxytetracycline, tetracycline, tigecycline), a streptogramin antibiotic (e.g., pristinamycin, quiupristin/dalfopristin), an aminoglycoside antibiotic (e.g., amikacin, gentamicin, kanamycin, neomycin, netilmicin, paromomycin, streptomycin, tobramycin), a cyclic lipopeptide antibiotic (e.g., daptomycin), a lipoglycopeptide antibiotic (e.g., telavancin), a glycopeptide antibiotic (e.g., vancomycin, teicoplanin), a glycylcycline antibiotic, an oxazolidinone antibiotic (e.g., linezolid, cycloserine), a tuberactinomycin antibiotic (e.g., viomycin, capreomycin), chloramphenicol, metronidazole, tinidazole, nitrofurantoin, or combinations thereof.

In some embodiments, the one or more antibacterial agent and any of the foregoing polypeptides or pharmaceutical compositions are administered within 28 days of each other (e.g., within 21, 14, 10, 7, 5, 4, 3, 2, or 1 days) or within 24 hours (e.g., 12, 6, 3, 2, or 1 hours; or concomitantly) each in an amount that together are effective to treat the subject.

Administration and Dosage

The present invention also features pharmaceutical compositions that contain a therapeutically effective amount of a polypeptide of the invention. The composition can be formulated for use in a variety of drug delivery systems. One or more physiologically acceptable excipients or carriers can also be included in the composition for proper formulation. Suitable formulations for use in the present invention are found in *Remington's Pharmaceutical Sciences, Mack Publishing Company, Philadelphia, Pa.*, 17th ed., 1985. For a brief review of methods for drug delivery, see, e.g., Langer (*Science* 249:1527-1533, 1990).

The pharmaceutical compositions are intended for parenteral, intranasal, topical, oral, or local administration, such as by a transdermal means, for prophylactic and/or therapeutic treatment. The pharmaceutical compositions can be administered parenterally (e.g., by intravenous, intramuscular, or subcutaneous injection), or by oral ingestion, or by topical application or intraarticular injection at areas affected by the vascular or cancer condition. Additional routes of administration include intravascular, intra-arterial, intratumor, intraperitoneal, intraventricular, intraepidural, as well as nasal, ophthalmic, intrascleral, intraorbital, rectal, topical, or aerosol inhalation administration. Sustained release administration is also specifically included in the invention, by such means as depot injections or erodible implants or components. Thus, the invention provides compositions for parenteral administration that include the above mention agents dissolved or suspended in an acceptable carrier, preferably an aqueous carrier, e.g., water, buffered water, saline, PBS, and the like. The compositions may contain pharmaceutically acceptable auxiliary substances as required to approximate physiological conditions, such as pH adjusting and buffering agents, tonicity adjusting agents, wetting agents, detergents and the like. The invention also provides compositions for oral delivery, which may contain inert ingredients such as binders or fillers for the formulation of a tablet, a capsule, and the like. Furthermore, this invention provides compositions for local administration, which may contain inert ingredients such as solvents or emulsifiers for the formulation of a cream, an ointment, and the like.

These compositions may be sterilized by conventional sterilization techniques, or may be sterile filtered. The resulting aqueous solutions may be packaged for use as is, or lyophilized, the lyophilized preparation being combined with a sterile aqueous carrier prior to administration. The pH of the preparations typically will be between 3 and 11, more preferably between 5 and 9 or between 6 and 8, and most preferably between 7 and 8, such as 7 to 7.5. The resulting compositions in solid form may be packaged in multiple single dose units, each containing a fixed amount of the above-mentioned agent or agents, such as in a sealed package of tablets or capsules. The composition in solid form can also be packaged in a container for a flexible quantity, such as in a squeezable tube designed for a topically applicable cream or ointment.

The compositions containing an effective amount can be administered for prophylactic or therapeutic treatments. In therapeutic applications, compositions are administered to a subject (e.g., a human) already suffering from a bacterial infection in an amount sufficient to cure or at least partially arrest the symptoms of the infection and its complications. An amount adequate to accomplish this purpose is defined as a "therapeutically effective amount," an amount of a polypeptide sufficient to substantially improve at least one symptom associated with the disease or a medical condition. For example, in the treatment of an infection, an agent or polypeptide that decreases, prevents, delays, suppresses, or arrests any symptom of the disease or condition would be therapeutically effective. A therapeutically effective amount of an agent or polypeptide is not required to cure a disease or condition but will provide a treatment for a disease or condition such that the onset of the disease or condition is delayed, hindered, or prevented, or the disease or condition symptoms are ameliorated, or the term of the disease or condition is changed or, for example, is less severe or recovery is accelerated in an individual.

Amounts effective for this use may depend on the severity of the disease or condition and the weight and general state of the subject. The therapeutically effective amount of the compositions of the invention and used in the methods of this invention applied to mammals (e.g., humans) can be determined by the ordinarily-skilled artisan with consideration of individual differences in age, weight, and the condition of the mammal. The agents of the invention are administered to a subject (e.g., a mammal, such as a human) in an effective amount, which is an amount that produces a desirable result in a treated subject. Therapeutically effective amounts can also be determined empirically by those of skill in the art.

Single or multiple administrations of the compositions of the invention including an effective amount can be carried out with dose levels and pattern being selected by the treating physician. The dose and administration schedule can be determined and adjusted based on the severity of the disease or condition in the subject, which may be monitored throughout the course of treatment according to the methods commonly practiced by clinicians or those described herein.

The polypeptides of the present invention may be used in combination with either conventional methods of treatment or therapy or may be used separately from conventional methods of treatment or therapy.

When the polypeptides of this invention are administered in combination therapies with other agents, they may be administered sequentially or concurrently to an individual. Alternatively, pharmaceutical compositions according to the present invention may be comprised of a combination of a polypeptide of the present invention in association with a pharmaceutically acceptable excipient, as described herein, and another therapeutic or prophylactic agent known in the art.

EXAMPLES

Example 1. Liposome Preparation 1-palmitoyl-2-oleoyl-sn-glycero-3-phosphocholine (POPC) and 1-palmitoyl-2-oleoyl-sn-glycero-3-phospho-(1'-rac-glycerol) (POPG) in chloroform (Avanti Polar Lipids Inc., AL, USA) were mixed in a 3:1 mol ratio (POPC:POPG) and dried into thin films. Lipid films were lyophilized overnight and brought up in 1 mL water, vortexed, frozen and lyophilized again. Lipids were then resuspended in 10 mM Tris buffer 10 mM NaCl pH 7.4 (5 mM) and freeze thawed 5× over dry ice and a water bath (50° C.). Lipids were then extruded using a 0.2 micron sized filter and left to equilibrate overnight. Samples were diluted further with buffer (2.5 mM) prior to addition to lyophilized peptide.

The lyophilized peptides added were:

Example 2. Determination of Helicity of Stapled Polypeptides by Circular Dichromism The helicity of the polypeptides described in Example 1 were tested by circular dichromism (CD) spectroscopy. The helicity of the polypeptides was determined in SDS micelles and in lipid bilayers.

The conditions in which the helicity in micelles were tested was stapled peptides (20 µM) in buffer (10 mM Tris HCl; 10 mM NaCl pH 7.4) and 140 mM SDS. The conditions in which the helicity in lipid bilayers were tested was 10 µM peptides in 2.5 mM POPC:POPG (3:1 mol ratio) (bacterial membrane mimetic lipid mixture).

Figure 1B:
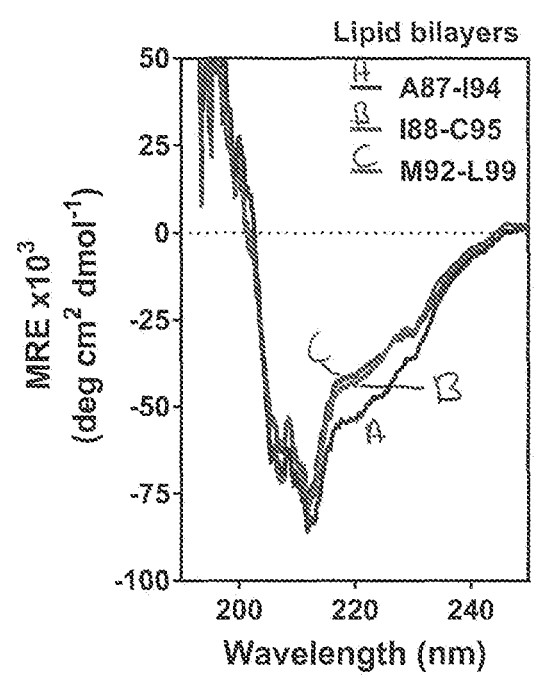

As shown in FIGS. 1A and 1B, all of the tested polypeptides were found to be helical in both micelles and lipid bilayers.

Example 3. Determination of Cell Toxicity of Stapled Polypeptides

E. coli K12 cells were grown overnight to saturation in LB (Luria broth). Cells were harvested and resus-pended in

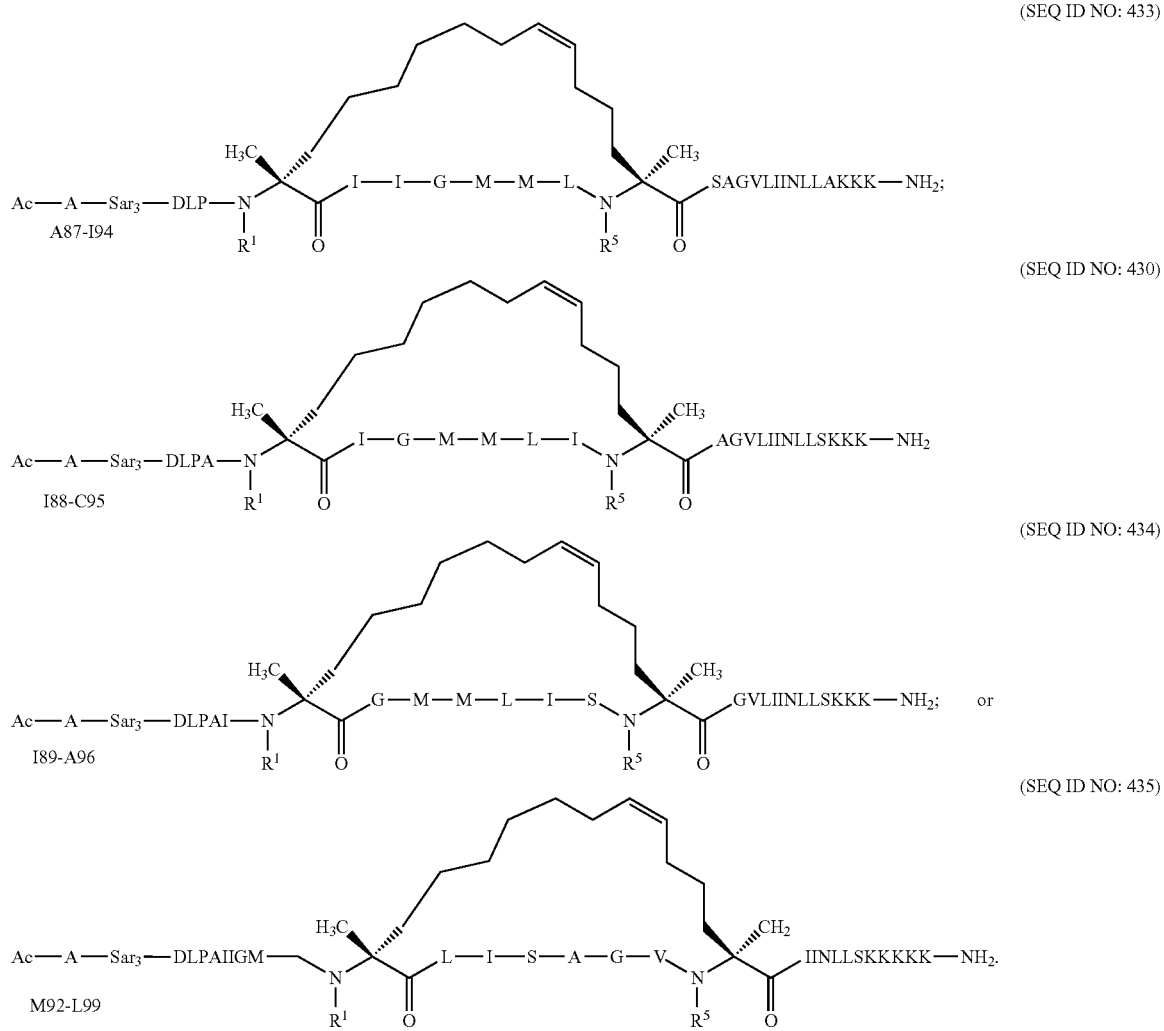

fresh media to a final OD600 of 0.1. Cells were then grown in the presence of DMSO (dimethyl sulfoxide) alone or in DMSO-solubilized peptide (4 µM) over 1 hour, while OD600 was recorded in 15-minute intervals. E. coli growth curves were normalized to the starting OD600. Growth in the presence of peptide was normalized to the growth of cells with DMSO alone, using:

$$\text{Growth} = \frac{OD_{600}^{+peptide}}{OD_{600}^{-peptide}}.$$

Figure 2:
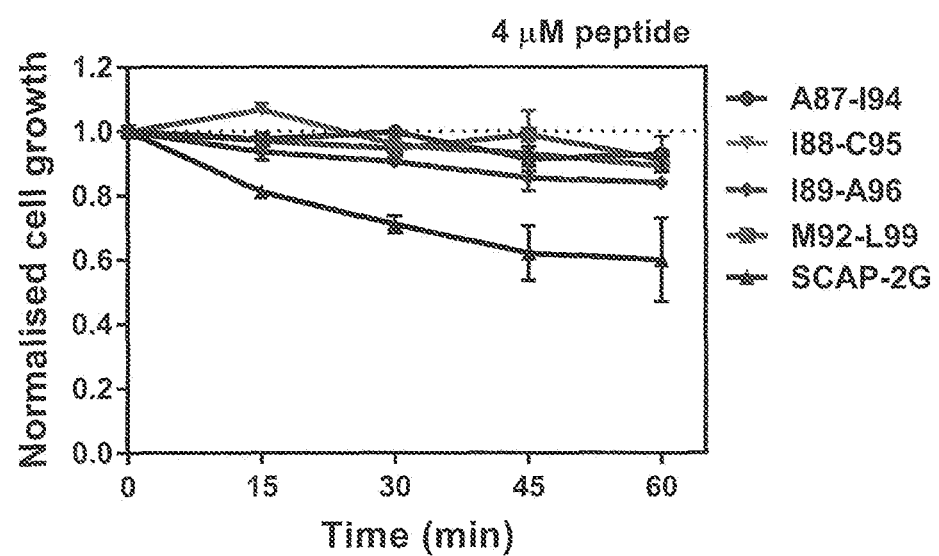
FIG. 2 is a graph illustrating the toxicity of polypeptides of the invention to *E. coli* cells.

As shown in FIG. 2, none of the four hydrocarbon-stapled peptides severely impact cell growth over the time tested. A dashed line at 1.0 represents the starting conditions of the cells. S-CAP-2G (sequence: KKKKKK-AGFAAWAAFGA (SEQ ID NO: 439), hydrocarbon staple indicated by underlined A) is a positive control for cell death. Data shown represents the average of at least 2 independent experiments. Error is indicated as SD.

Example 4. Inhibition of Efflux by Stapled Polypeptides

*E. coli* K12 cells were harvested by centrifugation, resuspended and diluted to an OD600=0.1 in Minimal Medium A. Cells were then treated with 80 µM carbonyl cyanide m-chlorophenyl hydrazine (CCCP) for 5 min at room temperature, before adding 1 µg/mL EtBr and either DMSO (8 µl) or peptide (4 µM) from a concentrated DMSO stock (1000 µM peptide). Cells were incubated at 37° C. with shaking (250 rpm) for 30 min, centrifuged for 10 min, resuspended in fresh Minimal Medium A supplemented with 1 µg/mL EtBr (without CCCP). Fluorescence decay was immediately measured using a spectropolarimeter (Photon Technology International, NJ, USA) over 2200s with stirring ($\lambda$ex=530 nm, slit width 2 nm, $\lambda$em=600 nm, slit width 4 nm, 1s intervals). Background fluorescence intensity (ethidium alone, as well as final plateau values for *E. coli* cells alone) was subtracted from fluorescence values. Efflux experiments were repeated three times.

Figure 3:
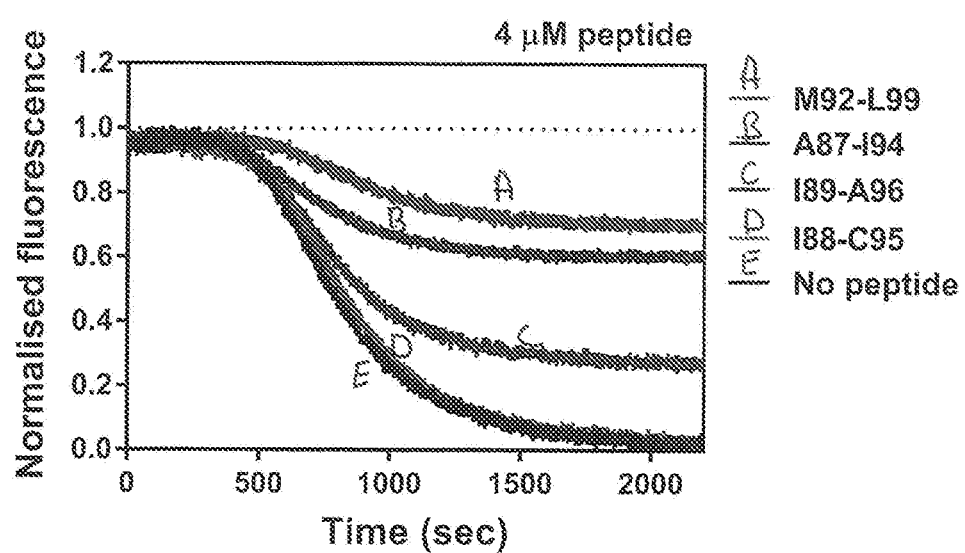
FIG. 3 is a graph illustrating the efflux of ethidium bromide from *E. coli* cells in the presence and absence of polypeptides of the invention.

As shown in FIG. 3, M92-L99 inhibits efflux activity by 68%, A87-I94 by 60%, I89-A96 by 26%. I88-C95 does show any inhibition of efflux activity. A dashed line at 1.0 represents 100% inhibition.

OTHER EMBODIMENTS

It is to be understood that while the present disclosure has been described in conjunction with the detailed description thereof, the foregoing description is intended to illustrate and not limit the scope of the present disclosure, which is defined by the scope of the appended claims. Other aspects, advantages, and alterations are within the scope of the following claims.

Those skilled in the art will recognize, or be able to ascertain using no more than routine experimentation, many equivalents to the specific embodiments in accordance with the invention described herein. The scope of the present invention is not intended to be limited to the above Description, but rather is as set forth in the appended claims.

In the claims, articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention includes embodiments in which more than one, or all of the group members are present in, employed in, or otherwise relevant to a given product or process.

It is also noted that the term "comprising" is intended to be open and permits but does not require the inclusion of additional elements or steps. When the term "comprising" is used herein, the term "consisting of" is thus also encompassed and disclosed.

Where ranges are given, endpoints are included. Furthermore, it is to be understood that unless otherwise indicated or otherwise evident from the context and understanding of one of ordinary skill in the art, values that are expressed as ranges can assume any specific value or subrange within the stated ranges in different embodiments of the invention, to the tenth of the unit of the lower limit of the range, unless the context clearly dictates otherwise.

In addition, it is to be understood that any particular embodiment of the present invention that falls within the prior art may be explicitly excluded from any one or more of the claims. Since such embodiments are deemed to be known to one of ordinary skill in the art, they may be excluded even if the exclusion is not set forth explicitly herein. Any particular embodiment of the compositions of the invention (e.g., any polynucleotide or protein encoded thereby; any method of production; any method of use) can be excluded from any one or more claims, for any reason, whether or not related to the existence of prior art.

The invention claimed is:

1. A polypeptide, or a pharmaceutically acceptable salt thereof, comprising a stabilized α-helix, wherein the polypeptide comprises the structure of Formula I:

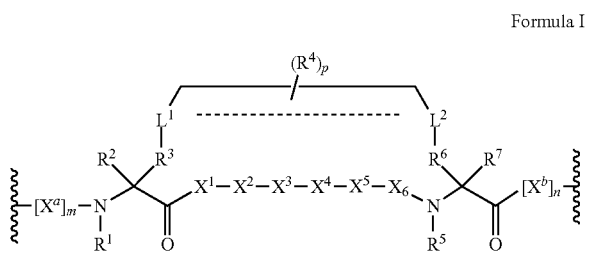

Formula I wherein the dotted line represents an optional double bond;

m is 1, 2, 3, 4, 5, or 6;

n is 6-m;

p is 0, 1, or 2;

each of $[X^a]_m$, $[X^b]_b$, and $X^1$-$X^6$ consist of consecutive amino acids of an α-helix of a monomer of a small multidrug resistance transporter, or conservative substitutions thereof;

$R^1$ and $R^5$ are, independently, hydrogen, optionally substituted acyl, or optionally substituted $C_1$-$C_6$ alkyl;

$R^2$ and $R^7$ are, independently, optionally substituted $C_1$-$C_6$ alkyl, optionally substituted $C_2$-$C_6$ alkenyl, optionally substituted $C_2$-$C_6$ alkynyl, optionally substituted $C_1$-$C_6$ heteroalkyl, optionally substituted $C_3$-$C_6$ carbocyclyl, or optionally substituted $C_2$-$C_9$ heterocyclyl;

$R^3$ and $R^6$ are, independently, optionally substituted $C_1$-$C_6$ alkylene, optionally substituted $C_1$-$C_6$ heteroalkylene, optionally substituted $C_3$-$C_6$ carbocyclyl, or optionally substituted $C_2$-$C_9$ heterocyclyl, or $R^1$ and $R^3$ or $R^5$ and $R^6$ combine with the atoms to which they are attached to form an optionally substituted $C_5$-$C_6$ heterocyclyl;

$L^1$ and $L^2$ are, independently, absent, optionally substituted $C_1$-$C_6$ alkylene, or —C(=O)OR$^{L1}$—, wherein each $R^{L1}$ is, independently, an optionally substituted $C_1$-$C_6$ alkyl; and each $R^4$ is, independently, optionally substituted $C_1$-$C_6$ alkyl, or optionally substituted $C_1$-$C_6$ heteroalkyl, wherein the polypeptide binds to the monomer of a small multidrug resistance transporter.

2. The polypeptide of claim 1, wherein $R^2$ is optionally substituted $C_1$-$C_6$ alkyl.

3. The polypeptide of claim 2, wherein the optionally substituted $C_1$-$C_6$ alkyl is methyl.

4. The polypeptide of claim 1, wherein $R^7$ is optionally substituted $C_1$-$C_6$ alkyl.

5. The polypeptide of claim 4, wherein the optionally substituted $C_1$-$C_6$ alkyl is methyl.

6. The polypeptide of claim 1, wherein $R^1$ is hydrogen.

7. The polypeptide of claim 1, wherein $R^5$ is hydrogen.

8. The polypeptide of claim 1, wherein p is 0.

9. The polypeptide of claim 1, wherein $R^6$ is optionally substituted $C_1$-$C_6$ alkylene.

10. The polypeptide of claim 9, wherein the optionally substituted $C_1$-$C_6$ alkylene is methylene.

11. The polypeptide of claim 1, wherein $R^3$ is optionally substituted $C_1$-$C_6$ alkylene.

12. The polypeptide of claim 11, wherein the optionally substituted $C_1$-$C_6$ alkylene is methylene.

13. The polypeptide of claim 1, wherein $L^1$ is optionally substituted $C_1$-$C_6$ alkylene.

14. The polypeptide of claim 13, wherein optionally substituted $C_1$-$C_6$ alkylene is pentylene.

15. The polypeptide of claim 1, wherein $L^2$ is optionally substituted $C_1$-$C_6$ alkylene.

16. The polypeptide of claim 15, wherein optionally substituted $C_1$-$C_6$ alkylene is ethylene.

17. The polypeptide of claim 1, wherein the dotted line represents a double bond.

18. The polypeptide of claim 1, wherein $X^1$ is glycine, alanine, valine, leucine, or isoleucine.

19. The polypeptide of claim 18, wherein $X^1$ is glycine.

20. The polypeptide of claim 1, wherein each $R^4$ is, independently, optionally substituted $C_1$-$C_6$ alkyl.

* * * * *